US012643889B2

(12) United States Patent
Zhang et al.

(10) Patent No.: US 12,643,889 B2
(45) Date of Patent: Jun. 2, 2026

(54) SYNTHESIS OF NOVEL EP4 ANTAGONIST AND USE IN CANCER AND INFLAMMATION

(71) Applicant: Wuhan Humanwell Innovative Drug Research And Development Center Limited Company, Wuhan (CN)

(72) Inventors: Xuejun Zhang, Wuhan (CN); Yang Zang, Wuhan (CN); Lie Li, Wuhan (CN); Jie Shen, Wuhan (CN); Zhe Liu, Wuhan (CN); Shaohua Chang, Wuhan (CN); Yonggang Wang, Wuhan (CN)

(73) Assignee: WUHAN HUMANWELL INNOVATIVE DRUG RESEARCH AND DEVELOPMENT CENTER LIMITED COMPANY, Hubei (CN)

( * ) Notice: Subject to any disclaimer, the term of this patent is extended or adjusted under 35 U.S.C. 154(b) by 781 days.

(21) Appl. No.: 17/905,559

(22) PCT Filed: Mar. 4, 2021

(86) PCT No.: PCT/CN2021/079073

§ 371 (c)(1),
(2) Date: Sep. 2, 2022

(87) PCT Pub. No.: WO2021/175283

PCT Pub. Date: Sep. 10, 2021

(65) Prior Publication Data

US 2023/0125494 A1 Apr. 27, 2023

(30) Foreign Application Priority Data

Mar. 4, 2020 (CN) ......................... 202010144983.1

(51) Int. Cl.
*C07D 409/12* (2006.01)
*A61K 45/06* (2006.01)
*C07D 231/20* (2006.01)

(52) U.S. Cl.
CPC ............ *C07D 409/12* (2013.01); *A61K 45/06* (2013.01); *C07D 231/20* (2013.01)

(58) Field of Classification Search
CPC .................................................... C07D 409/12
See application file for complete search history.

(56) References Cited

FOREIGN PATENT DOCUMENTS

| | | | |
|---|---|---|---|
| CN | 103097358 | A | 5/2013 |
| CN | 106572993 | A | 4/2017 |
| CN | 108929281 | A | 12/2018 |
| EP | 3061751 | A1 | 8/2016 |
| JP | 2007504210 | A | 3/2007 |
| JP | 2010500293 | A | 1/2010 |
| JP | 2013538825 | A | 10/2013 |
| JP | 2017516775 | A | 6/2017 |
| JP | 2018530595 | A | 10/2018 |
| KZ | 33902 | B | 9/2019 |
| WO | WO2009139373 | A1 | 11/2009 |
| WO | WO2012039972 | A1 | 3/2012 |
| WO | WO2015179615 | A1 | 11/2015 |
| WO | WO2022161418 | A1 | 8/2022 |

OTHER PUBLICATIONS

Bao et al (2015) : STN International, CAPLUS database, Accession No. 2015 : 1895598.*
Spyvee et al (2012) : STN International, CAPLUS database, Accession No. 2012 : 458190.*
Extended European Search Report mailed Feb. 27, 2024 for European Patent Application 21765389.8 a foreign counterpart to U.S. Appl. No. 17/905,559 7 pages.
Japanese Office Action dated Feb. 14, 2024 in Japanese Application No. 2022-552881, a corresponding foreign application of U.S. Appl. No. 17/905,559, 5 pages.
Office Action for Korean Application No. 10-2022-7031652, Dated Oct. 7, 2024, 22 pages.
Office Action for New Zealand Application No. 792763, Dated Sep. 26, 2024, 5 pages.

(Continued)

*Primary Examiner* — Golam M Shameem
(74) *Attorney, Agent, or Firm* — Lee & Hayes, P.C.

(57) ABSTRACT

The present disclosure provides a novel compound effective in antagonizing EP4, which is a compound represented by Formula I, or a tautomer, stereoisomer, hydrate, solvate, pharmaceutically acceptable salt or prodrug of the compound represented by Formula I:

I

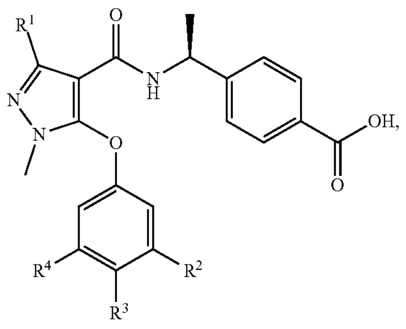

wherein: $R^1$ is selected from —$CH_3$, —$CHF_2$, and —$CF_3$; $R^2$ is selected from $C_2$-$C_6$ alkyl, $C_3$-$C_6$ cycloalkyl, $C_2$-$C_6$ halogen-substituted alkyl, $C_3$-$C_6$ halogen-substituted cycloalkyl; $R^3$ is selected from hydrogen, halogen, $C_1$-$C_2$ alkyl, $C_1$-$C_2$ fluorine- or chlorine-substituted alkyl; $R^4$ is selected from hydrogen, halogen, $C_1$-$C_6$ alkyl, $C_1$-$C_6$ alkoxyl, $C_1$-$C_6$ halogen-substituted alkyl, $C_1$-$C_6$ halogen-substituted alkoxyl.

13 Claims, 1 Drawing Sheet

(56) References Cited

OTHER PUBLICATIONS

Australian Office Action mailed Apr. 6, 2023 in Australian Application No. 2021229414, a corresponding foreign application of U.S. Appl. No. 17/905,559, 11 pages.
Australian Notice of Acceptance mailed Jun. 22, 2023 in Australian Application No. 2021229414, a corresponding foreign application of U.S. Appl. No. 17/905,559, 4 pages.
Indian Office Action mailed Jun. 12, 2023 in Indian Application No. 202227056257, a corresponding foreign application of U.S. Appl. No. 17/905,559, 6 pages.
Russian Office Action mailed Apr. 13, 2023 in Russian Application No. 2022125315/04, a corresponding foreign application of U.S. Appl. No. 17/905,559, 27 pages.
Yang et al., "Discovery and characterization of 1H-1,2,3-Triazole derivatives as novel prostanoid EP4 receptor antagonists for cancer immunotherapy," Journal of Medicainal Chemistry, 2020, 63:569-590.
Canadian Office Action mailed Nov. 3, 2023 in Canadian Application No. 3,170,288, a corresponding foreign application of U.S. Appl. No. 17/905,559, 6 pages.
Indian Office Action mailed Oct. 26, 2023 in Indian Application No. 202227056257, a corresponding foreign application of U.S. Appl. No. 17/905,559, 2 pages.
Japanese Office Action mailed Sep. 11, 2023 in Japanese Application No. 2022-552881, a corresponding foreign application of U.S. Appl. No. 17/905,559, 50 pages.
Office Action for Chinese Application No. 202110240347.3, Dated Apr. 29, 2024, 17 pages.
Office Action for Chinese Application No. 202110240347.3, Dated Jan. 22, 2025, 13 pages.
Office Action for Korean Application No. 2022-7031652, Dated Apr. 3, 2025, 6 pages.
Office Action for Korean Application No. 2022-7031652, Dated Dec. 20, 2024, 12 pages.
Schiffler, et al., "Discovery and Characterization of a Potent and Selctive EP4 Receptor Antagonist," Bioorganic & Medicinal Chemistry Letters, vol. 25, No. 16, Aug. 2015, pp. 3176-3178.
Bender et al., "Evaluation of a candidate anti-arthritic drug using the mouse collagen antibody induced arthritis model and clinically relevant biomarkers," Jan. 2013. Am J Transl Res, 5(1), 92-102.
International Search Report and Written Opinion mailed May 27, 2021 in Intenational Application No. PCT/CN2021/079073, 21 pages.

* cited by examiner

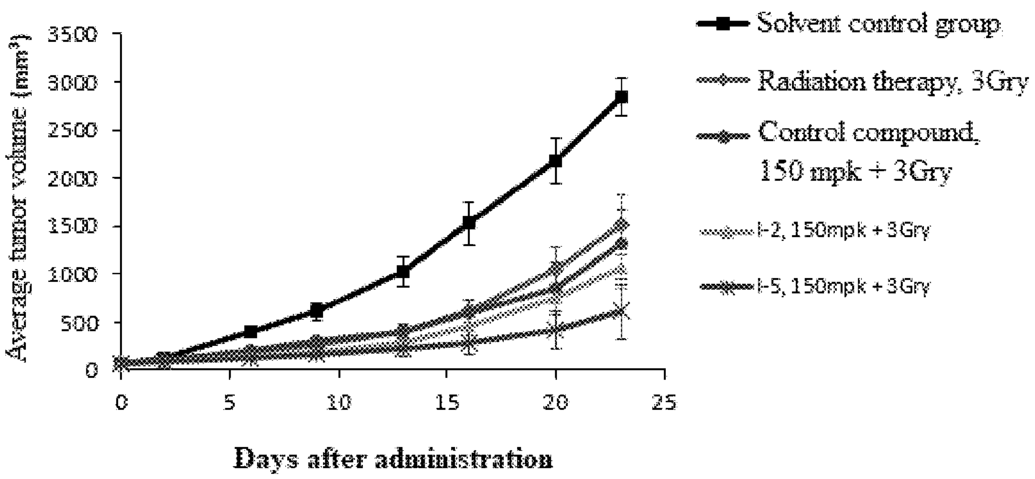
Solvent control group
Radiation therapy, 3Gry
Control compound, 150 mpk + 3Gry
I-2, 150mpk + 3Gry
I-5, 150mpk + 3Gry
Average tumor volume (mm³)
3500
3000
2500
2000
1500
1000
500
0
0
5
10
15
20
25
Days after administration

SYNTHESIS OF NOVEL EP4 ANTAGONIST AND USE IN CANCER AND INFLAMMATION

CROSS-REFERENCE TO RELATED APPLICATIONS

This application is a U.S. National Phase Application of International Application No. PCT/CN2021/079073, filed Mar. 4, 2021, which claims the priority of Chinese Patent Application No. 202010144983.1, filed on Mar. 4, 2020, which are incorporated herein by reference in their entirety.

FIELD

The present disclosure relates to the chemistry and medicine field, and in particular, to a pyrazole derivative and use thereof.

BACKGROUND

Prostaglandin $E_2$ ($PGE_2$) is an endogenous bioactive lipid. $PGE_2$ activates prostaglandin receptors to cause a broad upstream and downstream dependent biological response (Legler, D. F. et al, hit. J Biochem. Cell Biol. 2010, 42, p. 198-201), involved in the regulation of numerous physiological and pathological processes including inflammation, pain, renal function, cardiovascular system, pulmonary function, and cancer. It is reported that $PGE_2$ is highly expressed in cancerous tissues of various cancers, and it has been confirmed that $PGE_2$ is associated with the occurrence, growth and development of cancer and disease conditions in patients. It is generally believed that $PGE_2$ is associated with the activation of cell proliferation and cell death (apoptosis) and plays an important role in the processes of cancer cell proliferation, disease progression and cancer metastasis.

The receptors of $PGE_2$ are divided into 4 subtypes, i.e., EP1, EP2, EP3 and EP4, which are widely distributed in various tissues. Among these subtypes, $PGE_2$ effects on the EP4 receptor to interfere with inflammatory responses (including immunoinflammatory responses), smooth muscle relaxation, pains, lymphocyte differentiation, hypertrophy or proliferation of vascular mesangial cells, secretion of gastrointestinal mucus, and the like. Thus, it can be considered that EP4 receptor antagonists are promising as anti-inflammatory and/or analgesic agents for the treatment of diseases associated with the $PGE_2$-EP4 pathway, such as inflammatory diseases, diseases accompanied by various pains, and the like.

EP4 is the primary receptor involved in arthritic pain in rodent models of rheumatoid arthritis and osteoarthritis (for example, see J. Pharmacol. Exp. Ther., 325, 425 (2008)), which upon activation leads to an accumulation of the intracellular signaling molecule cAMP. There have been studies detecting EP4 receptor expression on peripheral nerve endings of pain receptors, macrophages, and neutrophils, and it has been confirmed that these cell types are extremely important for endometriosis. Studies have reported that oral EP4 antagonists can reduce proteinuria in type II diabetic mice, inhibiting the progression of diabetic nephropathy. Additional studies have reported that activation of EP4 and increased production of $PGE_2$ in the bladder mucosa may be the important causes of overactive bladder by prostatitis, and intravesical injection of EP4 antagonists may be effective in ameliorating overactive bladder following prostatitis. Thus, selective EP4 antagonists may be useful in the treatment of arthritis, including arthritis pain as well as endometriosis, diabetic nephropathy, overactive bladder. The existing treatments for arthritis are mainly conventional non-steroidal anti-inflammatory drugs (NSAIDs) or selective COX-2 inhibitors, which can produce cardiovascular and/or gastrointestinal side effects. However, the selective EP4 antagonists are less likely to produce cardiovascular side effects.

$PGE_2$ continuously activates EP receptors (abundantly produced by tumor cells) in the tumor microenvironment (Ochs et al, J Neurochem. 2016, 136, p. 1142-1154; Zelenay, S. et al, Cell 2015, 162, p. 1257-1270), which promotes the accumulation of a variety of immunosuppressive cells and enhances the activity thereof. The immunosuppressive cells include type II tumor-associated macrophages (TAMSs), Treg cells, and myeloid-derived suppressor cells (MDSC). One of the main features of the immunosuppressive tumor microenvironment is the presence of a large number of MDSCs and TAMs, which in turn are closely associated with low overall survival in patients with gastric, ovarian, breast, bladder, hepatocellular carcinoma (HCC), head and neck cancer, and other types of cancer. In addition, it was reported that $PGE_2$ can induce immune tolerance by suppressing the accumulation of antigen-presenting dendritic cells (DCs) in tumors as well as suppressing the activation of tumor-infiltrating DCs (Wang et al, Trends in Molecular Medicine 2016, 22, p. 1-3). All of these $PGE_2$-mediated effects may together help tumor cells evade immune surveillance. $PGE_2$ plays an important role in promoting the development of tumorigenesis. Increased expression levels of $PGE_2$ and its related receptors EP2 and EP4 have been found in various types of malignancies, including colon cancer, lung cancer, breast cancer, and head and neck cancer, and they are often closely associated with poor prognosis (Bhooshan, N. et al. Lung Cancer 101, 88-91). Thus, selective blockade of the EP2 and EP4 signaling pathways can suppress tumorigenesis by altering the tumor microenvironment and modulating tumor immune cells.

Existing preclinical research data indicate that EP2- and EP4-specific antagonists can prevent or inhibit tumor growth to varying degrees in animal models such as colon, esophageal, lung, and breast cancer. Among the $PGE_2$ receptor drugs entered into the clinic, Grapiprant, an EP4 antagonist developed by Pfizer, has been approved by the FDA for the treatment of arthritis in dogs, and meanwhile, it entered antitumor phase II clinical trials in 2015 for the treatment of multiple types of solid tumors such as prostate cancer, non-small cell lung cancer and breast cancer (De Vito, V. et al. J Pharm Biomed Anal 118, 251-258). E7046, an EP4 antagonist developed by Eisai, also launched a clinical phase I studies in 2015, and a phase Ib clinical trials in combination with radiotherapy or chemotherapy for rectal cancer was launched in 2017. ONO-4578, developed by Ono Pharmaceutical, entered a phase I clinical trials for advanced or metastatic solid tumors in 2017, and a phase I/II clinical trials for the treatment of advanced solid tumors either alone or in combination with nivolumab in 2018.

At present, EP4 antagonists have made some progress in the treatment of inflammatory diseases, pain, cancer, etc. However, it is still urgent to develop new drugs as improvements or replacements for current drugs.

SUMMARY

The present disclosure provides a compound capable of effectively antagonizing EP4, which can be used as an improvement or replacement of the current drugs or EP4 antagonists.

To this end, in a first aspect, the present disclosure provides a compound, which is a compound represented by Formula V, or a tautomer, stereoisomer, hydrate, solvate, salt or prodrug of the compound represented by Formula V:

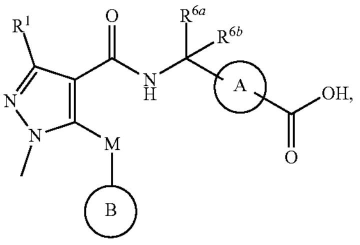

V in which the ring A is selected from

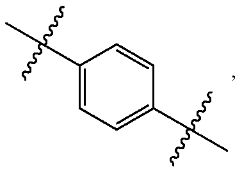

,

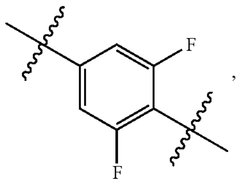

,

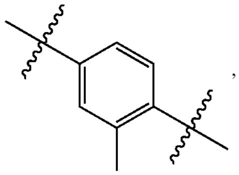

, and

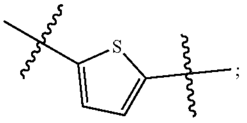

;

the ring B is selected from

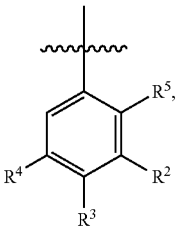

and

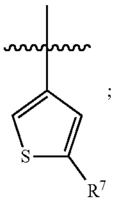

;

$R^1$ is selected from —$CH_3$, —$CHF_2$, and —$CF_3$;

$R^2$ is selected from $C_2$-$C_6$ alkyl, $C_3$-$C_6$ cycloalkyl, phenyl, trifluoromethyl, $C_2$-$C_6$ halogen-substituted alkyl, $C_3$-$C_6$ halogen-substituted cycloalkyl, $C_2$-$C_6$ hydroxy-substituted alkyl, $C_2$-$C_6$ cyano-substituted alkyl, —$SF_5$, and —X—$R^{2a}$, where X is selected from oxygen, sulfur, —CO—, —$SO_2$—, and SO—, and $R^{2a}$ is selected from $C_1$-$C_6$ alkyl and $C_1$-$C_6$ halogen-substituted alkyl;

$R^3$ is selected from hydrogen, halogen, $C_1$-$C_2$ alkyl, $C_1$-$C_2$ fluorine-substituted alkyl, and phenyl;

$R^4$ is selected from hydrogen, halogen, $C_1$-$C_6$ alkyl, $C_1$-$C_6$ alkoxyl, $C_1$-$C_6$ halogen-substituted alkyl, and $C_1$-$C_6$ halogen-substituted alkoxyl;

$R^5$ is selected from hydrogen and halogen;

one of $R^{6a}$ and $R^{6b}$ is hydrogen, and the other one of $R^{6a}$ and $R^{6b}$ is methyl; or $R^{6a}$ and $R^{6b}$ together form cyclobutyl;

$R^7$ is selected from —$CH_3$, —$CHF_2$, and —$CF_3$; and

M is selected from oxygen, sulfur, and methylene;

provided that:

when $R^2$ is trifluoromethyl, M is oxygen, one of $R^{6a}$ and $R^{6b}$ is hydrogen, and the other one of $R^{6a}$ and $R^{6b}$ is methyl, the ring A is selected from

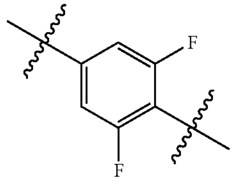

and

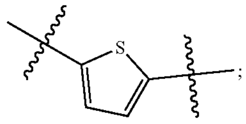

;

and when $R^2$ is trifluoromethyl, M is oxygen, and the ring A is

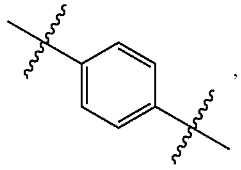 [SMILES: *c1ccc(*)cc1]

, $R^{6a}$ and $R^{6b}$ together form cyclobutyl.

According to the embodiments of the present disclosure, the above compound may further include at least one of the following additional technical features.

According to the embodiments of the present disclosure, the compound is a compound represented by Formula III, or the compound is a tautomer, stereoisomer, hydrate, solvate, salt or prodrug of the compound represented by Formula III:

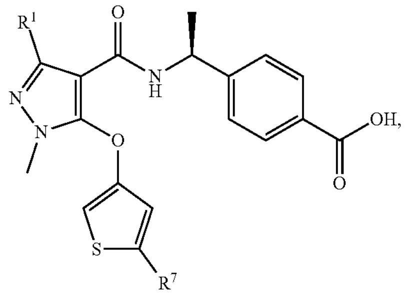

III in which $R^1$ is selected from —$CH_3$, —$CHF_2$, and —$CF_3$; $R^7$ is selected from —$CH_3$, —$CHF_2$, and —$CF_3$; and M is selected from oxygen, sulfur, and methylene.

According to the embodiments of the present disclosure, the compound is a compound represented by Formula II, or the compound is a tautomer, stereoisomer, hydrate, solvate, salt or prodrug of the compound represented by Formula II:

II

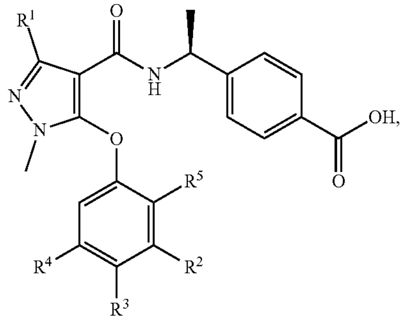

in which $R^1$ is selected from —$CH_3$, —$CHF_2$, and —$CF_3$, and preferably, $R^1$ is —$CHF_2$; $R^2$ is selected from ethyl, propyl, isopropyl, n-butyl, isobutyl, tert-butyl, fluoroethyl, fluoropropyl, fluoroisopropyl, fluorobutyl, fluoroisobutyl, hydroxyethyl, hydroxyisopropyl, cyanomethyl, cyanoethyl, phenyl, —$SF_5$, and —X—$R^{2a}$, where X is selected from oxygen, sulfur, and —CO—, and $R^{2a}$ is selected from methyl, ethyl, fluoromethyl, and fluoroethyl; $R^3$ is selected from hydrogen, fluorine, chlorine, methyl, ethyl, fluoromethyl, fluoroethyl, and phenyl; $R^4$ is selected from hydrogen, fluorine, chlorine, methyl, ethyl, fluoromethyl, and fluoroethyl; $R^5$ is selected from hydrogen, fluorine, and chlorine; and M is selected from oxygen, sulfur, and methylene.

According to the embodiments of the present disclosure, the compound is a compound represented by Formula I (also referred as to compound I), or the compound is a tautomer, stereoisomer, hydrate, solvate, salt or prodrug of the compound represented by Formula I:

I

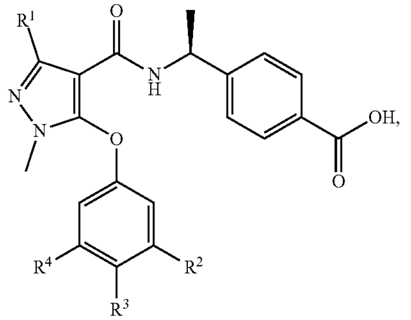

in which $R^1$ is selected from —$CH_3$, —$CHF_2$, and —$CF_3$; $R^2$ is selected from $C_2$-$C_6$ alkyl, $C_3$-$C_6$ cycloalkyl, $C_2$-$C_6$ halogen-substituted alkyl, and $C_3$-$C_6$ halogen-substituted cycloalkyl; $R^3$ is selected from hydrogen, halogen, $C_1$-$C_2$ alkyl, and $C_1$-$C_2$ fluorine-substituted alkyl; $R^4$ is selected from hydrogen, halogen, $C_1$-$C_6$ alkyl, $C_1$-$C_6$ alkoxyl, $C_1$-$C_6$ halogen-substituted alkyl, and $C_1$-$C_6$ halogen-substituted alkoxyl.

According to the embodiments of the present disclosure, the above compound may further include at least one of the following additional technical features.

According to the embodiments of the present disclosure, $R^2$ is selected from $C_2$-$C_3$ alkyl, $C_3$-$C_6$ cycloalkyl, $C_2$-$C_3$ fluorine-substituted alkyl, and $C_3$-$C_6$ fluorine-substituted cycloalkyl.

According to the embodiments of the present disclosure, $R^2$ is preferably selected from —$CH_2CH_3$, —$CH(CH_3)_2$, cyclopropyl, —$CF_2CH_3$, and —$CH_2CF_3$.

According to the embodiments of the present disclosure, $R^3$ is selected from hydrogen, fluorine, and chlorine.

According to the embodiments of the present disclosure, $R^4$ is selected from hydrogen, halogen, $C_1$-$C_6$ alkyl, $C_1$-$C_6$ alkoxyl, $C_1$-$C_6$ halogen-substituted alkyl, and $C_1$-$C_6$ halogen-substituted alkoxyl.

According to some embodiments of the present disclosure, $R^4$ is selected from hydrogen, fluorine, chlorine, $C_1$-$C_4$ alkyl, $C_1$-$C_4$ alkoxyl, $C_1$-$C_4$ fluorine- or chlorine-substituted alkyl, $C_1$-$C_4$ fluorine- or chlorine-substituted alkoxyl; and preferably, $R^4$ is selected from hydrogen, fluorine, and chlorine.

According to the embodiments of the present disclosure, the compound is any one of the following compounds, or the compound is a tautomer, stereoisomer, hydrate, solvate, pharmaceutically acceptable salt or prodrug of any one of the following compounds:

I-1

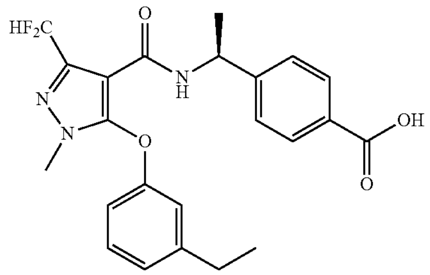

I-2

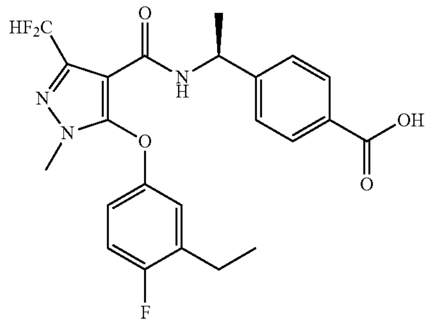

I-3

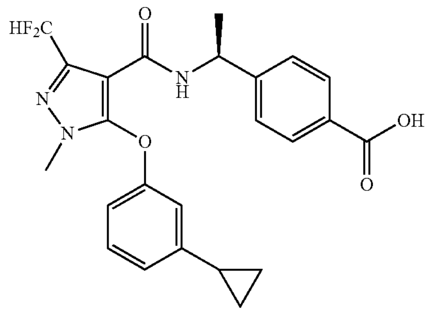

-continued
I-4
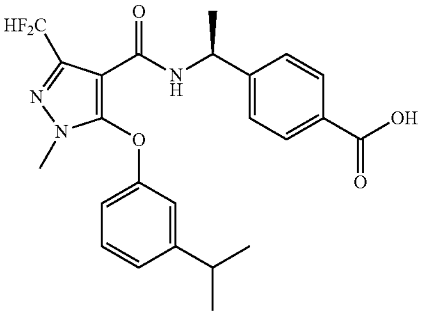
I-5
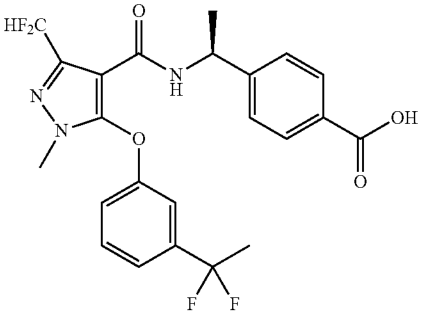
I-6
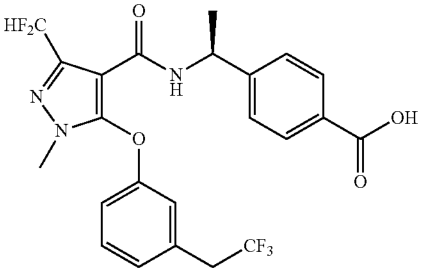
I-7
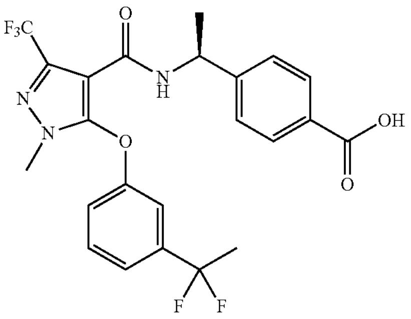
I-8
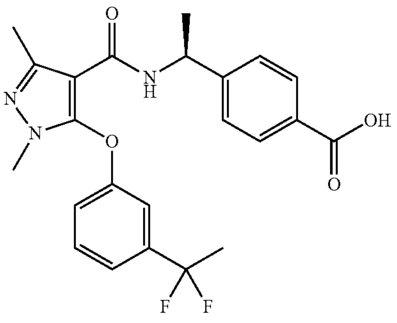
-continued
I-9
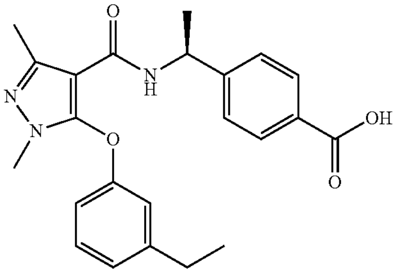
I-10
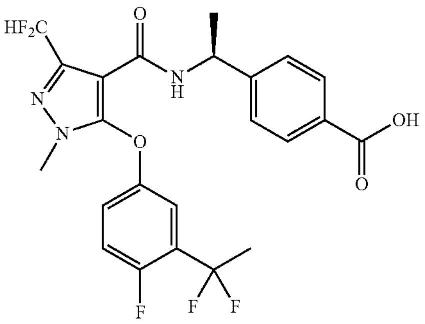
I-11
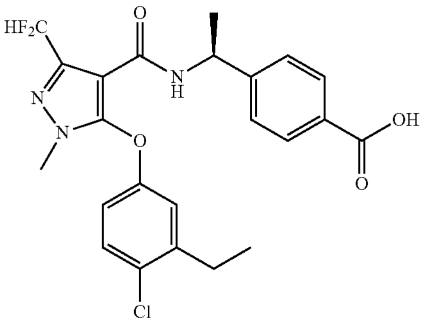
I-12
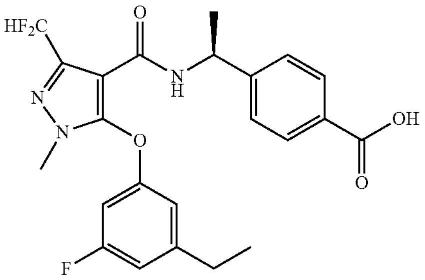
I-13
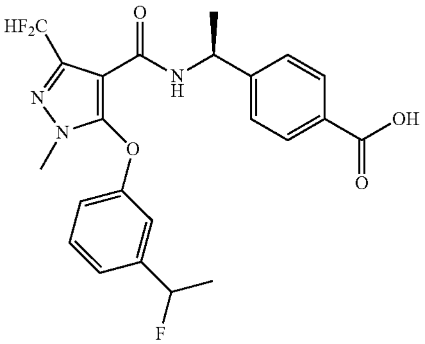

-continued
I-14
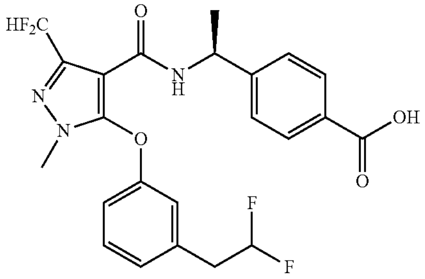
I-15
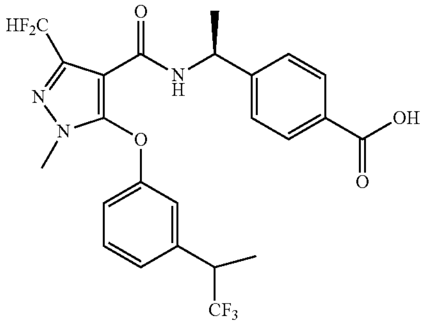
I-16
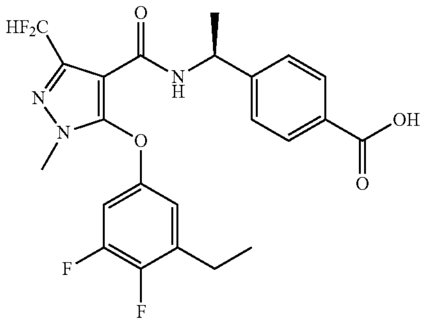
I-17
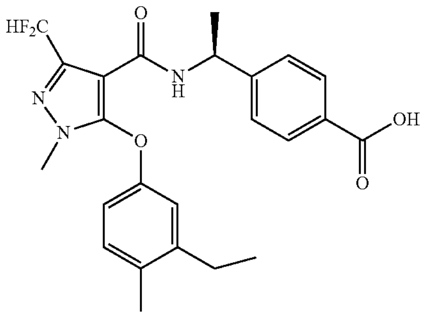
I-18
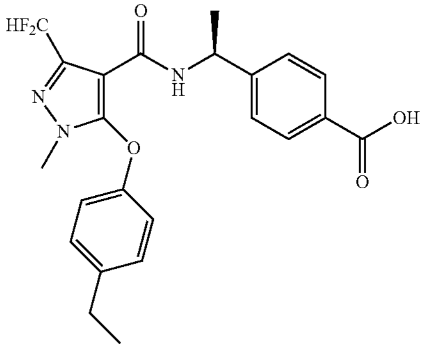
-continued
I-19
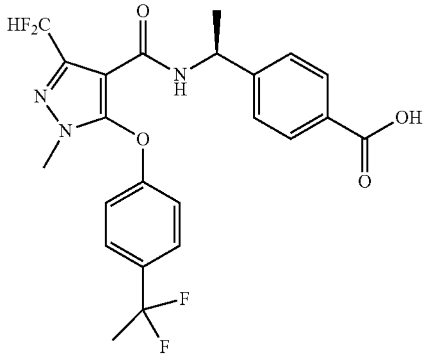
I-20
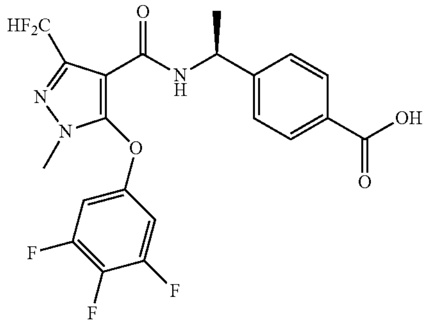
I-21
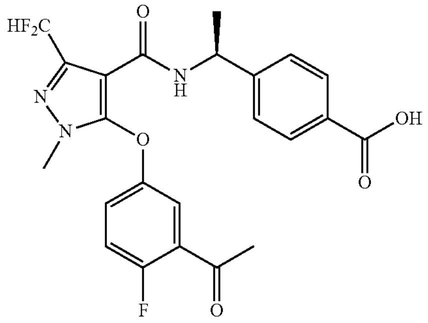
I-22
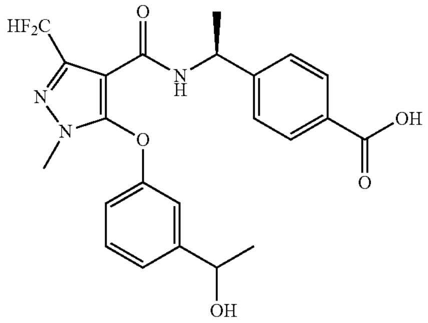

-continued
I-23
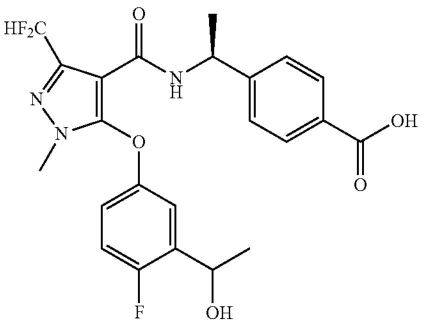
I-24
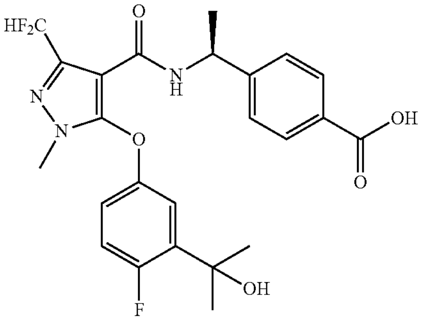
I-25
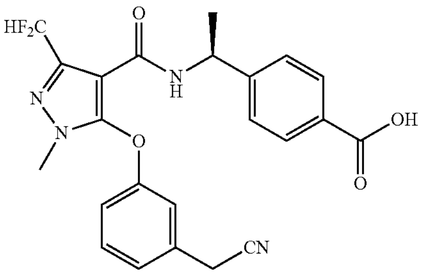
I-26
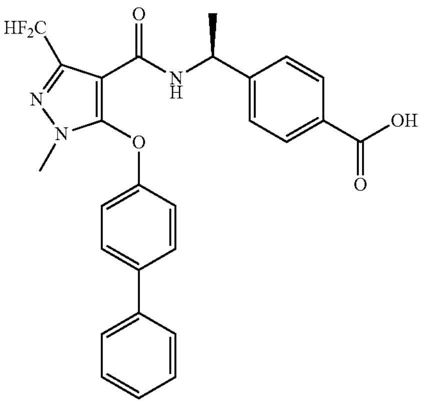
-continued
I-27
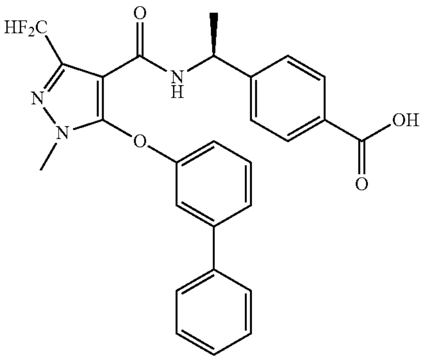
I-28
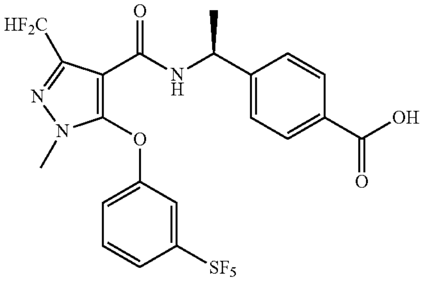
I-29
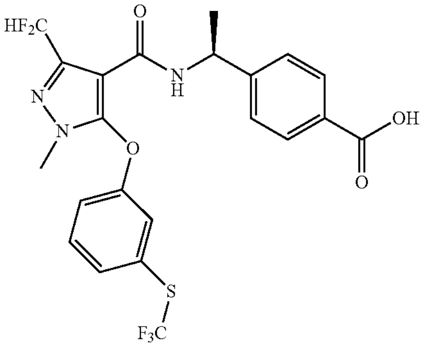
I-30
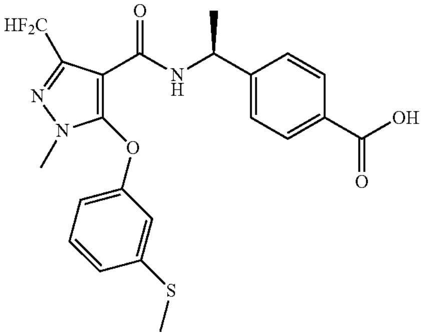

-continued
I-31
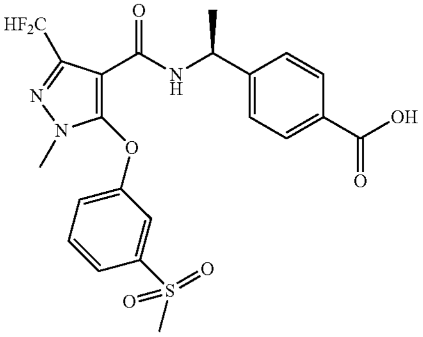
I-32
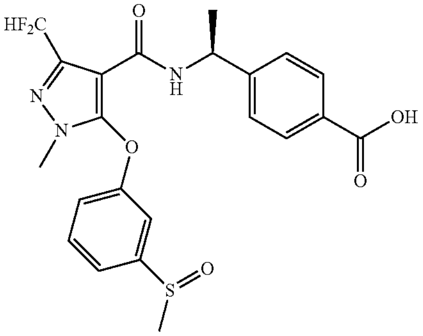
I-33
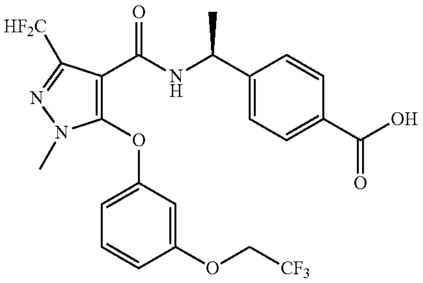
I-34
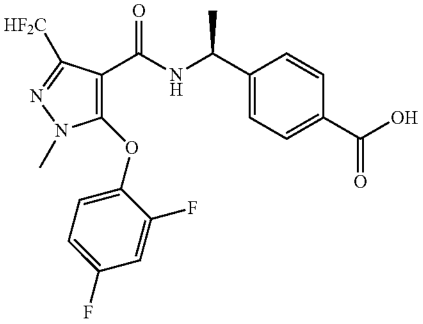
I-35
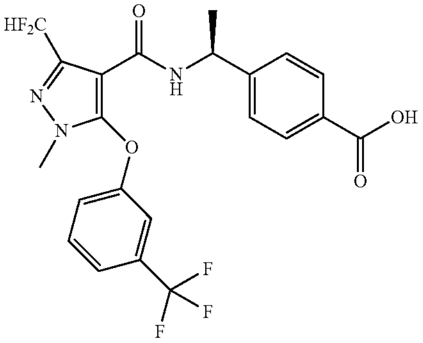
-continued
I-36
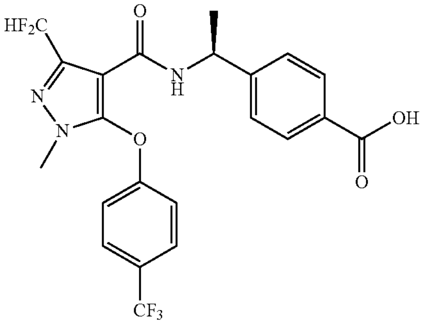
I-37
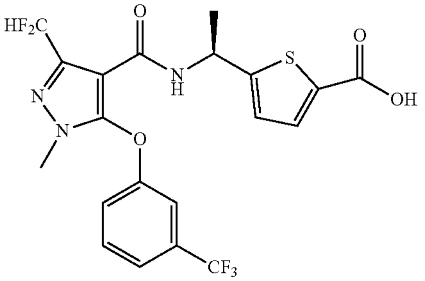
I-38
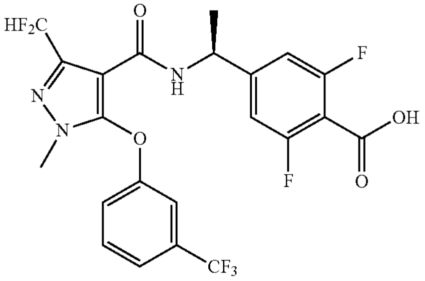
I-39
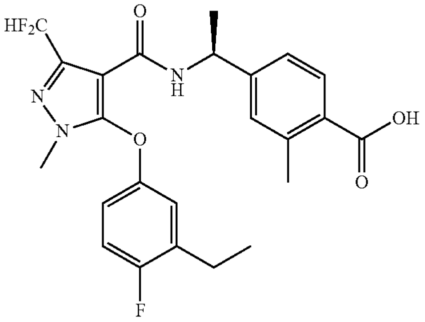
I-40
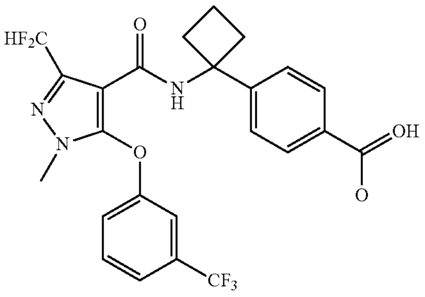

-continued

I-41

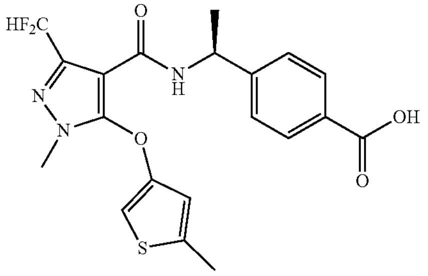

I-42

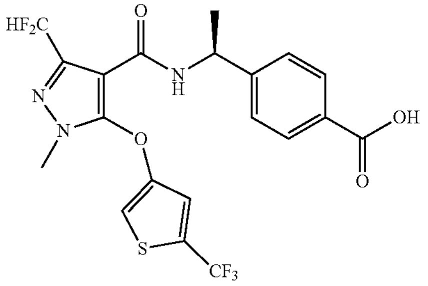

I-43

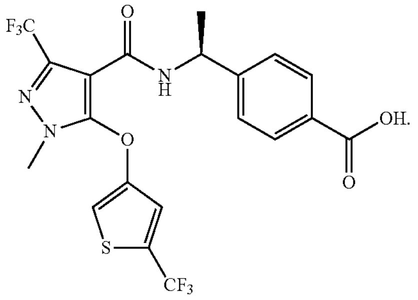

According to the embodiments of the present disclosure, the salt includes a pharmaceutically acceptable salt and is at least one selected from sulfuric acid, phosphoric acid, nitric acid, hydrobromic acid, hydrochloric acid, formic acid, acetic acid, propionic acid, benzenesulfonic acid, benzoic acid, phenylacetic acid, salicylic acid, alginic acid, anthranilic acid, camphoric acid, citric acid, vinyl sulfonic acid, formic acid, fumaric acid, furoic acid, gluconic acid, glucuronic acid, glutamic acid, glycolic acid, isethionic acid, lactic acid, maleic acid, malic acid, mandelic acid, mucic acid, pamoic acid, pantothenic acid, stearic acid, succinic acid, sulfanilic acid, tartaric acid, p-toluenesulfonic acid, malonic acid, 2-hydroxypropionic acid, oxalic acid, glycolic acid, glucuronic acid, galacturonic acid, citric acid, lysine, arginine, aspartic acid, cinnamic acid, p-toluenesulfonic acid, methanesulfonic acid, ethanesulfonic acid or trifluoromethanesulfonic acid. Those skilled in the art can understand that, in addition to pharmaceutically acceptable salts, other salts can also be used in the present disclosure, acting as intermediates in the purification of compounds or in the preparation of other pharmaceutically acceptable salts, or for identifying, characterizing or purifying the compounds of the present disclosure.

In a second aspect of the present disclosure, the present disclosure provides a pharmaceutical composition. According to the embodiments of the present disclosure, the pharmaceutical composition includes a pharmaceutically acceptable excipient, and the compound as described above.

In a third aspect of the present disclosure, the present disclosure provides uses of the compound as described above or the pharmaceutical composition as described above in the preparation of a medicament for the treatment or prevention of an EP4-related disease.

According to the embodiments of the present disclosure, the use may further include at least one of the following additional technical features.

According to an embodiment of the present disclosure, the EP4-related disease includes at least one selected from the group consisting of an inflammatory disease, a pain, a cancer, a metabolic disease and a urinary system disease.

According to an embodiment of the present disclosure, the inflammatory disease includes at least one selected from the group consisting of arthritis and rheumatoid arthritis.

According to an embodiment of the present disclosure, the pain includes osteoarthritis pain and endometriosis-induced pain.

According to an embodiment of the present disclosure, the compound or the pharmaceutical composition as described above may be administered in combination with a radiation therapy and/or an antibody therapy. The antibody therapy is selected from the group consisting of a CTLA4 antibody therapy, a PDL1 antibody therapy, a PD1 antibody therapy, and combinations thereof.

According to an embodiment of the present disclosure, the cancer includes a solid cancer.

According to embodiments of the present disclosure, the cancer includes breast cancer, cervical cancer, colorectal cancer, endometrial cancer, glioblastoma, head and neck cancer, kidney cancer, liver cancer, lung cancer, medulloblastoma, ovarian cancer, pancreatic cancer, prostate cancer, skin cancer, and urethral cancer.

According to an embodiment of the present disclosure, the metabolic disease includes diabetes, and the urinary disease includes overactive bladder.

According to an embodiment of the present disclosure, with the compound or pharmaceutical composition of the present disclosure, the patient in need thereof can be provided with a more optimal, more effective clinical treatment medication or regimen. According to the embodiments of the present disclosure, the present disclosure provides a series of EP4 antagonists having novel structures, better pharmacokinetic properties, better drug effect and good medicinal properties, which can effectively treat EP4-related diseases or disorders.

The present disclosure also relates to a method of treating a disease associated with EP4, the method including administering to a patient a therapeutically effective amount of a pharmaceutical formulation comprising a compound described herein, or a pharmaceutically acceptable salt thereof.

The present disclosure further provides a method of treating inflammatory diseases, pain, cancer, metabolic diseases, urinary system diseases. The method includes: administering, to a patient, a therapeutically effective amount of a pharmaceutical formulation containing the compound as described above or the pharmaceutically acceptable salt thereof. The present disclosure further provides a method for treating a disease by administering the compound or pharmaceutical composition in combination with a radiation therapy and/or an antibody therapy, in which the antibody therapy is selected from the group consisting of a CTLA4 antibody therapy, a PDL1 antibody therapy, a PD1 antibody therapy, and combinations thereof.

Term Definitions and Explanations

Unless otherwise stated, the definitions of groups and terms described in the specification and claims include actual definitions, exemplary definitions, preferred definitions, definitions recorded in tables, and definitions of specific compounds in the examples, etc., which can be arbitrarily combined and integrated with each other. The group definitions and compound structures that are combined and integrated should fall within the scope of the present disclosure.

Unless defined otherwise, all technical and scientific terms herein have the same meaning as commonly understood by one of ordinary skill in the art to which the claimed subject matter belongs. The patents, patent applications, publications cited herein are hereby incorporated by reference in their entireties, unless stated otherwise. When a term has multiple definitions, that defined in this chapter will prevail.

Unless otherwise indicated, conventional methods in the related art are employed, such as mass spectroscopy, NMR, IR and UV/Vis spectroscopy, and pharmacological methods. Unless specific definitions are set forth, the terms in the related description of analytical chemistry, organic synthetic chemistry, and medicinal and medicinal chemistry are those known in the art. Standard techniques may be used in chemical synthesis, chemical analysis, pharmaceutical preparation, formulation, and delivery, and treatment of patients. For example, reactions and purifications can be performed using the manufacturer's instructions of the kit, or in a manner well known in the related art or as described herein. The techniques and procedures described above may generally be performed with conventional methods well known in the art according to the description in a number of general and more specific documents cited and discussed throughout the present description. Throughout the description, groups and substituents thereof can be chosen by one skilled in the field to provide stable moieties and compounds. Where substituent groups are depicted by conventional chemical formulae, written from left to right, the substituent groups likewise encompass the chemically equivalent substituents that would result from writing the structural formula from right to left. For example, $CH_2O$ is equivalent to $OCH_2$.

As used herein, the description and claims recite numerical ranges, which, read as "integers", are to be understood as reciting both endpoints of the range and each integer within the range. For example, "an integer from 1 to 6" is to be understood as reciting each and every integer from 0, 1, 2, 3, 4, 5, and 6. When the numerical range is understood to be "a number", it is understood to recite both endpoints of the range and each integer within the range and each decimal number within the range. As an example, "a number from 1 to 10" is to be understood as reciting not only each of the integers 1, 2, 3, 4, 5, 6, 7, 8, 9, and 10, but also at least the sum of each of the integers with 0.1, 0.2, 0.3, 0.4, 0.5, 0.6, 0.7, 0.8, 0.9, respectively.

The term "pharmaceutically acceptable" means the compounds, materials, compositions and/or dosage forms that are suitable for use in contact with human and animal tissues without excess toxicity, irritation, allergic reactions or other problems or complications within the scope of reliable medical judgment, and are commensurate with a reasonable benefit/risk ratio.

The term "pharmaceutically acceptable salt" or "pharmaceutically acceptable salt thereof" refers to salts of pharmaceutically acceptable non-toxic acids or bases, including salts of inorganic acids and bases, organic acids and bases.

In addition to the pharmaceutically acceptable salts, other salts may be adopted in the present disclosure, and they can serve as intermediates in the purification of compounds or in the preparation of other pharmaceutically acceptable salts or can be used for identifying, characterizing, or purifying the compounds of the present disclosure.

The term "stereoisomer" refers to an isomer produced by a different spatial arrangement of atoms in the molecule. The definitions and rules of stereochemistry used in the present disclosure generally follow "McGraw-Hill Dictionary of Chemical Terms (1984)", S. P. Parker, Ed., McGraw-Hill Book Company, New York; and "Stereochemistry of Organic Compounds", Eliel, E. and Wilen, S., John Wiley & Sons, Inc., New York, 1994. The compound of the present disclosure may contain an asymmetric center or chiral center, and thus different stereoisomeric forms may exist. All stereoisomeric forms of the compound of the present disclosure, including, but not limited to, diastereoisomers, enantiomers, atropisomers, geometric (or conformational) isomers, and mixtures thereof such as racemic mixtures, shall be fall within the scope of the present disclosure.

Many organic compounds exist in optically active forms, i.e., they are capable of rotating a plane of plane-polarized light. When describing optically active compounds, the prefixes D and L, or R and S are used to denote the absolute configurations of the molecule with respect to one or more chiral centers. The prefixes D and L, or (+) and (−) are symbols used to specify a rotation of plane-polarized light caused by a compound, where (−) or L indicates that the compound is levorotatory, and the prefix (+) or D indicates that the compound is dextrorotatory. For a given chemical structure, these stereoisomers are identical except that these stereoisomers are mirror images of each other. The specific stereoisomers can be referred as to enantiomers, and a mixture of such isomers is called an enantiomeric mixture. A mixture of enantiomers in 50:50 is called a racemic mixture or a racemate, which may occur when there is no stereoselectivity or stereospecificity in a chemical reaction or process.

In accordance with the selection of raw materials and methods, the compound of the present disclosure may exist in the form of one of the possible isomers or a mixture thereof, for example, as a pure optical isomer, or as a mixture of isomers such as racemic isomer and diastereoisomeric mixture, depending on the number of asymmetric carbon atoms. The optically active (R)- or (S)-isomer can be prepared using chiral synthons or chiral preparations, or resolved using conventional techniques. If the compound contains a double bond, the substituents may be in E- or Z-configuration; if the compound contains a disubstituted cycloalkyl, the substituent of the cycloalkyl may has a cis- or trans-conformation.

When the bond with a chiral carbon in the formula of the present disclosure is depicted in a straight line, it should be understood that the two configurations (R) and (S) of the chiral carbon and both the resulting enantiomerically pure compound and mixture are included in the scope defined by the general formula. The diagrammatic presentation of the racemate or pure enantiomeric compound herein is from Maehr, J. Chem. Ed. 1985, 62: 114-120. Unless otherwise specified, the wedge bond and the dashed bond are used to represent the absolute configuration of a stereocenter.

The compounds of the present disclosure containing asymmetrically substituted carbon atoms can be separated in an optically active form or in a racemic form. The resolution of a racemic mixture of a compound can be carried out with any of a variety of methods known in the art. For example, the methods include fractional recrystallization using chiral resolving acids, which are optically active salt-forming organic acids. For example, the suitable resolving agents for fractional recrystallization are optically active acids, such as tartaric acid, diacetyl tartaric acid, dibenzoyl tartaric acid, mandelic acid, malic acid, lactic acid or various optically active camphorsulfonic acids such as the D and L forms of β-camphorsulfonic acid. Other resolving agents suitable for fractional crystallization include α-methyl-benzylamine in a pure stereoisomeric form (for example, S and R forms or a pure diastereomeric form), 2-phenylglycinol, norephedrine, ephedrine, N-methylephedrine, cyclohexylethylamine, 1,2-diaminocyclohexane, etc. The resolution of the racemic mixture can also be carried out by eluting a column filled with an optically active resolving agent (for example, dinitrobenzoylphenylglycine). High performance liquid chromatography (HPLC) or supercritical fluid chromatography (SFC) can also be employed. The specific method, elution conditions, and the chromatographic columns can be selected by those skilled in the art according to the structures of the compounds and the experimental results. Further, pure optically active starting materials or reagents with known configuration can also be used to obtain any enantiomers or diastereomers of the compounds described in the present disclosure through stereo-organic synthesis.

Many geometric isomers of olefins, C═N double bonds, or the like may also be present in the compounds described herein, and all these stable isomers are considered in the present disclosure. When the compound described herein contains an ethylenic double bond, such a double bond includes E- and Z-geometric isomers, unless otherwise specified.

The term "tautomer" refers to an isomer of a functional group resulting from a rapid movement of an atom between two positions in a molecule. The compound of the present disclosure may exhibit tautomerism. Tautomeric compounds can be present in two or more mutually convertible species. The protonotropic tautomer are resulted from a transfer of covalently bonded hydrogen atoms between two atoms. The tautomer generally exists in an equilibrium form. When trying to separate a single tautomer, a mixture is usually produced, the physical and chemical properties of which are consistent with the mixture of compounds. The position of equilibrium depends on the intramolecularly chemical properties. For example, for many aliphatic aldehydes and ketones, such as acetaldehyde, ketonic type is dominant; and for phenols, enol type is dominant. All tautomeric forms of the compounds are included in the present disclosure.

The term "pharmaceutical composition" refers to a mixture of one or more of the compounds described herein or physiologically/pharmaceutically acceptable salts or prodrugs thereof and other chemical components. The other chemical components can be, for example, physiologically/pharmaceutically acceptable carriers and excipients. The pharmaceutical composition aims to facilitate the administration of the compound to an organism.

The term "solvate" refers to the compound of the present disclosure or a salt thereof including a stoichiometric or non-stoichiometric solvent bonded through an intermolecular non-covalent force. When the solvent is water, the solvate is a hydrate.

The term "prodrug" can be converted into the compound of the present disclosure having biological activity under physiological conditions or through solvolysis. The prodrug of the present disclosure is prepared by modifying the functional groups in the compound, and the modification moiety can be removed by conventional operations or in vivo, so as to obtain the parent compound. The prodrug includes a compound, which is formed by connecting a moiety to a hydroxyl group or amino group in the compound of the present disclosure. When the prodrug of the compound of the present disclosure is administered to a mammal individual, the prodrug is dissociated to form a free hydroxyl or amino group.

The compound of the present disclosure may contain an unnatural ratio of atomic isotopes on one or more of the atoms constituting the compound. For example, the compound may be labeled with a radioisotope, such as tritium ($^3H$), iodine-125 ($^{125}I$) or C-14 ($^{14}C$). The transformation of all isotopic compositions of the compounds of the present disclosure, whether radioactive or not, are included within the scope of the present disclosure.

The term "excipient" refers to a pharmaceutically acceptable inert ingredient. Examples of the "excipient" include, but not limited to, binders, disintegrants, lubricants, glidants, stabilizers, fillers, diluents, and the like.

The term "$C_1$-$C_6$ alkyl" refers to a linear or branched, saturated, monovalent hydrocarbon group having 1, 2, 3, 4, 5 or 6 carbon atoms. Said alkyl is, for example, methyl, ethyl, propyl, butyl, pentyl, hexyl, isopropyl, isobutyl, sec-butyl, tert-butyl, isoamyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl, etc., or an isomer thereof. Specifically, said group has 1, 2 or 3 carbon atoms ("$C_1$-$C_3$ alkyl"), e.g., methyl, ethyl, n-propyl, or isopropyl.

The term "$C_3$-$C_6$ cycloalkyl" refers to a saturated, monovalent, mono- or bicyclic hydrocarbon ring having 3 to 6 carbon atoms, including fused or bridged polycyclic ring systems, e.g., cyclopropyl, cyclobutyl, cyclopentyl, and cyclohexyl.

The term "$C_1$-$C_6$ alkoxyl" is to be understood as —O—($C_{1-6}$ alkyl), in which the "$C_{1-6}$ alkyl" has the above definition.

The term "halogeno-group" or "halogen" is fluorine, chlorine, bromine, or iodine.

"Halogen-substituted alkyl" refers to a branched and straight-chain saturated aliphatic hydrocarbon group having a specified number of carbon atoms and substituted with one or more halogen atoms (e.g., —CvFw, where v=1 to 3, w=1 to (2v+1)). Examples of halogen-substituted alkyl include, but are not limited to, trifluoromethyl, trichloromethyl, pentafluoroethyl, pentachloroethyl, 2,2,2-trifluoroethyl, heptafluoropropyl, and heptachloropropyl.

Beneficial Effects

According to the embodiments of the present disclosure, the compounds and/or compositions thereof described herein have the activity of effectively antagonizing the EP4 receptor, and they have the advantages of superior hepatic metabolic stability and cardiac safety and also have better pharmacokinetic properties, higher in vivo exposure, lower dosing and a better compliance. Therefore, they have good application perspective in the preparation of medicaments for the treatment of EP4-related diseases.

Additional aspects and advantages of the present disclosure will be set forth in part in the following description, and in part will be obvious from the description, or may be learned by practice of the present disclosure.

BRIEF DESCRIPTION OF DRAWINGS

FIG. 1 is a result of tumor inhibition of the compounds according to an embodiment of the present disclosure.

DESCRIPTION OF EMBODIMENTS

Solutions of the present disclosure will be explained below in connection with the examples. It will be appreciated by those skilled in the art that the following examples are merely illustrative of the present disclosure and should not be taken as limiting the scope of the present disclosure. Techniques or conditions that are not specified in the examples shall be performed in accordance with the techniques or conditions described in the literatures in the field or in accordance with the product instruction. Reagents or instruments without indicating the manufacturer and are those commercially available.

Compounds of the present application are identified by nuclear magnetic resonance (NMR) and/or mass spectrometry (MS), unless otherwise specified. The unit of NMR shift is $10^{-6}$ (ppm). Solvents for NMR were deuterated dimethyl sulfoxide, deuterated chloroform, deuterated methanol, etc., and internal standard was tetramethylsilane (TMS).

Abbreviations in the present disclosure are defined as follows:

BAST: bis(2-methoxyethyl)aminosulfur trifluoride m-CPBA: m-chloroperoxybenzoic acid L-selectride: lithium tri-sec-butyl borohydride Pd (dppf) $Cl_2$: 1,1-bis(diphenylphosphino)ferrocene palladium chloride DCM: dichloromethane HATU: O-(7-Azabenzotriazol-1-yl)-N, N, N', N'-tetramethyluronium hexafluorophosphate DIPEA: diisopropylethylamine i.e., N, N-diisopropylethylamine DMF: N, N-dimethylformamide N: normality, e.g., 1N hydrochloric acid means 1 mol/L hydrochloric acid solution THF: tetrahydrofuran DMA: N, N-dimethylacetamide DMSO: dimethyl sulfoxide EA: ethyl acetate $IC_{50}$: half inhibitory concentration, indicating a concentration at which half of the maximal inhibitory effect is achieved.

CHO: Chinese hamster ovary cells

HBSS: Hank's Balanced Salt Solution

BSA: albumin from bovine serum

HEPES: hydroxyethylpiperazine ethanethiosulfonic acid

IBMX: 3-isobutyl-1-methyl-7H-xanthine

FLIPR: fluorescence imaging plate reader $EC_{80}$: a concentration at which 80% of maximal effect is achieved Unless otherwise indicated, the compounds exemplified herein are named and numbered using ChemBioDraw Ultra 13.0.

Control Example 1: Preparation of Control Compound

Control compound

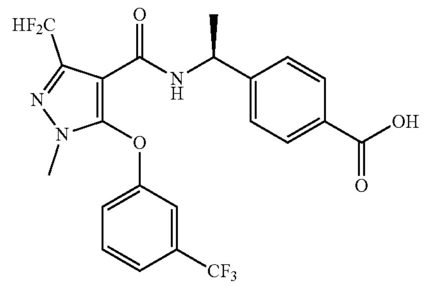

The control compound was synthesized with reference to patent application WO2012039972A1.

The control compounds in the following test examples are all referred to as the compound as described in Control Example 1.

Preparation Example 1: Preparation of Intermediate A

Methyl (S)-4-(1-(5-chloro-3-(difluoromethyl)-1-methyl-1H-pyrazole-4-carboxamido)ethyl)benzoate (Intermediate A)

A

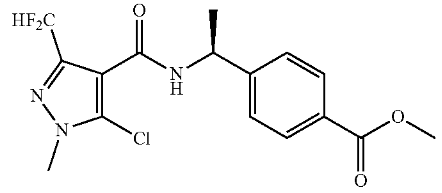

The synthesis scheme for Intermediate A is shown below:

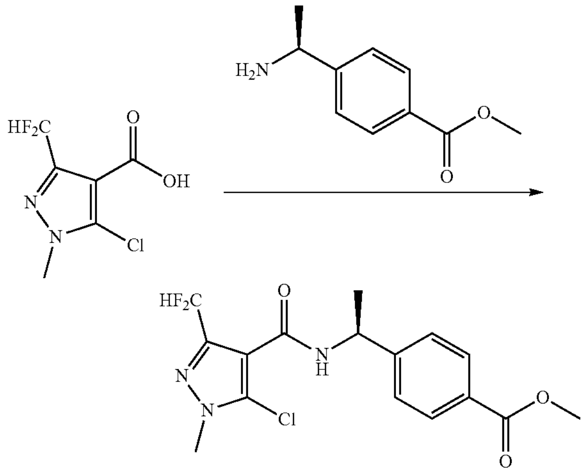

A

A starting material 5-chloro-3-(difluoromethyl)-1-methyl-1H-pyrazole-4-carboxylic acid (5 g, 23.8 mmol), which was synthesized with reference to patent application WO2011151369A1, was added to DCM (200 mL). Methyl (S)-4-(1-aminoethyl) benzoate (5.1 g, 28.6 mmol), HATU (10.9 g, 28.6 mmol) and DIPEA (4.6 g, 35.7 mmol) were added. The mixture was stirred at room temperature for 16 hours; water (200 mL) was added, and the mixture was extracted with DCM (50 mL×3) and separated, and the organic phases were combined, dried over anhydrous sodium sulfate, filtered and concentrated, and the residue was separated and purified by a silica gel column (petroleum ether:ethyl acetate (V/V)=3:1) to obtain a white solid of methyl (S)-4-(1-(5-chloro-3-(difluoromethyl)-1-methyl-1H-pyrazole-4-carboxamido)ethyl)benzoate.

LCMS (ESI) m/z: 372.5 [M+H]+

Preparative Example 2: Acidic Preparation Method A

This example is an example for product purification, in which the purification is performed using high performance liquid chromatography with the following purification conditions: Welch, Ultimate C18 column, 10 μm, 21.2 mm×250 mm.

The mobile phase A was 1‰ trifluoroacetic acid in pure water, the mobile phase B was acetonitrile. Gradient Conditions: within 0 to 3 min, the mobile phase A was kept at 90%; after gradient elution from 3 min to 18 min, the mobile phase A was changed from 90% to 5%, and the mobile phase A was kept at 5% from 18 min to 22 min).

The "Acidic Preparation Method A" described in the following Examples all refer to the Acidic Preparation Method A of the Preparation Example 2.

Example 1: Preparation of Compound I-1

(S)-4-(1-(3-(difluoromethyl)-5-(3-ethylphenoxy)-1-methyl-1H-pyrazole-4-carboxamido)ethyl)benzoic Acid (Compound I-1)

I-1

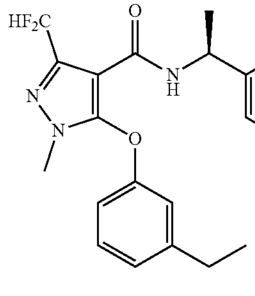

The synthesis scheme for Compound I-1 was shown below:

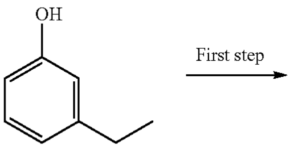

I-1A

-continued

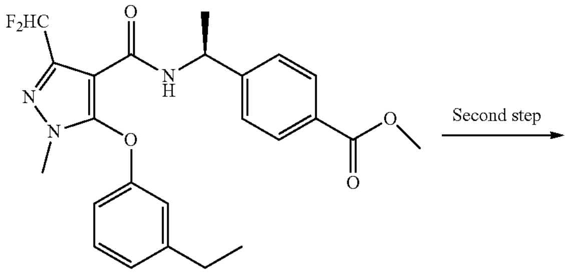

I-1B

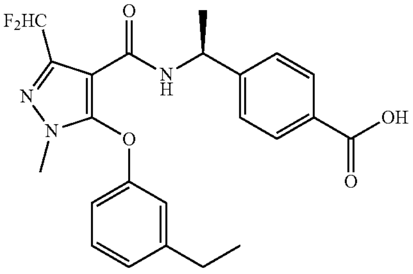

I-1

First Step: methyl (S)-4-(1-(3-(difluoromethyl)-5(3-ethylphenoxy)-1-methyl-1H-pyrazole-4-carboxamido)ethyl)benzoate (Compound I-1B)

I-1B

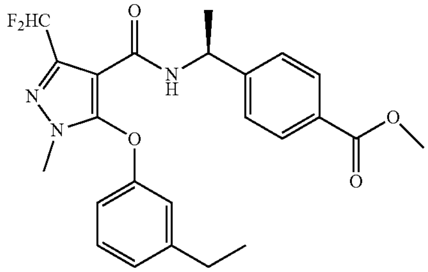

The compound methyl (S)-4-(1-(5-chloro-3-(difluoromethyl)-1-methyl-1H-pyrazole-4-carboxamido)ethyl)benzoate (Intermediate A) (370 mg, 1.0 mmol) was added to DMF (10 mL) at room temperature, and 3-ethylphenol (I-1A) (183 mg, 1.5 mmol) and KOH (168 mg, 3.0 mmol) were added; the mixture was heated to 120° C. and stirred for 6 h, and then was cooled to room temperature and diluted with water (40 mL); the pH was adjusted to 7 with 1N hydrochloric acid; the solution was extracted with ethyl acetate (20 mL×3) and separated the organic phases were combined and dried over anhydrous sodium sulfate, filtered and concentrated to obtain a colorless liquid crude product of methyl (S)-4-(1-(3-(difluoromethyl)-5-(3-ethylphenoxy)-1-methyl-1H-pyrazole-4-carboxamido)ethyl)benzoate (Compound I-1B) (220 mg, yield 48.1%).

LCMS (ESI) m/z: 458.1 $[M+H]^+$

Second Step: (S)-4-(1-(3-(difluoromethyl)-5-(3-ethylphenoxy)-1-methyl-1H-pyrazole-4-carboxamido)ethyl)benzoic Acid (Compound I-1)

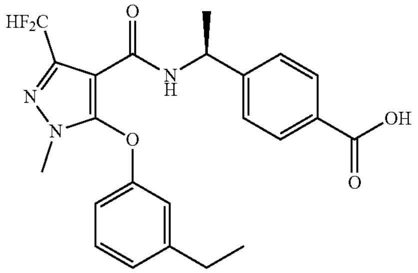

I-1

A starting material methyl (S)-4-(1-(3-(difluoromethyl)-5-(3-ethylphenoxy)-1-methyl-1H-pyrazole-4-carboxamido)ethyl)benzoate (Compound I-1B) (220 mg, 0.48 mmol) was added to THF (4 mL) at room temperature; water (2 mL) and lithium hydroxide monohydrate (42 mg, 1.0 mmol) were added. The mixture was stirred at room temperature for 16 hours. The reaction mixture was concentrated to obtain a white solid of (S)-4-(1-(3-(difluoromethyl)-5-(3-ethylphenoxy)-1-methyl-1H-pyrazole-4-carboxamido)ethyl)benzoic acid (Compound I-1) (80 mg, yield 37.5%).

$^1$H NMR (400 m Hz, DMSO-$d_6$) δ 12.8 (s, 1H), 7.90 (d, 1H), 7.71 (d, 2H), 7.32 (t, 1H), 7.25 (t, 1H), 7.12 (d, 2H), 7.07 (d, 1H), 6.90 (s, 1H), 6.76 (dd, 1H), 4.90 (t, 1H), 3.72 (s, 3H), 2.61 (q, 2H), 1.22 (d, 3H), 1.14 (t, 3H).

LCMS (ESI) m/z: 444.1 $[M+H]^+$

Example 2: Preparation of Compound I-2

(S)-4-(1-(3-(difluoromethyl)-5-(3-ethyl-4-fluorophenoxy)-1-methyl-1H-pyrazole-4-carboxamido)ethyl)benzoic Acid (Compound I-2)

I-2

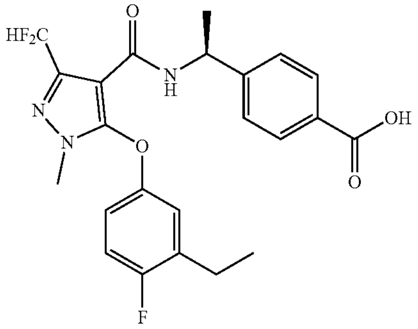

The synthesis scheme for Compound I-2 is shown below:

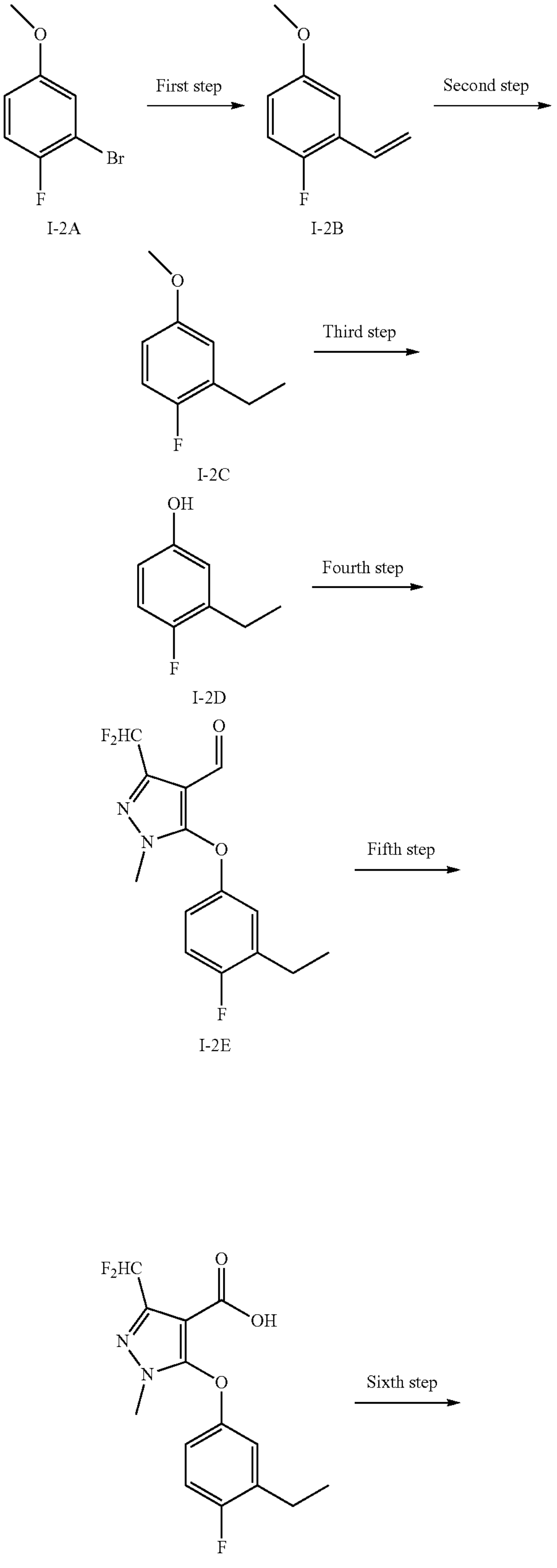

I-2A

I-2B

I-2C

I-2D

I-2E

I-2F

-continued

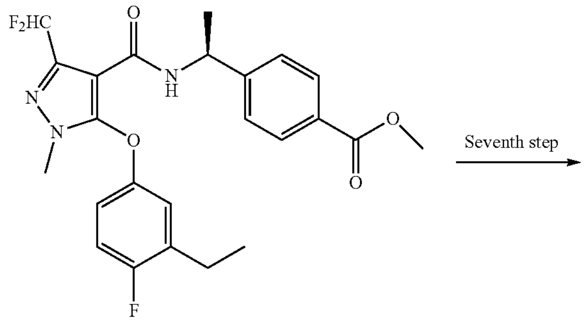

I-2G

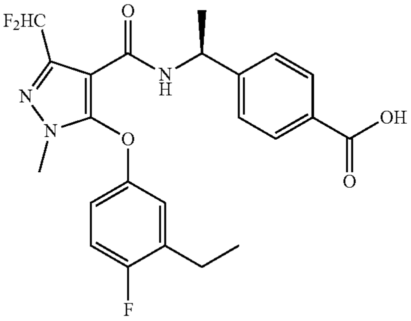

I-2

First Step: 1-fluoro-4-methoxy-2-vinylbenzene (Compound I-2B)

I-2B

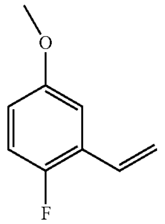

2-bromo-1-fluoro-4-methoxybenzene (Compound I-2A) (1.02 g, 5.0 mmol) was added to 1, 4-dioxane (20 mL) at room temperature; potassium vinylfluoroborate (740 mg, 5.52 mmol) and [1, 1-bis(diphenylphosphino) ferrocene] dichloropalladium (430 mg, 0.50 mmol) and potassium carbonate (1.52 g, 11.0 mmol) were added. The mixture was heated to 100° C. under nitrogen protection and stirred for 14 hours, and then cooled to room temperature, diluted with water (200 mL), extracted with DCM (80 mL×3) and separated. The organic phases were combined, dried over anhydrous sodium sulfate, filtered and concentrated, and the residue was separated and purified by a silica gel column (pure petroleum ether) to obtain a colorless liquid crude product of 1-fluoro-4-methoxy-2-vinylbenzene (Compound I-2B) (680 mg, yield 89.9%).

Second Step: 2-ethyl-1-fluoro-4-methoxybenzene (Compound I-2C)

I-2C

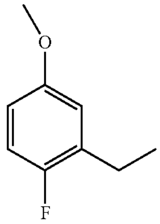

1-fluoro-4-methoxy-2-vinylbenzene (3.60 g, 23.7 mmol) was added to methanol (50 mL) at room temperature; 10% palladium on carbon (200 mg) was added; $H_2$ was purged, and then the solution was stirred for 16 hours at room temperature. The solution was filtrated and the filtrate washed with methanol (30 mL×3), and the organic phases were combined and concentrated to obtain a colorless liquid crude product of 2-ethyl-1-fluoro-4-methoxybenzene (Compound I-2C) (2.90 g, yield 79.5%).

Third Step: 3-ethyl-4-fluorophenol (Compound I-2D)

I-2D

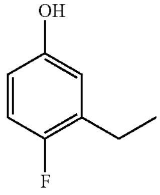

2-ethyl-1-fluoro-4-methoxybenzene (100 mg, 0.65 mmol) was added to DCM (3 mL) at room temperature, and then the mixture was cooled to −60° C. 1 mol/L $BBr_3$ DCM solution (2 mL) was added, the mixture was warmed up naturally to room temperature, and stirred at room temperature for 4H. The residue was purified by silica gel column (petroleum ether:ethyl acetate (V/V)=4:1) to obtain a colorless liquid of 3-ethyl-4-fluorophenol (Compound I-2D) (60 mg, yield 89.9%).

Fourth Step: 3-(difluoromethyl)-5-(3-ethyl-4-fluorophenoxy)-1-methyl-1H-pyrazole-4-carbaldehyde (Compound I-2E)

I-2E

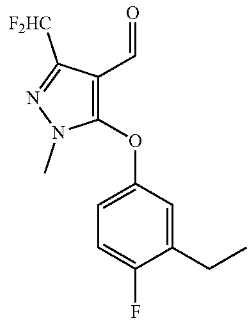

The compound 5-chloro-3-(difluoromethyl)-1-methyl-1H-pyrazole-4-carbaldehyde (350 mg, 1.18 mmol) was added to DMF (5 mL) at room temperature; 3-ethyl-4-fluorophenol (379 mg, 2.70 mmol) and potassium carbonate (546 mg, 3.95 mmol) were added; and the mixture was heated to 100° C. and stirred for 1.5 h. Then the mixture was cooled to room temperature, diluted with water (20 mL), extracted with ethyl acetate (15 mL×3) and separated. The organic phases were combined, dried over anhydrous sodium sulfate, filtered and concentrated, and the residue was separated and purified by a silica gel column (petroleum ether:ethyl acetate (V/V)=4:1) to obtain a colorless liquid crude product of 3-(difluoromethyl)-5-(3-ethyl-4-fluorophenoxy)-1-methyl-1H-pyrazole-4-carbaldehyde (Compound I-2E) (600 mg, yield 100%).

LCMS (ESI) m/z: 299.1 $[M+H]^+$

Fifth Step: 3-(difluoromethyl)-5-(3-ethyl-4-fluorophenoxy)-1-methyl-1H-pyrazole-4-carboxylic Acid (Compound I-2F)

I-2F

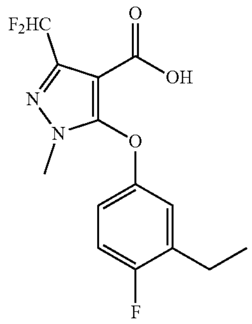

The compound 3-(difluoromethyl)-5-(3-ethyl-4-fluorophenoxy)-1-methyl-1H-pyrazole-4-carbaldehyde (350 mg, 1.80 mmol) was added to tert-butanol (10 mL) and water (2 mL) at room temperature; 2-methyl-2-butene (246 mg, 3.52 mmol), sodium chlorite (316 mg, 3.52 mmol) and sodium dihydrogen phosphate (281 mg, 2.34 mmol) were added. The mixture was stirred for 4 hours at room temperature. The solution was diluted with water (5 mL), extracted with ethyl acetate (10 mL×3) and separated, and the organic phases were combined and dried over anhydrous sodium sulfate, filtered and concentrated to obtain a colorless liquid crude product of 3-(difluoromethyl)-5-(3-ethyl-4-fluorophenoxy)-1-methyl-1H-pyrazole-4-carboxylic acid (Compound I-2F) (350 mg, yield 94.9%).

LCMS (ESI) m/z: 315.1 $[M+H]^+$

Sixth Step: methyl (S)-4-(1-(3-(difluoromethyl)-5-(3-ethyl-4-fluorophenoxy)-1-methyl-1H-pyrazole-4-carboxamido)ethyl)benzoate (Compound I-2G)

I-2G

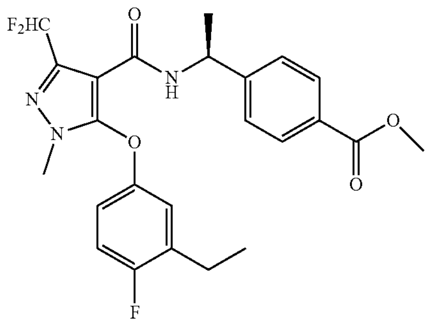

The compound 3-(difluoromethyl)-5-(3-ethyl-4-fluorophenoxy)-1-methyl-1H-pyrazole-4-carboxylic acid (350 mg, 1.11 mmol) was added to DMF (5 mL) at room temperature, and methyl (S)-4-(1-aminoethyl) benzoate (220 mg, 1.23 mmol), HATU (467 mg, 1.23 mmol) and DIPEA (301 mg, 2.33 mmol) were added. The mixture was stirred at room temperature for 16 hours, diluted with water (20 mL), extracted with ethyl acetate (10 mL×3) and separated, and the organic phases were combined, dried over anhydrous sodium sulfate, filtered, concentrated, and purified by silica gel column separation (petroleum ether:ethyl acetate (V/V)=4:1) to obtain a colorless liquid of methyl (S)-4-(1-(3-(difluoromethyl)-5-(3-ethyl-4-fluorophenoxy)-1-methyl-1H-pyrazole-4-carboxamido)ethyl)benzoate (Compound I-2G) (400 mg, yield 75.5%).

LCMS (ESI) m/z: 476.2 $[M+H]^+$

Seventh Step: (S)-4-(1-(3-(difluoromethyl)-5-(3-ethyl-4-fluorophenoxy)-1-methyl-1H-pyrazole-4-carboxamido)ethyl)benzoic Acid (Compound I-2)

I-2

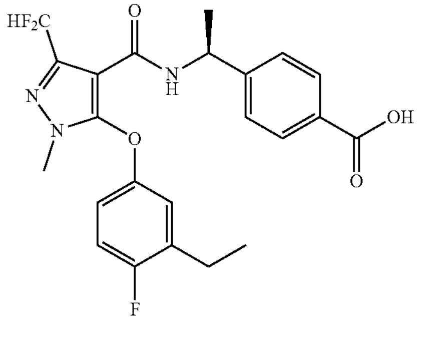

A starting material methyl (S)-4-(1-(3-(difluoromethyl)-5-(3-ethyl-4-fluorophenoxy)-1-methyl-1H-pyrazole-4-carboxamido)ethyl)benzoate (400 mg, 0.84 mmol) was added to THF (5 mL), water (5 mL) and methanol (5 mL) at room temperature, and lithium hydroxide monohydrate (141 mg, 3.36 mmol) was added. The mixture was stirred at room temperature for 16 hours, and the reaction mixture was concentrated to obtain a white solid of ((S)-4-(1-(3-(difluoromethyl)-5-(3-ethyl-4-fluorophenoxy)-1-methyl-1H-pyrazole-4-carboxamido)ethyl)benzoic acid (300 mg, 77.2% yield).

$^1$H NMR (400 m Hz, DMSO-d6) 12.8 (s, 1H), 8.03 (d, 1H), 7.74 (d, 2H), 7.17 (t, 1H), 7.14-7.10 (m, 3H), 7.01-6.97 (m, 1H), 6.82-6.79 (m, 1H), 4.92 (t, 1H), 3.73 (s, 3H), 2.59 (q, 2H), 1.25 (d, 3H), 1.11 (t, 3H).

LCMS (ESI) m/z: 462.2 [M+H]$^+$

Example 3: Preparation of Compound I-3

(S)-4-(1-(5-(3-cyclopropylphenoxy)-3-(difluoromethyl)-1-methyl-1H-pyrazole-4-carboxamido)ethyl) benzoic Acid (Compound I-3)

I-3

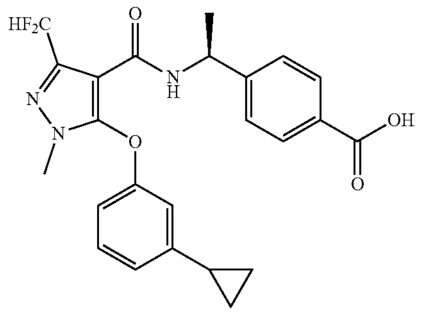

The synthesis scheme for Compound I-3 is shown below:

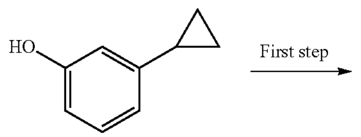

I-3A

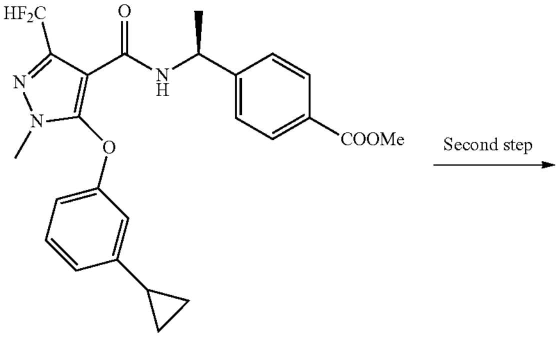

I-3B

-continued

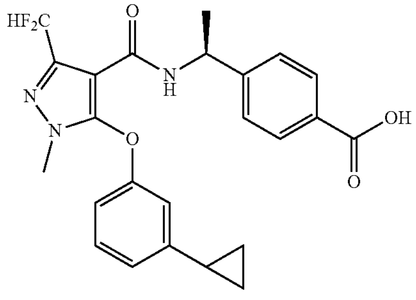

I-3

First Step: methyl (S)-4-(1-(5-(3-cyclopropylphenoxy)-3-(difluoromethyl)-1-methyl-1H-pyrazole-4-carboxamido)ethyl)benzoate (Compound I-3B)

I-3B

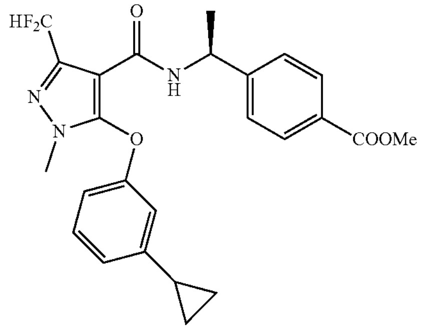

The compound methyl (S)-4-(1-(5-chloro-3-(difluoromethyl)-1-methyl-1H-pyrazole-4-carboxamido)ethyl)benzoate (Intermediate A) (145 mg, 0.39 mmol) was added to DMA (2 mL) at room temperature, 3-cyclopropylphenol (80 mg, 0.59 mmol) and KOH (34 mg, 0.61 mmol) was added, and the mixture was heated to 120° C., stirred for 2 hours, and then cooled to room temperature, diluted with water (100 mL), extracted with ethyl acetate (10 mL×3) and separated. The organic phases were combined and dried over anhydrous sodium sulfate, filtered and concentrated to obtain a colorless liquid crude product of methyl (S)-4-(1-(5-(3-cyclopropylphenoxy)-3-(difluoromethyl)-1-methyl-1H-pyrazole-4-carboxamido)ethyl)benzoate (Compound I-3B) (20 mg, yield 10.9%).

LCMS (ESI) m/z: 470.6 [M+H]$^+$

Second Step: (S)-4-(1-(5-(3-cyclopropylphenoxy)-3-(difluoromethyl)-1-methyl-1H-pyrazole-4-carboxamido)ethyl)benzoic Acid (Compound I-3)

I-3

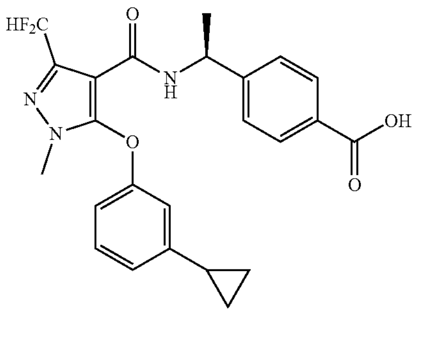

A starting material methyl (S)-4-(1-(5-(3-cyclopropylphenoxy)-3-(difluoromethyl)-1-methyl-1H-pyrazole-4-carboxamido)ethyl)benzoate (Compound I-3B) (20 mg, 0.04 mmol) was added to THF (1 mL) at room temperature, and water (1 mL) and lithium hydroxide monohydrate (2 mg, 0.048 mmol) were added. The mixture was stirred at room temperature for 16 hours. The reaction mixture was concentrated to obtain a white solid of (S)-4-(1-(5-(3-cyclopropylphenoxy)-3-(difluoromethyl)-1-methyl-1H-pyrazole-4-carboxamido)ethyl)benzoic acid (Compound I-3) (1.5 mg, 7.7% yield).

$^1$H NMR (400 m Hz, DMSO-$d_6$) δ 12.8 (s, 1H), 7.92 (d, 1H), 7.72 (d, 2H), 7.27 (t, 1H), 7.11 (t, 1H), 7.10 (d, 2H), 6.90 (d, 1H), 6.80 (t, 1H), 6.70 (dd, 1H), 4.90 (t, 1H), 3.72 (s, 3H), 1.92-1.98 (m, 1H), 1.23 (d, 3H), 0.96-0.92 (m, 2H), 0.66-0.27 (m, 2H).

LCMS (ESI) m/z: 456.6 $[M+H]^+$

Example 4: Preparation of Compound I-4

(S)-4-(1-(3-(difluoromethyl)-5-(3-isopropylphenoxy)-1-methyl-1H-pyrazole-4-carboxamido)ethyl) benzoic Acid (Compound I-4)

I-4

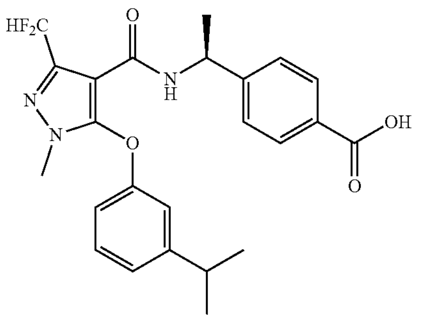

The synthesis scheme for Compound I-4 is shown below:

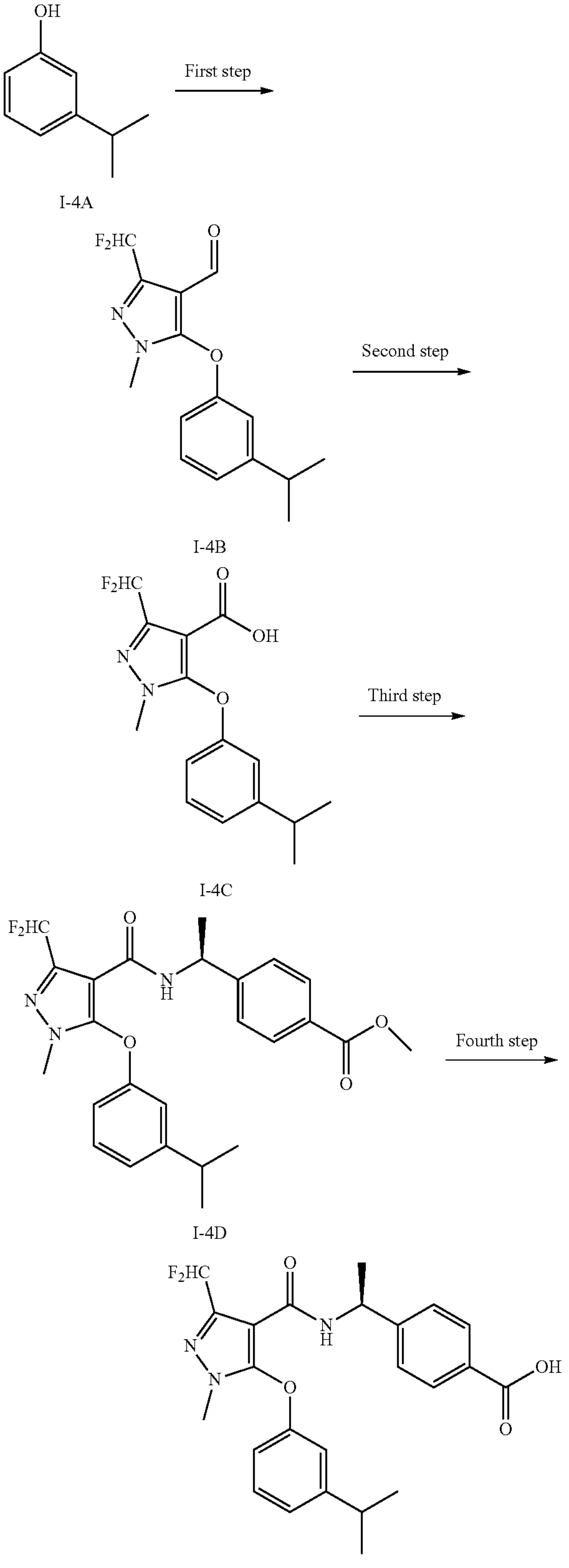

I-4A

I-4B

I-4C

I-4D

I-4

First Step: 3-(difluoromethyl)-5-(3-isopropylphenoxy)-1-methyl-1H-pyrazole-4-carbaldehyde (Compound I-4B)

I-4B

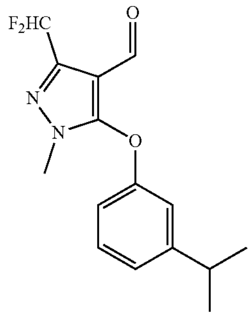

The compound 5-chloro-3-(difluoromethyl)-1-methyl-1H-pyrazole-4-carbaldehyde (500 mg, 2.57 mmol) was added to DMF (5 mL) at room temperature; 3-isopropylphenol (386 mg, 2.80 mmol) and KOH (216 mg, 3.85 mmol) were added; and the mixture was heated to 150° C. and stirred for 4 hours. Then, the mixture was cooled to room temperature, diluted with water (20 mL), extracted with ethyl acetate (15 mL×3) and separated. The organic phases were combined, dried over anhydrous sodium sulfate, filtered and concentrated, and the residue was separated and purified by a silica gel column (petroleum ether:ethyl acetate (V/V)=4:1) to obtain a light yellow liquid crude product of 3-(difluoromethyl)-5-(3-isopropylphenoxy)-1-methyl-1H-pyrazole-4-carbaldehyde (Compound I-4B) (750 mg, 98.9% yield).

LCMS (ESI) m/z: 295.1 $[M+H]^+$

Second Step: 3-(difluoromethyl)-5-(3-isopropylphenoxy)-1-methyl-1H-pyrazole-4-carboxylic Acid (Compound I-4C)

I-4C

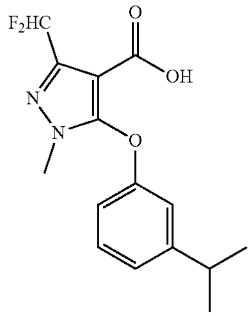

The compound 3-(difluoromethyl)-5-(3-isopropylphenoxy)-1-methyl-1H-pyrazole-4-carbaldehyde (750 mg, 2.55 mmol) was added to tert-butanol (6 mL) and water (7 mL) at room temperature, 2-methyl-2-butene (355 mg, 5.07 mmol), sodium chlorite (456 mg, 5.07 mmol), and sodium dihydrogen phosphate (669 mg, 5.57 mmol) were added. The mixture was stirred for 14 hours at room temperature. The mixture was diluted with water (15 mL) and extracted with ethyl acetate (30 mlL×3) and separated, and the organic phases were combined and dried over anhydrous sodium sulfate, filtered and concentrated to obtain a light yellow solid crude product of 3-(difluoromethyl)-5-(3-isopropylphenoxy)-1-methyl-1H-pyrazole-4-carboxylic acid (Compound I-4C) (800 mg, yield 100%).

LCMS (ESI) m/z: 311.1 $[M+H]^+$

Third Step: methyl (S)-4-(1-(3-(difluoromethyl)-5-(3-isopropylphenoxy)-1-methyl-1H-pyrazole-4-carboxamido)ethyl)benzoate (Compound I-4D)

I-4D

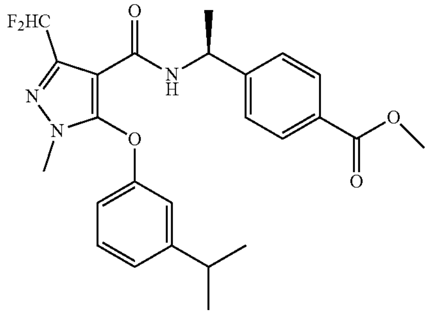

The compound 3-(difluoromethyl)-5-(3-isopropylphenoxy)-1-methyl-1H-pyrazole-4-carboxylic acid (800 mg, 2.58 mmol) was added to DCM (20 mL); (S)-methyl 4-(1-aminoethyl) benzoate (459 mg, 2.56 mmol), HATU (1.40 g, 3.68 mmol) and DIPEA (991 mg, 7.68 mmol) were added; and the mixture was stirred at room temperature for 16 hours, diluted with DCM (40 mL), washed with water (20 mL×3) and separated. The organic phases were dried over anhydrous sodium sulfate, filtered and concentrated, and the residue was separated and purified by a silica gel column (petroleum ether:ethyl acetate (V/V)=4:1) to obtain a light yellow liquid of methyl (S)-4-(1-(3-(difluoromethyl)-5-(3-isopropylphenoxy)-1-methyl-1H-pyrazole-4-carboxamido)ethyl)benzoate (Compound I-4D) (720 mg, yield 59.2%).

LCMS (ESI) m/z: 472.2 $[M+H]^+$

Fourth Step: (S)-4-(1-(3-(difluoromethyl)-5-(3-isopropylphenoxy)-1-methyl-1H-pyrazole-4-carboxamido)ethyl)benzoic Acid (Compound I-4)

I-4

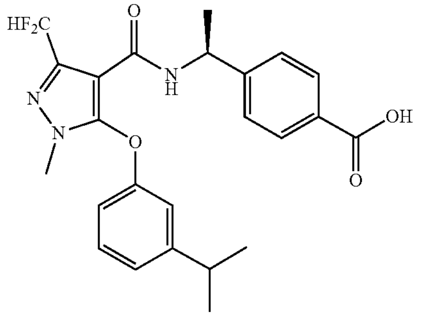

A starting material methyl (S)-4-(1-(3-(difluoromethyl)-5-(3-isopropylphenoxy)-1-methyl-1H-pyrazole-4-carboxamido)ethyl)benzoate (Compound I-4D) (440 mg, 0.93 mmol) was added to methanol (10 mL) and water (1 mL) at room temperature, and sodium hydroxide (93 mg, 2.32 mmol) was added. The mixture was stirred at room temperature for 16 hours. The reaction mixture was concentrated to obtain a white solid of (S)-4-(1-(3-(difluoromethyl)-5-(3-isopropylphenoxy)-1-methyl-1H-pyrazole-4-carboxamido)ethyl)benzoic acid (93 mg, 21.7% yield).

$^1H$ NMR (400 m Hz, DMSO-$d_6$) δ 12.7 (s, 1H), 7.89 (d, 1H), 7.70 (d, 2H), 7.32 (t, 1H), 7.12 (t, 1H), 7.10 (s, 1H), 7.06 (d, 2H), 6.99 (s, 1H), 6.72-6.70 (m, 1H), 4.91 (t, 1H), 3.73 (s, 3H), 2.91-2.85 (m, 1H), 1.21 (d, 3H), 1.17 (d, 6H).

LCMS (ESI) m/z: 458.3 $[M+H]^+$

Example 5: Preparation of Compound I-5

(S)-4-(1-(5-(3-(1,1-difluoroethyl)phenoxy)-3-(difluoromethyl)-1-methyl-1H-pyrazole-4-carboxamido)ethyl)benzoic Acid (Compound I-5)

I-5

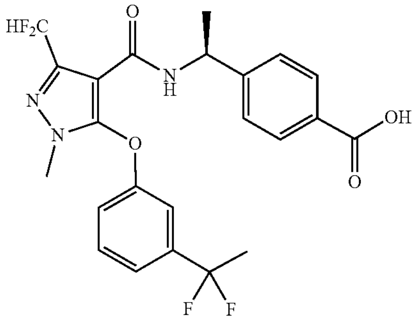

The synthesis scheme for Compound I-5 is shown below:

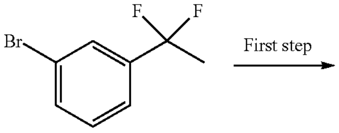

I-5A

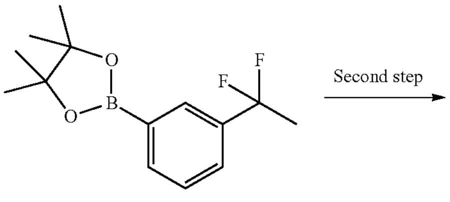

I-5B

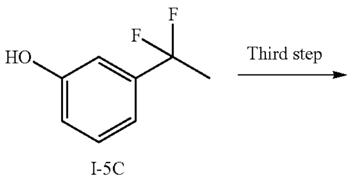

I-5C

-continued

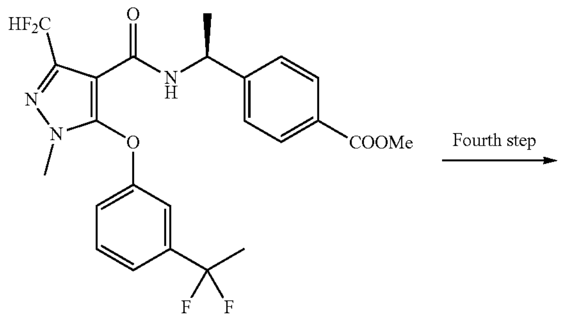

I-5D

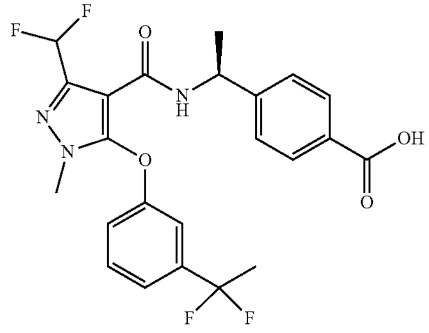

I-5

First Step: 2-(3-(1, 1-difluoroethyl)phenyl)-4,4,5,5-tetramethyl-1,3,2-dioxaborolane (Compound I-5B)

I-5B

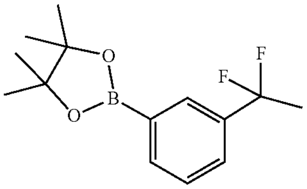

1-bromo-3-(1, 1-difluoroethyl) benzene (800 mg, 3.62 mmol) was added to 1, 4-dioxane (30 mL) at room temperature, and bis(pinacolato)diboron (17.0 g, 156.3 mmol), copper iodide (2.5 g, 13.0 mmol), L-proline (2.76 g, 10.86 mmol), potassium acetate (710 mg, 7.24 mmol) and [1, 1-bis(diphenylphosphino) ferrocene] dichloropalladium (295 mg, 0.36 mmol) were added. The mixture was heated to 90° C. under nitrogen protection and stirred for 16 hours, and then the mixture was cooled to room temperature, diluted with water (200 mL), extracted with dichloromethane (80 mL×3) and separated. The organic phases were combined and dried with anhydrous sodium sulfate, filtered and concentrated, and the residue was purified the by silica gel column separation (pure petroleum ether) to obtain a colorless liquid crude product of 2-(3-(1,1-difluoroethyl) phenyl)-4,4,5,5-tetramethyl-1,3,2-dioxaborolane (Compound I-5B) (900 mg, yield 92.7%).

Second Step: 3-(1,1-difluoroethyl)phenol (Compound I-5C)

I-5C

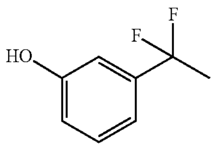

2-(3-(1,1-difluoroethyl)phenyl)-4,4,5,5-tetramethyl-1,3,2-dioxaborolane (Compound I-5B) (900 mg, 3.36 mmol) was added to THF (15 mL) and water (15 mL) at room temperature, and sodium perborate monohydrate (1.01 g, 10.07 mmol) was added. The mixture was stirred for 16 hours at room temperature, and the mixture was diluted with water (200 mL), extracted with DCM (50 mL×3) and separated. The organic phases were combined, dried over anhydrous sodium sulfate, filtered and concentrated, and the residue was separated and purified by a silica gel column (petroleum ether:ethyl acetate (V/V)=8:1) to obtain a colorless liquid of 3-(1,1-difluoroethyl)phenol (Compound I-5C) (280 mg, yield 52.7%).

Third Step: methyl (S)-4-(1-(5-(3-(1,1-difluoroethyl)phenoxy)-3-(difluoromethyl)-1-methyl-1H-pyrazole-4-carboxamido)ethyl)benzoate (Compound I-5D)

I-5D

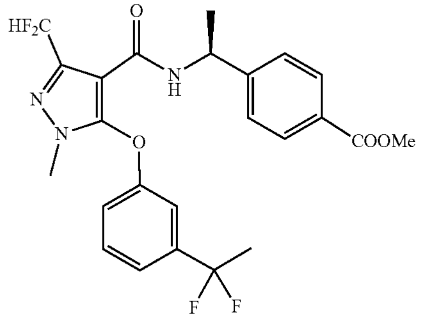

The compound methyl (S)-4-(1-(5-chloro-3-(difluoromethyl)-1-methyl-1H-pyrazole-4-carboxamido)ethyl)benzoate (Intermediate A) (650 mg, 1.75 mmol) was added to DMF (12 mL) at room temperature; 3-(1, 1-difluoroethyl) phenol (360 mg, 2.27 mmol) and potassium hydroxide (147 mg, 2.62 mmol) were added; and the mixture was heated to 120° C. and stirred for 2 hours. Then, the mixture was cooled to room temperature, diluted with water (200 mL), extracted with ethyl acetate (80 mL×3) and separated. The organic phases were combined, dried over anhydrous sodium sulfate, filtered, and concentrated to obtain a colorless liquid crude product of methyl (S)-4-(1-(5-(3-(1,1-difluoroethyl) phenoxy)-3-(difluoromethyl)-1-methyl-1H-pyrazole-4-carboxamido)ethyl)benzoate (Compound I-5D) (1.2 g, crude product).

LCMS (ESI) m/z: 494.6 [M+H]+.

Fourth Step: (S)-4-(1-(5-(3-(1,1-difluoroethyl)phenoxy)-3-(difluoromethyl)-1-methyl-1H-pyrazole-4-carboxamido)ethyl)benzoic Acid (Compound I-5)

I-5

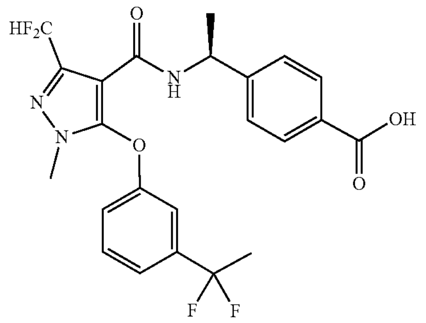

A starting material methyl (S)-4-(1-(5-(3-(1,1-difluoroethyl)phenoxy)-3-(difluoromethyl)-1-methyl-1H-pyrazole-4-carboxamido)ethyl)benzoate (Compound I-5D) (1.0 g, 2.03 mmol) was added to THF (5 mL) at room temperature, and water (4 mL) and lithium hydroxide monohydrate (340 mg, 8.11 mmol) were added. The mixture was stirred at room temperature for 16 hours. The reaction mixture was concentrated to obtain a white solid of (S)-4-(1-(5-(3-(1,1-difluoroethyl)phenoxy)-3-(difluoromethyl)-1-methyl-1H-pyrazole-4-carboxamido)ethyl)benzoic acid (Compound I-5) (88 mg, 7.9% yield).

LCMS (ESI) m/z: 480.5 $[M+H]^+$ $^1H$ NMR (400 m Hz, DMSO-$d_6$) δ 12.8 (s, 1H), 8.10 (d, 1H), 7.71 (d, 2H), 7.53 (t, 1H), 7.47 (d, 1H), 7.27 (d, 1H), 7.11 (t, 1H), 7.11 (d, 2H), 7.07 (dd, 1H), 4.88 (t, 1H), 3.74 (s, 3H), 1.96 (t, 3H), 1.96 (d, 3H).

Example 6: Preparation of Compound I-6

(S)-4-(1-(3-(difluoromethyl)-1-methyl-5-(3-(2,2,2-trifluoroethyl)phenoxy)-1H-pyrazole-4-carboxamido)ethyl)benzoic Acid (Compound I-6)

I-6

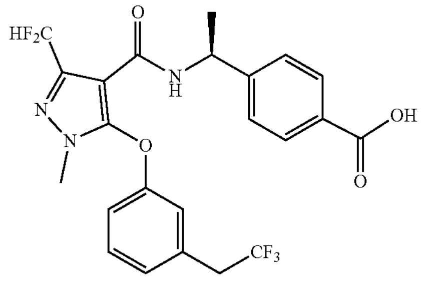

The synthesis scheme for Compound I-6 is shown below:

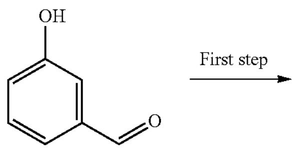

I-6A

-continued

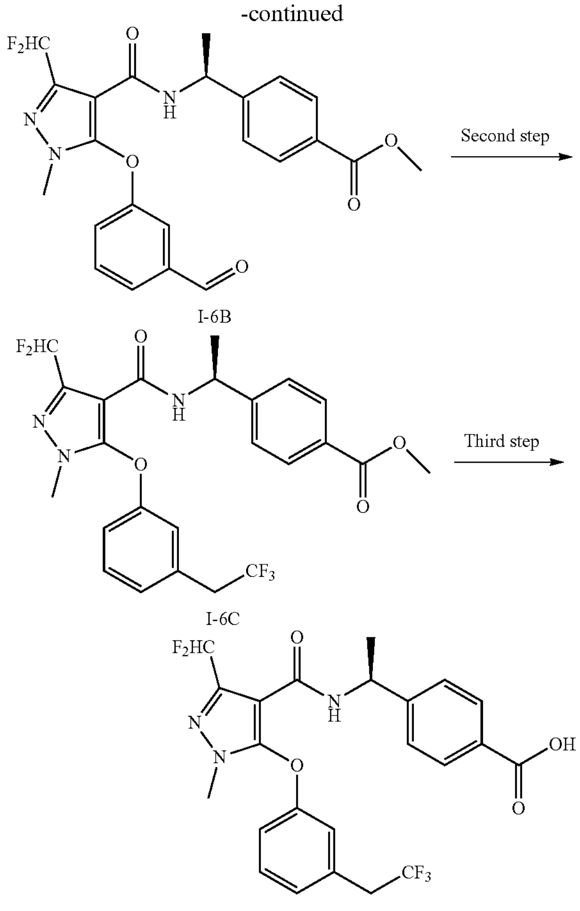

I-6B
I-6C
I-6

First Step: methyl (S)-4-(1-(3-(difluoromethyl)-5-(3-formylphenoxy)-1-methyl-1H-pyrazole-4-carboxamido)ethyl)benzoate (Compound I-6B)

I-6B

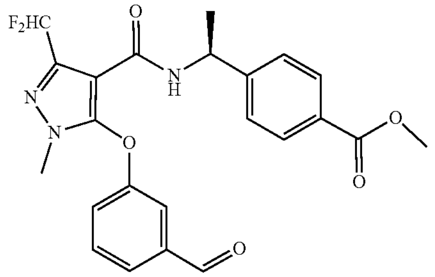

The compound methyl (S)-4-(1-(5-chloro-3-(difluoromethyl)-1-methyl-1H-pyrazole-4-carboxamido)ethyl)benzoat (Intermediate A) (371 mg, 1.0 mmol) was added to DMSO (5 mL) at room temperature, and 3-hydroxybenzaldehyde (122 mg, 1.0 mmol), $K_2CO_3$ (270 mg, 2.0 mmol) and cuprous iodide (76 mg, 0.4 mmol), phenanthroline (72 mg, 0.4 mmol) were added. The mixture was heated to 120° C. in the microwave under nitrogen protection and stirred for 2 hours. Then, the mixture was cooled to room temperature, diluted With water (20 ml), extracted With ethyl acetate (10 ml×3) and separated. The organic phases were combined, dried over anhydrous sodium sulfate, filtered and concentrated, and the residue was separated and purified by a silica gel column (petroleum ether:ethyl acetate (V/V)=8:1) to obtain a colorless liquid of methyl (S)-4-(1-(3-(difluoromethyl)-5-(3-formylphenoxy)-1-methyl-1H-pyrazole-4-carboxamido)ethyl)benzoate (Compound I-6B) (180 mg, yield 39.3%).

LCMS (ESI) m/z: 458.1 $[M+H]^+$

Second Step: (S)-4-(1-(3-(difluoromethyl)-1-methyl-5-(3-(2,2,2-trifluoroethyl)phenoxy)-1H-pyrazole-4-carboxamido)ethyl)benzoate (Compound I-6C)

I-6C

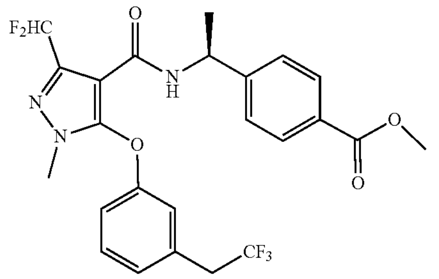

Methyl (S)-4-(1-(3-(difluoromethyl)-5-(3-formylphenoxy)-1-methyl-1H-pyrazole-4-carboxamido)ethyl)benzoate (Compound I-6B) (41.4 mg, 0.09 mmol) was added to DMF (2 mL) and 2,2-difluoro-2-triphenylphosphaniumylacetate (64 mg, 0.18 mmol) was added at room temperature, and the mixture was heated to 60° C., and stirred for 2 hours. A solution of tetrabutylammonium fluoride in tetrahydrofuran (0.3 mL, 0.30 mmol) was added and stirring was continued for 4 hours. Then, the mixture was cooled to room temperature, the reaction mixture was concentrated and the residue was purified by silica gel column (petroleum ether: ethyl acetate (V/V)=8:1) to obtain a colorless solid of (S)-4-(1-(3-(difluoromethyl)-1-methyl-5-(3-(2,2,2-trifluoroethyl)phenoxy)-1H-pyrazole-4-carboxamido)ethyl)benzoate (Compound I-6C) (40 mg, 91.2% yield).

LCMS (ESI) m/z: 512.1 $[M+H]^+$

Third Step: (S)-4-(1-(3-(difluoromethyl)-1-methyl-5-(3-(2,2,2-trifluoroethyl)phenoxy)-1H-pyrazole-4-carboxamido)ethyl)benzoic Acid (Compound I-6)

I-6

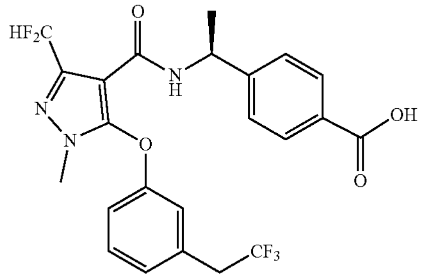

A starting material (S)-4-(1-(3-(difluoromethyl)-1-methyl-5-(3-(2,2,2-trifluoroethyl)phenoxy)-1H-pyrazole-4-carboxamido)ethyl)benzoate (Compound I-6C) (40 mg, 0.082 mmol) was added to methanol (2 mL) at room temperature, and water (2 mL) and lithium hydroxide monohydrate (12 mg, 0.3 mmol) were added. The mixture was stirred at room temperature for 16 hours. The reaction mixture was concentrated to obtain a white solid of (S)-4-(1-(3-(difluoromethyl)-1-methyl-5-(3-(2,2,2-trifluoroethyl) phenoxy)-1H-pyrazole-4-carboxamido)ethyl)benzoic acid (Compound I-6) (4.8 mg, 12.3% yield).

$^1$H NMR (400 m Hz, DMSO-$d_6$) δ 12.7 (s, 1H), 7.95 (d, 1H), 7.73 (d, 2H), 7.43 (t, 1H), 7.22 (d, 1H), 7.13 (t, 1H), 7.12 (d, 2H), 7.10 (s, 1H), 6.97 (dd, 1H), 4.89 (t, 1H), 3.74 (s, 3H), 3.72-3.63 (m, 2H), 1.24 (d, 3H).

LCMS (ESI) m/z: 498.5 $[M+H]^+$

Example 7: Preparation of Compound I-7

(S)-4-(1-(5-(3-(1,1-difluoroethyl)phenoxy)-1-methyl-3-(trifluoromethyl)-1H-pyrazole-4-carboxamido)ethyl)benzoic Acid (Compound I-7)

I-7

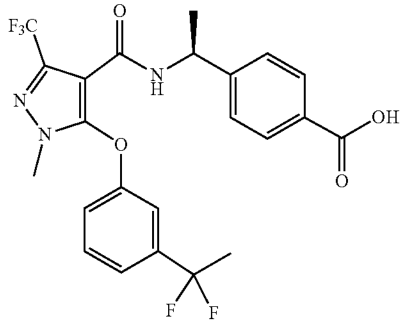

The synthesis scheme for Compound I-7 is shown below:

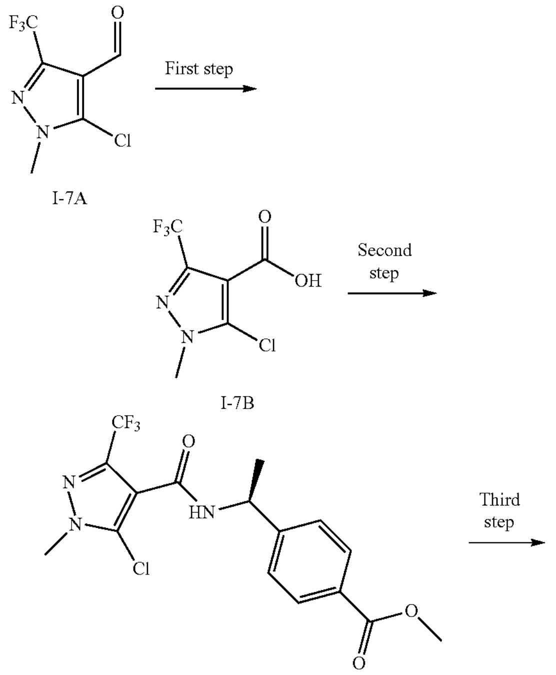

I-7A

I-7B

I-7C

-continued

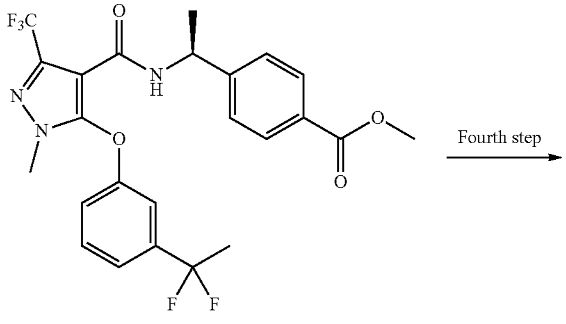

I-7D

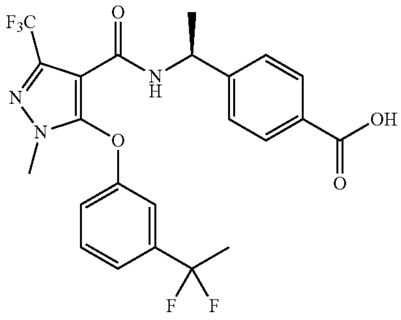

I-7

First Step: 5-chloro-1-methyl-3-(trifluoromethyl)-1H-pyrazole-4-carboxylic Acid (Compound I-7B)

I-7B

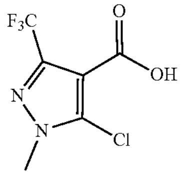

A compound 5-chloro-1-methyl-3-(trifluoromethyl)-1H-pyrazole-4-carbaldehyde (700 mg, 3.30 mmol) was added to tert-butanol (20 mL) and water (5 mL) at room temperature, and 2-methyl-2-butene (1.80 g, 25.7 mmol), sodium chlorite (1.48 g, 16.4 mmol) and sodium dihydrogen phosphate (3.10 g, 25.8 mmol) were added. The mixture was stirred for 14 hours at room temperature, and then the mixture was diluted with water (50 mL) and extracted with ethyl acetate (30 mL×3) and separated. The organic phases were combined and dried over anhydrous sodium sulfate, filtered and concentrated to obtain the crude residue. The crude residue was then purified by silica gel column separation (petroleum ether:ethyl acetate (V/V)=1:1) to obtain a colorless solid of 5-chloro-1-methyl-3-(trifluoromethyl)-1H-pyrazole-4-carboxylic acid (Compound I-7B) (680 mg, yield 90.3%).

LCMS (ESI) m/z: 229.6 $[M+H]^+$

Second Step: methyl (S)-4-(1-(5-chloro-1-methyl-3-(trifluoromethyl)-1H-pyrazole-4-carboxamido)ethyl) benzoate (Compound I-7C)

I-7C

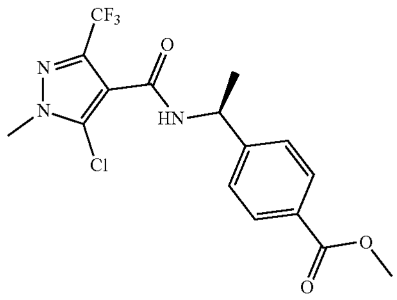

The compound 5-chloro-1-methyl-3-(trifluoromethyl)-1H-pyrazole-4-carboxylic acid (Compound I-7B) (680 mg, 2.98 mmol) was added to DMF (20 mL), and methyl (S)-4-(1-aminoethyl) benzoate (537 mg, 3.00 mmol), HATU (1.70 g, 4.47 mmol) and DIPEA (1.90 g, 14.7 mmol) were added. The mixture was stirred at room temperature for 16 hours. Then, the mixture was diluted with water (200 mL), extracted with ethyl acetate (30 mL×3) and separated. The organic phases were combined, dried over anhydrous sodium sulfate, filter and concentrated, and the residue was separated and purified by a silica gel column (petroleum ether:ethyl acetate (V/V)=1:1) to obtain a colorless solid of methyl (S)-4-(1-(5-chloro-1-methyl-3-(trifluoromethyl)-1H-pyrazole-4-carboxamido)ethyl)benzoate (Compound I-7C) (700 mg, 60.3% yield).

LCMS (ESI) m/z: 390.5 $[M+H]^+$

Third Step: methyl (S)-4-(1-(5-(3-(1,1-difluoroethyl)phenoxy)-1-methyl-3-(trifluoromethyl)-1H-pyrazole-4-carboxamido)ethyl)benzoate (Compound I-7D)

I-7D

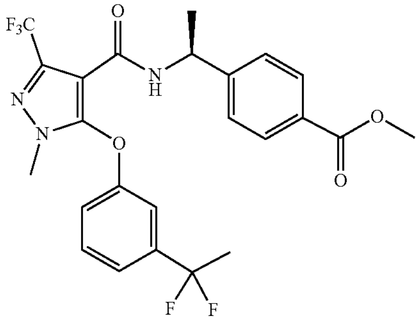

The compound methyl (S)-4-(1-(5-chloro-1-methyl-3-(trifluoromethyl)-1H-pyrazole-4-carboxamido)ethyl)benzoate (Compound I-7C) (700 mg, 1.00 mmol) was added to DMF (10 mL) at room temperature, and 3-(1, 1-difluoroethyl) phenol (284 mg, 1.00 mmol) and KOH (264 mg, 4.63 mmol) were added. The mixture was heated to 120° C. and stirred for 16 hours. Then, the mixture was cooled to room temperature, diluted with water (20 mL), extracted with ethyl acetate (20 mL×3) and separated. The organic phases were combined and dried over anhydrous sodium sulfate, filtered, and concentrated to obtain a colorless liquid crude product of methyl (S)-4-(1-(5-(3-(1,1-difluoroethyl)phenoxy)-1-methyl-3-(trifluoromethyl)-1H-pyrazole-4-carboxamido)ethyl)benzoate (Compound I-7D) (100 mg, yield 10.8%).

LCMS (ESI) m/z: 512.3 $[M+H]^+$

Fourth Step: (S)-4-(1-(5-(3-(1,1-difluoroethyl)phenoxy)-1-methyl-3-(trifluoromethyl)-1H-pyrazole-4-carboxamido)ethyl)benzoic Acid (Compound I-7)

I-7

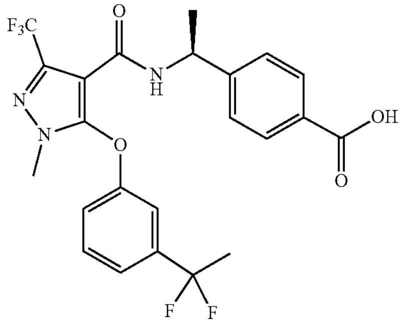

A starting material methyl (S)-4-(1-(5-(3-(1,1-difluoroethyl)phenoxy)-1-methyl-3-(trifluoromethyl)-1H-pyrazole-4-carboxamido)ethyl)benzoate (Compound I-7D) (100 mg, 0.19 mmol) was added to THF (5 mL) at room temperature, and water (4 mL) and lithium hydroxide monohydrate (10 mg, 0.24 mmol) were added. The mixture was stirred at room temperature for 16 hours. The reaction mixture was concentrated to obtain a white solid of (S)-4-(1-(5-(3-(1,1-difluoroethyl)phenoxy)-1-methyl-3-(trifluoromethyl)-1H-pyrazole-4-carboxamido)ethyl)benzoic acid (Compound I-7) (47.2 mg, 48.5% yield).

$^1H$ NMR (400 m Hz, DMSO-$d_6$) δ 12.8 (s, 1H), 8.58 (d, 1H), 7.73 (d, 2H), 7.53 (t, 1H), 7.40 (d, 1H), 7.27 (s, 1H), 7.15 (d, 2H), 7.11 (d, 1H), 4.85 (t, 1H), 3.29 (s, 3H), 1.96 (t, 3H), 1.17 (d, 3H).

LCMS (ESI) m/z: 498.3 $[M+H]^+$

Example 8: Preparation of Compound I-8

(S)-4-(1-(5-(3-(1,1-difluoroethyl)phenoxy)-1,3-dimethyl-1H-pyrazole-4-carboxamido)ethyl)benzoic Acid (Compound I-8)

I-8

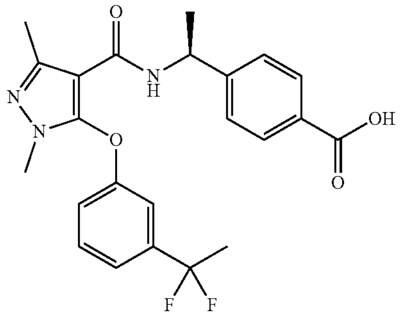

The synthesis scheme for Compound I-8 is shown below:

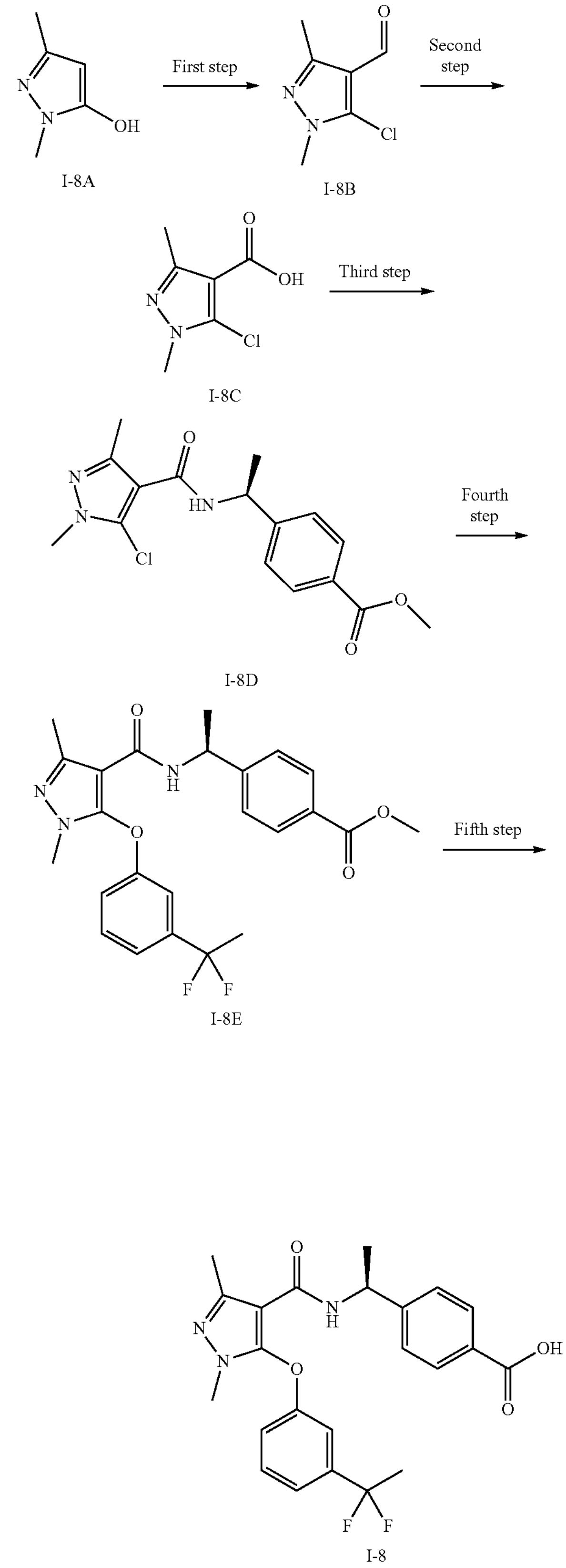

First Step:
5-chloro-1,3-dimethyl-1H-pyrazole-4-carbaldehyde (Compound I-8B)

I-8B

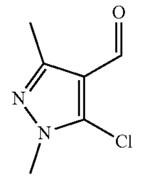

1, 3-dimethyl-5-hydroxypyrazole (5.5 g, 49.1 mmol) was added to DMF (10.9 g) at room temperature, and the mixture was cooled to 0° C., and $POCl_3$ (53.0 g, 346.4 mmol) was added and then naturally warmed to room temperature, heated to 120° C. and stirred for 1 h. Then, the mixture was cooled to room temperature, diluted with water (200 mL), extracted with EA (200 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a colorless liquid of 5-chloro-1,3-dimethyl-1H-pyrazole-4-carbaldehyde (Compound I-8B) (4.3 g, yield 55.4%).

LCMS (ESI) m/z: 159.6 $[M+H]^+$

Second Step:
5-chloro-1,3-dimethyl-1H-pyrazole-4-carboxylic Acid (Compound I-8C)

I-8C

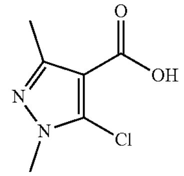

The compound 5-chloro-1,3-dimethyl-1H-pyrazole-4-carbaldehyde (Compound I-8B) (3.20 g, 20.2 mmol) was added to tert-butanol (50 mL) and water (15 mL) at room temperature; and 2-methyl-2-butene (11.3 g, 161.4 mmol), sodium chlorite (9.10 g, 101.1 mmol) and sodium dihydrogen phosphate (19.4 g, 161.6 mmol) were added. The mixture was stirred for 14 hours at room temperature; and then the mixture was diluted with water (50 mL), extracted with ethyl acetate (100 mL×3) and separated. The organic phases were combined and dried over anhydrous sodium sulfate, filtered and concentrated to obtain the crude colorless liquid residue of the captioned compound. The residue was separated and purified by a silica gel column (petroleum ether:ethyl acetate (V/V)=1:1) to obtain a colorless solid of 5-chloro-1,3-dimethyl-1H-pyrazole-4-carboxylic acid (Compound I-8C) (3.10 g, yield 87.9%).

LCMS (ESI) m/z: 175.6 $[M+H]^+$

Third Step: methyl (S)-4-(1-(5-chloro-1,3-dimethyl-1H-pyrazole-4-carboxamido)ethyl)benzoate (Compound I-8D)

I-8D

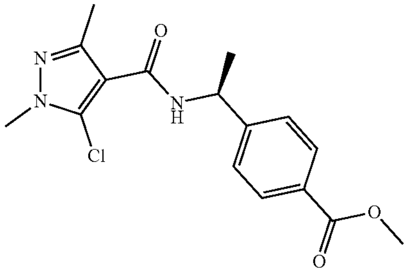

The compound 5-chloro-1,3-dimethyl-1H-pyrazole-4-carboxylic acid (Compound I-8C) (1.20 g, 6.89 mmol) was added to DMF (30 mL); and (S)-methyl 4-(1-aminoethyl) benzoate (1.23 g, 6.87 mmol), HATU (3.90 g, 10.1 mmol) and DIPEA (4.50 g, 34.8 mmol) were added. The mixture was stirred at room temperature for 16 hours, diluted with water (200 mL), extracted with ethyl acetate (100 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a colorless solid of methyl (S)-4-(1-(5-chloro-1,3-dimethyl-1H-pyrazole-4-carboxamido)ethyl)benzoate (Compound I-8D) (1.90 g, yield 82.2%).

LCMS (ESI) m/z: 336.6 $[M+H]^+$

Fourth Step: methyl (S)-4-(1-(5-(3-(1,1-difluoroethyl)phenoxy)-1,3-dimethyl-1H-pyrazole-4-carboxamido)ethyl)benzoate (Compound I-8E)

I-8E

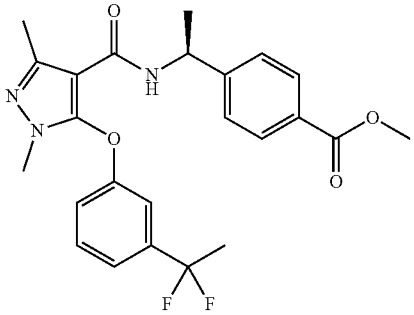

The compound methyl (S)-4-(1-(5-chloro-1,3-dimethyl-1H-pyrazole-4-carboxamido)ethyl)benzoate (Compound I-8D) (335 mg, 1.00 mmol) was added to DMF (10 mL) at room temperature, and 3-(1, 1-difluoroethyl) phenol (158 mg, 1.00 mmol) and KOH (150 mg, 2.67 mmol) were added. The mixture was heated to 120° C. and stirred for 16 hours. Then the mixture was cooled to room temperature, diluted with water (20 mL), extracted with ethyl acetate (20 mL×3) and separated. The organic phases were combined and dried with anhydrous sodium sulfate, filtered and concentrated to obtain a colorless liquid crude product of ethyl (S)-4-(1-(5-(3-(1,1-difluoroethyl)phenoxy)-1,3-dimethyl-1H-pyrazole-4-carboxamido)ethyl)benzoate (Compound I-8E) (170 mg, yield 37.1%).

LCMS (ESI) m/z: 458.5 $[M+H]^+$

Fifth Step: (S)-4-(1-(5-(3-(1,1-difluoroethyl)phenoxy)-1,3-dimethyl-1H-pyrazole-4-carboxamido) ethyl)benzoic Acid (Compound I-8)

I-8

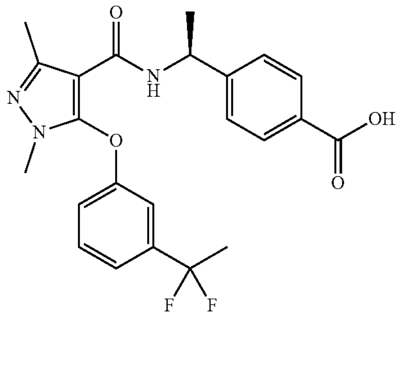

A starting material ethyl (S)-4-(1-(5-(3-(1,1-difluoroethyl)phenoxy)-1,3-dimethyl-1H-pyrazole-4-carboxamido) ethyl)benzoate (Compound I-8E) (500 mg, 1.09 mmol) was added to THF (5 mL) at room temperature, and water (4 mL) and lithium hydroxide monohydrate (340 mg, 8.11 mmol) were added. The mixture was stirred at room temperature for 16 hours. The reaction mixture was concentrated to obtain a white solid of (S)-4-(1-(5-(3-(1,1-difluoroethyl)phenoxy)-1,3-dimethyl-1H-pyrazole-4-carboxamido)ethyl)benzoic acid (Compound I-8) (53 mg, 10.9% yield).

$^1H$ NMR (400 m Hz, DMSO-$d_6$) δ 12.8 (s, 1H), 7.73 (d, 2H), 7.71 (d, 1H), 7.52 (t, 1H), 7.37 (d, 1H), 7.21 (s, 1H), 7.14 (d, 2H), 7.01 (dd, 1H), 4.91 (t, 1H), 3.59 (s, 3H), 2.27 (s, 3H), 1.96 (t, 3H), 1.22 (d, 3H).

LCMS (ESI) m/z: 444.5 $[M+H]^+$

Example 9: Preparation of Compound I-9

(S)-4-(1-(5-(3-ethylphenoxy)-1,3-dimethyl-1H-pyrazole-4-carboxamido)ethyl) benzoic Acid (Compound I-9)

The synthesis scheme for Compound I-9 is shown below:

I-9

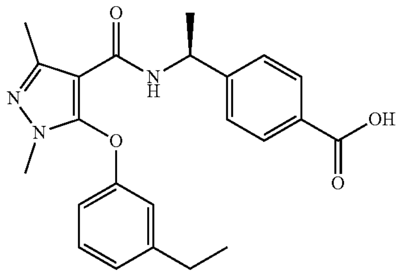

The synthesis scheme for Compound I-9 is shown below:

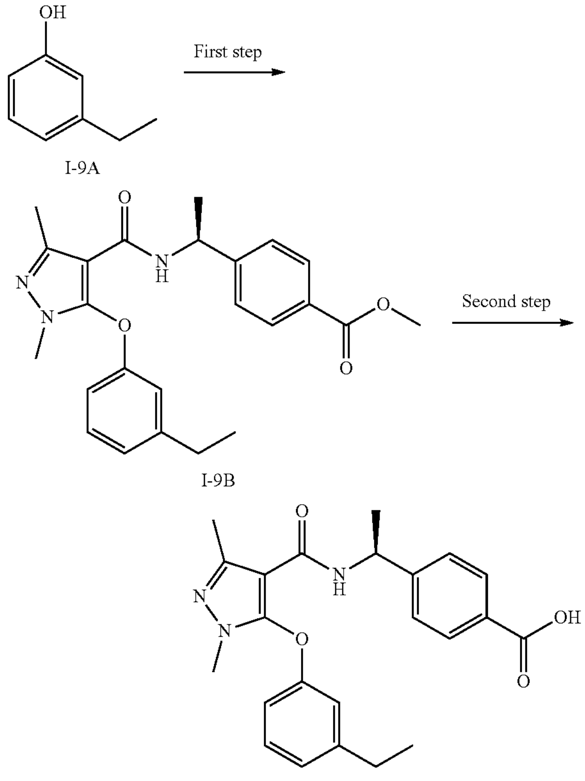

I-9A

I-9B

I-9

First Step: methyl (S)-4-(1-(5-(3-ethylphenoxy)-1,3-dimethyl-1H-pyrazole-4-carboxamido)ethyl)benzoate (Compound I-9B)

I-9B

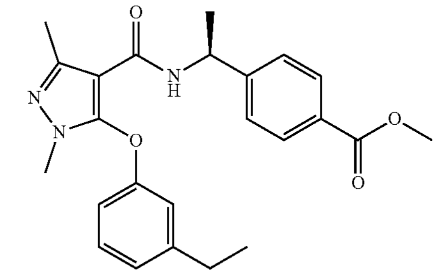

The compound methyl (S)-4-(1-(5-chloro-1,3-dimethyl-1H-pyrazole-4-carboxamido)ethyl)benzoate (Compound I-8D) (100 mg, 0.30 mmol) was added to DMF (3 mL) at room temperature; 3-ethylphenol (36 mg, 0.30 mmol) and KOH (49 mg, 0.86 mmol) were added; and the mixture was heated to 120° C. and stirred for 16 hours. Then, the mixture was cooled to room temperature, diluted with water (20 mL), extracted with ethyl acetate (20 mL×3) and separated. The organic phases were combined and dried over anhydrous sodium sulfate, filtered and concentrated to obtain a colorless liquid crude product of methyl (S)-4-(1-(5-(3-ethylphenoxy)-1,3-dimethyl-1H-pyrazole-4-carboxamido)ethyl)benzoate (Compound I-9B) (60 mg, 47.7% yield).

LCMS (ESI) m/z: 422.6 $[M+H]^+$

Second Step: (S)-4-(1-(5-(3-ethylphenoxy)-1,3-dimethyl-1H-pyrazole-4-carboxamido)ethyl)benzoic Acid (Compound I-9)

I-9

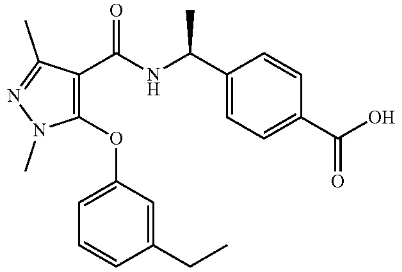

A starting material methyl (S)-4-(1-(5-(3-ethylphenoxy)-1,3-dimethyl-1H-pyrazole-4-carboxamido)ethyl)benzoate (Compound I-9B) (60 mg, 0.14 mmol) was added to THF (2 mL) at room temperature, and water (2 mL) and lithium hydroxide monohydrate (6 mg, 0.14 mmol) were added. The mixture was stirred at room temperature for 16 hours. The reaction mixture was concentrated to obtain a white solid of (S)-4-(1-(5-(3-ethylphenoxy)-1,3-dimethyl-1H-pyrazole-4-carboxamido)ethyl)benzoic acid (Compound I-9) (10 mg, 17.2% yield).

$^1H$ NMR (400 m Hz, DMSO-$d_6$) δ 12.6 (s, 1H), 7.72 (d, 2H), 7.50 (d, 1H), 7.31 (t, 1H), 7.12 (d, 2H), 7.04 (d, 1H), 6.85 (s, 1H), 6.71 (dd, 1H), 4.92 (t, 1H), 3.56 (s, 3H), 2.67 (q, 2H), 2.27 (s, 3H), 1.24 (d, 3H), 1.14 (t, 3H).

LCMS (ESI) m/z: 408.6 $[M+H]^+$

Example 10: Preparation of Compound I-10

(S)-4-(1-(5-(3-(1,1-difluoroethyl)-4-fluorophenoxy)-3-(difluoromethyl)-1-methyl-1H-pyrazole-4-carboxamido)ethyl)benzoic Acid (Compound I-10)

I-10

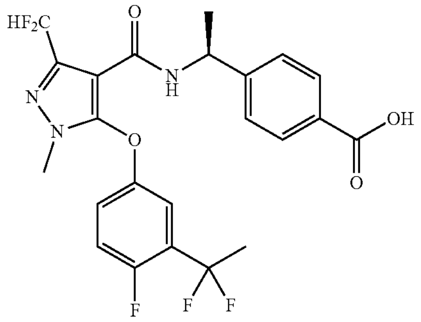

The synthesis scheme for Compound I-10 is shown below:

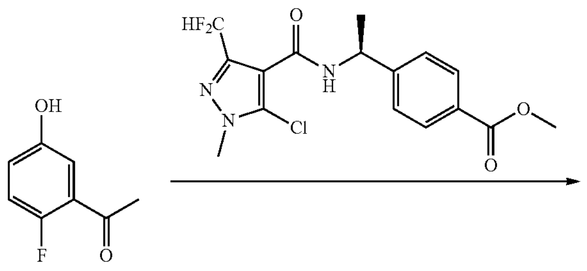

I-10A

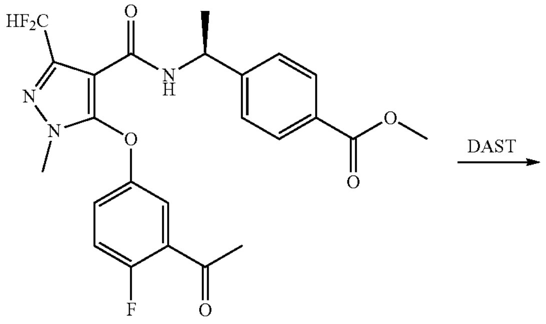

I-10B

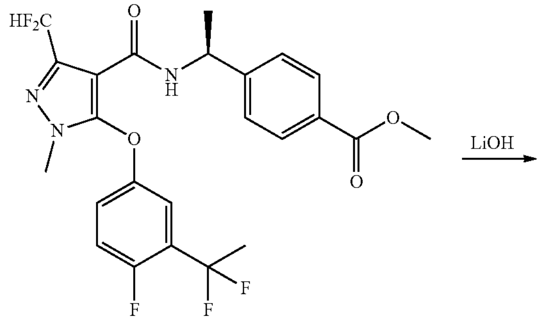

I-10C

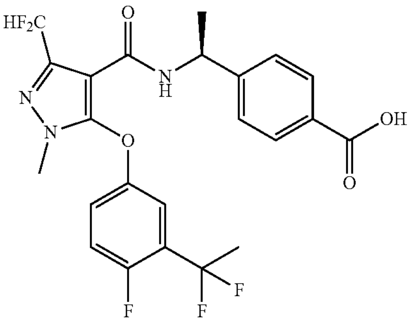

I-10

First Step: methyl (S)-4-(1-(5-(3-acetyl-4-fluorophenoxy)-3-(difluoromethyl)-1-methyl-1H-pyrazole-4-carboxamido)ethyl)benzoate (Compound I-10B)

I-10B

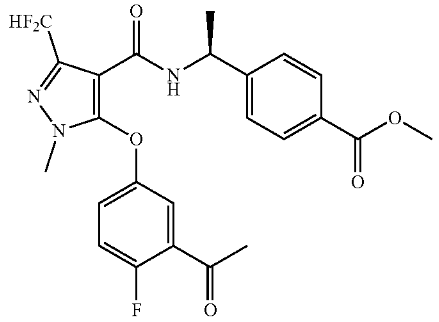

The compound 1-(2-fluoro-5-hydroxyphenyl) ethan-1-one (1.58 g, 10.8 mmol) was added to N, N-dimethylformamide (30 mL) at room temperature; methyl (S)-4-(1-(5-chloro-3-(difluoromethyl)-1-methyl-1H-pyrazole-4-carboxamido)ethyl)benzoat (Intermediate A) (2.0 g, 5.4 mmol) and potassium hydroxide (450 mg, 8.1 mmol) were added; and the mixture was heated to 120° C. in the microwave under nitrogen protection and stirred for 2 hours. The mixture was cooled to room temperature and added with water (30 mL), extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=10:1) to obtain a white solid of methyl (S)-4-(1-(5-(3-acetyl-4-fluorophenoxy)-3-(difluoromethyl)-1-methyl-1H-pyrazole-4-carboxamido) ethyl) benzoate (Compound I-10B) (346 mg, 13% yield).

LC-MS, M/Z (ESI): 490.2 $[M+H]^+$

Second Step: methyl (S)-4-(1-(5-(3-(1,1-difluoroethyl)-4-fluorophenoxy)-3-(difluoromethyl)-1-methyl-1H-pyrazole-4-carboxamido)ethyl)benzoate (Compound I-10C)

I-10C

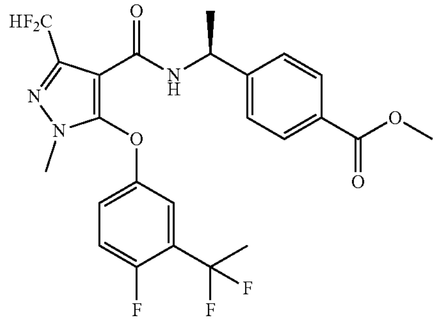

The compound methyl (S)-4-(1-(5-(3-acetyl-4-fluorophenoxy)-3-(difluoromethyl)-1-methyl-1H-pyrazole-4-carboxamido)ethyl)benzoate (Compound I-10B) (346 mg, 0.71 mmol) was added to (diethylamino) sulfur trifluoride (10 mL) at room temperature. The mixture was heated to 50° C. and stirred for 16 hours. Then, the mixture was cooled to 0°

C., diluted with water (50 mL), extracted with EA (100 mL×3) and separated. The organic phases were combined and dried over anhydrous sodium sulfate, filtered and concentrated to obtain a white crude product of methyl (S)-4-(1-(5-(3-(1,1-difluoroethyl)-4-fluorophenoxy)-3-(difluoromethyl)-1-methyl-1H-pyrazole-4-carboxamido)ethyl) benzoate (Compound I-10C) (390 mg, yield 100%).

LC-MS, M/Z (ESI): 512.2 $[M+H]^+$

Third step 3: (S)-4-(1-(5-(3-(1,1-difluoroethyl)-4-fluorophenoxy)-3-(difluoromethyl)-1-methyl-1H-pyrazole-4-carboxamido)ethyl)benzoic Acid (Compound I-10)

I-10

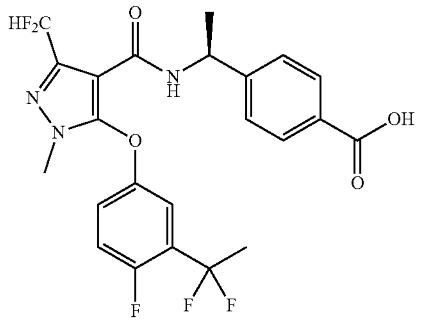

The compound methyl (S)-4-(1-(5-(3-(1,1-difluoroethyl)-4-fluorophenoxy)-3-(difluoromethyl)-1-methyl-1H-pyrazole-4-carboxamido)ethyl)benzoate (Compound I-10C) (390 mg, 0.76 mmol) was added to tetrahydrofuran (10 mL), methanol (10 mL) and water (3 mL) at room temperature, and lithium hydroxide (64 mg, 1.52 mmol) was added. The mixture was stirred at room temperature for 36 hours, and then the pH was adjusted to 7 with 1N hydrochloric acid. The mixture was concentrated to obtain, by the acidic preparation method, a white solid of (S)-4-(1-(5-(3-(1,1-difluoroethyl)-4-fluorophenoxy)-3-(difluoromethyl)-1-methyl-1H-pyrazole-4-carboxamido)ethyl)benzoic acid (Compound I-10) (116 mg, 31% yield).

LC-MS, M/Z (ESI): 498.1 $[M+H]^+$ $^1H$ NMR (400 mHz, DMSO-d6) δ 12.10 (s, 1H), 8.19 (d, 1H), 7.75 (d, 2H), 7.39 (t, 1H), 7.26 (t, 1H), 7.15 (d, 2H), 7.13 (d, 1H), 7.12 (t, 1H), 4.90 (t, 1H), 3.75 (s, 3H), 2.01 (t, 3H), 1.22 (d, 3H).

Example 11: Preparation of Compound I-11

(S)-4-(1-(5-(4-chloro-3-ethylphenoxy)-3-(difluoromethyl)-1-methyl-1H-pyrazole-4-carboxamido)ethyl) benzoic Acid (Compound I-11)

I-11

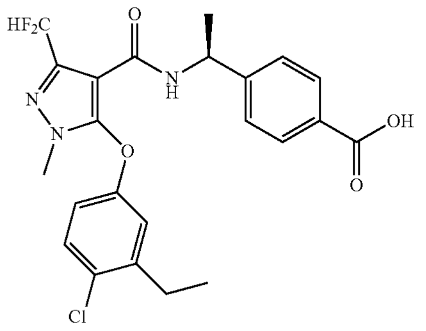

The synthesis scheme for Compound I-11 is shown below:

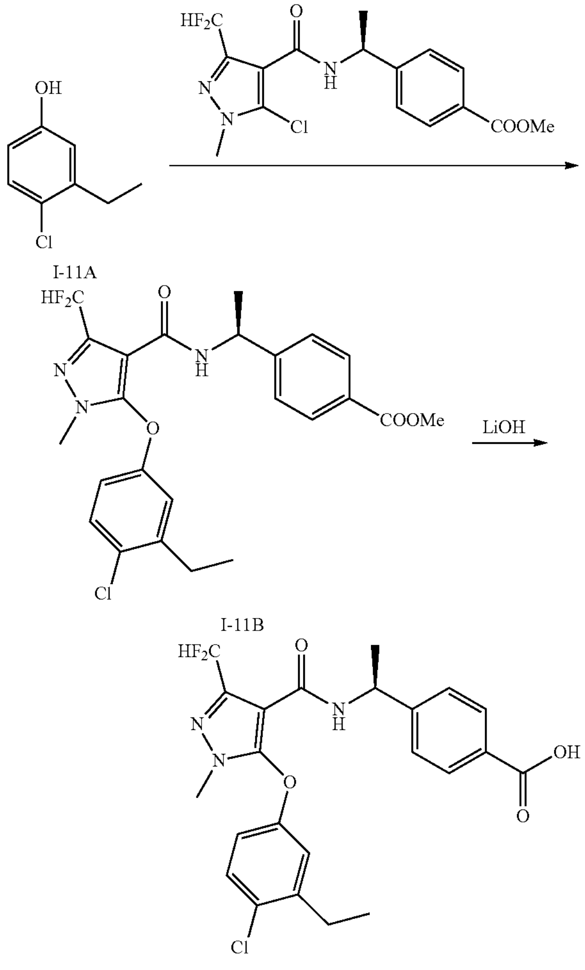

I-11A

I-11B

I-11

First Step: methyl (S)-4-(1-(5-(4-chloro-3-ethylphenoxy)-3-(difluoromethyl)-1-methyl-1H-pyrazole-4-carboxamido)ethyl)benzoate (Compound I-11B)

I-11B

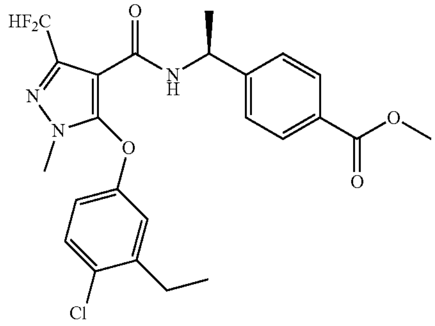

The compound methyl (S)-4-(1-(5-chloro-3-(difluoromethyl)-1-methyl-1H-pyrazole-4-carboxamido)ethyl)benzoat (Intermediate A) (371 mg, 1.00 mmol) was added to dimethyl sulfoxide (3 mL) at room temperature; 4-chloro-3-ethylphenol (156 mg, 1.00 mmol) and potassium hydroxide (112 mg, 2.00 mmol) were added; and the mixture was heated to 120° C. and stirred for 16 hours. Then, the mixture was cooled to room temperature, diluted with water (10 mL), extracted with ethyl acetate (10 mL×3) and separated. The organic phases were combined and dried over anhydrous sodium sulfate, filtered and concentrated to obtain a colorless liquid crude product of methyl (S)-4-(1-(5-(4-chloro-3-ethylphenoxy)-3-(difluoromethyl)-1-methyl-1H-pyrazole-4-carboxamido)ethyl)benzoate (Compound I-11B) (80 mg, yield 16%).

LC-MS, M/Z (ESI): 492.3 (M+1).

Second Step: (S)-4-(1-(5-(4-chloro-3-ethylphenoxy)-3-(difluoromethyl)-1-methyl-1H-pyrazole-4-carboxamido)ethyl)benzoic Acid (Compound I-11)

I-11

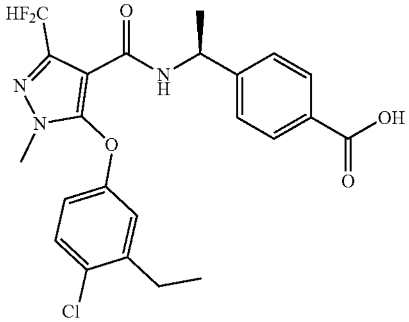

A starting material methyl (S)-4-(1-(5-(4-chloro-3-ethylphenoxy)-3-(difluoromethyl)-1-methyl-1H-pyrazole-4-carboxamido)ethyl)benzoate (Compound I-11B) (80 mg, 0.16 mmol) was added to tetrahydrofuran (1 mL) at room temperature; and water (1 mL) and lithium hydroxide monohydrate (21 mg, 0.48 mmol) were added. The mixture was stirred at room temperature for 16 hours. The reaction mixture was concentrated to obtain a white solid of (S)-4-(1-(5-(4-chloro-3-ethylphenoxy)-3-(difluoromethyl)-1-methyl-1H-pyrazole-4-carboxamido)ethyl)benzoic acid (Compound I-11) (13.3 mg, 17% yield).

$^1$H NMR (400 m Hz, DMSO-d6) δ 12.8 (s, 1H), 8.04 (d, 1H), 7.73 (d, 2H), 7.41 (d, 1H), 7.11 (t, 1H), 7.10 (d, 2H), 7.08 (d, 1H), 6.82 (d, 1H), 4.91 (t, 1H), 3.73 (s, 3H), 2.67 (q, 2H), 1.24 (d, 3H), 1.11 (t, 3H).

LC-MS, M/Z (ESI): 478.3 (M+1)

Example 12: Preparation of Compound I-12

(S)-4-(1-(3-(difluoromethyl)-5-(3-ethyl-5-fluorophenoxy)-1-methyl-1H-pyrazole-4-carboxamido)ethyl) benzoic Acid (Compound I-12)

I-12

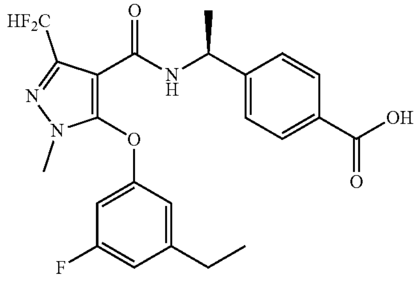

The synthesis scheme for Compound I-12 is shown below:

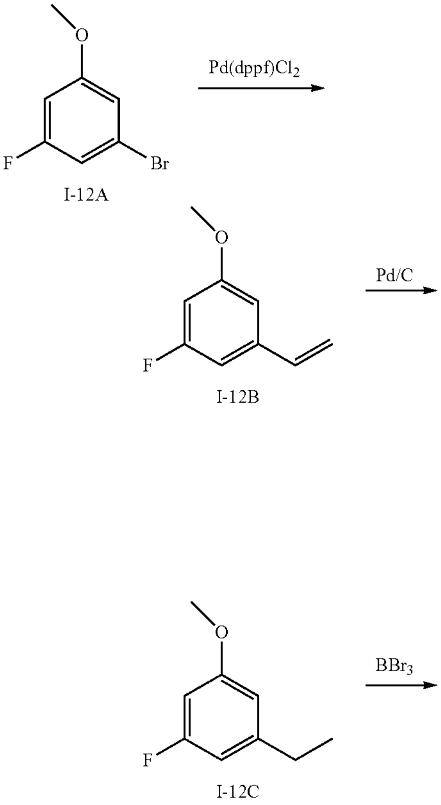

-continued

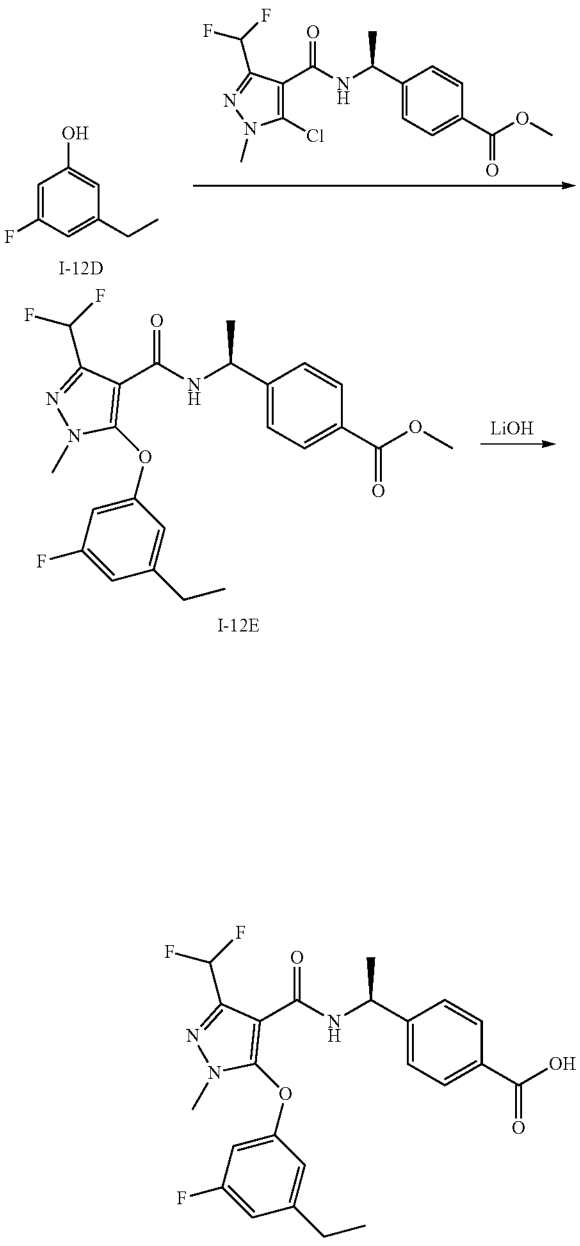

I-12D

I-12E

I-12

First Step: 1-fluoro-3-methoxy-5-vinylbenzene (Compound I-12B)

I-12B

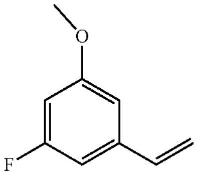

1-bromo-3-fluoro-5-methoxybenzene (2.0 g, 9.7 mmol) was added to 1, 4-dioxane (50 mL) at room temperature; potassium vinylfluoroborate (1.6 g, 11.7 mmol); [1, 1-bis (diphenylphosphino) ferrocene] dichloropalladium (1.4 g, 1.96 mmol) and potassium carbonate (2.7 g, 19.6 mmol) were added; and the mixture was heated to 100° C. under nitrogen protection and stirred for 16 hours. Then, the mixture was cooled to room temperature, diluted with water (200 mL), extracted with dichloromethane (80 mL×3) and separated. The organic phases were combined, dried over anhydrous sodium sulfate, filtered and concentrated, and the residue was separated and purified by a silica gel column (pure petroleum ether) to obtain 1-fluoro-3-methoxy-5-vinylbenzene (Compound I-12B) (600 mg, yield 40%).

Second Step: 1-ethyl-3-fluoro-5-methoxybenzene (Compound I-12C)

I-12C

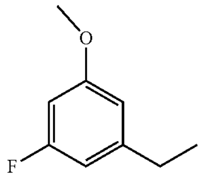

1-fluoro-3-methoxy-5-vinylbenzene (300 mg, 1.97 mmol) was added to methanol (20 mL) at room temperature and 10% palladium on carbon (200 mg) was added. Under the introduction of $H_2$, the mixture was stirred at room temperature for 16 hours. The mixture was filtered and washed with methanol (30 mL×3), and the organic phases were combined and concentrated to obtain a colorless liquid crude product of 1-ethyl-3-fluoro-5-methoxybenzene (Compound I-12C) (200 mg, yield 66%).

Third Step: 3-ethyl-5-fluorophenol (Compound I-12D)

I-12D

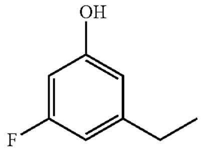

1-ethyl-3-fluoro-5-methoxybenzene (200 mg, 1.3 mmol) was added to dichloromethane (2 mL) at room temperature. The mixture was cooled to 0° C., and $BBr_3$ (1 mol/L in dichloromethane, 2 mL) was added. The mixture was naturally warmed to room temperature, and stirred at room temperature for 4 hours. The reaction was quenched by adding water (3 mL), and the mixture was extracted with dichloromethane (5 mL×3) and separated. The organic phases were combined and dried over anhydrous sodium sulfate, filtered, and concentrated to obtain a colorless liquid crude product of 3-ethyl-5-fluorophenol (Compound I-12D) (180 mg, yield 99%).

Fourth Step: methyl (S)-4-(1-(3-(difluoromethyl)-5-(3-ethyl-5-fluorophenoxy)-1-methyl-1H-pyrazole-4-carboxamido)ethyl)benzoate (Compound I-12E)

I-12E

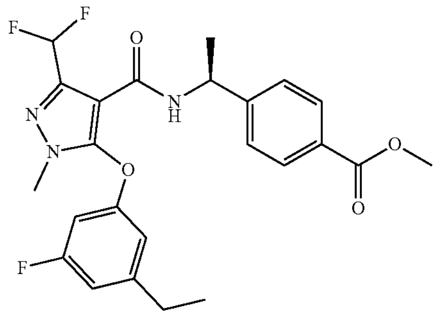

A compound methyl (S)-4-(1-(5-chloro-3-(difluoromethyl)-1-methyl-1H-pyrazole-4-carboxamido)ethyl)benzoat (Intermediate A) (250 mg, 0.67 mmol) was added to N, N-dimethylformamide (15 mL) and heated to 120° C.; 3-ethyl-5-fluorophenol (180 mg, 1.28 mmol), potassium carbonate (270 mg, 1.96 mmol), cuprous iodide (50 mg, 0.26 mmol) and 1, 10-phenanthroline (90 mg, 0.50 mmol) were added. The mixture was stirred for 1 hour at room temperature. Then, the mixture was cooled to room temperature, diluted with water (30 mL), extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=4:1) to obtain a colorless liquid of methyl (S)-4-(1-(3-(difluoromethyl)-5-(3-ethyl-5-fluorophenoxy)-1-methyl-1H-pyrazole-4-carboxamido)ethyl)benzoate (Compound I-12E) (200 mg, yield 62%).

LC-MS, M/Z (ESI): 476.2 (M+1).

Fifth Step: (S)-4-(1-(3-(difluoromethyl)-5-(3-ethyl-5-fluorophenoxy)-1-methyl-1H-pyrazole-4-carboxamido)ethyl)benzoic Acid (Compound I-12)

I-12

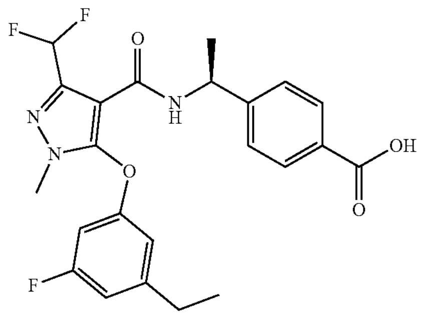

A starting material methyl (S)-4-(1-(3-(difluoromethyl)-5-(3-ethyl-5-fluorophenoxy)-1-methyl-1H-pyrazole-4-carboxamido)ethyl)benzoate (200 mg, 0.42 mmol) was added to tetrahydrofuran (10 mL) and water (5 mL) at room temperature, and lithium hydroxide monohydrate (53 mg, 1.26 mmol) was added. The mixture was stirred at room temperature for 16 hours. The reaction mixture was concentrated to obtain a white solid of the compound (S)-4-(1-(3-(difluoromethyl)-5-(3-ethyl-5-fluorophenoxy)-1-methyl-1H-pyrazole-4-carboxamido)ethyl)benzoic acid (130 mg, 67% yield).

$^1$H NMR (400 m Hz, DMSO-d6) δ 12.8 (s, 1H), 8.10 (d, 1H), 7.74 (d, 2H), 7.16 (d, 2H), 7.11 (t, 1H), 6.93 (d, 1H), 6.72 (s, 1H), 6.69 (d, 1H), 4.92 (t, 1H), 3.73 (s, 3H), 2.58-2.54 (m, 2H), 1.25 (d, 3H), 1.13 (t, 3H).

LC-MS, M/Z (ESI): 462.1 (M+1)

Example 13: Preparation of Compound I-13

4-((1S)-1-(3-(difluoromethyl)-5-(3-(1-fluoroethyl)phenoxy)-1-methyl-1H-pyrazole-4-carboxamido)ethyl)benzoic Acid (Compound I-13)

I-13

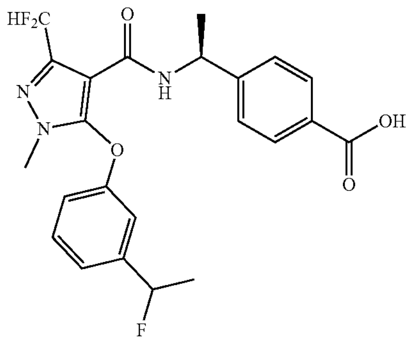

The synthesis scheme for Compound I-13 is shown below:

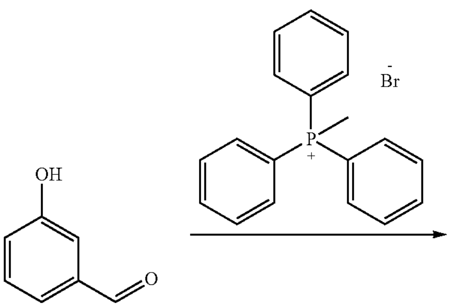

I-13A

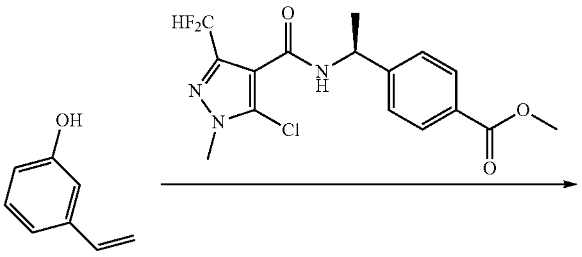

I-13B

-continued

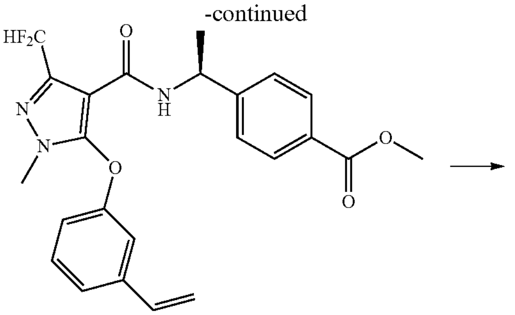

I-13C

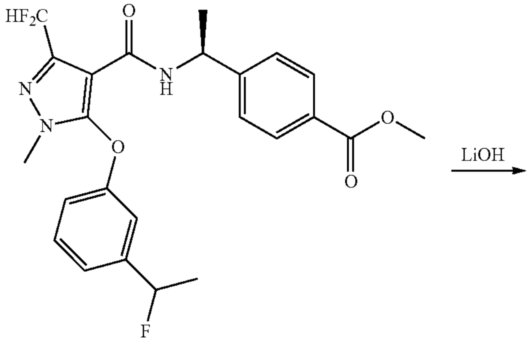

I-13D

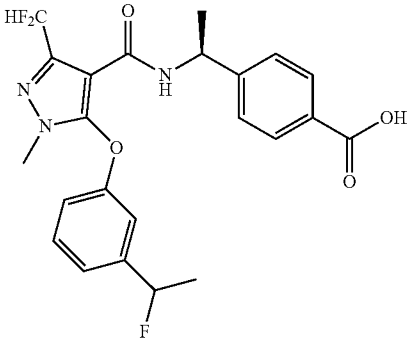

I-13

First Step: 3-vinylphenol (Compound I-13B)

I-13B

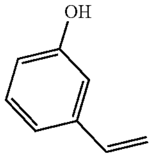

A compound methyltriphenylphosphine bromide (7.30 g, 20.5 mmol) was added to anhydrous tetrahydrofuran (40 mL) at 0° C., and potassium tert-butoxide (2.3 g, 20.5 mmol) was added. The mixture was stirred at low temperature for 2 hours. A solution of 3-hydroxybenzaldehyde (1.0 g, 8.20 mmol) and tetrahydrofuran (15 mL) was added dropwise, and after completion of addition, the mixture was warmed up naturally to room temperature and stirred for 16 hours. The mixture was diluted with water (100 mL), extracted with ethyl acetate (100 mL×3) and separated. The organic phases were combined, dried over anhydrous sodium sulfate, filtered and concentrated, and the residue was separated and purified by a silica gel column (petroleum ether:ethyl acetate (V/V)=10:1) to obtain a yellow liquid of 3-vinylphenol (Compound I-13B) (500 mg, yield 49%).

Second Step: methyl (S)-4-(1-(3-(difluoromethyl)-1-methyl-5-(3-vinylphenoxy)-1H-pyrazole-4-carboxamido)ethyl)benzoate (Compound I-13C)

I-13C

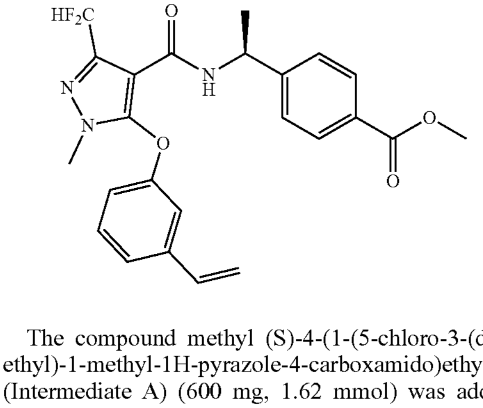

The compound methyl (S)-4-(1-(5-chloro-3-(difluoromethyl)-1-methyl-1H-pyrazole-4-carboxamido)ethyl)benzoat (Intermediate A) (600 mg, 1.62 mmol) was added to N, N-dimethylformamide (18 mL) at room temperature; and 3-vinylphenol (Compound I-13B) (388 mg, 3.23 mmol) and potassium hydroxide (181 mg, 3.23 mmol) were added. The mixture was heated to 120° C. in the microwave and stirred for 2 hours. Then, the mixture was cooled to room temperature, diluted with water (60 mL), extracted with ethyl acetate (60 mL×3) and separated. The organic phases were combined, dried over anhydrous sodium sulfate, filtered and concentrated, and the residue was separated and purified by a silica gel column (petroleum ether:ethyl acetate (V/V)=10:1) to obtain a white solid of methyl (S)-4-(1-(3-(difluoromethyl)-1-methyl-5-(3-vinylphenoxy)-1H-pyrazole-4-carboxamido)ethyl)benzoate (Compound I-13C) (200 mg, yield 27%).

LC-MS, M/Z (ESI): 456.2 (M+1).

Third Step: methyl 4-((1S)-1-(3-(difluoromethyl)-5-(3-(1-fluoroethyl)phenoxy)-1-methyl-1H-pyrazole-4-carboxamido)ethyl)benzoate (Compound I-13D)

I-13D

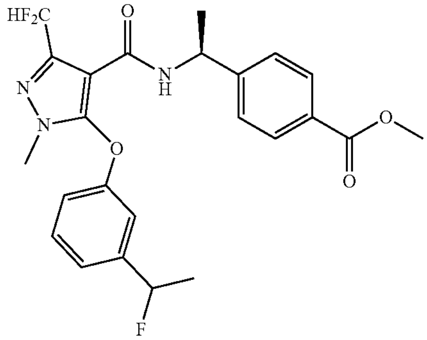

A starting material methyl (S)-4-(1-(3-(difluoromethyl)-1-methyl-5-(3-vinylphenoxy)-1H-pyrazole-4-carboxamido)ethyl)benzoate (Compound I-13C) (100 mg, 0.22 mmol)

was added to acetonitrile (25 mL); and a selective fluorinating reagent (233 mg, 0.66 mmol), palladium tetrakistriphenylphosphonium (25 mg, 0.02 mmol) and triethylsilane (40.0 mg, 0.33 mmol) were added at room temperature. The mixture was stirred for 16 hours under nitrogen protection at room temperature. Then, the mixture was diluted with water (60 mL), extracted with ethyl acetate (60 mL×3) and separated. The organic phases were combined, dried over anhydrous sodium sulfate, filtered, concentrated, and the residue purified by silica gel column separation (petroleum ether: ethyl acetate (V/V)=5:1) to obtain a white solid of methyl 4-((1S)-1-(3-(difluoromethyl)-5-(3-(1-fluoroethyl)phenoxy)-1-methyl-1H-pyrazole-4-carboxamido)ethyl)benzoate (Compound I-13D) (65.0 mg, yield 62%).

LC-MS, M/Z (ESI): 476.3 (M+1)

Fourth Step: 4-((1S)-1-(3-(difluoromethyl)-5-(3-(1-fluoroethyl)phenoxy)-1-methyl-1H-pyrazole-4-carboxamido)ethyl)benzoic Acid (Compound I-13)

I-13

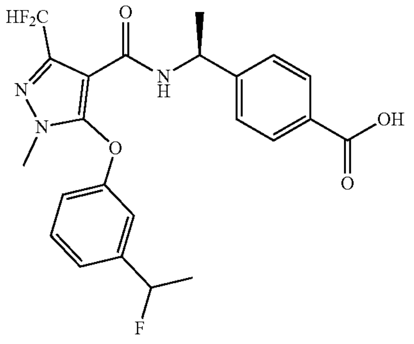

A starting material methyl 4-((1S)-1-(3-(difluoromethyl)-5-(3-(1-fluoroethyl)phenoxy)-1-methyl-1H-pyrazole-4-carboxamido)ethyl)benzoate (Compound I-13D) (150 mg, 0.19 mmol) was added to tetrahydrofuran (24 mL); and water (12 mL) and methanol (12 mL), lithium hydroxide (15.0 mg, 0.36 mmol) were added at room temperature. The mixture was stirred for 4 hours at room temperature. The reaction mixture was concentrated to obtain, by the acidic preparation method A, a white solid of 4-((1S)-1-(3-(difluoromethyl)-5-(3-(1-fluoroethyl)phenoxy)-1-methyl-1H-pyrazole-4-carboxamido)ethyl)benzoic acid (Compound I-13) (50.0 mg, 32% yield).

$^1$H NMR (400 m Hz, DMSO-d6) δ 12.8 (s, 1H), 8.03 (d, 1H), 7.72 (d, 2H), 7.45 (t, 1H), 7.25 (t, 1H), 7.11 (d, 2H), 6.98 (t, 1H), 6.94 (t, 1H), 5.78 (dd, 1H), 4.89 (m, 1H), 3.73 (s, 3H), 3.60 (s, 1H), 1.55 (dd, 3H), 1.24 (d, 3H).

LC-MS, M/Z (ESI): 462.3 (M+1)

Example 14: Preparation of Compound I-14

(S)-4-(1-(5-(3-(2,2-difluoroethyl)phenoxy)-3-(difluoromethyl)-1-methyl-1H-pyrazole-4-carboxamido)ethyl)benzoic Acid (Compound I-14)

I-14

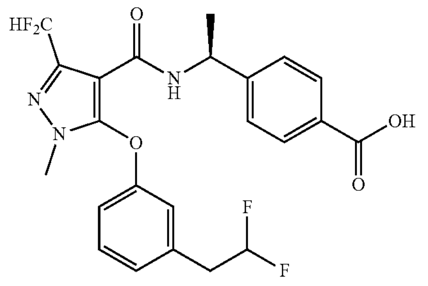

The synthesis scheme for Compound I-14 is shown below:

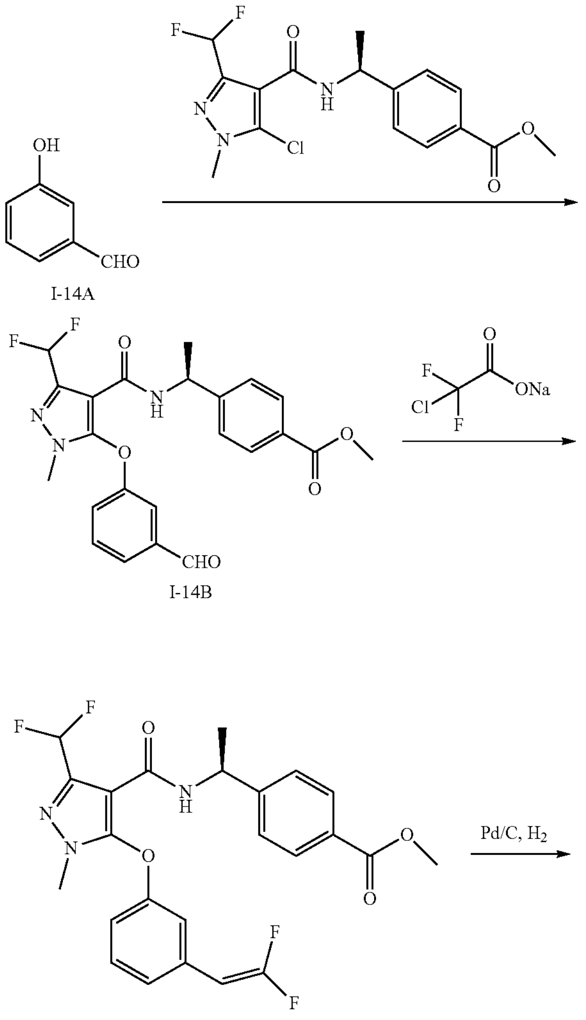

I-14A

I-14B

I-14C

-continued

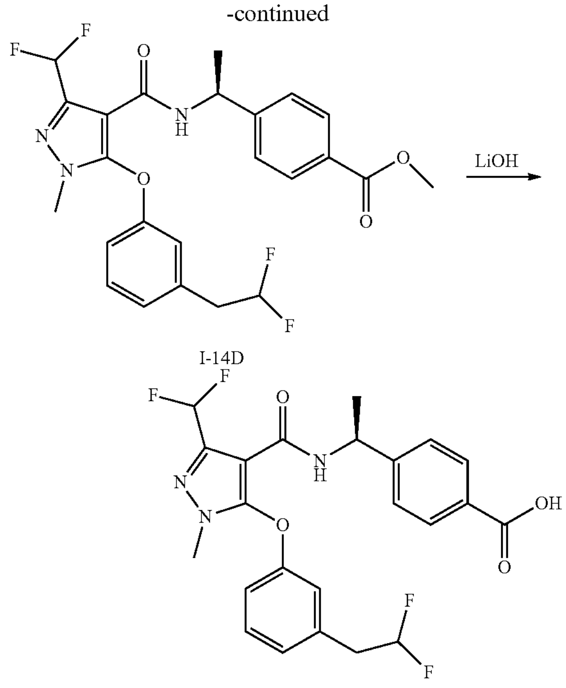

I-14D

I-14

First Step: methyl (S)-4-(1-(3-(difluoromethyl)-5-(3-formylphenoxy)-1-methyl-1H-pyrazole-4-carboxamido)ethyl)benzoate (Compound I-14B)

I-14B

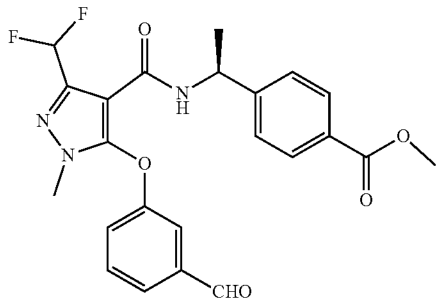

The compound methyl (S)-4-(1-(5-chloro-3-(difluoromethyl)-1-methyl-1H-pyrazole-4-carboxamido)ethyl)benzoat (Intermediate A) (574 mg, 1.54 mmol) was added to N, N-dimethylformamide (15 mL) at room temperature; and 3-hydroxybenzaldehyde (378 mg, 3.09 mmol), copper iodide (60 mg, 0.31 mmol), 1, 10-phenanthroline (114 mg, 0.62 mmol) and cesium carbonate (1.50 g, 4.62 mmol) were added. The mixture was heated to 120° C. in the microwave under nitrogen protection and stirred for 2 hours. Then, the mixture was cooled to room temperature, diluted with water (50 mL), and the pH was adjusted to 4 with 1N hydrochloric acid. The mixture was extracted with ethyl acetate (50 mL×3) and separated. The organic phases were combined, dried over anhydrous sodium sulfate, filtered and concentrated, and the residue was purified by silica gel column (petroleum ether:ethyl acetate (V/V)=3:1) to obtain a light yellow solid of methyl (S)-4-(1-(3-(difluoromethyl)-5-(3-formylphenoxy)-1-methyl-1H-pyrazole-4-carboxamido) ethyl)benzoate (Compound I-14B) (280 mg, yield 40%).

LC-MS, M/Z (ESI): 458.3 [M+H]+.

Second Step: methyl (S)-4-(1-(3-(difluoromethyl)-5-(3-(2,2-difluorovinyl)phenoxy)-1-methyl-1H-pyrazole-4-carboxamido)ethyl)benzoate (Compound I-14C)

I-14C

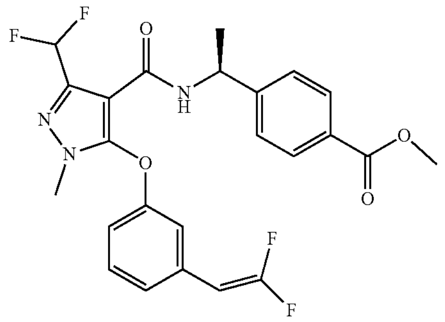

The compound methyl (S)-4-(1-(3-(difluoromethyl)-5-(3-formylphenoxy)-1-methyl-1H-pyrazole-4-carboxamido) ethyl)benzoate (Compound I-14B) (280 mg, 0.61 mmol) was added to N, N-dimethylformamide (15 mL) at room temperature, and triphenylphosphine (200 mg, 0.76 mmol) and sodium difluorochloroacetate (140 mg, 0.92 mmol) were added, and the mixture was heated to 100° C. in the microwave under nitrogen protection and stirred for 1 h. The mixture was cooled to room temperature, diluted by addition of water (50 mL), and the pH was adjusted to 4 with TN hydrochloric acid, and the mixture was extracted with ethyl acetate (50 mL×3) and separated. The organic phases were combined, dried over anhydrous sodium sulfate, filtered and concentrated, and the residue was separated and purified on a thin-layer silica gel plate (petroleum ether:ethyl acetate (V/V)=4:1) to obtain a light yellow solid of methyl (S)-4-(1-(3-(difluoromethyl)-5-(3-(2,2-difluorovinyl)phenoxy)-1-methyl-1H-pyrazole-4-carboxamido)ethyl)benzoate (Compound I-14C) (120 mg, yield 40%).

LC-MS, M/Z (ESI): 492.4 [M+H]+.

Third Step: methyl (S)-4-(1-(5-(3-(2,2-difluoroethyl)phenoxy)-3-(difluoromethyl)-1-methyl-1H-pyrazole-4-carboxamido)ethyl)benzoate (Compound I-14D)

I-14D

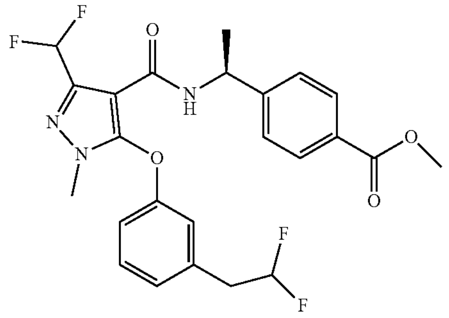

The compound methyl (S)-4-(1-(3-(difluoromethyl)-5-(3-(2,2-difluorovinyl)phenoxy)-1-methyl-1H-pyrazole-4-carboxamido)ethyl)benzoate (Compound I-14C) (120 mg, 0.24 mmol) was added to methanol (20 mL) at room temperature; 10% palladium on carbon (20 mg) was added; and hydrogen was introduced. The mixture was stirred at room temperature for 16 hours. The mixture was filtered and concentrated to obtain a light yellow solid crude product methyl (S)-4-(1-(5-(3-(2,2-difluoroethyl)phenoxy)-3-(difluoromethyl)-1-methyl-1H-pyrazole-4-carboxamido)ethyl)benzoate (Compound I-14D) (120 mg, 99% yield).

LC-MS, M/Z (ESI): 494.4 [M+H]+.

Fourth Step: (S)-4-(1-(5-(3-(2,2-difluoroethyl)phenoxy)-3-(difluoromethyl)-1-methyl-1H-pyrazole-4-carboxamido)ethyl)benzoic Acid (Compound I-14)

I-14

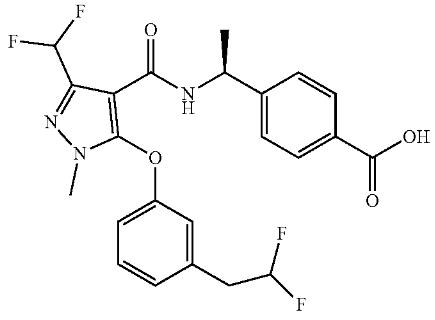

A starting material methyl (S)-4-(1-(5-(3-(2,2-difluoroethyl)phenoxy)-3-(difluoromethyl)-1-methyl-1H-pyrazole-4-carboxamido)ethyl)benzoate (Compound I-14D) (120 mg, 0.24 mmol) was added to tetrahydrofuran (5 mL) and water (5 mL) at room temperature, and then lithium hydroxide (31 mg, 0.72 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(5-(3-(2,2-difluoroethyl)phenoxy)-3-(difluoromethyl)-1-methyl-1H-pyrazole-4-carboxamido)ethyl)benzoic acid (Compound I-14) (90 mg, 77% yield).

$^1$H NMR (400 m Hz, DMSO-d6) δ 12.8 (s, 1H), 7.95 (d, 1H), 7.74 (d, 2H), 7.39 (t, 1H), 7.25 (t, 1H), 7.16 (d, 2H), 7.13 (d, 1H), 7.04 (d, 1H), 6.91 (t, 1H), 6.34 (dt, 1H), 4.91 (t, 1H), 3.71 (s, 3H), 3.22 (q, 2H), 1.22 (d, 3H).

LC-MS, M/Z (ESI): 480.4 [M+H]$^+$

Example 15: Preparation of Compound I-15

4-((1S)-1-(3-(difluoromethyl)-1-methyl-5-(3-(1,1,1-trifluoropropan-2-yl)phenoxy)-1H-pyrazole-4-carboxamido)ethyl)benzoic Acid (Compound I-15)

I-15

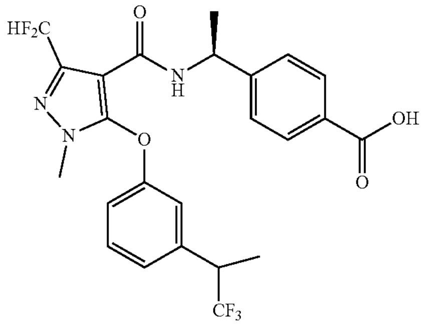

The synthesis scheme for Compound I-15 is shown below:

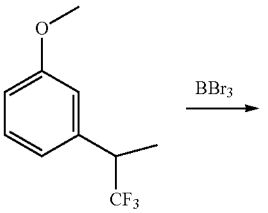

I-15A

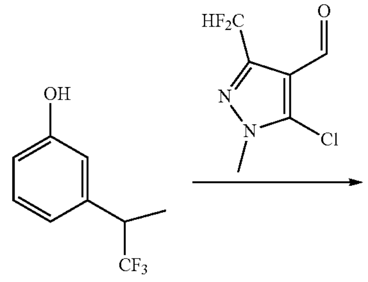

I-15B

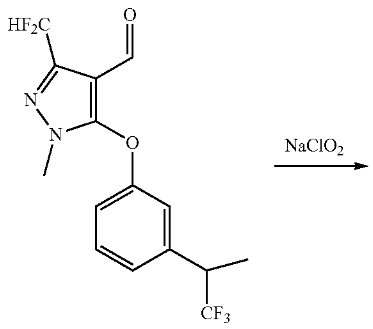

I-15C

-continued

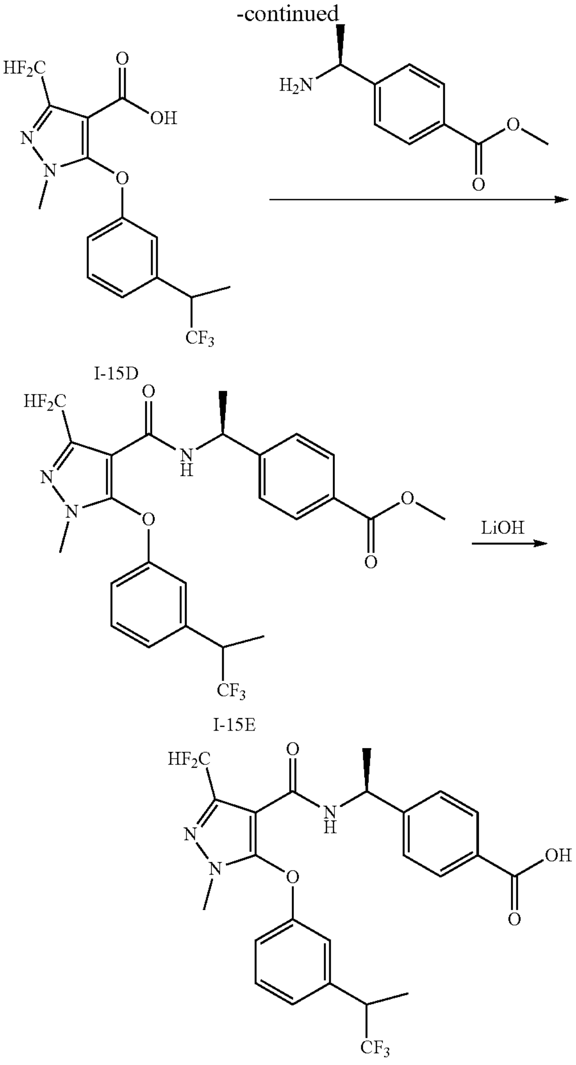

I-15D

I-15E

I-15

First Step: 3-(1,1,1-trifluoropropan-2-yl)phenol (Compound I-15B)

I-15B

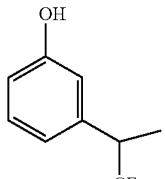

A compound 1-methoxy-3-(1, 1, 1-trifluoropropan-2-yl) benzene (800 mg, 0.72 mmol) was added to dichloromethane (1 mL) at room temperature, and then the mixture was cooled to −78° C., and then boron tribromide (1.50 g, 5.88 mmol) was added. The mixture was stirred at room temperature for 4 hours; and then the mixture was diluted with water (50 mL), extracted with dichloromethane (50 mL×3) and separated. The organic phases were combined, dried over anhydrous sodium sulfate, filtered, concentrated and the residue purified by silica gel column separation (petroleum ether:ethyl acetate (V/V)=5:1) to obtain a light yellow liquid of 3-(1,1,1-trifluoropropan-2-yl)phenol (Compound I-15B) (640 mg, 86% yield).

Second Step: 3-(difluoromethyl)-1-methyl-5-(3-(1,1,1-trifluoropropan-2-yl)phenoxy)-1H-pyrazole-4-carbaldehyde (Compound I-15C)

I-15C

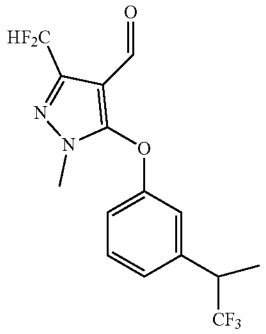

The compound 5-chloro-3-(difluoromethyl)-1-methyl-1H-pyrazole-4-carbaldehyde (660 mg, 3.37 mmol) was added to N, N dimethylformamide (6 mL) at room temperature, and then 3-(1, 1, 1-trifluoropropan-2-yl) phenol (640 mg, 3.37 mmol) and potassium carbonate (930 mg, 6.72 mmol) were added. The mixture was heated to 100° C. under nitrogen protection and stirred for 8 h; and then the mixture was cooled to room temperature, diluted with water (50 mL), extracted with ethyl acetate (50 mL×3) and separated. The organic phases were combined, dried over anhydrous sodium sulfate, filtered and concentrated, and the residue was purified by silica gel column (petroleum ether:ethyl acetate (V/V)=5:1) to obtain a light yellow liquid of 33-(difluoromethyl)-1-methyl-5-(3-(1,1,1-trifluoropropan-2-yl) phenoxy)-1H-pyrazole-4-carbaldehyde (Compound I-15C) (1.0 g, yield 18%).

LC-MS, M/Z (ESI): 349.2 [M+H]+.

Third Step: 3-(difluoromethyl)-1-methyl-5-(3-(1,1,1-trifluoropropan-2-yl)phenoxy)-1H-pyrazole-4-carboxylic Acid (Compound I-15D)

I-15D

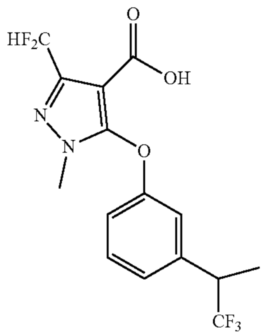

A compound 3-(difluoromethyl)-1-methyl-5-(3-(1,1,1-trifluoropropan-2-yl)phenoxy)-1H-pyrazole-4-carbaldehyde (800 mg, 2.30 mmol) was added to tert-butanol (8 mL) and water (8 mL) at room temperature. 2-methyl-2-butene (322 mg, 4.60 mmol), sodium chlorite (414 mg, 4.60 mmol) and sodium dihydrogen phosphate (617 mg, 5.06 mmol) were added. The mixture was stirred at room temperature for 8 h; and then the mixture was diluted with water (15 mL), the pH was adjusted to 4 with 1N hydrochloric acid, and the mixture was extracted with ethyl acetate (30 mL×3) and separated. The organic phases were combined and dried over anhydrous sodium sulfate, filtered and concentrated to obtain a light yellow solid of crude 3-(difluoromethyl)-1-methyl-5-(3-(1,1,1-trifluoropropan-2-yl)phenoxy)-1H-pyrazole-4-carboxylic acid (Compound I-15D) (850 mg, yield 100%).

LC-MS, M/Z (ESI): 365.1 $[M+H]^+$.

Fourth Step: methyl 4-((1S)-1-(3-(difluoromethyl)-1-methyl-5-(3-(1,1,1-trifluoropropan-2-yl)phenoxy)-1H-pyrazole-4-carboxamido)ethyl)benzoate (Compound I-15E)

I-15E

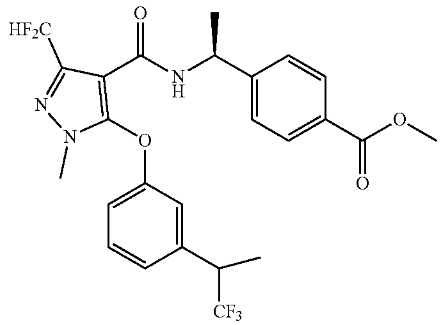

A compound 3-(difluoromethyl)-1-methyl-5-(3-(1,1,1-trifluoropropan-2-yl)phenoxy)-1H-pyrazole-4-carboxylic acid (850 mg, 2.34 mmol) was added to N, N-dimethylformamide (10 mL); and methyl (S)-4-(1-aminoethyl) benzoate (418 mg, 2.34 mmol), O-(7-azabenzotriazol-1-yl)-N, N, N, N-tetramethyluronium hexafluorophosphate (1.3 g, 3.50 mmol) and N, N-diisopropylethylamine (900 mg, 7.0 mmol) were added. The mixture was stirred at room temperature for 16 hours, diluted with water (40 mL), extracted with ethyl acetate (40 mL×3) and separated. The organic phases were combined, dried over anhydrous sodium sulfate, filtered, concentrated and purified by silica gel column (petroleum ether:ethyl acetate (V/V)=3:1) to obtain a light yellow liquid of methyl 4-((1S)-1-(3-(difluoromethyl)-1-methyl-5-(3-(1,1,1-trifluoropropan-2-yl)phenoxy)-1H-pyrazole-4-carboxamido)ethyl)benzoate (Compound I-15E) (1.0 g, yield 81%).

LC-MS, M/Z (ESI): 526.3 $[M+H]^+$.

Fifth Step: 4-((1S)-1-(3-(difluoromethyl)-1-methyl-5-(3-(1,1,1-trifluoropropan-2-yl)phenoxy)-1H-pyrazole-4-carboxamido)ethyl)benzoic Acid (Compound I-15)

I-15

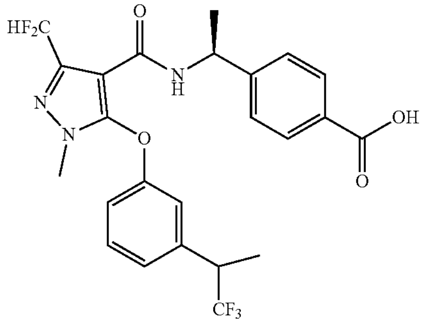

The starting material methyl 4-((1S)-1-(3-(difluoromethyl)-1-methyl-5-(3-(1,1,1-trifluoropropan-2-yl)phenoxy)-1H-pyrazole-4-carboxamido)ethyl)benzoate (Compound I-15E) (1.0 g, 1.90 mmol) was added to tetrahydrofuran (10 mL); and water (2 mL) at room temperature; and lithium hydroxide (200 mg, 4.76 mmol) was added. The mixture was stirred at room temperature for 16 hours; the pH was adjusted to 4 by 1N hydrochloric acid; and the reaction mixture was concentrated to prepare, by the acidic preparative method A, a white solid of 4-((1S)-1-(3-(difluoromethyl)-1-methyl-5-(3-(1,1,1-trifluoropropan-2-yl)phenoxy)-1H-pyrazole-4-carboxamido)ethyl)benzoic acid (Compound I-15) (356 mg, 37% yield).

$^1$H NMR (400 m Hz, DMSO-d6) δ 12.8 (s, 1H), 7.97 (dd, 1H), 7.73 (d, 2H), 7.43 (dd, 1H), 7.28 (d, 1H), 7.25 (t, 1H), 7.13 (d, 2H), 7.11 (d, 1H), 6.99 (t, 1H), 4.90 (t, 1H), 3.89-3.85 (m, 1H), 3.73 (s, 3H), 1.41 (d, 3H), 1.21 (t, 3H).

LC-MS, M/Z (ESI): 512.3 $[M+H]^+$

Example 16: Preparation of Compound I-16

(S)-4-(1-(3-(difluoromethyl)-5-(3-ethyl-4,5-difluorophenoxy)-1-methyl-1H-pyrazole-4-carboxamido)ethyl)benzoic Acid (Compound I-16)

I-16

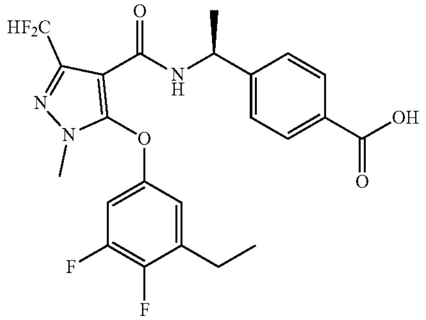

The synthesis scheme for Compound I-16 is shown below:

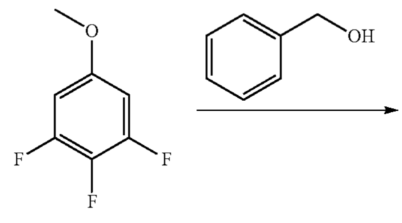

I-16A

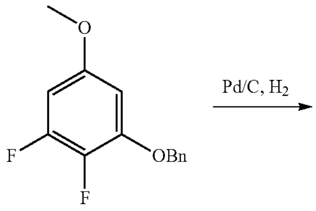

I-16B

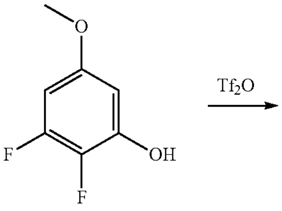

I-16C

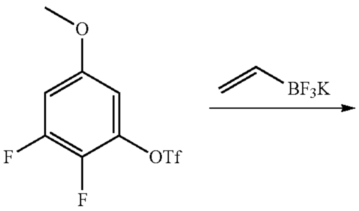

I-16D

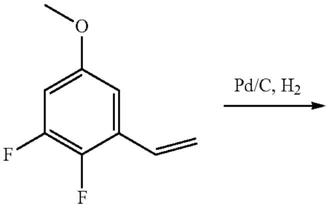

I-16E

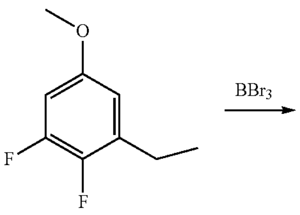

I-16F

-continued

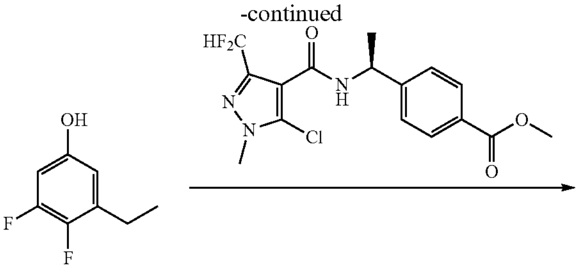

I-16G

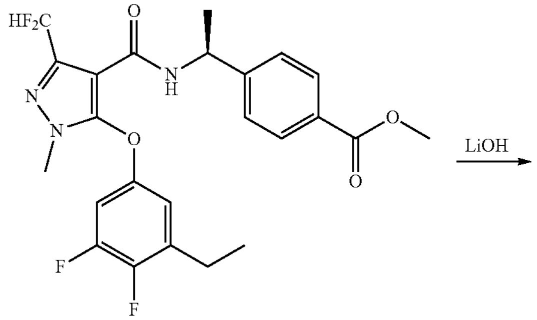

I-16H

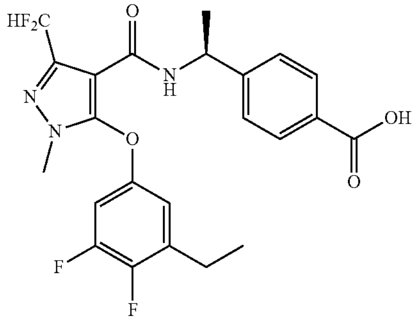

I-16

First Step: 1-(benzyloxy)-2,3-difluoro-5-methoxybenzene (Compound I-16B)

I-16B

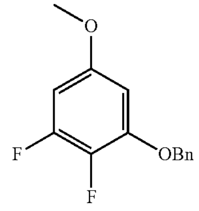

A Compound 1, 2, 3-trifluoro-5-methoxybenzene (8.5 g, 52.4 mmol) was added to toluene (100 mL) at room temperature; benzyl alcohol (11.3 g, 104 mmol) and potassium hydroxide (5.86 g, 104 mmol) were added; and the mixture was heated to 120° C. and stirred for 16 hours. Then, the mixture was cooled to room temperature, diluted with water (500 mL), and the pH was adjusted to 7-8 with 1N hydrochloric acid. The mixture was extracted with dichloromethane (100 mL×3) and separated. The organic phases were combined and dried over anhydrous sodium sulfate, filtered and concentrated, and the residue was separated and purified by a silica gel column (petroleum ether:ethyl acetate (V/V), 20:1) to obtain a colorless liquid of 1-(benzyloxy)-2,3-difluoro-5-methoxybenzene (compound I-16B) (5.2 g, yield 40%).

Second Step: 2,3-difluoro-5-methoxyphenol (Compound I-16C)

I-16C

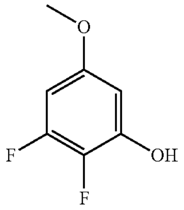

A compound 1-(benzyloxy)-2,3-difluoro-5-methoxybenzene (5.2 g, 20.8 mmol) was added to tetrahydrofuran (100 mL) at room temperature; 10% palladium on carbon (520 mg) was added; and hydrogen was introduced. The mixture was stirred at room temperature for 16 hours. Then, the mixture was filtrated, concentrated, and purified by silica gel column (petroleum ether:ethyl acetate (V/V)=5:1) to obtain a colorless liquid crude product of 2,3-difluoro-5-methoxyphenol (Compound I-16C) (3.8 g, 100% yield).

Third Step: 2,3-difluoro-5-methoxyphenyl trifluoromethanesulfonate (Compound I-16D)

I-16D

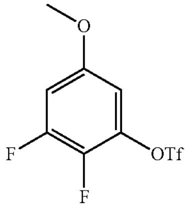

A compound 2,3-difluoro-5-methoxyphenol (500 mg, 3.12 mmol) was added to dichloromethane (20 mL) at room temperature; and trifluoromethanesulfonic anhydride (881 mg, 3.12 mmol) and pyridine (493 mg, 6.25 mmol) were added. The mixture was stirred for 4 hours at room temperature; saturated sodium bicarbonate (20 mL) was added and then the mixture was separated and the organic phases were dried over anhydrous sodium sulfate, filtered and concentrated to obtain a colorless liquid crude product of 2,3-difluoro-5-methoxyphenyl trifluoromethanesulfonate (Compound I-16D) (600 mg, yield 66%).

Fourth Step: 1,2-difluoro-5-methoxy-3-vinylbenzene (Compound I-16E)

I-16E

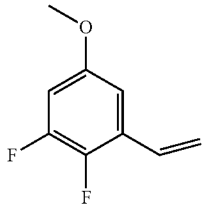

A compound 2,3-difluoro-5-methoxyphenyl trifluoromethanesulfonate (600 mg, 2.05 mmol) was added to 1, 4-dioxane (50 mL) at room temperature; potassium vinyltrifluoroborate (1.25 g, 9.37 mmol); potassium carbonate (1.30 g, 9.37 mmol) and dichloro [1, 1'-bis(diphenylphosphino) ferrocene] palladium (254 mg, 0.31 mmol) were added; and the mixture was heated to 90° C. under nitrogen protection and stirred for 16 hours. Then, the mixture was cooled to room temperature, diluted with water (200 mL), extracted with dichloromethane (50 mL×3) and separated. The organic phases were combined, dried over anhydrous sodium sulfate, filtered and concentrated, and the residue was separated and purified by a silica gel column (petroleum ether:ethyl acetate (V/V)=100:1) to obtain a light yellow liquid of 1,2-difluoro-5-methoxy-3-vinylbenzene (Compound I-16E) (200 mg, yield 57%).

Fifth Step: 1-ethyl-2,3-difluoro-5-methoxybenzene (Compound I-16F)

I-16F

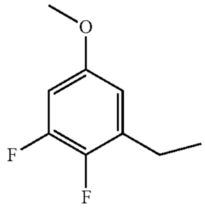

A compound 1,2-difluoro-5-methoxy-3-vinylbenzene (130 mg, 0.82 mmol) was added to methanol (15 mL) at room temperature; 10% palladium on carbon (20 mg) was added; and hydrogen was introduced under stirring at room temperature for 16 hours. The mixture was filtered and concentrated to obtain 1-ethyl-2,3-difluoro-5-methoxybenzene (Compound I-16F) (100 mg, 76% yield) a light yellow liquid.

Sixth Step: 3-ethyl-4,5-difluorophenol (Compound I-16G)

I-16G

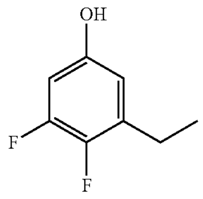

A compound 1-ethyl-2,3-difluoro-5-methoxybenzene (100 mg, 0.58 mmol) was added to dichloromethane (10 mL) at room temperature; boron tribromide (726 mg, 2.90 mmol) was added at 0° C. under stirring for 3 h; and the mixture was diluted by addition of water (20 mL), extracted with dichloromethane (30 mL×3) and separated. The organic phases were combined and dried over anhydrous sodium sulfate, filtered and concentrated to obtain a light yellow liquid crude product of 3-ethyl-4,5-difluorophenol (Compound I-16G) (60 mg, yield 66%).

Seventh Step: methyl (S)-4-(1-(3-(difluoromethyl)-5-(3-ethyl-4,5-difluorophenoxy)-1-methyl-1H-pyrazole-4-carboxamido)ethyl)benzoate (Compound I-16H)

I-16H

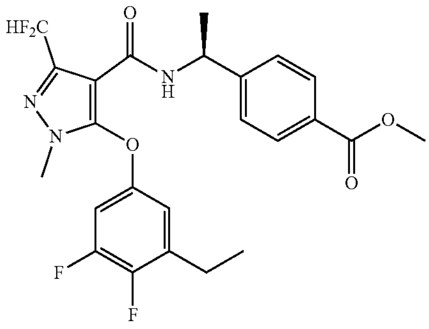

A compound methyl (S)-4-(1-(5-chloro-3-(difluoromethyl)-1-methyl-1H-pyrazole-4-carboxamido) ethyl) benzoate (600 mg, 1.61 mmol) was added to N, N-dimethylformamide (15 mL) at room temperature; and 3-ethyl-4, 5-difluorophenol (450 mg, 3.0 mmol) and potassium hydroxide (210 mg, 3.9 mmol) were added. The mixture was heated to 120° C. in the microwave and stirred for 2 hours. Then, the mixture was cooled to room temperature, diluted with water (50 mL), the pH was adjusted to 4 with TN hydrochloric acid. The mixture was extracted with ethyl acetate (60 mL×3) and separated. The organic phases were combined, dried over anhydrous sodium sulfate, filtered, concentrated and the residue purified by silica gel column separation (petroleum ether:ethyl acetate (V/V)=4:1) to obtain a light yellow solid of methyl (S)-4-(1-(3-(difluoromethyl)-5-(3-ethyl-4,5-difluorophenoxy)-1-methyl-1H-pyrazole-4-carboxamido)ethyl)benzoate (Compound I-16H) (350 mg, yield 44%).

LC-MS, M/Z (ESI): 494.4 $[M+H]^+$.

Eighth Step: (S)-4-(1-(3-(difluoromethyl)-5-(3-ethyl-4,5-difluorophenoxy)-1-methyl-1H-pyrazole-4-carboxamido)ethyl)benzoic Acid (Compound I-16)

I-16

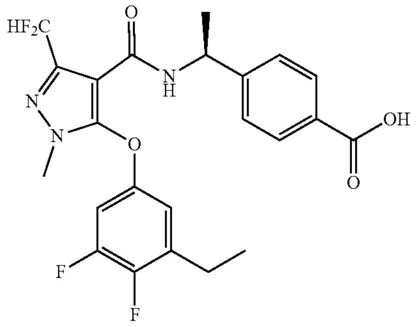

A starting material methyl (S)-4-(1-(3-(difluoromethyl)-5-(3-ethyl-4,5-difluorophenoxy)-1-methyl-1H-pyrazole-4-carboxamido)ethyl)benzoate (325 mg, 0.66 mmol) was added to tetrahydrofuran (15 mL), methanol (3 mL) and water (3 mL) at room temperature; and lithium hydroxide (32 mg, 1.32 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(3-(difluoromethyl)-5-(3-ethyl-4,5-difluorophenoxy)-1-methyl-1H-pyrazole-4-carboxamido) ethyl)benzoic acid (170 mg, 54% yield).

$^1H$ NMR (400 m Hz, DMSO-d6) δ 12.8 (s, 1H), 8.15 (d, 1H), 7.76 (d, 2H), 7.24 (t, 1H), 7.18 (d, 2H), 7.01 (t, 1H), 6.80 (d, 1H), 4.94 (t, 1H), 3.74 (s, 3H), 2.62 (q, 2H), 1.27 (d, 3H), 1.11 (t, 3H).

LC-MS, M/Z (ESI): 480.4 $[M+H]^+$

Example 17: Preparation of Compound I-17

(S)-4-(1-(3-(difluoromethyl)-5-(3-ethyl-4-methylphenoxy)-1-methyl-1H-pyrazole-4-carboxamido) ethyl)benzoic Acid (Compound I-17)

I-17

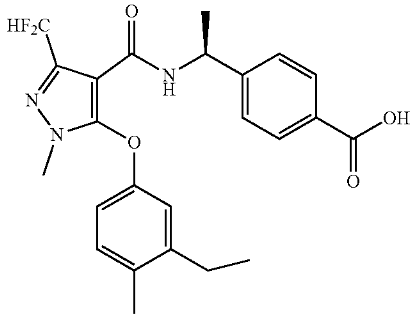

The synthesis scheme for Compound I-17 is shown below:

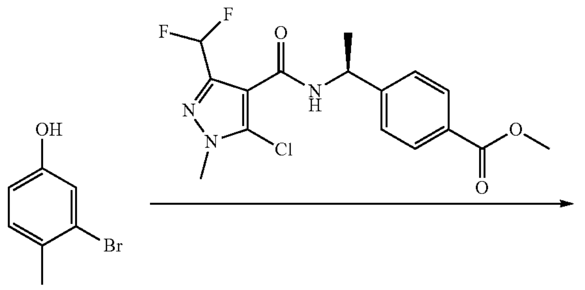

I-17A

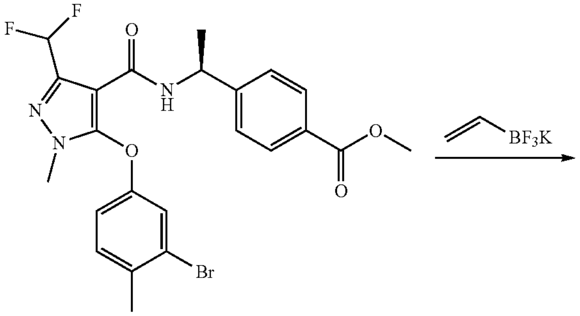

I-17B

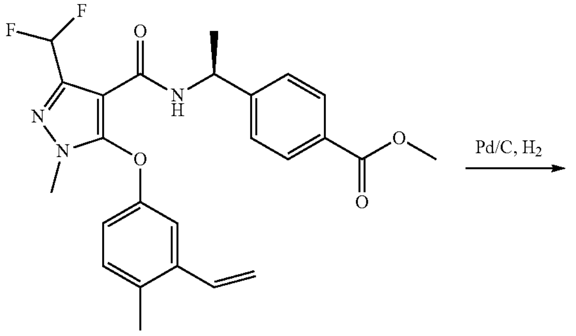

I-17C

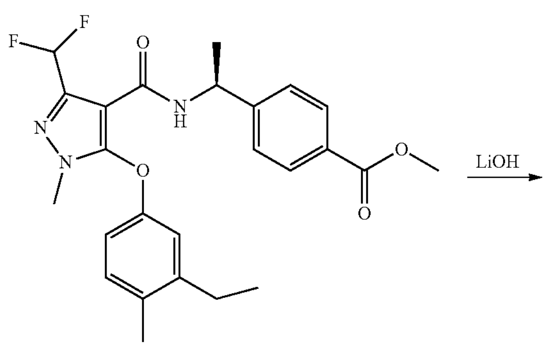

I-17D

-continued

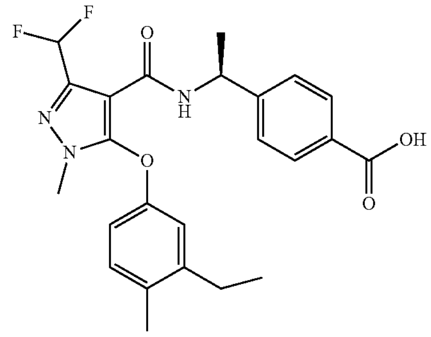

I-17

First Step: methyl (S)-4-(1-(5-(3-bromo-4-methylphenoxy)-3-(difluoromethyl)-1-methyl-1H-pyrazole-4-carboxamido)ethyl)benzoate (Compound I-17B)

I-17B

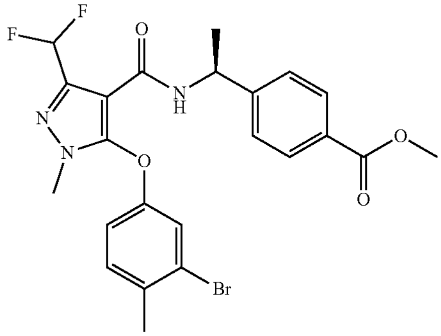

The compound methyl (S)-4-(1-(5-chloro-3-(difluoromethyl)-1-methyl-1H-pyrazole-4-carboxamido)ethyl)benzoat (Intermediate A) (500 mg, 1.35 mmol) was added to N, N-dimethylformamide (10 mL) at room temperature; 3-bromo-4-methylphenol (380 mg, 2.02 mmol), cuprous iodide (100 mg, 0.52 mmol), 1, 10-phenanthroline (180 mg, 1.0 mmol) and cesium carbonate (1.30 g, 4.05 mmol) were added. The mixture was heated to 120° C. in the microwave under nitrogen protection and stirred for 2 hours. Then, the mixture was cooled to room temperature, diluted with water (50 mL), and the pH was adjusted to 4 with 1N hydrochloric acid. The mixture was extracted with ethyl acetate (50 mL×3) and separated. The organic phases were combined, dried over anhydrous sodium sulfate, filtered and concentrated, and the residue was purified by silica gel column (petroleum ether:ethyl acetate (V/V)=3:1) to obtain a light yellow solid of methyl (S)-4-(1-(5-(3-bromo-4-methylphenoxy)-3-(difluoromethyl)-1-methyl-1H-pyrazole-4-carboxamido)ethyl)benzoate (Compound I-17B) (270 mg, yield 38%).

LC-MS, M/Z (ESI): 522.3 [M+H]+.

Second Step: methyl (S)-4-(1-(3-(difluoromethyl)-1-methyl-5-(4-methyl-3-vinylphenoxy)-1H-pyrazole-4-carboxamido)ethyl)benzoate (Compound I-17C)

I-17C

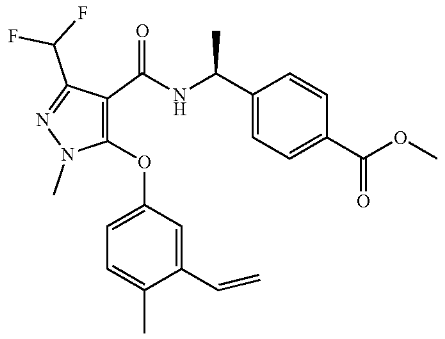

The compound methyl (S)-4-(1-(5-(3-bromo-4-methylphenoxy)-3-(difluoromethyl)-1-methyl-1H-pyrazole-4-carboxamido)ethyl)benzoate (Compound I-17B) (260 mg, 0.50 mmol) was added to 1, 4-dioxane (5 mL) at room temperature; dichloro[1, 1'-bis(diphenylphosphino)ferrocene]palladium (73 mg, 0.10 mmol), potassium vinyltrifluoroborate (100 mg, 0.75 mmol), and potassium carbonate (140 mg, 1.0 mmol) were added; and the mixture was heated to 100° C. under nitrogen protection and stirred for 16 hours. Then, the mixture was cooled to room temperature, diluted with water (50 mL); the pH was adjusted to 4 with 1N hydrochloric acid; and the mixture was extracted with ethyl acetate (50 mL×3) and separated. The organic phases were combined, dried over anhydrous sodium sulfate, filtered and concentrated. The residue was separated and purified on a thin-layer silica gel plate (petroleum ether:ethyl acetate (V/V)=4:1) to obtain a light yellow solid of methyl (S)-4-(1-(3-(difluoromethyl)-1-methyl-5-(4-methyl-3-vinylphenoxy)-1H-pyrazole-4-carboxamido)ethyl)benzoate (Compound I-17C) (160 mg, yield 68%).

LC-MS, M/Z (ESI): 470.3 $[M+H]^+$.

Third Step: methyl (S)-4-(1-(3-(difluoromethyl)-5-(3-ethyl-4-methylphenoxy)-1-methyl-1H-pyrazole-4-carboxamido)ethyl)benzoate (Compound I-17D)

I-17D

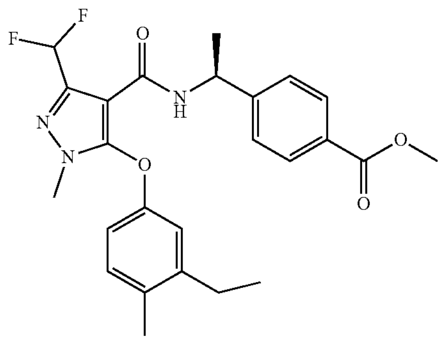

The compound methyl (S)-4-(1-(3-(difluoromethyl)-1-methyl-5-(4-methyl-3-vinylphenoxy)-1H-pyrazole-4-carboxamido)ethyl)benzoate (160 mg, 0.34 mmol) was added to methanol (10 mL) at room temperature and 10% palladium on carbon (20 mg) was added; and hydrogen was introduced under stirring for 16 hours at room temperature; and the mixture was filtered and concentrated to obtain a light yellow solid crude product of methyl (S)-4-(1-(3-(difluoromethyl)-5-(3-ethyl-4-methylphenoxy)-1-methyl-1H-pyrazole-4-carboxamido)ethyl)benzoate (Compound I-17D) (150 mg, yield 93%).

LC-MS, M/Z (ESI): 472.3 $[M+H]^+$

Fourth Step: (S)-4-(1-(3-(difluoromethyl)-5-(3-ethyl-4-methylphenoxy)-1-methyl-1H-pyrazole-4-carboxamido)ethyl)benzoic Acid (Compound I-17)

I-17

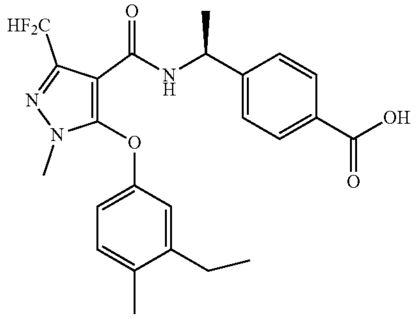

The starting material methyl (S)-4-(1-(3-(difluoromethyl)-5-(3-ethyl-4-methylphenoxy)-1-methyl-1H-pyrazole-4-carboxamido)ethyl)benzoate (Compound I-17D) (150 mg, 0.32 mmol) was added to tetrahydrofuran (5 mL) and water (5 mL) at room temperature, and lithium hydroxide (24 mg, 1.0 mmol) was added. The mixture was stirred at room temperature for 16 hours; the pH was adjusted to 4 by IN hydrochloric acid; and the reaction mixture was concentrated to prepare, by the acidic preparation method A, a white solid of (S)-4-(1-(3-(difluoromethyl)-5-(3-ethyl-4-methylphenoxy)-1-methyl-1H-pyrazole-4-carboxamido)ethyl)benzoic acid (85 mg, 58% yield).

$^1H$ NMR (400 m Hz, DMSO-d6) δ 12.7 (s, 1H), 7.90 (d, 1H), 7.69 (d, 2H), 7.25 (t, 1H), 7.13 (d, 1H), 7.11 (d, 2H), 6.85 (d, 1H), 6.64 (dd, 1H), 4.93 (t, 1H), 3.71 (s, 3H), 2.55 (q, 2H), 2.23 (s, 3H), 1.24 (d, 3H), 1.07 (t, 3H).

LC-MS, M/Z (ESI): 458.3 $[M+H]^+$

Example 18: Preparation of Compound I-18

(S)-4-(1-(3-(difluoromethyl)-5-(4-ethylphenoxy)-1-methyl-1H-pyrazole-4-carboxamido)ethyl) benzoic Acid (Compound I-18)

I-18

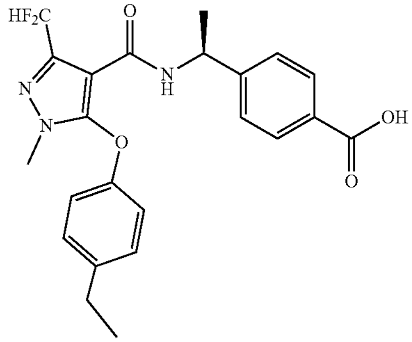

The synthesis scheme for Compound I-18 is shown below:

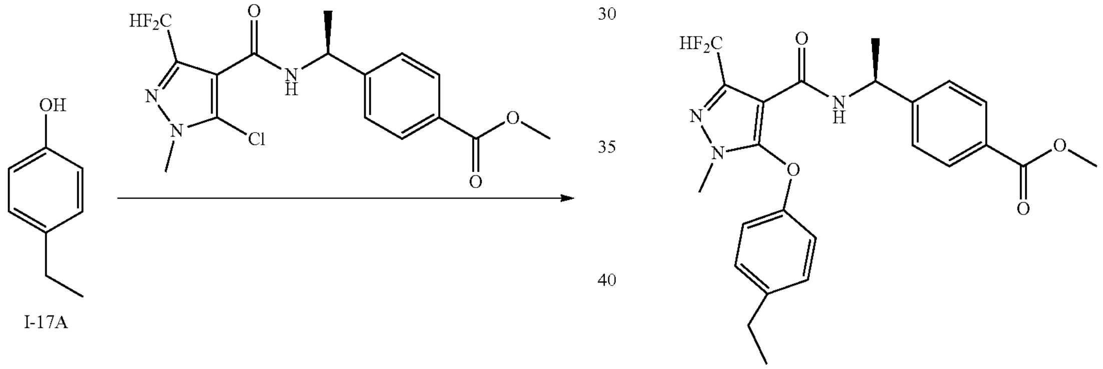

I-17A

I-18B

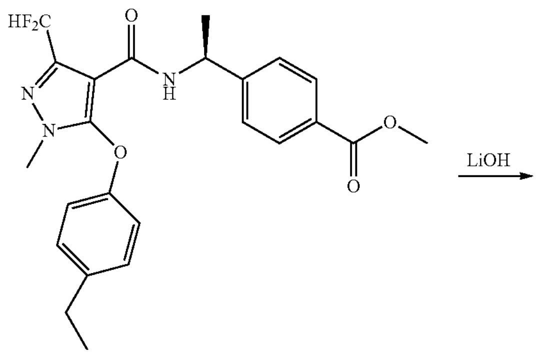

I-18B

-continued

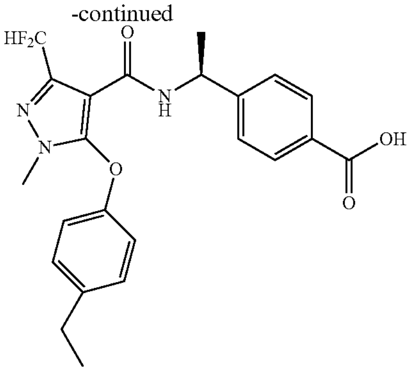

I-18

First Step: methyl (S)-4-(1-(3-(difluoromethyl)-5-(4-ethylphenoxy)-1-methyl-1H-pyrazole-4-carboxamido)ethyl)benzoate (Compound I-18B)

The compound methyl (S)-4-(1-(5-chloro-3-(difluoromethyl)-1-methyl-1H-pyrazole-4-carboxamido)ethyl)benzoat (Intermediate A) (371 mg, 1.0 mmol) was added to dimethyl sulfoxide (3 mL) at room temperature; 4-ethylphenol (122 mg, 1.0 mmol) and potassium hydroxide (114 mg, 2.0 mmol) were added; and the mixture was heated to 120° C. in the microwave and stirred for 20 min. Then, the mixture was cooled to room temperature and diluted with water (20 mL); the pH was adjusted to 4 with TN hydrochloric acid; and the mixture was extracted with ethyl acetate (20 mL×3) and separated. The organic phases were combined and dried over anhydrous sodium sulfate, filtered and concentrated to obtain a white solid crude product of methyl (S)-4-(1-(3-(difluoromethyl)-5-(4-ethylphenoxy)-1-methyl-1H-pyrazole-4-carboxamido)ethyl)benzoate (Compound I-18B) (175 mg, yield 38%).

LC-MS, M/Z (ESI): 458.3 $[M+H]^+$

Second Step: (S)-4-(1-(3-(difluoromethyl)-5-(4-ethylphenoxy)-1-methyl-1H-pyrazole-4-carboxamido)ethyl)benzoic Acid (Compound I-18)

I-18

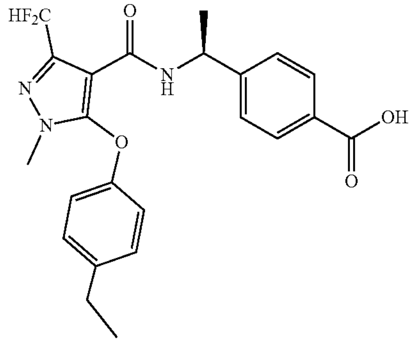

The starting material methyl (S)-4-(1-(3-(difluoromethyl)-5-(4-ethylphenoxy)-1-methyl-1H-pyrazole-4-carboxamido)ethyl)benzoate (Compound I-18B) (175 mg, 0.38 mmol) was added to tetrahydrofuran (2 mL), methanol (2 mL) and water (1 mL) at room temperature; and lithium hydroxide (3 mg, 0.16 mmol) was added. The mixture was stirred for 12 hours at room temperature; the pH was adjusted to 4 with 1N hydrochloric acid; and the reaction mixture was concentrated to prepare, by the acidic preparation method A, a white solid of (S)-4-(1-(3-(difluoromethyl)-5-(4-ethylphenoxy)-1-methyl-1H-pyrazole-4-carboxamido)ethyl)benzoic acid (Compound I-18) (40 mg, 24% yield).

$^{1}$H NMR (400 mHz, DMSO-d6) δ 12.7 (s, 1H), 7.95 (d, 1H), 7.71 (d, 2H), 7.24 (d, 2H), 7.21 (t, 1H), 7.11 (d, 2H), 6.92 (d, 2H), 4.91 (t, 1H), 3.72 (s, 3H), 2.62 (q, 2H), 1.24 (d, 3H), 1.19 (t, 3H).

LC-MS, M/Z (ESI): 444.3 [M+H]$^+$

Example 19: Preparation of Compound I-19

(S)-4-(1-(5-(4-(1,1-difluoroethyl)phenoxy)-3-(difluoromethyl)-1-methyl-1H-pyrazole-4-carboxamido)ethyl)benzoic Acid (Compound I-19)

I-19

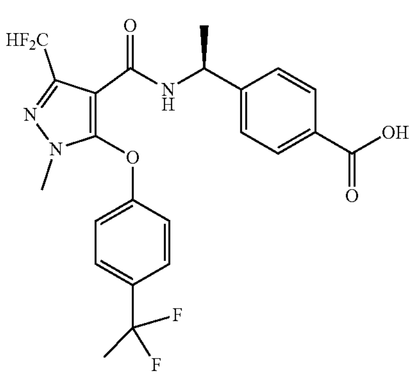

The synthesis scheme for Compound I-19 is shown below:

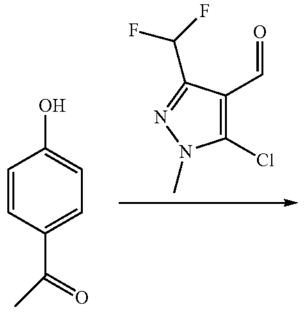

I-19A

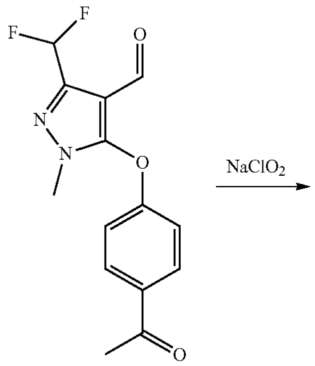

I-19B

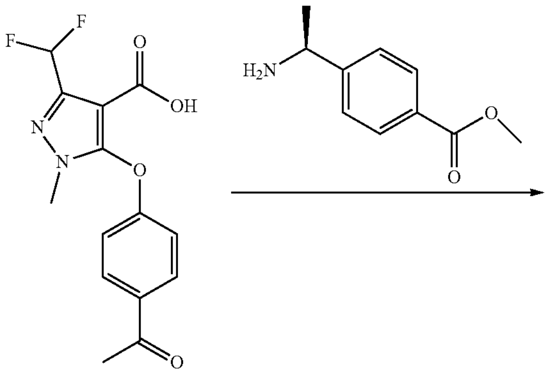

I-19C

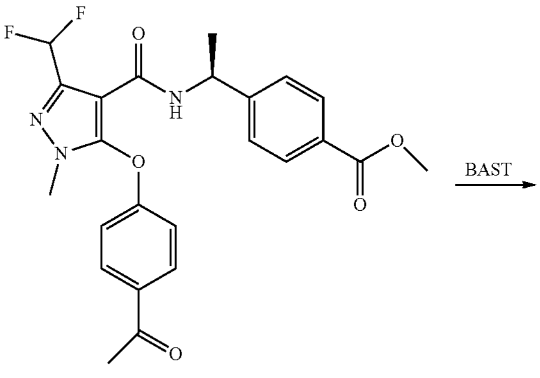

I-19D

-continued

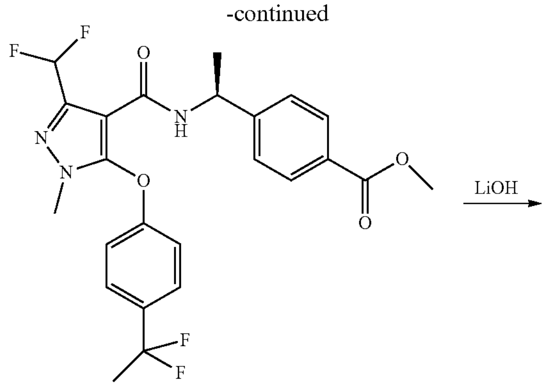

I-19E

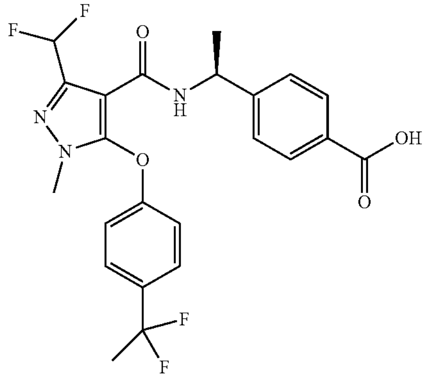

I-19

First Step: 5-(4-acetylphenoxy)-3-(difluoromethyl)-1-methyl-1H-pyrazole-4-carbaldehyde (Compound I-19B)

I-19B

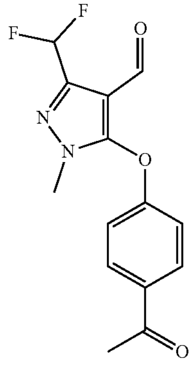

A compound 5-chloro-3-(difluoromethyl)-1-methyl-1H-pyrazole-4-carbaldehyde (1.0 g, 5.15 mmol) was added to N, N-dimethylformamide (15 mL) at room temperature; 4-acetylphenol (1.05 g, 7.73 mmol), cuprous iodide (918 mg, 5.15 mmol), 1, 10-phenanthroline (1.05 g, 7.73 mmol) and potassium carbonate (1.42 g, 10.3 mmol) were added; and the mixture was heated to 100° C. under nitrogen protection and stirred for 2 hours. Then, the mixture was cooled to room temperature, diluted with water (50 mL), extracted with ethyl acetate (50 mL×3) and separated. The organic phases were combined, dried over anhydrous sodium sulfate, filtered and concentrated, and the residue was purified by silica gel column (petroleum ether:ethyl acetate (V/V)=3:1) to obtain a light yellow solid crude product of 5-(4-acetylphenoxy)-3-(difluoromethyl)-1-methyl-1H-pyrazole-4-carbaldehyde (Compound I-19B) (270 mg, yield 18%).

LC-MS, M/Z (ESI): 295.1 $[M+H]^+$

Second Step: 5-(4-acetylphenoxy)-3-(difluoromethyl)-1-methyl-1H-pyrazole-4-carboxylic Acid (Compound I-19C)

I-19C

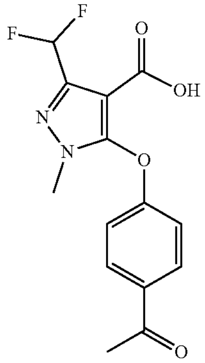

The compound 5-(4-acetylphenoxy)-3-(difluoromethyl)-1-methyl-1H-pyrazole-4-carbaldehyde (Compound I-19B) (400 mg, 1.36 mmol) was added to tert-butanol (9 mL) and water (3 mL) at room temperature; and 2-methyl-2-butene (476 mg, 6.80 mmol), sodium chlorite (369 mg, 4.08 mmol) and sodium dihydrogen phosphate (408 mg, 3.40 mmol) were added. The mixture was stirred for 14 hours at room temperature; the mixture was diluted by addition of water (15 mL), the pH was adjusted to 4 with 1N hydrochloric acid, and the mixture was extracted with ethyl acetate (30 mL×3) and separated. The organic phases were combined and dried over anhydrous sodium sulfate, filtered and concentrated to obtain crude 5-(4-acetylphenoxy)-3-(difluoromethyl)-1-methyl-1H-pyrazole-4-carboxylic acid (compound I-19C) (350 mg, yield 100%) alight yellow solid.

LC-MS, M/Z (ESI): 311.1 [M+H]+.

Third Step: methyl (S)-4-(1-(5-(4-acetylphenoxy)-3-(difluoromethyl)-1-methyl-1H-pyrazole-4-carboxamido)ethyl)benzoate (Compound I-19D)

I-19D

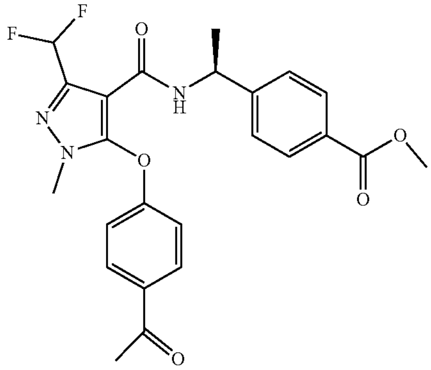

A compound 3-(difluoromethyl)-5-(3-isopropylphenoxy)-1-methyl-1H-pyrazole-4-carboxylic acid (350 mg, 1.13 mmol) was added to N, N-dimethylformamide (7 mL); methyl (S)-4-(1-aminoethyl) benzoate (242 mg, 1.36 mmol), O-(7-azabenzotriazol-1-yl)-N, N, N, N-tetramethyluronium hexafluorophosphate (650 mg, 1.71 mmol) and N, N-diisopropylethylamine (437 mg, 3.67 mmol) were added; and the mixture was stirred at room temperature for 16 hours, diluted with water (40 mL), extracted with ethyl acetate (40 mL×3) and separated. The organic phases were combined, dried over anhydrous sodium sulfate, filtered, concentrated, and purified by silica gel column (petroleum ether:ethyl acetate (V/V)=4:1) to obtain a light yellow liquid of methyl (S)-4-(1-(5-(4-acetylphenoxy)-3-(difluoromethyl)-1-methyl-1H-pyrazole-4-carboxamido)ethyl)benzoate (Compound I-19D) (500 mg, yield 94%).

LC-MS, M/Z (ESI): 472.2 [M+H]$^+$

Fourth Step: methyl (S)-4-(1-(5-(4-(1,1-difluoroethyl)phenoxy)-3-(difluoromethyl)-1-methyl-1H-pyrazole-4-carboxamido)ethyl)benzoate (Compound I-19E)

I-19E

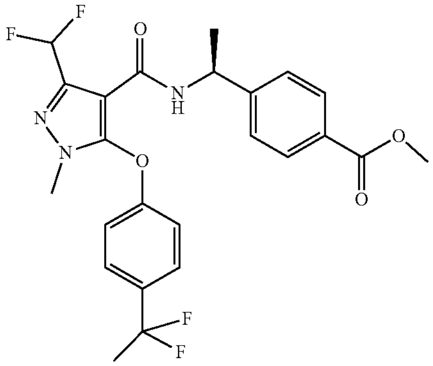

The compound methyl (S)-4-(1-(5-(4-acetylphenoxy)-3-(difluoromethyl)-1-methyl-1H-pyrazole-4-carboxamido) ethyl)benzoate (Compound I-19D) (50 mg, 0.53 mmol) was added to bis(2-methoxyethyl)aminosulfur trifluoride (5 mL) at room temperature. The mixture was heated to 50° C. and stirred for 48 h; then the mixture was cooled to room temperature, and added dropwise to a saturated solution of sodium bicarbonate (50 mL) and extracted with ethyl acetate (40 mL×3) and separated. The organic phases were combined and dried over anhydrous sodium sulfate, filtered and concentrated to obtain a light yellow solid crude product of methyl (S)-4-(1-(5-(4-(1,1-difluoroethyl)phenoxy)-3-(difluoromethyl)-1-methyl-1H-pyrazole-4-carboxamido)ethyl) benzoate (Compound I-19E) (250 mg, yield 96%).

LC-MS, M/Z (ESI): 494.5 [M+H]$^+$.

Fifth Step: (S)-4-(1-(5-(4-(1,1-difluoroethyl)phenoxy)-3-(difluoromethyl)-1-methyl-1H-pyrazole-4-carboxamido)ethyl)benzoic Acid (Compound I-19)

I-19

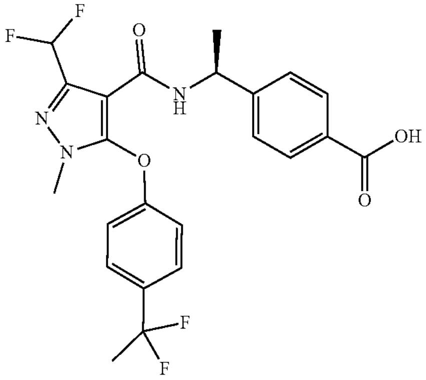

A starting material methyl (S)-4-(1-(5-(4-(1,1-difluoroethyl)phenoxy)-3-(difluoromethyl)-1-methyl-1H-pyrazole-4-carboxamido)ethyl)benzoate (Compound I-19E) (250 mg, 0.51 mmol) was added to tetrahydrofuran (4 mL); and methanol (2 mL) and water (2 mL) at room temperature and lithium hydroxide (61 mg, 2.55 mmol) was added. The mixture was stirred at room temperature for 16 hours; the pH was adjusted to 4 with TN hydrochloric acid; and the reaction mixture was concentrated to prepare, by the acidic preparation method A, a white solid of (S)-4-(1-(5-(4-(1,1-difluoroethyl)phenoxy)-3-(difluoromethyl)-1-methyl-1H-pyrazole-4-carboxamido)ethyl)benzoic acid (Compound I-19) (19 mg, 8% yield).

$^1$H NMR (400 m Hz, DMSO-d6) δ 12.8 (s, 1H), 8.11 (d, 1H), 7.71 (d, 2H), 7.60 (d, 2H), 7.25 (t, 1H), 7.12 (d, 2H), 7.08 (d, 2H), 4.90 (t, 1H), 3.73 (s, 3H), 2.01 (t, 3H), 1.23 (d, 3H).

LC-MS, M/Z (ESI): 480.5 [M+H]$^+$

Example 20: Preparation of Compound I-20

(S)-4-(1-(3-(difluoromethyl)-1-methyl-5-(3,4,5-trifluorophenoxy)-1H-pyrazole-4-carboxamido)ethyl) benzoic Acid (Compound I-20)

I-20

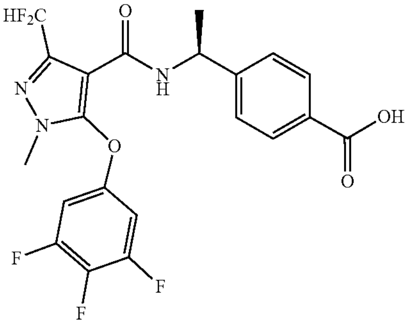

The synthesis scheme for Compound I-20 is shown below:

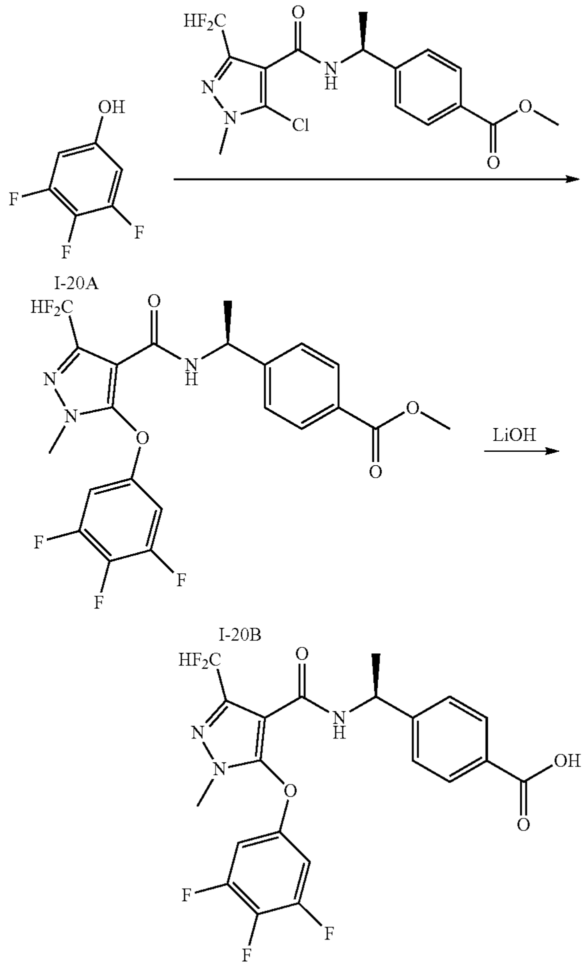

I-20A

I-20B

I-20

First Step: methyl (S)-4-(1-(3-(difluoromethyl)-1-methyl-5-(3,4,5-trifluorophenoxy)-1H-pyrazole-4-carboxamido)ethyl)benzoate (Compound I-20B)

I-20B

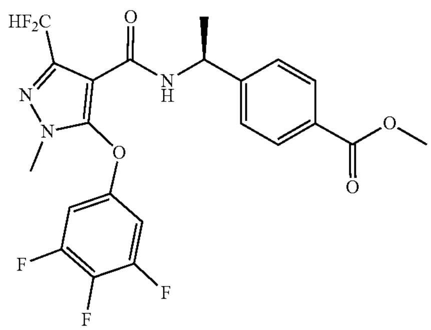

The compound methyl (S)-4-(1-(5-chloro-3-(difluoromethyl)-1-methyl-1H-pyrazole-4-carboxamido)ethyl)benzoat (Intermediate A) (370 mg, 1.0 mmol) was added to N, N dimethylformamide (10 mL) at room temperature; 3, 4, 5-trifluorophenol (222 mg, 1.5 mmol) and potassium hydroxide (168 mg, 3.0 mmol) were added; and the mixture was heated to 120° C. and stirred for 6 hours. The mixture was cooled to room temperature and diluted with water (50 mL); the pH was adjusted to 4 with 1N hydrochloric acid; and the mixture was extracted with ethyl acetate (60 mL×3) and separated. The organic phases were combined and dried over anhydrous sodium sulfate, filtered and concentrated to obtain a white solid crude product of methyl (S)-4-(1-(3-(difluoromethyl)-1-methyl-5-(3,4,5-trifluorophenoxy)-1H-pyrazole-4-carboxamido)ethyl)benzoate (Compound I-20B) (80 mg, yield 17%).

LC-MS, M/Z (ESI): 484.1 [M+H]+.

Second Step: (S)-4-(1-(3-(difluoromethyl)-1-methyl-5-(3,4,5-trifluorophenoxy)-1H-pyrazole-4-carboxamido)ethyl)benzoic Acid (Compound I-20)

I-20

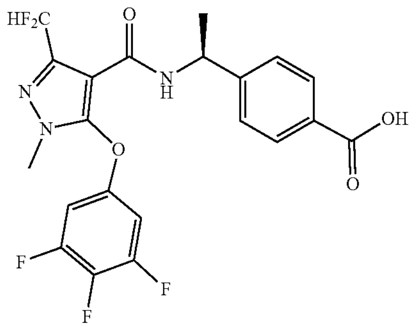

The starting material methyl (S)-4-(1-(3-(difluoromethyl)-1-methyl-5-(3,4,5-trifluorophenoxy)-1H-pyrazole-4-carboxamido)ethyl)benzoate (80 mg, 0.16 mmol) was added to tetrahydrofuran (2 mL) and water (1 mL) at room temperature; lithium hydroxide (17 mg, 0.40 mmol) was added; and the mixture was heated to 50° C. and stirred for 2 hours. Then, the mixture was cooled to room temperature; the pH was adjusted to 4 with 1N hydrochloric acid; and the reaction mixture was concentrated to prepare, by the acidic preparation method A, a white solid of (S)-4-(1-(3-(difluoromethyl)-1-methyl-5-(3,4,5-trifluorophenoxy)-1H-pyrazole-4-carboxamido)ethyl)benzoic acid (Compound I-20) (7 mg, 9.0% yield).

$^1H$ NMR (400 mHz, DMSO-d6) δ 12.8 (s, 1H), 8.24 (d, 1H), 7.78 (d, 2H), 7.24 (d, 2H), 7.22 (t, 1H), 7.09 (d, 1H), 7.02 (d, 1H), 4.96 (t, 1H), 3.73 (s, 3H), 1.30 (d, 3H).

LC-MS, M/Z (ESI): 470.1 $[M+H]^+$

Example 21: Preparation of Compound I-21

(S)-4-(1-(5-(3-acetyl-4-fluorophenoxy)-3-(difluoromethyl)-1-methyl-1H-pyrazole-4-carboxamido)ethyl)benzoic Acid (Compound I-21)

I-21

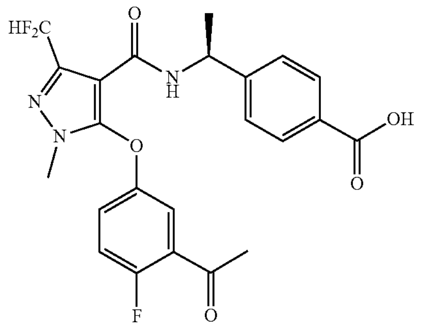

The synthesis scheme for Compound I-21 is shown below:

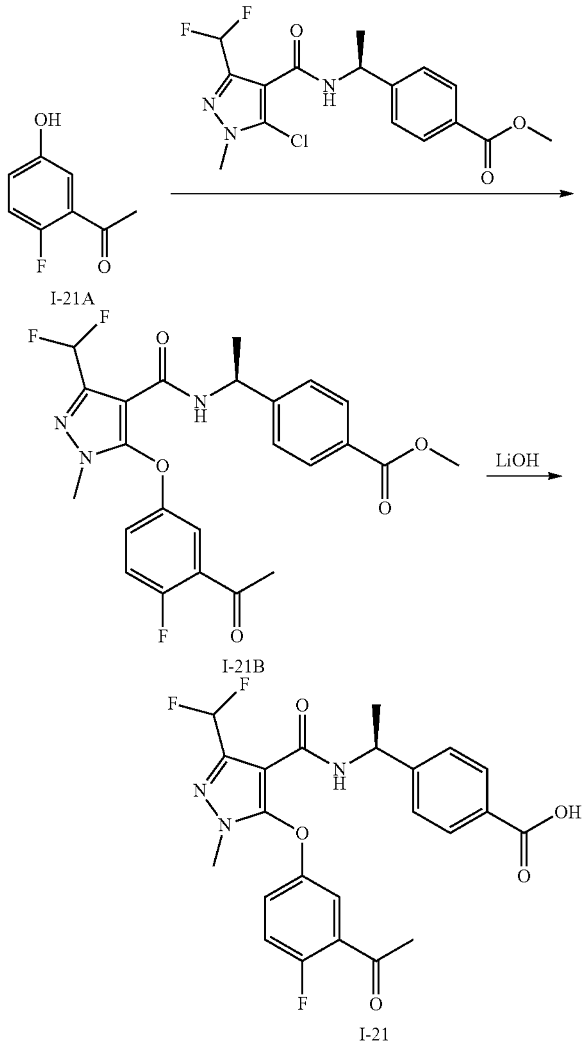

First Step: methyl (S)-4-(1-(5-(3-acetyl-4-fluorophenoxy)-3-(difluoromethyl)-1-methyl-1H-pyrazole-4-carboxamido)ethyl)benzoate (Compound I-21B)

I-21B

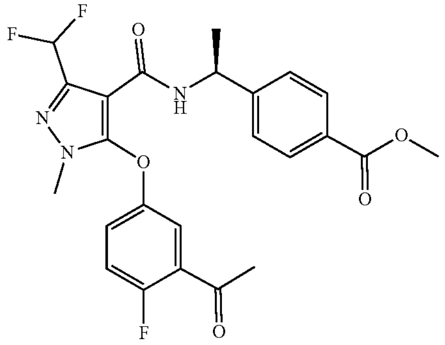

A compound 1-(2-fluoro-5-hydroxyphenyl) ethan-1-one (1.58 g, 10.8 mmol) was added to N, N-dimethylformamide (30 mL) at room temperature; and methyl (S)-4-(1-(5-chloro-3-(difluoromethyl)-1-methyl-1H-pyrazole-4-carboxamido)ethyl)benzoat (Intermediate A) (2.0 g, 5.4 mmol) and potassium hydroxide (450 mg, 8.1 mmol) were added. The mixture was heated to 120° C. in the microwave under nitrogen protection and stirred for 2 hours; the mixture was cooled to room temperature and added with water (30 mL); the pH was adjusted to 4 with 1N hydrochloric acid; and the mixture was extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=10:1) to obtain a white solid of methyl (S)-4-(1-(5-(3-acetyl-4-fluorophenoxy)-3-(difluoromethyl)-1-methyl-1H-pyrazole-4-carboxamido)ethyl)benzoate (Compound I-21B) (346 mg, yield 13%).

LC-MS, M/Z (ESI): 490.2 [M+H]+

Second Step: (S)-4-(1-(5-(3-acetyl-4-fluorophenoxy)-3-(difluoromethyl)-1-methyl-1H-pyrazole-4-carboxamido)ethyl)benzoic Acid (Compound I-21)

I-21

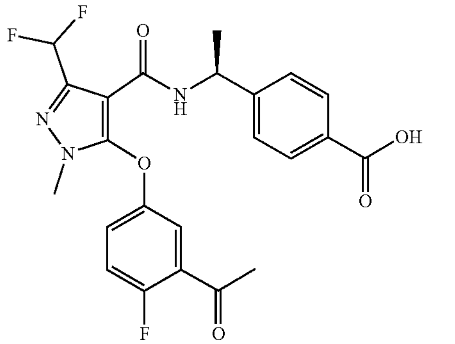

The starting material methyl (S)-4-(1-(5-(3-acetyl-4-fluorophenoxy)-3-(difluoromethyl)-1-methyl-1H-pyrazole-4-carboxamido)ethyl)benzoate (compound I-21B) (65 mg, 0.13 mmol) was added to tetrahydrofuran (5 mL), methanol (5 mL) and water (1 mL) at room temperature; and lithium hydroxide (20 mg, 0.47 mmol) was added. The mixture was stirred at room temperature for 5 hours; the pH was adjusted to 4 with TN hydrochloric acid; and the reaction mixture was concentrated to prepare, by the acidic preparation method A, a white solid of (S)-4-(1-(5-(3-acetyl-4-fluorophenoxy)-3-(difluoromethyl)-1-methyl-1H-pyrazole-4-carboxamido) ethyl)benzoic acid (Compound I-21) (30 mg, 66% yield).

$^1$H NMR (400 mHz, DMSO-d6) δ 12.8 (s, 1H), 8.18 (d, 1H), 7.72 (d, 2H), 7.38-7.32 (m, 2H), 7.29-7.24 (m, 1H), 7.26 (t, 1H), 7.16 (d, 2H), 4.91 (t, 1H), 3.73 (s, 3H), 2.54 (d, 3H), 1.24 (d, 3H).

LC-MS, M/Z (ESI): 476.1 $[M+H]^+$

Example 22: Preparation of Compound I-22

4-((1S)-1-(3-(difluoromethyl)-5-(3-(1-hydroxyethyl) phenoxy)-1-methyl-1H-pyrazole-4-carboxamido) ethyl)benzoic Acid (Compound I-22)

I-22

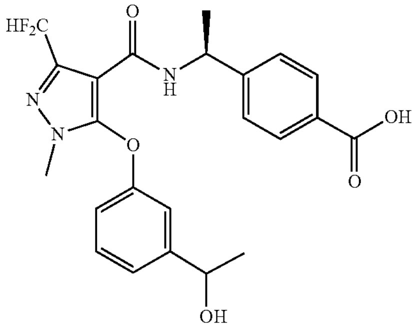

The synthesis scheme for Compound I-22 is shown below:

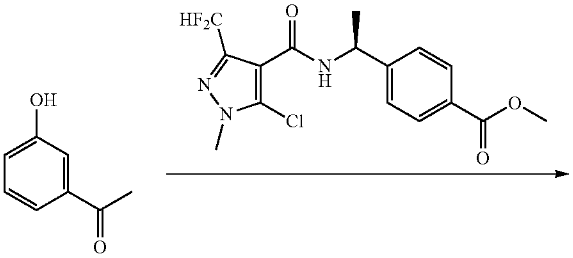

I-22A

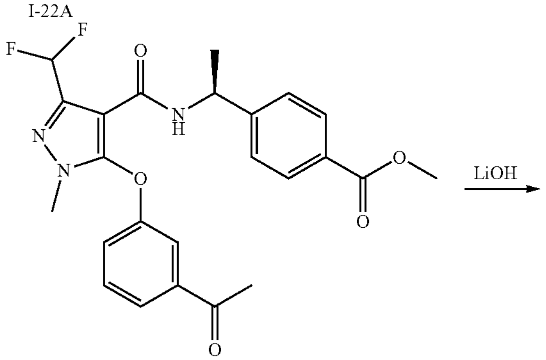

I-22B

-continued

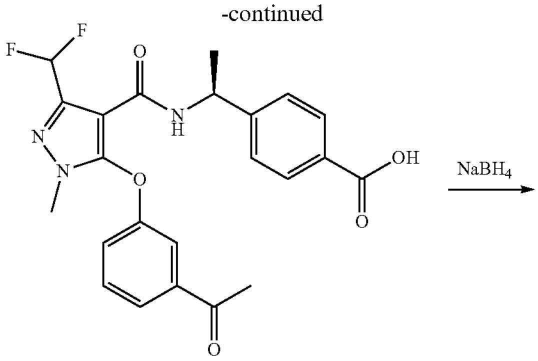

I-22C

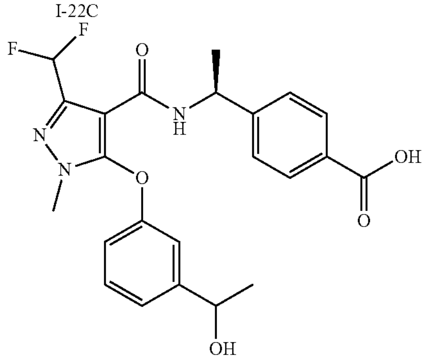

I-22

First Step: methyl (S)-4-(1-(5-(3-acetylphenoxy)-3-(difluoromethyl)-1-methyl-1H-pyrazole-4-carboxamido)ethyl)benzoate (Compound I-22B)

I-22

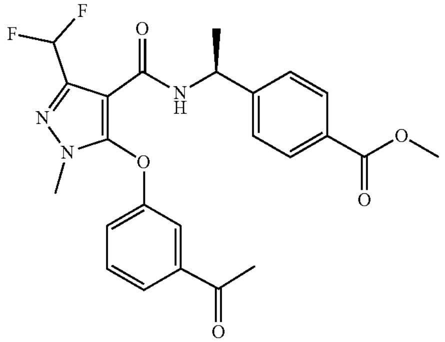

A compound 1-(3-hydroxyphenyl) ethan-1-one (275 mg, 2.02 mmol) was added to N, N-dimethylformamide (6 mL) at room temperature; and methyl (S)-4-(1-(5-chloro-3-(difluoromethyl)-1-methyl-1H-pyrazole-4-carboxamido)ethyl) benzoat (Intermediate A) (500 mg, 1.35 mmol), copper iodide (100 mg, 0.52 mmol), 1, 10-phenanthroline (180 mg, 1.0 mmol) and cesium carbonate (1.30 g, 4.05 mmol) were added. The mixture was heated to 120° C. in the microwave under nitrogen protection and stirred for 2 hours. Then the mixture was cooled to room temperature and added with water (30 mL); the pH was adjusted to 4 with 1N hydrochloric acid; and the mixture was extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=3:1) to obtain a white solid of methyl (S)-4-(1-(5-(3-acetylphenoxy)-3-(difluoromethyl)-1-methyl-1H-pyrazole-4-carboxamido)ethyl)benzoate (Compound I-22B) (300 mg, yield 47%).

LC-MS, M/Z (ESI): 472.3 $[M+H]^+$

Second Step: (S)-4-(1-(5-(3-acetylphenoxy)-3-(difluoromethyl)-1-methyl-1H-pyrazole-4-carboxamido)ethyl)benzoic Acid (Compound I-22C)

I-22C

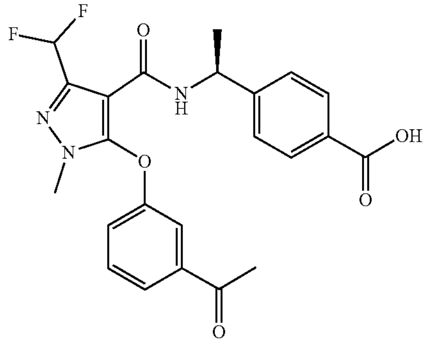

The starting material methyl (S)-4-(1-(5-(3-acetylphenoxy)-3-(difluoromethyl)-1-methyl-1H-pyrazole-4-carboxamido)ethyl)benzoate (Compound I-22B) (290 mg, 0.62 mmol) was added to tetrahydrofuran (5 mL) and water (5 mL) at room temperature; and lithium hydroxide (45 mg, 1.87 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(5-(3-acetylphenoxy)-3-(difluoromethyl)-1-methyl-1H-pyrazole-4-carboxamido)ethyl)benzoic acid (Compound I-22C) (180 mg, 64% yield).

LC-MS, M/Z (ESI): 458.3 $[M+H]^+$

Third Step: 4-((1S)-1-(3-(difluoromethyl)-5-(3-(1-hydroxyethyl)phenoxy)-1-methyl-1H-pyrazole-4-carboxamido)ethyl)benzoic Acid (Compound I-22)

I-22

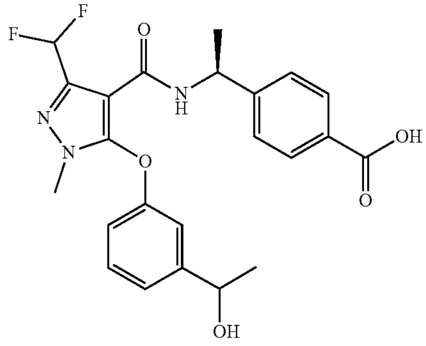

The compound (S)-4-(1-(5-(3-acetylphenoxy)-3-(difluoromethyl)-1-methyl-1H-pyrazole-4-carboxamido)ethyl)benzoic acid (Compound I-22C) (170 mg, 0.37 mmol) was added to methanol (15 mL) and water (15 mL) at room temperature; and sodium borohydride (15 mg, 0.39 mmol) was added. The mixture was stirred for 2 hours at room temperature; and the pH was adjusted to 4 with 1N hydrochloric acid and concentrated to obtain 4-((1S)-1-(3-(difluoromethyl)-5-(3-(1-hydroxyethyl)phenoxy)-1-methyl-1H-pyrazole-4 carboxamido)ethyl)benzoic acid (Compound I-22) (168 mg, 98% yield) a white solid by the acidic preparation method A.

LC-MS, M/Z (ESI): 460.3 $[M+H]^+$ $^1H$ NMR (400 mHz, DMSO-d6) δ 12.7 (s, 1H), 7.92 (d, 1H), 7.73 (d, 2H), 7.36 (t, 1H), 7.26 (t, 1H), 7.18 (d, 1H), 7.13 (d, 2H), 7.11 (t, 1H), 6.83 (dd, 1H), 5.26 (d, 1H), 4.92 (t, 1H), 4.71 (s, 1H), 3.72 (s, 3H), 1.28 (dd, 3H), 1.22 (d, 3H).

LC-MS, M/Z (ESI): 478.1 $[M+H]^+$

Example 23: Preparation of Compound I-23

4-((1S)-1-(3-(difluoromethyl)-5-(4-fluoro-3-(1-hydroxyethyl)phenoxy)-1-methyl-1H-pyrazole-4-carboxamido)ethyl)benzoic Acid (Compound I-23)

I-23

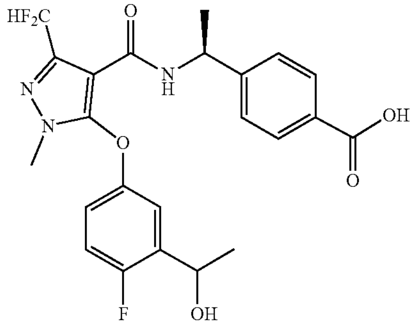

The synthesis scheme for Compound I-23 is shown below:

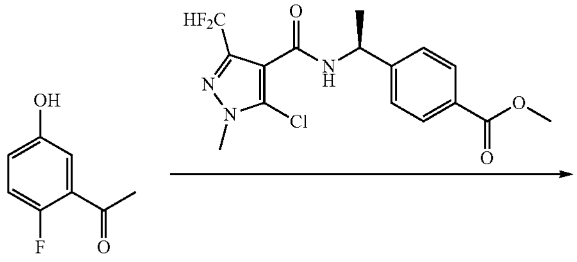

I-23A

-continued

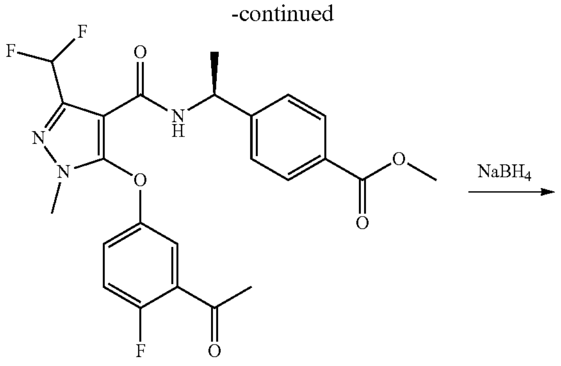

I-23B

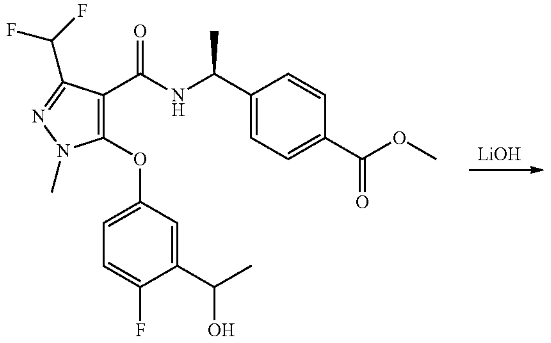

I-23C

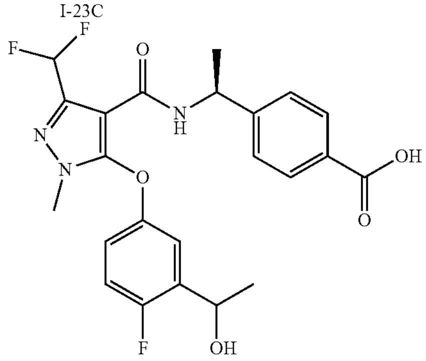

I-23

First Step: methyl (S)-4-(1-(5-(3-acetyl-4-fluorophenoxy)-3-(difluoromethyl)-1-methyl-1H-pyrazole-4-carboxamido)ethyl)benzoate (Compound I-23B)

I-23B

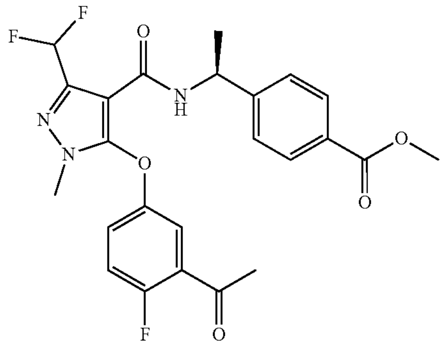

A compound 1-(2-fluoro-5-hydroxyphenyl) ethan-1-one (1.58 g, 10.8 mmol) was added to N, N-dimethylformamide (30 mL) at room temperature; and methyl (S)-4-(1-(5-chloro-3-(difluoromethyl)-1-methyl-1H-pyrazole-4-carboxamido)ethyl)benzoat (Intermediate A) (2.0 g, 5.4 mmol) and potassium hydroxide (450 mg, 8.1 mmol) were added. The mixture was heated to 120° C. in the microwave under nitrogen protection and stirred for 2 hours; the mixture was cooled to room temperature and added with water (30 mL); the pH was adjusted to 4 with 1N hydrochloric acid; and the mixture was extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=10:1) to obtain a white solid of methyl (S)-4-(1-(5-(3-acetyl-4-fluorophenoxy)-3-(difluoromethyl)-1-methyl-1H-pyrazole-4-carboxamido) ethyl)benzoate (Compound I-23B) (346 mg, 13% yield).

LC-MS, M/Z (ESI): 490.2 $[M+H]^+$

Second Step: methyl 4-((1S)-1-(3-(difluoromethyl)-5-(4-fluoro-3-(1-hydroxyethyl)phenoxy)-1-methyl-1H-pyrazole-4-carboxamido)ethyl)benzoate (Compound I-23C)

I-23C

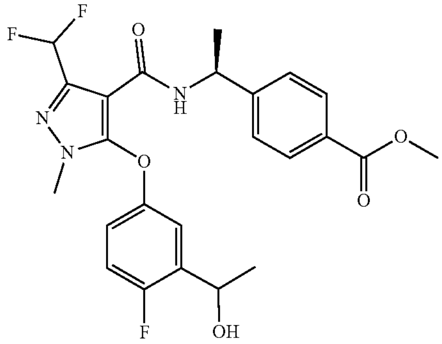

The compound methyl (S)-4-(1-(5-(3-acetyl-4-fluorophenoxy)-3-(difluoromethyl)-1-methyl-1H-pyrazole-4-carboxamido)ethyl)benzoate (Compound I-23B) (100 mg, 0.20 mmol) was added to tetrahydrofuran (10 mL) at room temperature, cooled to 0° C.; and sodium borohydride (23 mg, 0.60 mmol) was added. The mixture was stirred at room temperature for 3 h; the mixture was diluted by addition of water (100 mL), extracted with ethyl acetate (80 mL×3) and separated. The organic phases were combined, dried over anhydrous sodium sulfate, filtered and concentrated, and the residue was separated and purified on a thin-layer silica gel plate (petroleum ether:ethyl acetate (V/V)=4:1) to obtain a white solid of crude product of methyl 4-((1S)-1-(3-(difluoromethyl)-5-(4-fluoro-3-(1-hydroxyethyl)phenoxy)-1-methyl-1H-pyrazole-4-carboxamido)ethyl)benzoate (Compound I-23C) (75 mg, yield 75%).

LC-MS, M/Z (ESI): 492.1 $[M+H]^+$.

4-((1S)-1-(3-(difluoromethyl)-5-(4-fluoro-3-(1-hydroxyethyl)phenoxy)-1-methyl-1H-pyrazole-4-carboxamido)ethyl)benzoic Acid (Compound I-23)

I-23

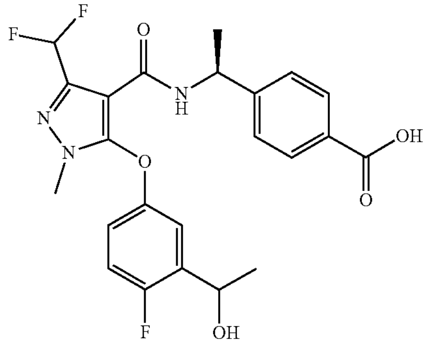

The starting material methyl 4-((1S)-1-(3-(difluoromethyl)-5-(4-fluoro-3-(1-hydroxyethyl)phenoxy)-1-methyl-1H-pyrazole-4-carboxamido)ethyl)benzoate (Compound I-23C) (75 mg, 0.15 mmol) was added to tetrahydrofuran (5 mL), methanol (5 mL) and water (1 mL) at room temperature; and lithium hydroxide monohydrate (20 mg, 0.47 mmol) was added. The mixture was stirred at room temperature for 5 hours; the pH was adjusted to 4 with 1N hydrochloric acid; and the reaction mixture was concentrated to prepare, by the acidic preparative method A, a white solid of 4-((1S)-1-(3-(difluoromethyl)-5-(4-fluoro-3-(1-hydroxyethyl)phenoxy)-1-methyl-1H-pyrazole-4-carboxamido)ethyl)benzoic acid (Compound I-23) (48 mg, 66% yield).

$^1$H NMR (400 mHz, DMSO-d6) δ 12.8 (s, 1H), 8.02 (d, 1H), 7.74 (d, 2H), 7.25 (t, 1H), 7.21-7.10 (m, 4H), 6.90-6.81 (m, 1H), 4.96-4.86 (m, 2H), 3.72 (s, 3H), 3.67 (s, 1H), 1.28 (d, 3H), 1.24 (d, 3H).

LC-MS, M/Z (ESI): 478.1 $[M+H]^+$

Example 24: Preparation of Compound I-24

(S)-4-(1-(3-(difluoromethyl)-5-(4-fluoro-3-(2-hydroxypropan-2-yl)phenoxy)-1-methyl-1H-pyrazole-4-carboxamido)ethyl)benzoic Acid (Compound I-24)

I-24

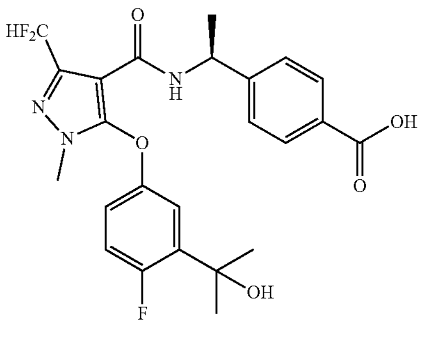

The synthesis scheme for Compound I-24 is shown below:

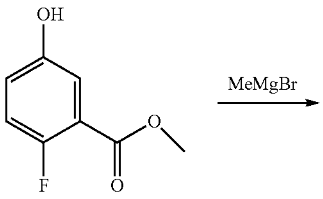

I-24A

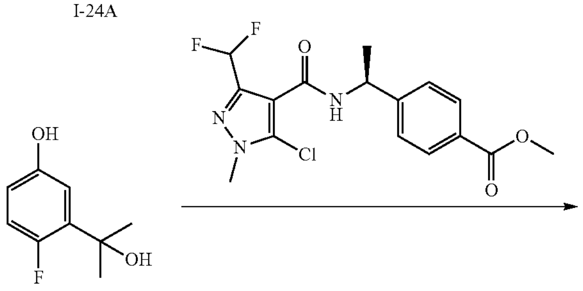

I-24B

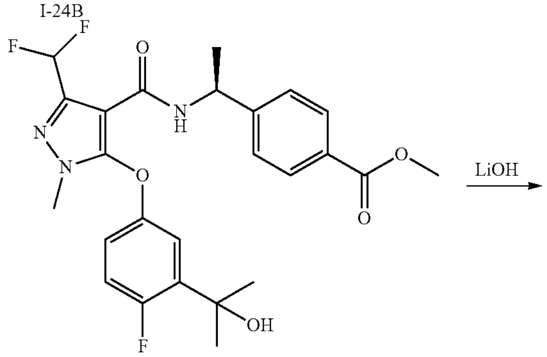

I-24C

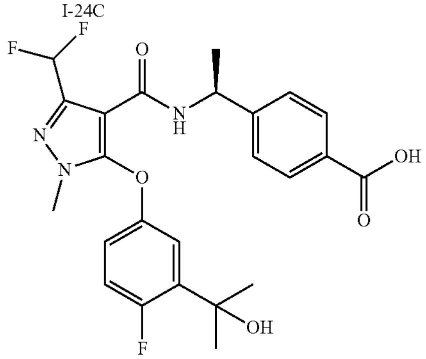

I-24

First Step: 4-fluoro-3-(2-hydroxypropan-2-yl)phenol (Compound I-24B)

I-24B

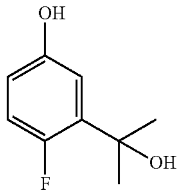

A compound methyl 2-fluoro-5-hydroxybenzoate (340 mg, 2.0 mmol) was added to a solution of methyl magnesium bromide (1 mol/L) in tetrahydrofuran (5 mL) at room temperature and stirred for 16 hours; a saturated solution of ammonium chloride (10 mL) was added and extracted with dichloromethane (30 mL×3) and separated. The organic phases were combined and dried over anhydrous sodium sulfate, filtered and concentrated to obtain a colorless liquid crude product of 4-fluoro-3-(2-hydroxypropan-2-yl)phenol (Compound I-24B) (340 mg, yield 100%).

Second Step: methyl (S)-4-(1-(3-(difluoromethyl)-5-(4-fluoro-3-(2-hydroxypropan-2-yl)phenoxy)-1-methyl-1H-pyrazole-4-carboxamido)ethyl)benzoate (Compound I-24C)

I-24C

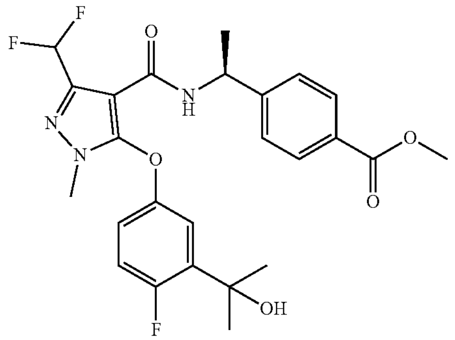

The compound 4-fluoro-3-(2-hydroxypropan-2-yl)phenol (Compound I-24B) (340 mg, 2.0 mmol) was added to N, N-dimethylformamide (9 mL) at room temperature; and methyl (S)-4-(1-(5-chloro-3-(difluoromethyl)-1-methyl-1H-pyrazole-4-carboxamido)ethyl)benzoat (Intermediate A) (495 mg, 1.34 mmol), cuprous iodide (100 mg, 0.52 mmol), 1, 10-phenanthroline (180 mg, 1.0 mmol) and cesium carbonate (1.30 g, 4.05 mmol) were added. The mixture was heated to 120° C. in the microwave under nitrogen protection and stirred for 2 hours. Then, the mixture was cooled to room temperature and added with water (30 mL); the pH was adjusted to 4 with 1N hydrochloric acid; and the mixture was extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=3:1) to obtain a white solid of methyl (S)-4-(1-(3-(difluoromethyl)-5-(4-fluoro-3-(2-hydroxypropan-2-yl)phenoxy)-1-methyl-1H-pyrazole-4-carboxamido)ethyl)benzoate (Compound I-24C) (120 mg, yield 32%).

LC-MS, M/Z (ESI): 506.3 $[M+1]^+$

Third Step: (S)-4-(1-(3-(difluoromethyl)-5-(4-fluoro-3-(2-hydroxypropan-2-yl)phenoxy)-1-methyl-1H-pyrazole-4-carboxamido)ethyl)benzoic Acid (Compound I-24)

I-24

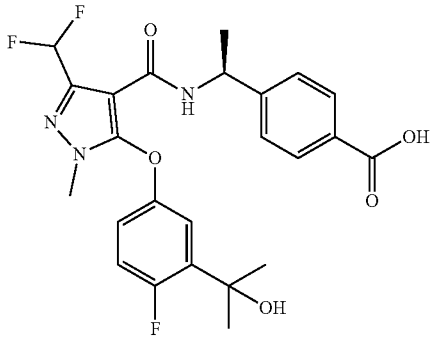

A starting material methyl (S)-4-(1-(3-(difluoromethyl)-5-(4-fluoro-3-(2-hydroxypropan-2-yl)phenoxy)-1-methyl-1H-pyrazole-4-carboxamido)ethyl)benzoate (Compound I-24C) (120 mg, 0.24 mmol) was added to tetrahydrofuran (5 mL), and water (1 mL) at room temperature; and lithium hydroxide (20 mg, 0.47 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(3-(difluoromethyl)-5-(4-fluoro-3-(2-hydroxypropan-2-yl)phenoxy)-1-methyl-1H-pyrazole-4-carboxamido)ethyl)benzoic acid (Compound I-24) (22 mg, 19% yield).

$^1H$ NMR (400 mHz, DMSO-d6) δ 12.8 (s, 1H), 7.96 (d, 1H), 7.73 (d, 2H), 7.33 (t, 1H), 7.26 (t, 1H), 7.17 (d, 2H), 7.14 (t, 1H), 6.85 (t, 1H), 4.92 (t, 1H), 3.73 (s, 3H), 3.72 (s, 1H), 1.44 (s, 6H), 1.25 (d, 3H).

LC-MS, M/Z (ESI): 492.3 $[M+1]^+$

Example 25: Preparation of Compound I-25

(S)-4-(1-(5-(3-(cyanomethyl)phenoxy)-3-(difluoromethyl)-1-methyl-1H-pyrazole-4-carboxamido)ethyl) benzoic Acid (Compound I-25)

I-25

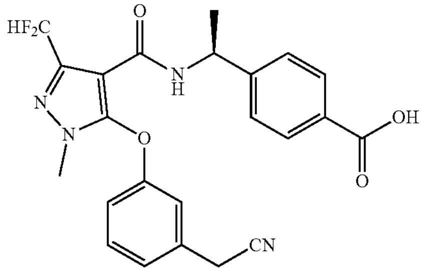

The synthesis scheme for Compound I-25 is shown below:

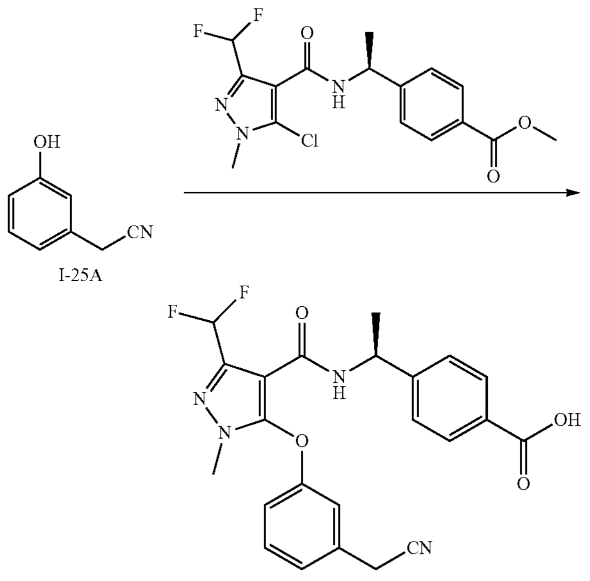

I-25A

I-25

First Step: (S)-4-(1-(5-(3-(cyanomethyl)phenoxy)-3-(difluoromethyl)-1-methyl-1H-pyrazole-4-carboxamido)ethyl)benzoic Acid (Compound I-25)

I-25

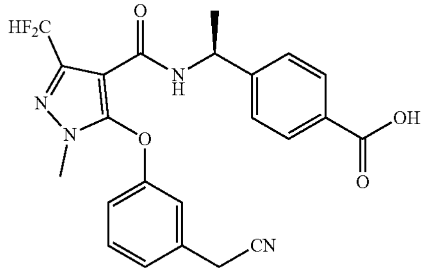

A compound 2-(3-hydroxyphenyl) acetonitrile (72 mg, 0.40 mmol) was added to N, N dimethylformamide (2 mL) at room temperature; and methyl (S)-4-(1-(5-chloro-3-(difluoromethyl)-1-methyl-1H-pyrazole-4-carboxamido)ethyl) benzoat (Intermediate A) (100 mg, 0.27 mmol) and potassium hydroxide (30 mg, 0.53 mmol) were added. The mixture was heated to 170° C. in the microwave under nitrogen protection and stirred for 5 min; and then, the mixture was cooled to room temperature and added with water (30 mL). The mixture was stirred for 0.5 hour; the pH was adjusted to 4 with 1N hydrochloric acid; and the reaction mixture was concentrated to prepare, by the acidic preparation method A, a white solid of (S)-4-(1-(5-(3-(cyanomethyl)phenoxy)-3-(difluoromethyl)-1-methyl-1H-pyrazole-4-carboxamido)ethyl)benzoic acid (10 mg, yield 8%).

$^1$H NMR (400 mHz, CDCl3) δ12.7 (s, 1H), 7.93 (d, 2H), 7.38 (t, 1H), 7.25 (t, 1H), 7.19 (d, 1H), 7.16 (d, 2H), 6.94 (s, 1H), 6.82 (t, 1H), 6.35 (d, 1H), 5.18 (t, 1H), 3.73 (s, 2H), 3.70 (s, 3H), 1.41 (d, 3H).

LC-MS, M/Z (ESI): 455.5 $[M+H]^+$

Example 26: Preparation of Compound I-26

(S)-4-(1-(5-([1,1'-biphenyl]-4-yloxy)-3-(difluoromethyl)-1-methyl-1H-pyrazole-4-carboxamido)ethyl) benzoic Acid (Compound I-26)

I-26

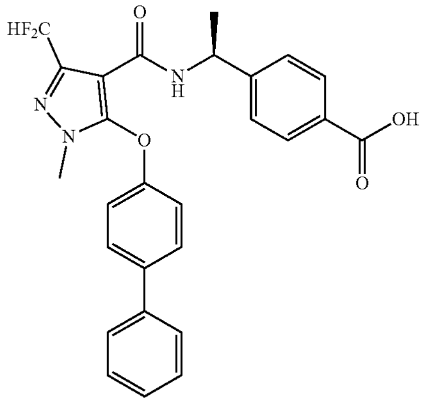

The synthesis scheme for Compound I-26 is shown below:

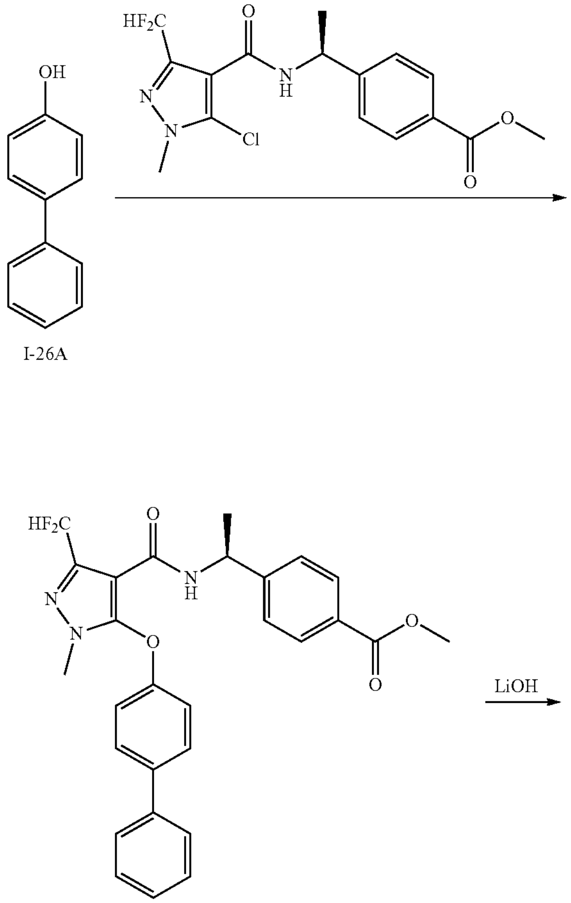

I-26A

I-26B

-continued

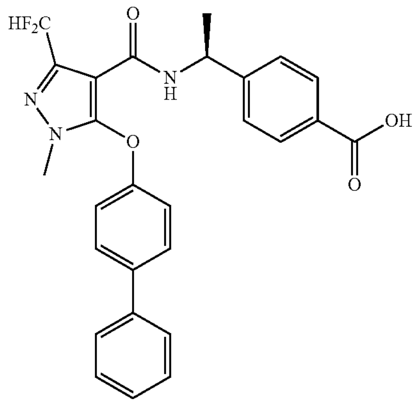

I-26

First Step: methyl (S)-4-(1-(5-([1,1'-biphenyl]-4-yloxy)-3-(difluoromethyl)-1-methyl-1H-pyrazole-4-carboxamido)ethyl)benzoate (Compound I-26B)

I-26B

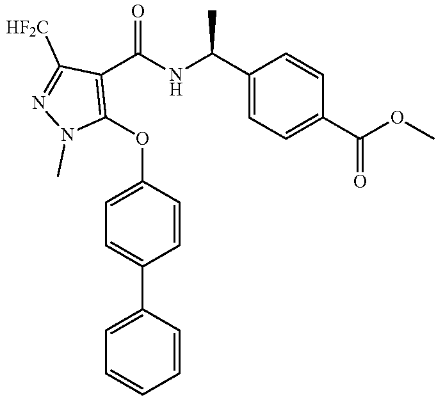

A compound [1, 1'-biphenyl]-4-ol (458 mg, 2.70 mmol) was added to N, N-dimethylformamide (10 mL) at room temperature; and methyl (S)-4-(1-(5-chloro-3-(difluoromethyl)-1-methyl-H-pyrazole-4-carboxamido)ethyl)benzoat (Intermediate A) (500 mg, 1.35 mmol) and potassium hydroxide (227 mg, 4.05 mmol) were added. The mixture was heated to 120° C. in the microwave under nitrogen protection and stirred for 1 hour. Then, the mixture was cooled to room temperature and added with water (30 mL); the pH was adjusted to 4 with 1N hydrochloric acid; and the mixture was extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a white solid crude product of methyl (S)-4-(1-(5-([1,1'-biphenyl]-4-yloxy)-3-(difluoromethyl)-1-methyl-1H-pyrazole-4-carboxamido)ethyl)benzoate (Compound I-26B) (500 mg, yield 73%).

LC-MS, M/Z (ESI): 506.4 $[M+H]^+$

Second Step: (S)-4-(1-(5-([1,1'-biphenyl]-4-yloxy)-3-(difluoromethyl)-1-methyl-1H-pyrazole-4-carboxamido)ethyl)benzoic Acid (Compound I-26)

I-26

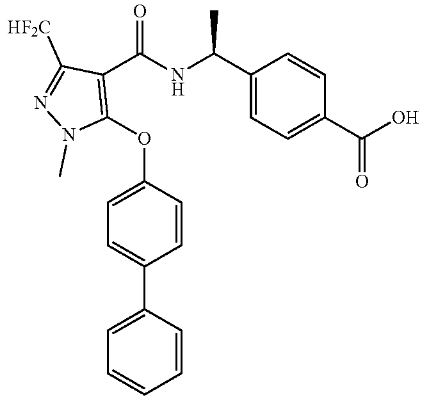

A starting material methyl (S)-4-(1-(5-([1,1'-biphenyl]-4-yloxy)-3-(difluoromethyl)-1-methyl-1H-pyrazole-4-carboxamido)ethyl)benzoate (Compound I-26B) (450 mg, 0.89 mmol) was added to tetrahydrofuran (10 mL), methanol (5 mL) and water (4 mL) at room temperature; and lithium hydroxide (108 mg, 4.5 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(5-([1,1'-biphenyl]-4-yloxy)-3-(difluoromethyl)-1-methyl-1H-pyrazole-4-carboxamido)ethyl)benzoic acid (Compound I-26) (70 mg, 16% yield).

$^1H$ NMR (400 mHz, DMSO-d6) δ 12.8 (s, 1H), 8.08 (d, 1H), 7.71 (d, 2H), 7.69 (d, 2H), 7.63 (d, 2H), 7.48 (t, 2H), 7.38 (t, 1H), 7.26 (t, 1H), 7.15 (d, 2H), 7.12 (d, 2H), 4.92 (t, 1H), 3.76 (s, 3H), 1.25 (d, 3H).

LC-MS, M/Z (ESI): 492.4 $[M+H]^+$

Example 27: Preparation of Compound I-27

(S)-4-(1-(5-([1,1'-biphenyl]-3-yloxy)-3-(difluoromethyl)-1-methyl-1H-pyrazole-4-carboxamido)ethyl)benzoic Acid (Compound I-27)

I-27

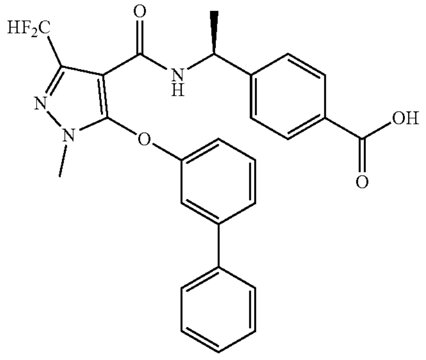

The synthesis scheme for Compound I-27 is shown below:

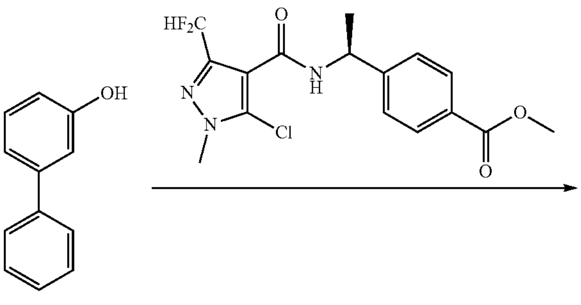

I-27A

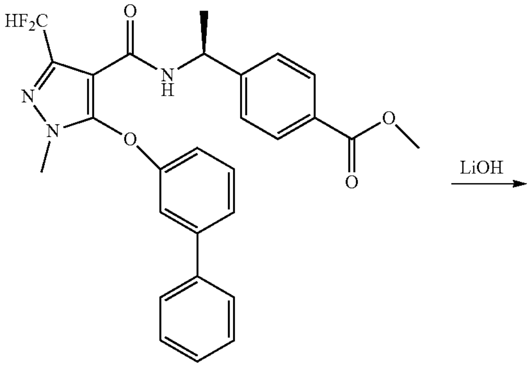

I-27B

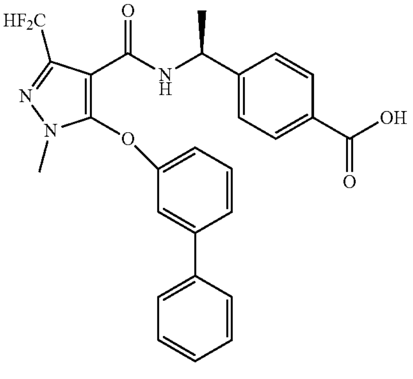

I-27

First Step: methyl (S)-4-(1-(5-([1,1'-biphenyl]-3-yloxy)-3-(difluoromethyl)-1-methyl-1H-pyrazole-4-carboxamido)ethyl)benzoate (Compound I-27B)

I-27B

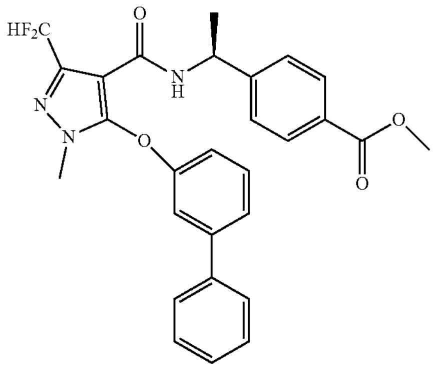

A compound [1, 1'-biphenyl]-3-ol (458 mg, 2.70 mmol) was added to N, N-dimethylformamide (10 mL) at room temperature; and methyl (S)-4-(1-(5-chloro-3-(difluoromethyl)-1-methyl-1H-pyrazole-4-carboxamido)ethyl)benzoat (Intermediate A) (500 mg, 1.35 mmol) and potassium hydroxide (227 mg, 4.05 mmol) were added. The mixture was heated to 120° C. in the microwave under nitrogen protection and stirred for 1 hour. Then, the mixture was cooled to room temperature and added with water (30 mL); the pH was adjusted to 4 with 1N hydrochloric acid; and the mixture was extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a white solid crude product of methyl (S)-4-(1-(5-([1,1'-biphenyl]-3-yloxy)-3-(difluoromethyl)-1-methyl-1H-pyrazole-4-carboxamido)ethyl)benzoate (Compound I-27B) (450 mg, yield 66%).

LC-MS, M/Z (ESI): 506.4 $[M+H]^+$

Second Step: (S)-4-(1-(5-([1,1'-biphenyl]-3-yloxy)-3-(difluoromethyl)-1-methyl-1H-pyrazole-4-carboxamido)ethyl)benzoic Acid (Compound I-27)

I-27

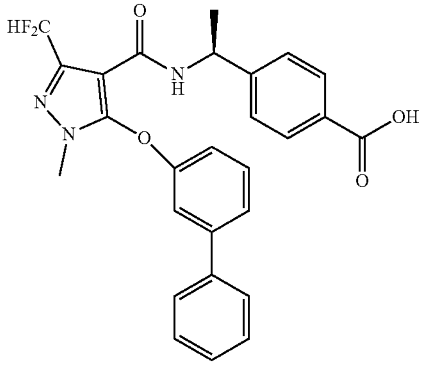

The starting material methyl (S)-4-(1-(5-([1,1'-biphenyl]-3-yloxy)-3-(difluoromethyl)-1-methyl-1H-pyrazole-4-carboxamido)ethyl)benzoate (Compound I-27B) (400 mg, 0.79 mmol) was added to tetrahydrofuran (10 mL), methanol (5 mL) and water (5 mL) at room temperature; and lithium hydroxide (96 mg, 4.0 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(5-([1,1'-biphenyl]-3-yloxy)-3-(difluoromethyl)-1-methyl-1H-pyrazole-4-carboxamido)ethyl)benzoic acid (Compound I-27) (115 mg, 30% yield).

$^1$H NMR (400 mHz, DMSO-d6) δ 12.8 (s, 1H), 8.07 (d, 1H), 7.68 (d, 2H), 7.62 (d, 2H), 7.50-7.44 (m, 4H), 7.41 (d, 1H), 7.31 (s, 1H), 7.25-6.96 (m, 4H), 4.89 (t, 1H), 3.77 (s, 3H), 1.19 (d, 3H).

LC-MS, M/Z (ESI): 492.4 [M+H]$^+$

Example 28: Preparation of Compound I-28

(S)-4-(1-(3-(difluoromethyl)-1-methyl-5-(3-(pentafluoro-λ$^6$-sulfanyl)phenoxy)-1H-pyrazole-4-carboxamido)ethyl)benzoic Acid (Compound I-28)

I-28

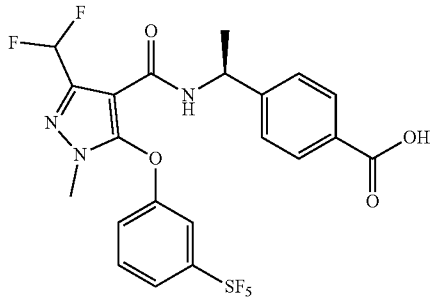

The synthesis scheme for Compound I-28 is shown below:

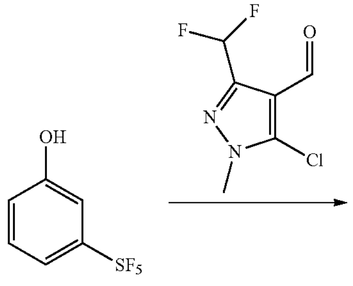

I-28A

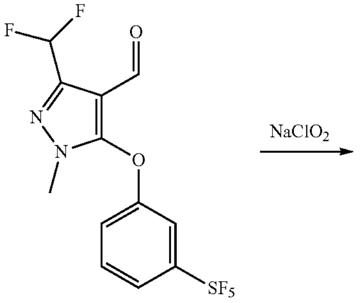

I-28B

-continued

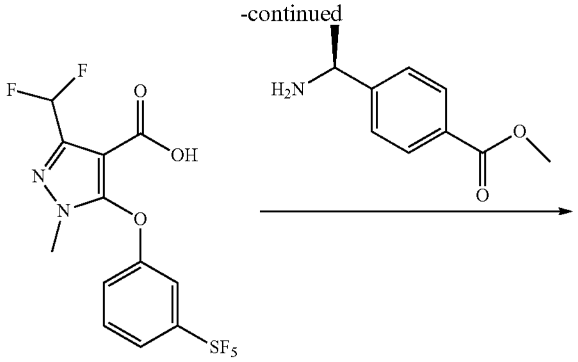

I-28C

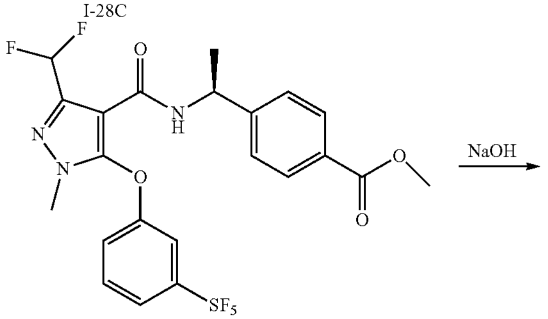

I-28D

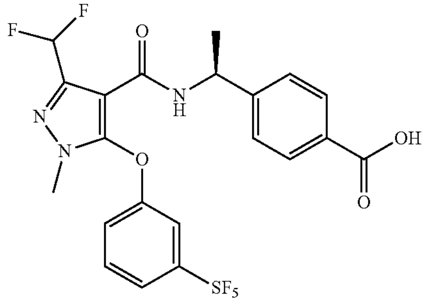

I-28

First Step: 3-(difluoromethyl)-1-methyl-5-(3-(pentafluoro-λ$^6$-sulfanyl)phenoxy)-1H-pyrazole-4-carbaldehyde (Compound I-28B)

I-28B

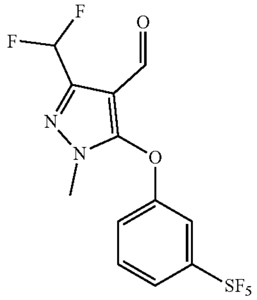

A compound 5-chloro-3-(difluoromethyl)-1-methyl-1H-pyrazole-4-carbaldehyde (500 mg, 2.57 mmol) was added to N, N-dimethylformamide (5 mL) at room temperature; 3-(pentafluoro-λ$^6$-sulfanyl) phenol (386 mg, 2.80 mmol) and potassium hydroxide (216 mg, 3.85 mmol) were added;

and the mixture was heated to 150° C. and stirred for 4 hours. Then, the mixture was cooled to room temperature, diluted with water (20 mL), the pH was adjusted to 4 with 1N hydrochloric acid, and the mixture was extracted with ethyl acetate (15 mL×3) and separated. The organic phases were combined, dried over anhydrous sodium sulfate, filtered and concentrated, and the residue was purified by silica gel column (petroleum ether:ethyl acetate (V/V)=4:1) to obtain a light yellow liquid crude product of 3-(difluoromethyl)-1-methyl-5-(3-(pentafluoro-$\lambda^6$-sulfanyl)phenoxy)-1H-pyrazole-4-carbaldehyde (Compound I-28B) (750 mg, 98% yield).

LC-MS, M/Z (ESI): 379.1 $[M+H]^+$

Second Step: 3-(difluoromethyl)-1-methyl-5-(3-(pentafluoro-$\lambda^6$-sulfanyl)phenoxy)-1H-pyrazole-4-carboxylic Acid (Compound I-28C)

I-28C

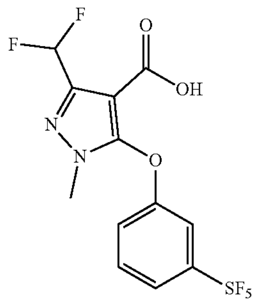

The compound 3-(difluoromethyl)-1-methyl-5-(3-(pentafluoro-$\lambda^6$-sulfanyl)phenoxy)-1H-pyrazole-4-carbaldehyde (Compound I-28B) (750 mg, 2.55 mmol) was added to tert-butanol (6 mL) and water (7 mL) at room temperature; and 2-methyl-2-butene (355 mg, 5.07 mmol), sodium chlorite (456 mg, 5.07 mmol) and sodium dihydrogen phosphate (669 mg, 5.57 mmol) were added. The mixture was stirred for 14 hours at room temperature; the mixture was diluted with water (15 mL) and the pH was adjusted to 4 with 1N hydrochloric acid; and the mixture was extracted with ethyl acetate (30 mL×3) and separated. The organic phases were combined and dried over anhydrous sodium sulfate, filtered and concentrated to obtain a light yellow solid crude product of 3-(difluoromethyl)-1-methyl-5-(3-(pentafluoro-$\lambda^6$-sulfanyl)phenoxy)-1H-pyrazole-4-carboxylic acid (Compound I-28C) (800 mg, yield 100%).

LC-MS, M/Z (ESI): 395.1 $[M+H]^+$

Third Step: methyl (S)-4-(1-(3-(difluoromethyl)-1-methyl-5-(3-(pentafluoro-$\lambda^6$-sulfanyl)phenoxy)-1H-pyrazole-4-carboxamido)ethyl)benzoate (Compound I-28D)

I-28D

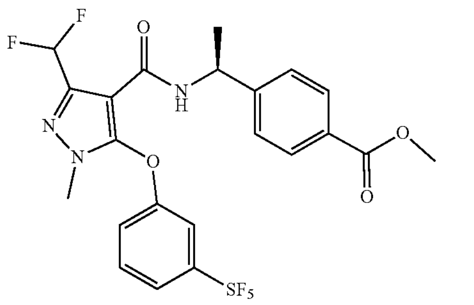

The compound 3-(difluoromethyl)-1-methyl-5-(3-(pentafluoro-$\lambda^6$-sulfanyl)phenoxy)-1H-pyrazole-4-carboxylic acid (compound I-28C) (800 mg, 2.58 mmol) was added to dichloromethane (20 mL); and methyl (S)-4-(1-aminoethyl) benzoate (459 mg, 2.56 mmol), O-(7-azabenzotriazol-1-yl)-N, N, N, N-tetramethyluronium hexafluorophosphate (1.40 g, 3.68 mmol) and N, N-diisopropylethylamine (991 mg, 7.68 mmol) were added. The mixture was stirred at room temperature for 16 hours, diluted with dichloromethane (40 mL), washed with water (20 mL×3) and separated. The organic phases were dried over anhydrous sodium sulfate, filtered and concentrated, and the residue was purified by silica gel column separation (petroleum ether:ethyl acetate (V/V)=4:1) to obtain a light yellow liquid of (S)-4-(1-(3-(difluoromethyl)-1-methyl-5-(3-(pentafluoro-$\lambda^6$-sulfanyl) phenoxy)-1H-pyrazole-4-carboxamido)ethyl)benzoate (Compound I-28D) (720 mg, yield 59%).

LC-MS, M/Z (ESI): 556.1 $[M+H]^+$

Fourth Step: (S)-4-(1-(3-(difluoromethyl)-1-methyl-5-(3-(pentafluoro-$\lambda^6$-sulfanyl)phenoxy)-1H-pyrazole-4-carboxamido)ethyl)benzoic Acid (Compound I-28)

I-28

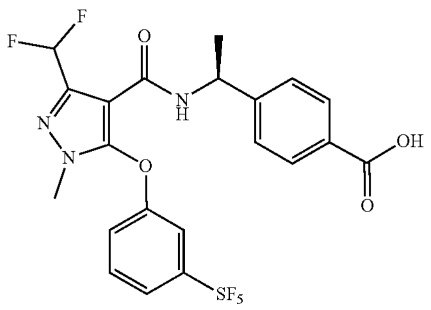

The starting material (S)-4-(1-(3-(difluoromethyl)-1-methyl-5-(3-(pentafluoro-$\lambda^6$-sulfanyl)phenoxy)-1H-pyrazole-4-carboxamido)ethyl)benzoate (Compound I-28D) (440 mg, 0.93 mmol) was added to methanol (10 mL) and water (1 mL) at room temperature; and sodium hydroxide (93 mg, 2.32 mmol) was added. The mixture was stirred at room temperature for 16 hours; the pH was adjusted to 4 with 1N hydrochloric acid; and the reaction mixture was concentrated to obtain a white solid of (S)-4-(1-(3-(difluoromethyl)-1-methyl-5-(3-(pentafluoro-$\lambda^6$-sulfanyl)phenoxy)-1H-pyrazole-4-carboxamido)ethyl)benzoic acid (Compound I-28) (93 mg, 22% yield).

$^1$H NMR (400 m Hz, DMSO-d6) δ 12.7 (s, 1H), 8.18 (d, 1H), 7.74 (d, 2H), 7.73 (d, 1H), 7.71 (d, 1H), 7.65 (t, 1H), 7.26 (d, 1H), 7.23 (t, 1H), 7.21 (d, 2H), 4.89 (t, 1H), 3.78 (s, 3H), 1.11 (d, 3H).

LC-MS, M/Z (ESI): 542.1 [M+H]$^+$

Example 29: Preparation of Compound I-29

(S)-4-(1-(3-(difluoromethyl)-1-methyl-5-(3-((trifluoromethyl)thio)phenoxy)-1H-pyrazole-4-carboxamido)ethyl)benzoic Acid (Compound I-29)

I-29

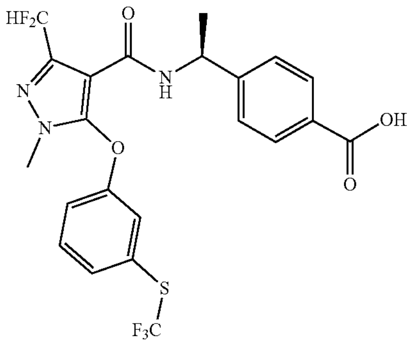

The synthesis scheme for Compound I-29 is shown below:

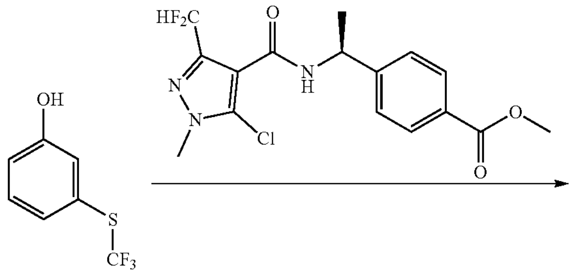

I-29A

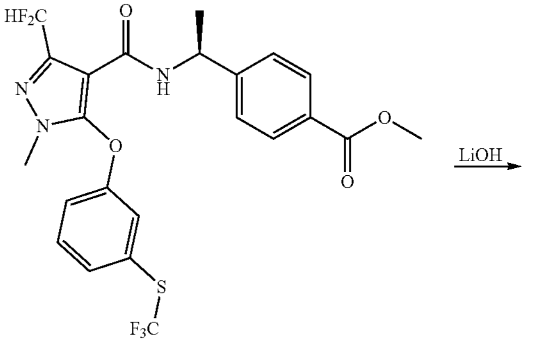

I-29B

-continued

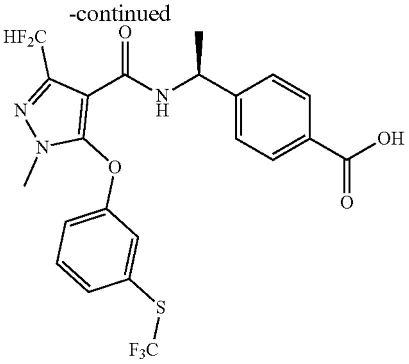

I-29

First Step: methyl (S)-4-(1-(3-(difluoromethyl)-1-methyl-5-(3-((trifluoromethyl)thio)phenoxy)-1H-pyrazole-4-carboxamido)ethyl)benzoate (Compound I-29B)

I-29B

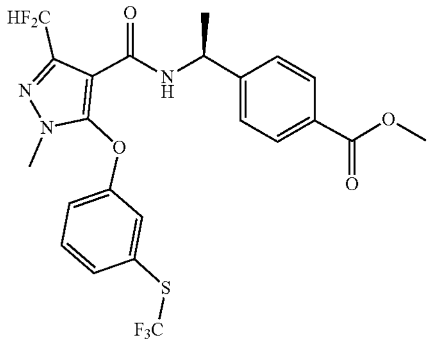

The compound methyl (S)-4-(1-(5-chloro-3-(difluoromethyl)-1-methyl-1H-pyrazole-4-carboxamido)ethyl)benzoat (Intermediate A) (186 mg, 0.50 mmol) was added to N, N-dimethylformamide (5 mL) at room temperature; 3-((trifluoromethyl) sulfanyl) phenol (120 mg, 0.60 mmol) and potassium hydroxide (45 mg, 0.80 mmol) were added; and the mixture was heated to 120° C. and stirred for 12 hours. Then, the mixture was cooled to room temperature, diluted with water (20 mL), the pH was adjusted to 4 with 1N hydrochloric acid, and the mixture was extracted with ethyl acetate (15 mL×3) and separated. The organic phases were combined, dried over anhydrous sodium sulfate, filtered and concentrated, and the residue was separated and purified on a thin-layer silica gel plate (petroleum ether:ethyl acetate (V/V)=4:1) to obtain a white solid of methyl (S)-4-(1-(3-(difluoromethyl)-1-methyl-5-(3-((trifluoromethyl)thio)phenoxy)-1H-pyrazole-4-carboxamido)ethyl)benzoate (Compound I-29B) (20 mg, yield 7.5%).

LC-MS, M/Z (ESI): 530.2 [M+H]$^+$

Second Step: (S)-4-(1-(3-(difluoromethyl)-1-methyl-5-(3-((trifluoromethyl)thio)phenoxy)-1H-pyrazole-4-carboxamido)ethyl)benzoic Acid (Compound I-29)

I-29

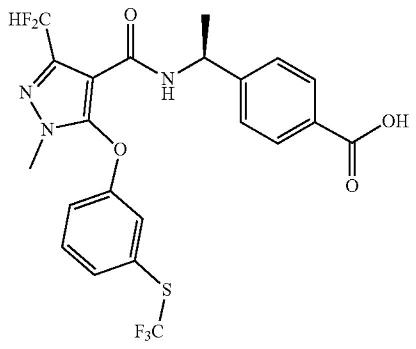

The starting material methyl (S)-4-(1-(3-(difluoromethyl)-1-methyl-5-(3-((trifluoromethyl)thio)phenoxy)-1H-pyrazole-4-carboxamido)ethyl)benzoate (compound I-29B) (20 mg, 0.04 mmol) was added to tetrahydrofuran (2 mL), methanol (2 mL) and water (1 mL) at room temperature; lithium hydroxide (3 mg, 0.16 mmol) was added; and the mixture was heated to 50° C. and stirred for 4 hours. Then, the mixture was cooled to room temperature and the pH was adjusted to 4 with 1N hydrochloric acid; and the reaction mixture was concentrated to prepare, by the acidic preparative method A, a white solid of (S)-4-(1-(3-(difluoromethyl)-1-methyl-5-(3-((trifluoromethyl)thio)phenoxy)-1H-pyrazole-4-carboxamido)ethyl)benzoic acid (Compound I-29) (14 mg, 72% yield).

$^1$H NMR (400 mHz, DMSO-$d_6$) δ 12.8 (s, 1H), 8.16 (d, 1H), 7.74 (d, 2H), 7.57 (t, 2H), 7.39 (s, 1H), 7.22-6.69 (m, 4H), 4.91-4.84 (m, 1H), 3.74 (s, 3H), 1.21 (d, 3H).

LC-MS, M/Z (ESI): 516.2 [M+H]$^+$

Example 30: Preparation of Compound I-30

(S)-4-(1-(3-(difluoromethyl)-1-methyl-5-(3-(methylthio)phenoxy)-1H-pyrazole-4-carboxamido)ethyl) benzoic Acid (Compound I-30)

I-30

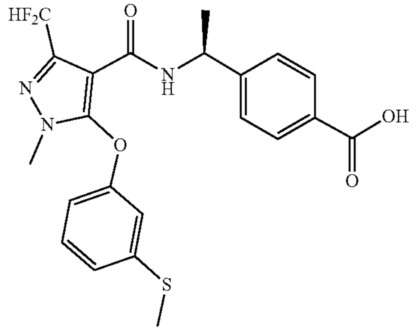

The synthesis scheme for Compound I-30 is shown below:

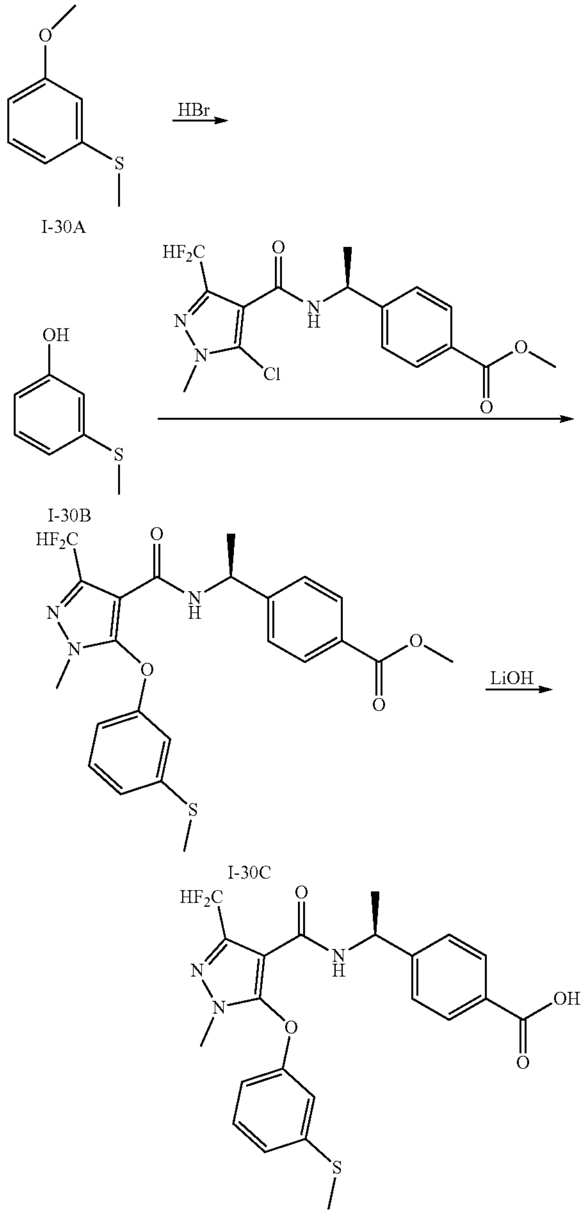

I-30A
I-30B
I-30C
I-30

First Step: 3-(methylthio)phenol (Compound I-30B)

I-30B

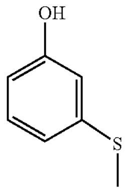

A compound (3-methoxyphenyl) (methyl) sulfide (4.0 g, 26 mmol) was added to a solution of 30% hydrobromic acid in acetic acid (12 mL) and a solution of 48% hydrobromic acid in water (3 mL) at room temperature; the mixture was heated to reflux under $N_2$ protection and stirred for 6 hours; and then the mixture was cooled to room temperature, diluted with water (100 mL), extracted with diethyl ether (100 mL×3) and separated. The organic phases were combined and dried over anhydrous sodium sulfate, filtered, and concentrate to obtain a colorless liquid crude product of 3-(methylthio)phenol (Compound I-30B) (3.8 g, yield 100%).

Second Step: methyl (S)-4-(1-(3-(difluoromethyl)-1-methyl-5-(3-(methylthio)phenoxy)-1H-pyrazole-4-carboxamido)ethyl)benzoate (Compound I-30C)

I-30C

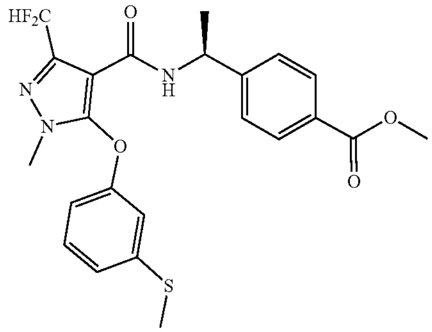

The compound methyl (S)-4-(1-(5-chloro-3-(difluoromethyl)-1-methyl-1H-pyrazole-4-carboxamido)ethyl)benzoat (Intermediate A) (700 mg, 1.89 mmol) was added to N, N-dimethylformamide (5 mL) at room temperature; and 3-(methylthio) phenol (528 mg, 3.77 mmol) and potassium hydroxide (318 mg, 5.67 mmol) were added. The mixture was heated to 150° C. in the microwave and stirred for 2 hours. Then, the mixture was cooled to room temperature and diluted with water (20 mL), the pH was adjusted to 4 with 1N hydrochloric acid, and the mixture was extracted with ethyl acetate (30 mL×3) and separated. The organic phases were combined and dried over anhydrous sodium sulfate, filtered and concentrated to obtain a white solid crude product of methyl (S)-4-(1-(3-(difluoromethyl)-1-methyl-5-(3-(methylthio)phenoxy)-1H-pyrazole-4-carboxamido)ethyl)benzoate (Compound I-30C) (800 mg, 89% yield).

LC-MS, M/Z (ESI): 476.5 $[M+H]^+$

Third Step: (S)-4-(1-(3-(difluoromethyl)-1-methyl-5-(3-(methylthio)phenoxy)-1H-pyrazole-4-carboxamido)ethyl)benzoic Acid (Compound I-30)

I-30

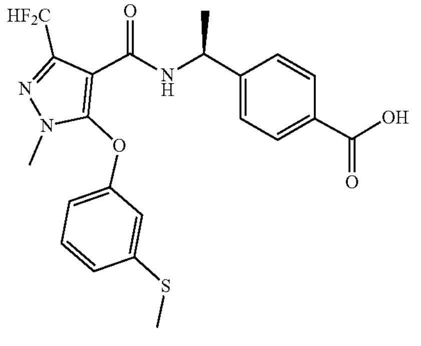

The starting material methyl (S)-4-(1-(3-(difluoromethyl)-1-methyl-5-(3-(methylthio)phenoxy)-1H-pyrazole-4-carboxamido)ethyl)benzoate (Compound I-30C) (800 mg, 1.68 mmol) was added to tetrahydrofuran (10 mL), methanol (10 mL) and water (2 mL) at room temperature; lithium hydroxide (121 mg, 5.0 mmol) was added; and the mixture was heated to 50° C. and stirred for 4 hours. Then, the mixture was cooled to room temperature and the pH was adjusted to 4 with 1N hydrochloric acid; and the reaction mixture was concentrated to prepare, by the acidic preparation method A, a white solid of (S)-4-(1-(3-(difluoromethyl)-1-methyl-5-(3-(methylthio)phenoxy)-1H-pyrazole-4-carboxamido)ethyl)benzoic acid (Compound I-30) (165 mg, yield 21%).

$^1H$ NMR (400 mHz, DMSO-d6) δ 12.8 (s, 1H), 8.03 (d, 1H), 7.74 (d, 2H), 7.34 (t, 2H), 7.14 (d, 2H), 7.11 (t, 1H), 6.97 (t, 1H), 6.70 (d, 1H), 4.91 (t, 1H), 3.73 (s, 3H), 2.45 (s, 3H), 1.24 (d, 3H).

LC-MS, M/Z (ESI): 462.5 $[M+H]^+$

Example 31: Preparation of Compound I-31

(S)-4-(1-(3-(difluoromethyl)-1-methyl-5-(3-(methylsulfonyl)phenoxy)-1H-pyrazole-4-carboxamido)ethyl)benzoic Acid (Compound I-31)

I-31

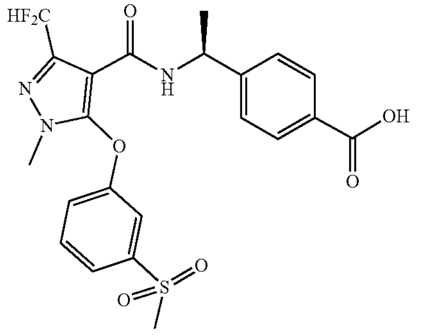

The synthesis scheme for Compound I-31 is shown below:

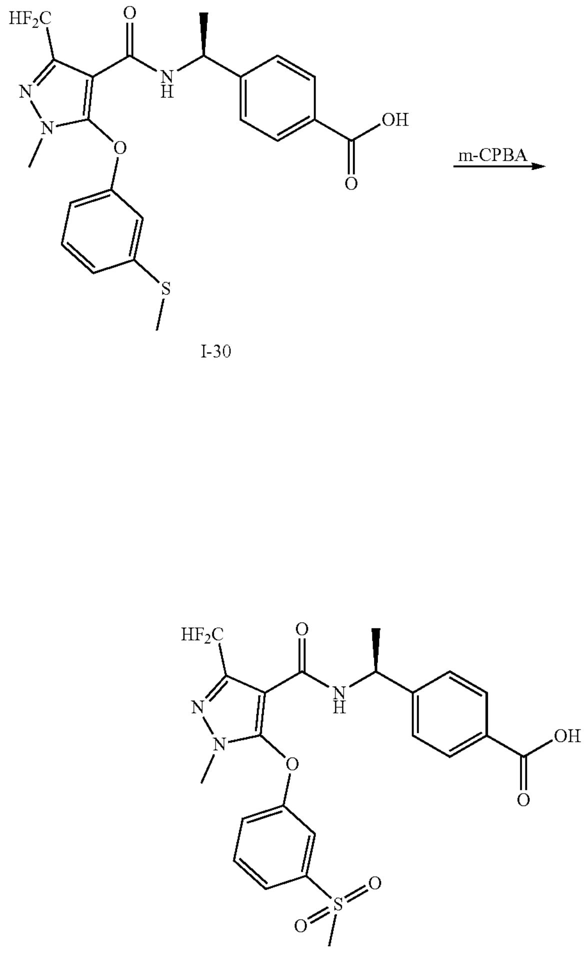

I-30

I-31

The starting material (S)-4-(1-(3-(difluoromethyl)-1-methyl-5-(3-(methylthio)phenoxy)-1H-pyrazole-4-carboxamido)ethyl)benzoic acid (Compound I-30) (80 mg, 0.17 mmol) was added to dichloromethane (5 mL); and m-chloroperoxybenzoic acid (83 mg, 0.48 mmol) was added at room temperature and stirred for 3 hours at room temperature. The reaction mixture was concentrated to prepare, by the acidic preparation method A, a white solid of (S)-4-(1-(3-(difluoromethyl)-1-methyl-5-(3-(methylsulfonyl)phenoxy)-1H-pyrazole-4-carboxamido)ethyl)benzoic acid (Compound I-31) (64 mg, 75% yield).

$^1$H NMR (400 mHz, DMSO-d6) δ 12.8 (s, 1H), 8.21 (d, 1H), 7.77 (d, 2H), 7.75 (d, 1H), 7.70 (t, 1H), 7.59 (t, 1H), 7.37 (d, 1H), 7.25 (t, 1H), 7.15 (d, 2H), 4.87 (t, 1H), 3.77 (s, 3H), 3.19 (s, 3H), 1.19 (d, 3H).

LC-MS, M/Z (ESI): 494.1 $[M+H]^+$

Example 32: Preparation of Compound I-32

4-((1S)-1-(3-(difluoromethyl)-1-methyl-5-(3-(methylsulfinyl)phenoxy)-1H-pyrazole-4-carboxamido)ethyl)benzoic Acid (Compound I-32)

I-32

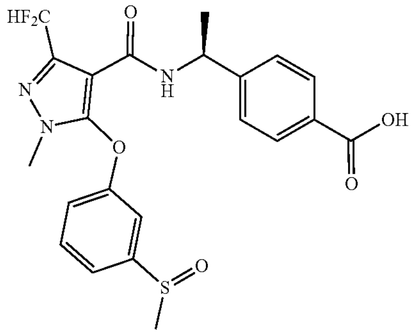

The synthesis scheme for Compound I-32 is shown below:

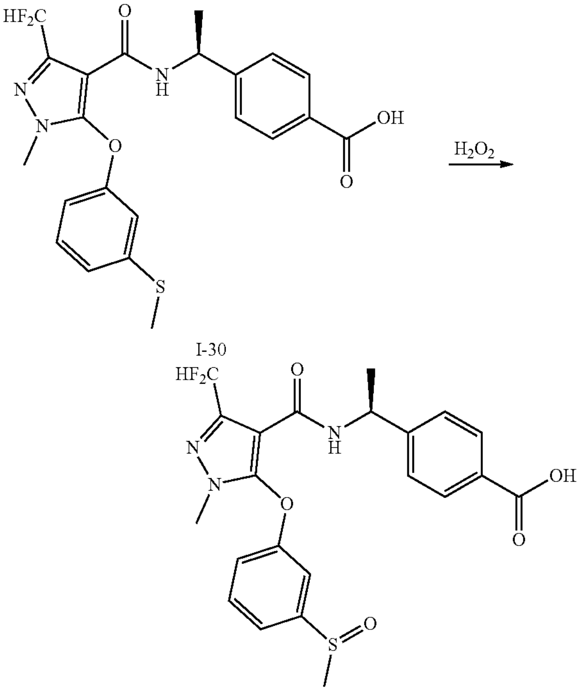

I-30

I-32

The starting material (S)-4-(1-(3-(difluoromethyl)-1-methyl-5-(3-(methylthio)phenoxy)-1H-pyrazole-4-carboxamido)ethyl)benzoic acid (Compound I-30) (60 mg, 0.13 mmol) was added to tetrahydrofuran (5 mL); 30% hydrogen peroxide (1 mL) was added; and the mixture was heated to 60° C. and stirred for 7 h at room temperature. Then, the mixture was cooled to room temperature and was concentrated to prepare, by the acidic preparation method A, a white solid of 4-((1S)-1-(3-(difluoromethyl)-1-methyl-5-(3-(methylsulfinyl)phenoxy)-1H-pyrazole-4-carboxamido)ethyl)benzoic acid (Compound I-32) (35 mg, yield 75%).

$^1$H NMR (400 mHz, DMSO-d6) δ 12.8 (s, 1H), 8.15 (d, 1H), 7.73 (d, 2H), 7.61 (d, 1H), 7.50 (t, 1H), 7.36 (s, 1H), 7.25 (t, 1H), 7.15 (d, 1H), 7.13 (d, 2H), 4.87 (t, 1H), 3.75 (s, 3H), 2.69 (s, 3H), 1.20 (d, 3H).

LC-MS, M/Z (ESI): 478.2 [M+H]$^+$

Example 33: Preparation of Compound I-33

(S)-4-(1-(3-(difluoromethyl)-1-methyl-5-(3-(2,2,2-trifluoroethoxy)phenoxy)-1H-pyrazole-4-carboxamido)ethyl)benzoic Acid (Compound I-33)

I-33

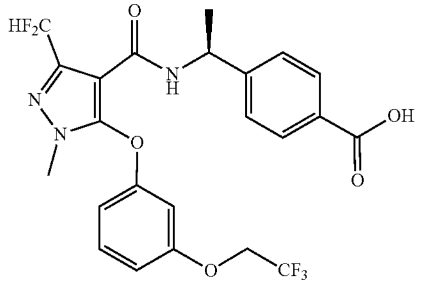

The synthesis scheme for Compound I-33 is shown below:

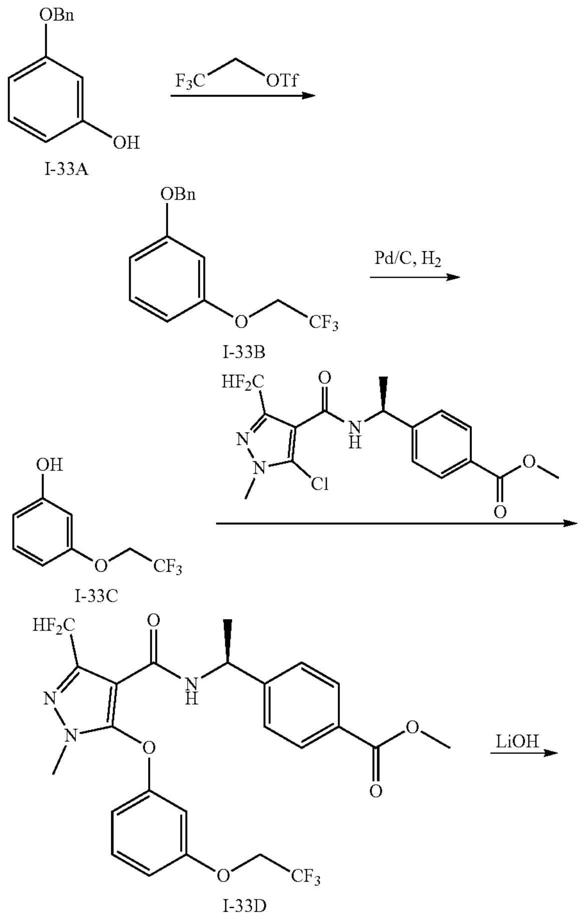

-continued

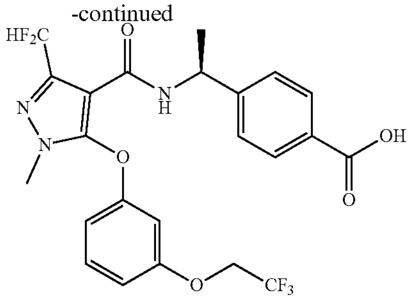

I-33

First Step: 1-(benzyloxy)-3-(2,2,2-trifluoroethoxy) benzene (Compound I-33B)

I-33B

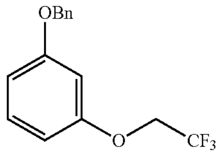

A compound 3-(benzyloxy) phenol (600 mg, 3.0 mmol) was added to N, N-dimethylformamide (10 mL) at room temperature; trifluoro-2, 2, 2-trifluoroethane-1-sulfonate (840 mg, 3.6 mmol) and potassium carbonate (1.24 g, 9.0 mmol) were added; and the mixture was heated to 60° C. and stirred for 16 hours. Then, the mixture was cooled to room temperature, diluted with water (30 mL), extracted with ethyl acetate (30 mL×3) and separated. The organic phases were combined and dried over anhydrous sodium sulfate, filtered, and concentrated; the residue was separated and purified on a thin-layer silica gel plate (petroleum ether:ethyl acetate (V/V)=10:1) to obtain a colorless liquid of 1-(benzyloxy)-3-(2,2,2-trifluoroethoxy)benzene (Compound I-33B) (380 mg, yield 45%).

Second Step: 3-(2,2,2-trifluoroethoxy)phenol (Compound I-33C)

I-33C

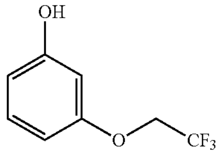

The compound 1-(benzyloxy)-3-(2,2,2-trifluoroethoxy) benzene (Compound I-33B) (520 mg, 1.84 mmol) was added to ethanol (10 mL) at room temperature; 10% palladium on carbon (50 mg) was added; and a drop of formic acid was added. Then, hydrogen was introduced, and the mixture was stirred for 12 hours; and the mixture was diluted with water (20 mL), extracted with ethyl acetate (30 mL×3) and separated. The organic phases were combined, dried over anhydrous sodium sulfate, filtered and concentrated, and the residue was separated and purified on a thin-layer silica gel plate (petroleum ether:ethyl acetate (V/V)=4:1) to obtain a white solid of the captioned compound, i.e., 3-(2,2,2-trifluoroethoxy)phenol (Compound I-33C) (210 mg, yield 59%).

Third Step: methyl (S)-4-(1-(3-(difluoromethyl)-1-methyl-5-(3-(2,2,2-trifluoroethoxy)phenoxy)-1H-pyrazole-4-carboxamido)ethyl)benzoate (Compound I-33D)

I-33D

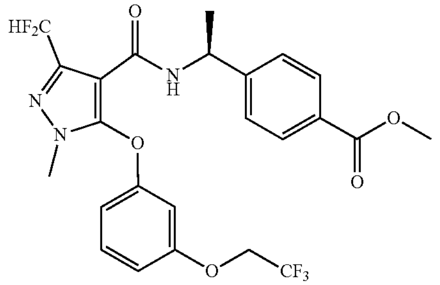

The compound methyl (S)-4-(1-(5-chloro-3-(difluoromethyl)-1-methyl-1H-pyrazole-4-carboxamido)ethyl)benzoat (Intermediate A) (371 mg, 1.0 mmol) was added to N, N-dimethylformamide (5 mL) at room temperature; 3-(2,2,2-trifluoroethoxy)phenol (Compound I-33C) (210 mg, 1.1 mmol), copper iodide (191 mg, 1.0 mmol), cesium carbonate (1.0 g, 3.1 mmol), and 1, 10-phenanthroline (72 mg, 0.40 mmol) were added; and the mixture was heated to 120° C. in the microwave and stirred for 2 hours. Then, the mixture was cooled to room temperature, diluted with water (20 mL), extracted with ethyl acetate (30 mL×3) and separated. The organic phases were combined, dried over anhydrous sodium sulfate, filtered and concentrated; and the residue was separated and purified on a thin-layer silica gel plate (petroleum ether:ethyl acetate (V/V)=4:1) to obtain a white solid of methyl (S)-4-(1-(3-(difluoromethyl)-1-methyl-5-(3-(2,2,2-trifluoroethoxy)phenoxy)-1H-pyrazole-4-carboxamido)ethyl)benzoate (Compound I-33D) (120 mg, yield 8%).

LC-MS, M/Z (ESI): 528.2 $[M+H]^+$

Fourth Step: (S)-4-(1-(3-(difluoromethyl)-1-methyl-5-(3-(2,2,2-trifluoroethoxy)phenoxy)-1H-pyrazole-4-carboxamido)ethyl)benzoic Acid (Compound I-33)

I-33

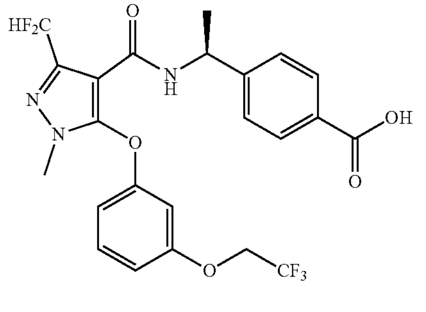

The starting material methyl (S)-4-(1-(3-(difluoromethyl)-1-methyl-5-(3-(2,2,2-trifluoroethoxy)phenoxy)-1H-pyrazole-4-carboxamido)ethyl)benzoate (Compound I-33D)

(120 mg, 0.23 mmol) was added to tetrahydrofuran (5 mL), methanol (5 mL) and water (1 mL) at room temperature; and lithium hydroxide (20 mg, 0.83 mmol) was added. The mixture was stirred for 16 hours at room temperature; the pH was adjusted to 4 with TN hydrochloric acid; and the reaction mixture was concentrated to prepare, by the acidic preparation method A, a white solid of (S)-4-(1-(3-(difluoromethyl)-1-methyl-5-(3-(2,2,2-trifluoroethoxy)phenoxy)-1H-pyrazole-4-carboxamido)ethyl)benzoic acid (Compound I-33) (45 mg, 72% yield).

$^1H$ NMR (400 mHz, DMSO-d6) δ 12.8 (s, 1H), 8.02 (d, 1H), 7.74 (d, 2H), 7.38 (t, 1H), 7.16 (t, 1H), 7.14 (d, 2H), 6.93 (d, 1H), 6.76 (t, 1H), 6.65 (d, 1H), 4.92 (t, 1H), 4.78 (dd, 2H), 3.72 (s, 3H), 1.25 (d, 3H).

LC-MS, M/Z (ESI): 514.2 $[M+H]^+$

Example 34: Preparation of Compound I-34

(S)-4-(1-(3-(difluoromethyl)-5-(2,4-difluorophenoxy)-1-methyl-1H-pyrazole-4-carboxamido)ethyl)benzoic Acid (Compound I-34)

I-34

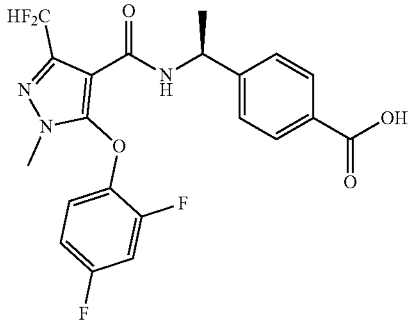

The synthesis scheme for Compound I-34 is shown below:

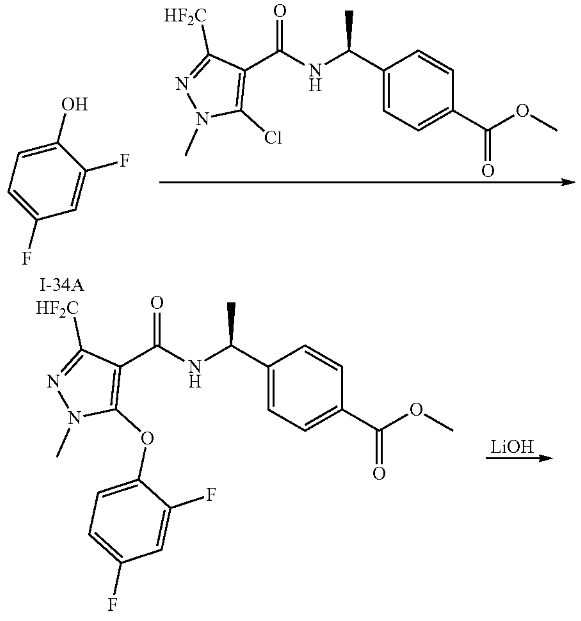

-continued

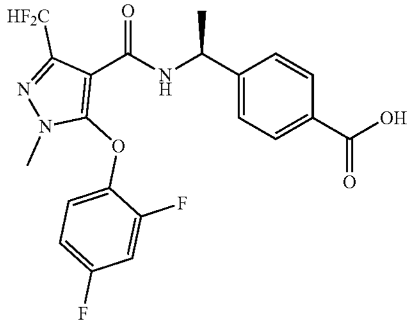

I-34

First Step: methyl (S)-4-(1-(3-(difluoromethyl)-5-(2,4-difluorophenoxy)-1-methyl-1H-pyrazole-4-carboxamido)ethyl)benzoate (Compound I-34B)

I-34B

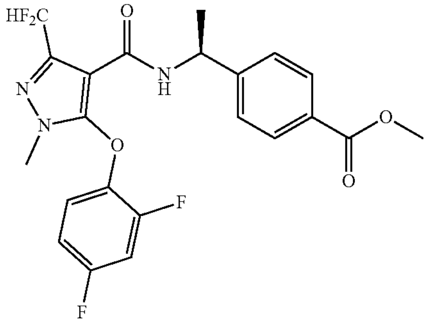

The compound methyl (S)-4-(1-(5-chloro-3-(difluoromethyl)-1-methyl-1H-pyrazole-4-carboxamido)ethyl)benzoat (Intermediate A) (370 mg, 1.0 mmol) was added to N,N-dimethylformamide (10 mL) at room temperature; 2,4-difluorophenol (195 mg, 1.5 mmol) and potassium hydroxide (168 mg, 3.0 mmol) were added; and the mixture was heated to 120° C. and stirred for 6 hours. Then, the mixture was cooled to room temperature and diluted with water (50 mL), the pH was adjusted to 4 with 1N hydrochloric acid, and the mixture was extracted with ethyl acetate (60 mL×3) and separated. The organic phases were combined and dried over anhydrous sodium sulfate, filtered and concentrated to obtain a white solid crude product of methyl (S)-4-(1-(3-(difluoromethyl)-5-(2,4-difluorophenoxy)-1-methyl-1H-pyrazole-4-carboxamido)ethyl)benzoate (Compound I-34B) (160 mg, yield 34%).

LC-MS, M/Z (ESI): 466.1 $[M+H]^+$

Second Step: (S)-4-(1-(3-(difluoromethyl)-5-(2,4-difluorophenoxy)-1-methyl-1H-pyrazole-4-carboxamido)ethyl)benzoic Acid (Compound I-34)

I-34

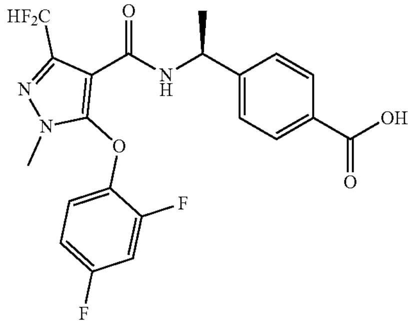

The starting material methyl (S)-4-(1-(3-(difluoromethyl)-5-(2,4-difluorophenoxy)-1-methyl-1H-pyrazole-4-carboxamido)ethyl)benzoate (Compound I-34B) (160 mg, 0.34 mmol) was added to tetrahydrofuran (4 mL) and water (2 mL) at room temperature; lithium hydroxide (32 mg, 0.76 mmol) was added; and the mixture was heated to 50° C. and stirred for 2 hours. Then, the mixture was cooled to room temperature and the pH was adjusted to 4 with 1N hydrochloric acid; and the reaction mixture was concentrated to prepare, by the acidic preparation method A, a white solid of (S)-4-(1-(3-(difluoromethyl)-5-(2,4-difluorophenoxy)-1-methyl-1H-pyrazole-4-carboxamido)ethyl)benzoic acid (Compound I-34) (11 mg, yield 7.0%).

$^1H$ NMR (400 mHz, DMSO-d6) δ 12.7 (s, 1H), 8.28 (d, 1H), 7.78 (d, 2H), 7.45 (t, 1H), 7.21 (d, 2H), 7.17 (t, 1H), 7.04 (d, 1H), 7.02 (d, 1H), 4.88 (t, 1H), 3.76 (s, 3H), 1.26 (d, 3H).

LC-MS, M/Z (ESI): 452.1 $[M+H]^+$

Example 35: Preparation of Compound I-35

(S)-4-(1-(3-(difluoromethyl)-1-methyl-5-((3-(trifluoromethyl)phenyl)thio)-1H-pyrazole-4-

I-35

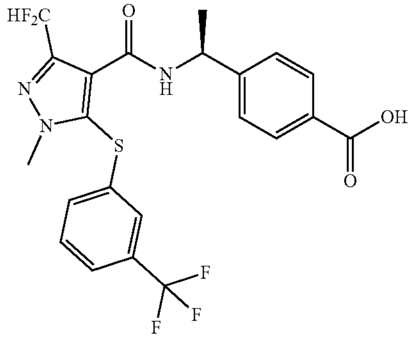

The synthesis scheme for Compound I-35 is shown below:

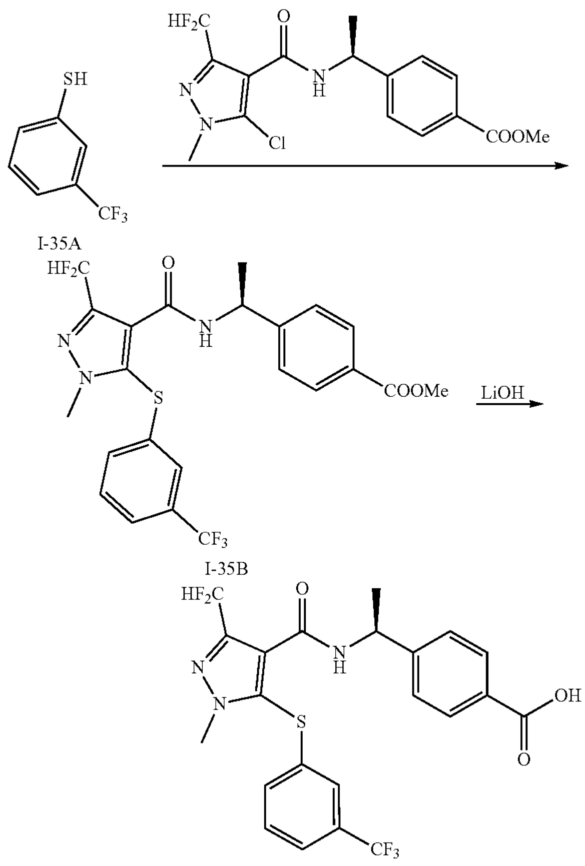

I-35A

I-35B

I-35

First Step: methyl (S)-4-(1-(3-(difluoromethyl)-1-methyl-5-((3-(trifluoromethyl)phenyl)thio)-1H-pyrazole-4-carboxamido)ethyl)benzoate (Compound I-35B)

I-35B

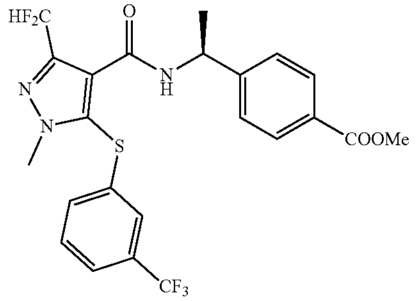

A compound 3-(trifluoromethyl) benzenethiol (215 mg, 1.20 mmol) was added to N, N-dimethylformamide (20 mL) at room temperature; and sodium hydride (80 mg, 2.00 mmol) was added. The mixture was stirred for 0.5 hour; methyl (S)-4-(1-(5-chloro-3-(difluoromethyl)-1-methyl-1H-pyrazole-4-carboxamido)ethyl)benzoat (Intermediate A) (375 mg, 1.00 mmol) was added; and the mixture was heated to 120° C. and stirred for 8 h. Then, the mixture was cooled to room temperature, diluted with water (100 mL), extracted with ethyl acetate (100 mL×3) and separated. The organic phases were combined, dried over anhydrous sodium sulfate, filtered and concentrated; the residue purified by silica gel column separation (petroleum ether:ethyl acetate (V/V) =4:1) to obtain a white solid of methyl (S)-4-(1-(3-(difluoromethyl)-1-methyl-5-((3-(trifluoromethyl)phenyl)thio)-1H-pyrazole-4-carboxamido)ethyl)benzoate (Compound I-35B) (350 mg, yield 67%).

LC-MS, M/Z (ESI): 514.2 (M+1).

Second Step: (S)-4-(1-(3-(difluoromethyl)-1-methyl-5-((3-(trifluoromethyl)phenyl)thio)-1H-pyrazole-4-carboxamido)ethyl)benzoic Acid (Compound I-35)

I-35

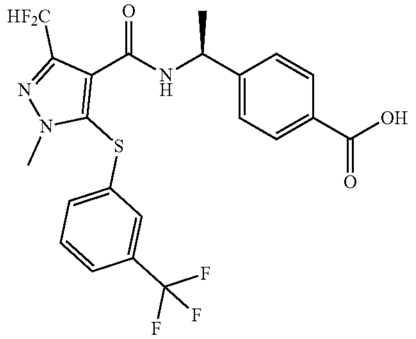

A starting material methyl (S)-4-(1-(3-(difluoromethyl)-1-methyl-5-((3-(trifluoromethyl)phenyl)thio)-1H-pyrazole-4-carboxamido)ethyl)benzoate (Compound I-35B) (220 mg, 0.43 mmol) was added to tetrahydrofuran (5 mL) at room temperature; water (5 mL), methanol (5 mL), and lithium hydroxide (30 mg, 1.25 mmol) were added; and the mixture was heated to 50° C. and stirred for 18 hours. The reaction mixture was concentrated to prepare, by the acidic preparation method A, a white solid of (S)-4-(1-(3-(difluoromethyl)-1-methyl-5-((3-(trifluoromethyl)phenyl)thio)-1H-pyrazole-4-carboxamido)ethyl)benzoic acid (Compound I-35) (105 mg, 49% yield).

$^1$H NMR (400 m Hz, DMSO-d6) δ 12.8 (s, 1H), 8.68 (d, 1H), 7.79 (d, 2H), 7.63 (d, 1H), 7.58 (t, 2H), 7.39 (d, 2H), 7.27 (t, 1H), 7.14 (t, 1H), 5.10-5.03 (m, 1H), 3.89 (s, 3H), 1.38 (d, 3H).

LC-MS, M/Z (ESI): 500.2 (M+1)

Example 36: Preparation of Compound I-36

(S)-4-(1-(3-(difluoromethyl)-1-methyl-5-(4-(trifluoromethyl)benzyl)-1H-pyrazole-4-carboxamido)ethyl) benzoic Acid (Compound I-36)

I-36

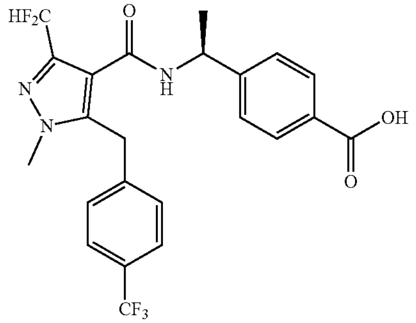

The synthesis scheme for Compound I-36 is shown below:

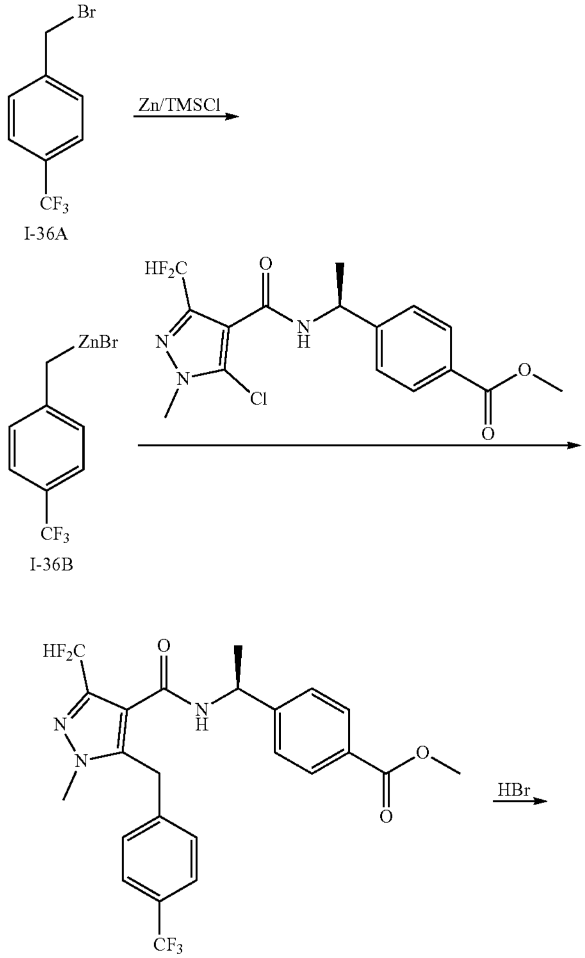

I-36A

I-36B

I-36C

-continued

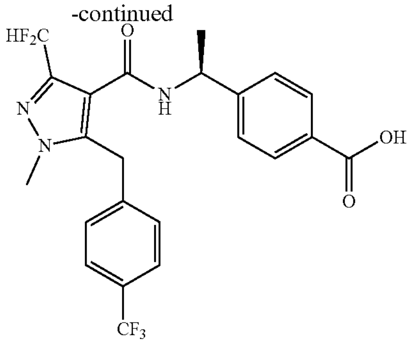

I-36

First Step: (4-(trifluoromethyl)benzyl)zinc(II) bromide (Compound I-36B)

I-36B

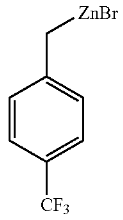

Zinc powder (2.60 g, 40.0 mmol) was added to anhydrous tetrahydrofuran (15 mL) at room temperature; 1, 2-dibromoethane (0.02 mL) was added under nitrogen protection; and the mixture was heated to 60° C. Then, chlorotrimethylsilane (0.02 mL) was added, and the mixture was stirred for 15 min and cooled to 0° C. A solution of 4-(trifluoromethyl) benzyl bromide (4.80 g, 20.0 mmol) in tetrahydrofuran (5 mL) was added dropwise; and then the mixture was heated to 60° C. and stirred for 1 hour. The mixture was cooled to room temperature to obtain a solution (1 mol/L) of (4-(trifluoromethyl)benzyl)zinc(II) bromide (Compound I-36B) in tetrahydrofuran (20 mL).

Second Step: methyl (S)-4-(1-(3-(difluoromethyl)-1-methyl-5-(4-(trifluoromethyl)benzyl)-1H-pyrazole-4-carboxamido)ethyl)benzoate (Compound I-36C)

I-36C

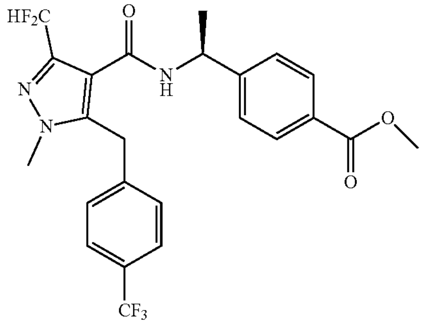

The compound (4-(trifluoromethyl) benzyl) zinc bromide in tetrahydrofuran (Compound I-36B) (2.70 mL, 2.70 mmol)

was added to N, N-dimethylformamide (15 mL) at room temperature; and methyl (S)-4-(1-(5-chloro-3-(difluoromethyl)-1-methyl-1H-pyrazole-4-carboxamido)ethyl)benzoat (Intermediate A) (500 mg, 1.35 mmol), 4, 4'-di-tert-butyl-2, 2'-bipyridine (35 mg, 0.13 mmol) and nickel chloride glyme complex (30 mg, 0.13 mmol) were added. The mixture was heated to 100° C. in the microwave under nitrogen protection and stirred for 1 hour; the mixture was cooled to room temperature and added with water (50 mL); and the mixture was extracted with ethyl acetate (100 mL×3) and separated. The organic phases were combined, dried over anhydrous sodium sulfate, filtered and concentrated, and the residue was separated and purified by a silica gel column (petroleum ether:ethyl acetate (V/V)=3:1) to obtain a white solid of methyl (S)-4-(1-(3-(difluoromethyl)-1-methyl-5-(4-(trifluoromethyl)benzyl)-1H-pyrazole-4-carboxamido)ethyl)benzoate (Compound I-36C) (180 mg, yield 27%).

LC-MS, M/Z (ESI): 496.3 [M+1]+.

Third Step: (S)-4-(1-(3-(difluoromethyl)-1-methyl-5-(4-(trifluoromethyl)benzyl)-1H-pyrazole-4-carboxamido)ethyl)benzoic Acid (Compound I-36)

I-36

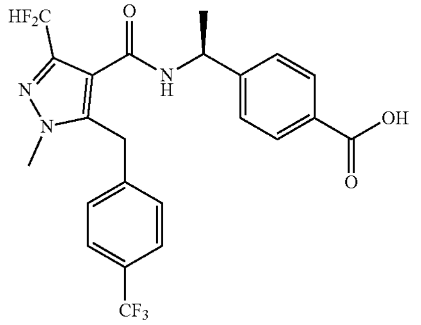

A starting material methyl (S)-4-(1-(3-(difluoromethyl)-1-methyl-5-(4-(trifluoromethyl)benzyl)-1H-pyrazole-4-carboxamido)ethyl)benzoate (Compound I-36C) (150 mg, 0.30 mmol) was added to 48% hydrobrominated acetic acid solution (3 mL) at room temperature, and the mixture was heated to 65° C. and stirred for 16 hours. The mixture was then cooled to room temperature, and the reaction mixture was concentrated to prepare, by the acidic preparation method A, a white solid of (S)-4-(1-(3-(difluoromethyl)-1-methyl-5-(4-(trifluoromethyl)benzyl)-1H-pyrazole-4-carboxamido)ethyl)benzoic acid (Compound I-36) (90 mg, yield 62%).

$^1$H NMR (400 mHz, DMSO-d6) δ 12.8 (s, 1H), 8.47 (d, 1H), 7.86 (d, 2H), 7.62 (d, 2H), 7.41 (d, 2H), 7.33 (d, 2H), 7.23 (t, 1H), 5.12 (t, 1H), 4.37 (dd, 2H), 3.77 (s, 3H), 1.41 (s, 3H).

LC-MS, M/Z (ESI): 482.3 [M+1]+

Example 37: Preparation of Compound I-37

(S)-5-(1-(3-(difluoromethyl)-1-methyl-5-(3-(trifluoromethyl)phenoxy)-1H-pyrazole-4-carboxamido)ethyl)thiophene-2-carboxylic Acid (Compound I-37)

I-37

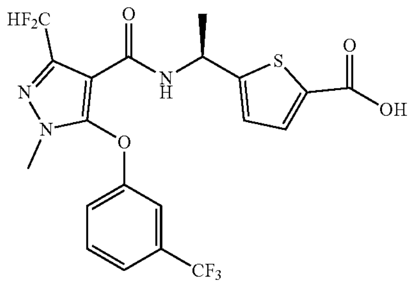

The synthesis scheme for Compound I-37 is shown below:

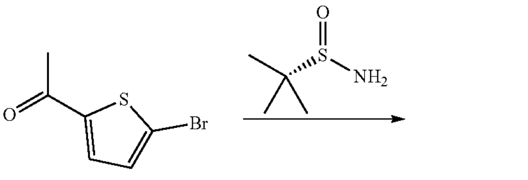

I-37A

I-37B

I-37C

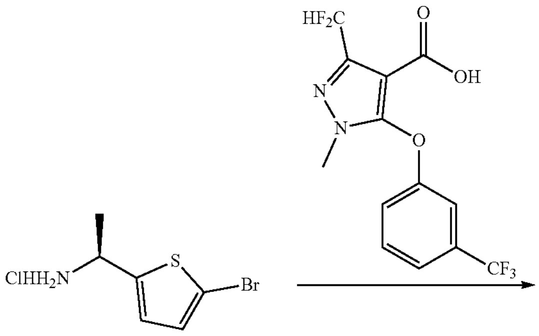

I-37D

-continued

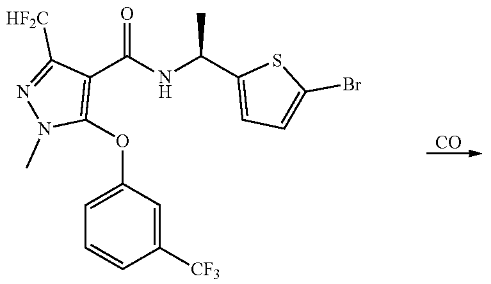

I-37E

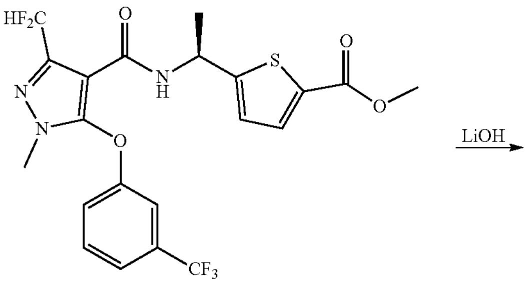

I-37F

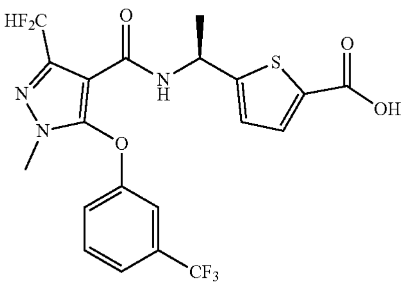

I-37

First Step: (R, E)-N-(1-(5-bromothiophen-2-yl)ethylidene)-2-methylpropane-2-sulfinamide (Compound I-37B)

I-37B

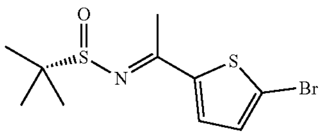

A compound 1-(5-bromothiophen-2-yl) ethan-1-one (2.05 g, 10.0 mmol) was added to dichloromethane (50 mL) at room temperature; (R)-tert-butylsulfinyl (1.8 g, 15.0 mmol) and tetraethyl titanate (5.70 g, 25.0 mmol) were added; and the mixture was heated to 50° C., stirred for 20 hours, and added with water (80 mL). The mixture was extracted with ethyl acetate (50 mL×3) and separated. The organic phases were combined, dried over anhydrous sodium sulfate, filtered and concentrated, and the residue was separated and purified by a silica gel column (petroleum ether:ethyl acetate (V/V)=10:1) to obtain a white solid of (R, E)-N-(1-(5-bromothiophen-2-yl)ethylidene)-2-methylpropane-2-sulfinamide (Compound I-37B) (500 mg, yield 16%).

Second Step: (R)—N—((S)-1-(5-bromothiophen-2-yl)ethyl)-2-methylpropane-2-sulfinamide (Compound I-37C)

I-37C

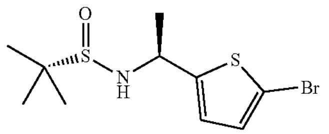

The compound (R, E)-N-(1-(5-bromothiophen-2-yl)ethylidene)-2-methylpropane-2-sulfinamide (Compound I-37B) (500 mg, 1.62 mmol) was added to tetrahydrofuran (10 mL) at room temperature; the mixture was cooled to −78° C., and added with 1 mol/L solution of lithium tri-sec-butylborohydride in tetrahydrofuran (2.4 mL, 2.4 mmol); and then the mixture was warmed naturally to room temperature and stirred for 16 hours. The pH was adjusted to 4 with 1N hydrochloric acid, and the mixture was diluted with water (50 mL), extracted with ethyl acetate (50 mL×3) and separated. The organic phases were combined, dried over anhydrous sodium sulfate, filtered and concentrated; the residue was separated and purified on a thin-layer silica gel plate (petroleum ether:ethyl acetate (V/V)=4:1) to obtain a white solid of (R)—N—((S)-1-(5-bromothiophen-2-yl) ethyl)-2-methylpropane-2-sulfinamide (Compound I-37C) (320 mg, yield 64%).

LC-MS, M/Z (ESI): 310.2 $[M+H]^+$.

Third Step: (S)-1-(5-bromothiophen-2-yl)ethan-1-amine Hydrochloride (Compound I-37D)

I-37D

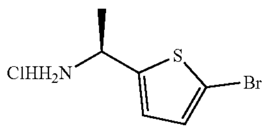

The starting material (R)—N—((S)-1-(5-bromothiophen-2-yl)ethyl)-2-methylpropane-2-sulfinamide (Compound I-37C) (310 mg, 1.0 mmol) was added to methanol (10 mL) at room temperature, and 4 mol/L solution of dioxane hydrochloride (0.5 mL, 2.0 mmol) was added. The mixture was stirred at room temperature for 16 hours; the reaction mixture was concentrated and diethyl ether (10 mL) was added; the mixture was filtered to obtain (S)-1-(5-bromothiophen-2-yl)ethan-1-amine hydrochloride (60097D) (190 mg, yield 78%) as a white solid.

Fourth Step: (S)—N-(1-(5-bromothiophen-2-yl)ethyl)-3-(difluoromethyl)-1-methyl-5-(3-(trifluoromethyl)phenoxy)-1H-pyrazole-4-carboxamide (Compound I-37E)

I-37E

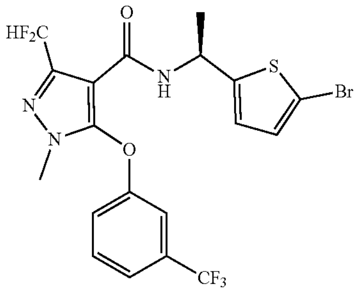

A compound 3-(difluoromethyl)-1-methyl-5-(3-(trifluoromethyl) phenoxy)-1H-pyrazole-4-carboxylic acid (140 mg, 0.41 mmol) was added to dichloromethane (5 mL) and N, N-dimethylformamide (5 mL) at room temperature; (S)-1-(5-bromothiophen-2-yl)ethan-1-amine hydrochloride (Compound I-37D) (118 mg, 0.49 mmol), O-(7-azabenzotriazol-1-yl)-N, N, N, N-tetramethyluronium hexafluorophosphate (239 mg, 0.63 mmol) and N, N-diisopropylethylamine (135 mg, 1.05 mmol) were added. The mixture was stirred for 16 hours at room temperature. Then, the mixture was diluted with water (50 mL), extracted with ethyl acetate (50 mL×3) and separated. The organic phases were combined, dried over anhydrous sodium sulfate, filtered and concentrated; and the residue was purified by thin-layer silica gel separation (petroleum ether:ethyl acetate (V/V)=4:1) to obtain a white solid crude product of (S)—N-(1-(5-bromothiophen-2-yl)ethyl)-3-(difluoromethyl)-1-methyl-5-(3-(trifluoromethyl)phenoxy)-1H-pyrazole-4-carboxamide (Compound I-37E) (170 mg, yield 78%).

LC-MS, M/Z (ESI): 524.2 $[M+H]^+$

Fifth Step: methyl (S)-5-(1-(3-(difluoromethyl)-1-methyl-5-(3-(trifluoromethyl)phenoxy)-1H-pyrazole-4-carboxamido)ethyl)thiophene-2-carboxylate (Compound I-37F)

I-37F

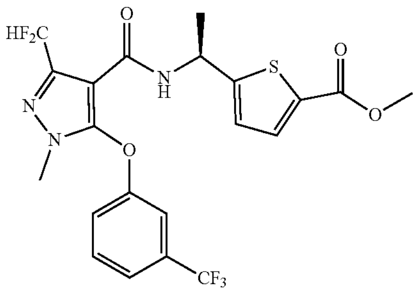

A compound (S)—N-(1-(5-bromothiophen-2-yl)ethyl)-3-(difluoromethyl)-1-methyl-5-(3-(trifluoromethyl)phenoxy)-1H-pyrazole-4-carboxamide (Compound I-37E) (170 mg, 0.32 mmol) was added to methanol (5 mL) at room temperature; triethylamine (320 mg, 3.20 mmol) and [1, 1'-bis (diphenylphosphino) ferrocene] dichloropalladium (53 mg, 0.06 mmol) were added; carbon monoxide was introduced; and the mixture was heated to 120° C. and stirred for 48 h. Then, mixture was diluted with water (20 mL), extracted with ethyl acetate (50 mL×3) and separated. The organic phases were combined, dried over anhydrous sodium sulfate, filtered and concentrated; and the residue was separated and purified on a thin-layer silica gel plate (petroleum ether:ethyl acetate (V/V)=3:1) to obtain a white solid of methyl (S)-5-(1-(3-(difluoromethyl)-1-methyl-5-(3-(trifluoromethyl)phenoxy)-1H-pyrazole-4-carboxamido)ethyl)thiophene-2-carboxylate (Compound I-37F) (140 mg, yield 86%).

LC-MS, M/Z (ESI): 504.5 $[M+H]^+$

Sixth Step: (S)-5-(1-(3-(difluoromethyl)-1-methyl-5-(3-(trifluoromethyl)phenoxy)-1H-pyrazole-4-carboxamido)ethyl)thiophene-2-carboxylic Acid (Compound I-37)

I-37

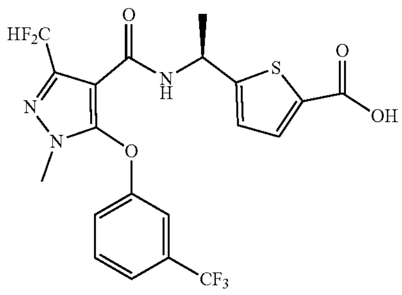

The starting material methyl (S)-5-(1-(3-(difluoromethyl)-1-methyl-5-(3-(trifluoromethyl)phenoxy)-1H-pyrazole-4-carboxamido)ethyl)thiophene-2-carboxylate (Compound I-37F) (140 mg, 0.28 mmol) was added to tetrahydrofuran (5 mL) and water (5 mL) at room temperature, and lithium hydroxide (20 mg, 0.47 mmol) was added. The mixture was stirred at room temperature for 16 hours; the pH was adjusted to 4 with 1N hydrochloric acid; and the reaction mixture was concentrated to prepare, by the acidic preparation method A, (S)-5-(1-(3-(difluoromethyl)-1-methyl-5-(3-(trifluoromethyl)phenoxy)-1H-pyrazole-4-carboxamido)ethyl)thiophene-2-carboxylic acid (Compound I-37) (110 mg, yield 81%) as a white solid.

$^1H$ NMR (400 mHz, DMSO-d6) δ 12.7 (s, 1H), 8.32 (d, 1H), 7.62 (t, 1H), 7.54 (t, 1H), 7.42 (d, 2H), 7.28 (t, 1H), 7.23 (t, 1H), 6.75 (d, 1H), 5.51-5.04 (m, 1H), 3.76 (s, 3H), 1.27 (d, 3H).

LC-MS, M/Z (ESI): 490.5 $[M+H]^+$

Example 38: Preparation of Compound I-38

(S)-4-(1-(3-(difluoromethyl)-1-methyl-5-(3-(trifluoromethyl)phenoxy)-1H-pyrazole-4-carboxamido)ethyl)-2,6-difluorobenzoic Acid (Compound I-38)

I-38

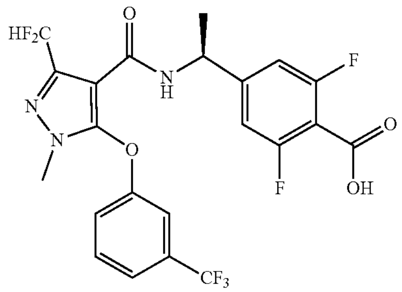

The synthesis scheme for Compound I-38 is shown below:

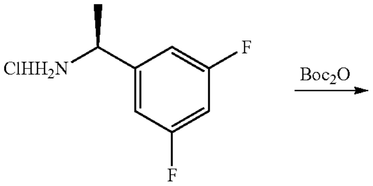

I-38A

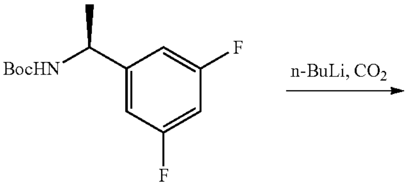

I-38B

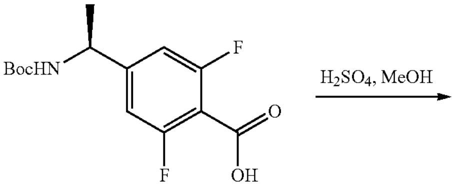

I-38C

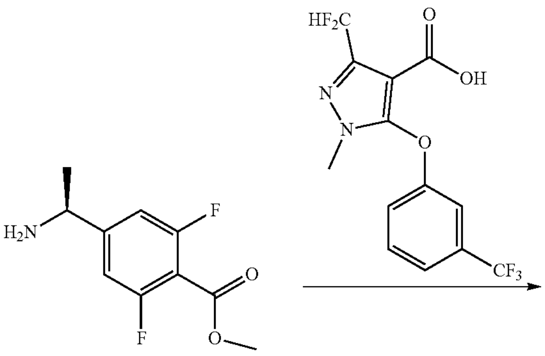

I-38D

-continued

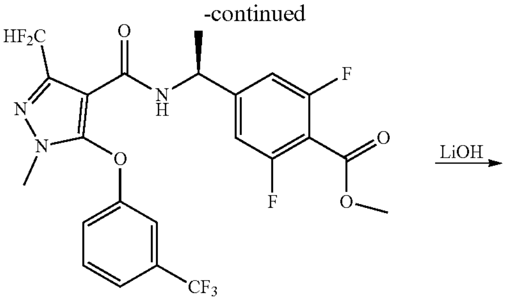

I-38E

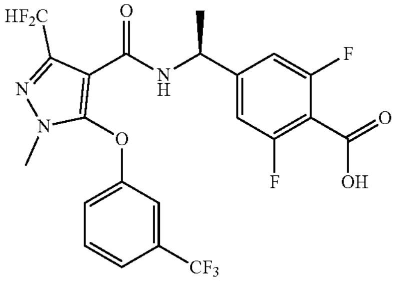

I-38

First Step: tert-butyl (S)-(1-(3,5-difluorophenyl)ethyl)carbamate (Compound I-38B)

I-38B

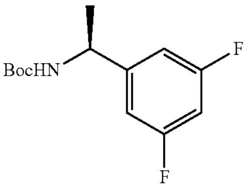

A compound (S)-1-(3, 5-difluorophenyl) ethan-1-amino-hydrochloride (2.0 g, 10.3 mmol) was added to dichloromethane (50 mL) at room temperature; di-tert-butyl dicarbonate (4.5 g, 20.7 mmol) and triethylamine (3.1 g, 31.0 mmol) were added. The mixture was stirred for 16 hours at room temperature; then the reaction mixture was concentrated, and the residue was separated and purified by a silica gel column (petroleum ether:ethyl acetate (V/V)=10:1) to obtain tert-butyl (S)-(1-(3,5-difluorophenyl)ethyl)carbamate (Compound I-38B) (2.2 g, 72% yield) as a white solid.

Second Step: (S)-4-(1-((tert-butoxycarbonyl)amino)ethyl)-2,6-difluorobenzoic Acid (Compound I-38C)

I-38C

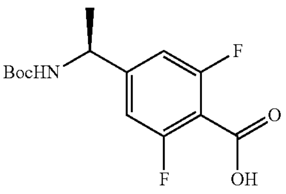

A compound (S)-tert-butyl (1-(3, 5-difluorophenyl)ethyl) carbamate (500 mg, 2.50 mmol) was added to tetrahydrofuran (10 mL) at room temperature. The mixture was cooled to −78° C., and added with 2.5 mol/L solution of butyllithium in THF (2.0 mL, 5.0 mmol). The mixture was stirred for 2 hours; carbon dioxide was introduced at low temperature. The mixture was warmed up naturally to room temperature and stirred for 16 hours; the pH was adjusted to 2 with 1N hydrochloric acid; and the mixture was diluted with water (50 mL), extracted with ethyl acetate (50 mL×3) and separated. The organic phases were combined, dried over anhydrous sodium sulfate, filtered and concentrated to obtain a white solid crude product of (S)-4-(1-((tert-butoxycarbonyl)amino)ethyl)-2,6-difluorobenzoic acid (Compound I-38C) (550 mg, yield 90%).

Third Step: methyl (S)-4-(1-aminoethyl)-2,6-difluorobenzoate (Compound I-38D)

I-38D

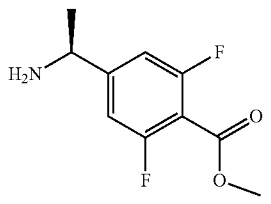

The starting material (S)-4-(1-((tert-butoxycarbonyl)amino)ethyl)-2,6-difluorobenzoic acid (Compound I-38C) (500 mg, 2.0 mmol) was added to methanol (100 mL) at room temperature and added with concentrated sulfuric acid (20 mL). The mixture was heated to 80° C. and stirred for 6 hours; and then the mixture was diluted by addition of water (100 mL), extracted with ethyl acetate (100 mL×3) and separated. The organic phases were combined and dried over anhydrous sodium sulfate, filtered and concentrated to obtain a white solid crude product of methyl (S)-4-(1-aminoethyl)-2,6-difluorobenzoate (Compound I-38D) (1.2 g, yield 100%).

Fourth Step: methyl (S)-4-(1-(3-(difluoromethyl)-1-methyl-5-(3-(trifluoromethyl)phenoxy)-1H-pyrazole-4-carboxamido)ethyl)-2,6-difluorobenzoate (Compound I-38E)

I-38E

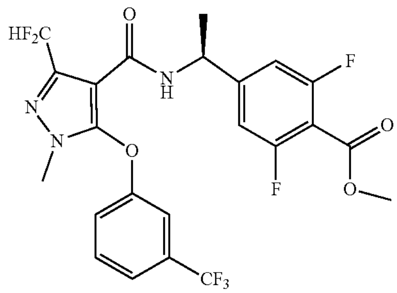

A compound 3-(difluoromethyl)-1-methyl-5-(3-(trifluoromethyl) phenoxy)-1H-pyrazole-4-carboxylic acid (100 mg, 0.30 mmol) was added to dichloromethane (8 mL) and N, N-dimethylformamide (2 mL) at room temperature; methyl (S)-4-(1-aminoethyl)-2,6-difluorobenzoate (Compound I-38D) (78 mg, 0.36 mmol) was added; and then O-(7-azabenzotriazol-1-yl)-N, N, N, N-tetramethyluronium hexafluorophosphate (171 mg, 0.45 mmol) and N, N-diisopropylethylamine (58 mg, 0.45 mmol) were added. The mixture was stirred for 16 hours at room temperature, and the mixture was diluted with water (50 mL), extracted with ethyl acetate (50 mL×3) and separated. The organic phases were combined, dried over anhydrous sodium sulfate, filtered and concentrated; the residue was separated and purified by a thin-layer silica gel plate (petroleum ether:ethyl acetate (V/V)=3:1) to obtain a white solid of methyl (S)-4-(1-(3-(difluoromethyl)-1-methyl-5-(3-(trifluoromethyl)phenoxy)-1H-pyrazole-4-carboxamido)ethyl)-2,6-difluorobenzoate (Compound I-38E) (82 mg, yield 52%).

LC-MS, M/Z (ESI): 534.3 $[M+H]^+$

Fifth Step: (S)-4-(1-(3-(difluoromethyl)-1-methyl-5-(3-(trifluoromethyl)phenoxy)-1H-pyrazole-4-carboxamido)ethyl)-2,6-difluorobenzoic Acid (Compound I-38)

I-38

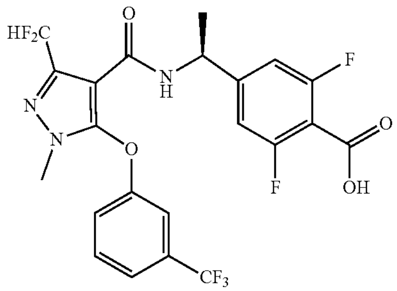

A starting material methyl (S)-4-(1-(3-(difluoromethyl)-1-methyl-5-(3-(trifluoromethyl)phenoxy)-1H-pyrazole-4-carboxamido)ethyl)-2,6-difluorobenzoate (82 mg, 0.15 mmol) was added to tetrahydrofuran (2 mL) and water (4 mL) at room temperature, and lithium hydroxide (18.9 mg, 0.45 mmol) was added. The mixture was stirred at room temperature for 16 hours; the pH was adjusted to 4 with 1N hydrochloric acid; and the reaction mixture was concentrated to prepare, by the acidic preparation method A, a white solid of (S)-4-(1-(3-(difluoromethyl)-1-methyl-5-(3-(trifluoromethyl)phenoxy)-1H-pyrazole-4-carboxamido)ethyl)-2,6-difluorobenzoic acid (Compound I-38) (16 mg, 20% yield).

$^1H$ NMR (400 mHz, DMSO-d6) δ 12.8 (s, 1H), 8.12 (d, 1H), 7.61 (t, 1H), 7.56 (t, 1H), 7.45 (s, 1H), 7.27 (t, 1H), 7.25 (t, 1H), 6.62 (d, 2H), 4.76 (t, 1H), 3.76 (s, 3H), 1.13 (d, 3H).

LC-MS, M/Z (ESI): 520.3 $[M+H]^+$

Example 39: Preparation of Compound I-39

(S)-4-(1-(3-(difluoromethyl)-5-(3-ethyl-4-fluorophenoxy)-1-methyl-1H-pyrazole-4-carboxamido)ethyl)-2-methylbenzoic Acid (Compound I-39)

I-39

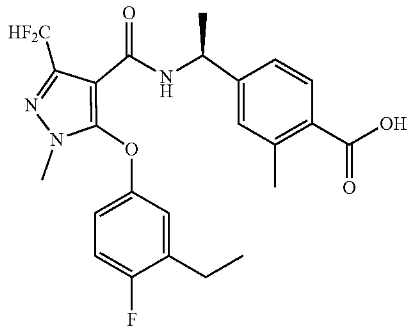

The synthesis scheme for Compound I-39 is shown below:

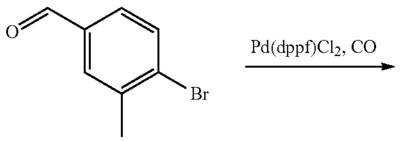

I-39A

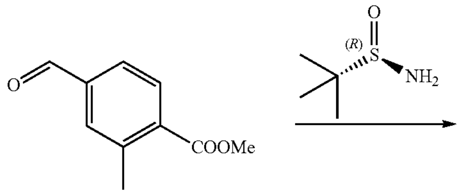

I-39B

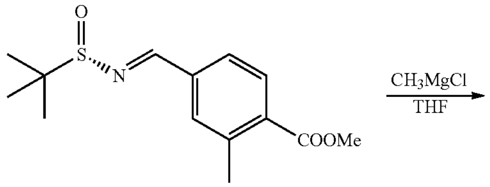

I-39C

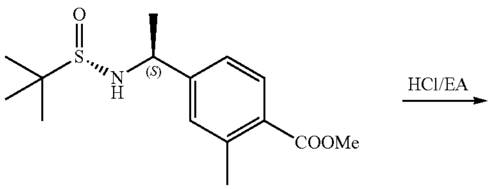

I-39D

-continued

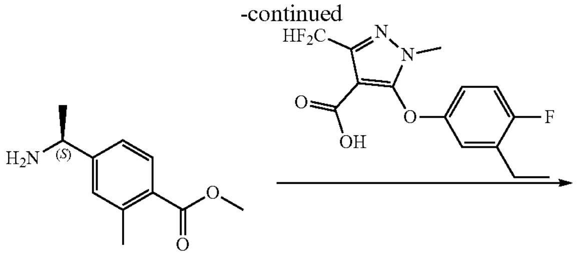

I-39E

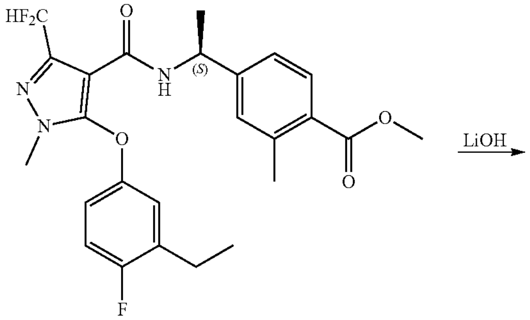

I-39F

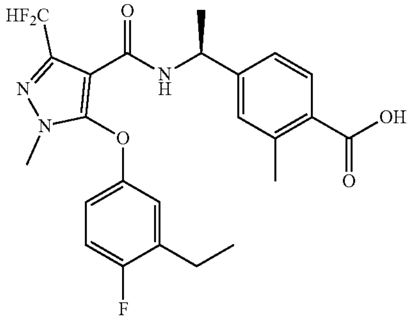

I-39

First Step: Synthesis of methyl 4-formyl-2-methylbenzoate (Compound I-39B)

I-39B

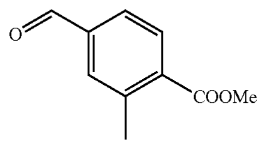

4-bromo-3-methylbenzaldehyde (Compound I-39A) (10.0 g, 50.2 mmol) and triethylamine (15.3 g, 151 mmol) were added to methanol (200 mL); and 1, 1-bis(diphenylphosphonium) ferrocene palladium chloride (2.94 g, 4.02 mmol) was added at room temperature. The mixture was replaced by carbon monoxide for 3 times, and then reacted for 15 hours at 65° C. under the pressure of 50 Psi; and then the mixture was cooled to room temperature and filtered through celite. The filter cake was washed with ethyl acetate 3 times and the filtrate was concentrated to obtain the crude product, which was separated and purified by a silica gel column (petroleum ether:ethyl acetate (V/V)=100: 1-5:1) to obtain the compound methyl 4-formyl-2-methylbenzoate (Compound I-39B) (8.0 g, yield 89%).

Second Step: Synthesis of methyl (S,E)-4-(((tert-butylsulfinyl)imino)methyl)-2-methylbenzoate (Compound I-39C)

I-39C

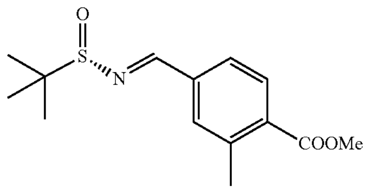

Methyl 4-formyl-2-methylbenzoate (Compound I-39B) (8.0 g, 44.9 mmol) and R-(+)-tert-butylsulfinamide (6.53 g, 53.9 mmol) and cesium carbonate (17.6 g, 53.9 mmol) were added to dichloromethane (200 mL). The mixture was reacted at 50° C. for 15 h, added with water (200 mL) and dichloromethane (200 mL), and the aqueous phase was extracted with dichloromethane (200 mL×3), combined and washed with brine (100 mL), dried over sodium sulfate, filtered, and spin-dried to obtain a crude product. The crude product was separated and purified by a silica gel column (petroleum ether:ethyl acetate (V/V)=100: 1-1:1) to obtain a compound methyl (S, E)-4-(((tert-butylsulfinyl)imino) methyl)-2-methylbenzoate (Compound I-39C) (10.0 g, 79% yield).

Third Step: Synthesis of methyl 4-((S)-1-(((S)-tert-butylsulfinyl)amino)ethyl)-2-methylbenzoate (Compound I-39D)

I-39D

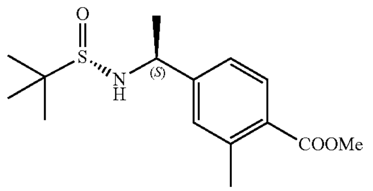

Methyl (S, E)-4-(((tert-butylsulfinyl)imino)methyl)-2-methylbenzoate (Compound I-39C) (1.0 g, 3.55 mmol) was added to tetrahydrofuran (20 mL); and the mixture was cooled to −10° C. Then, methyl magnesium chloride (7.1 mL, 21.3 mmol, 3 mol/L) was slowly added dropwise and reacted at room temperature for 15 hours; water (50 mL) and ethyl acetate (100 mL) were added to the reaction. The aqueous phase was extracted with ethyl acetate (100 mL×3); the combined extract liquor was washed with brine (100 mL), dried over sodium sulfate, filtered and spin-dried to obtain a crude product. The crude product was separated and purified by a silica gel column (petroleum ether:ethyl acetate (V/V)=20: 1-1:1) to obtain a compound methyl 4-((S)-1-(((S)-tert-butylsulfinyl)amino)ethyl)-2-methylbenzoate (Compound I-39D) (0.7 g, yield 66%).

Fourth Step: Synthesis of methyl (S)-4-(1-aminoethyl)-2-methylbenzoate (Compound I-39E)

I-39E

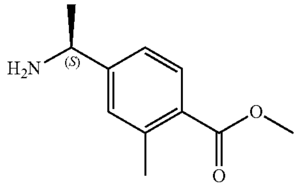

Methyl 4-((S)-1-(((S)-tert-butylsulfinyl)amino)ethyl)-2-methylbenzoate (Compound I-39D) (0.7 g, 2.35 mmol) was added to ethyl acetate (10 mL); a solution (10 mL) of ethyl acetate/hydrogen chloride was added at room temperature. The reaction mixture was reacted at room temperature for 2 hours, and was spin-dried to obtain methyl (S)-4-(1-aminoethyl)-2-methylbenzoate (Compound I-39E) (0.4 g, yield 88%).

Fifth Step: Synthesis of methyl (S)-4-(1-(3-(difluoromethyl)-5-(3-ethyl-4-fluorophenoxy)-1-methyl-1H-pyrazole-4-carboxamido)ethyl)-2-methylbenzoate (Compound I-39F)

I-39F

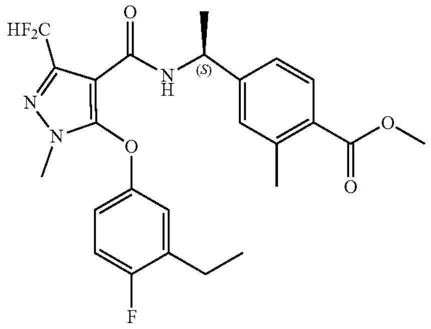

Methyl (S)-4-(1-aminoethyl)-2-methylbenzoate (Compound I-39E) (0.1 g, 0.52 mmol), O-(7-azabenzotriazol-1-yl)-N, N, N, N-tetramethyluronium hexafluorophosphate (0.24 g, 0.62 mmol), N, N-diisopropylethylamine (0.20 g, 1.55 mmol), and 3-(difluoromethyl)-5-(3-ethyl-4-fluorophenoxy)-1-methyl-1H-pyrazole-4-carboxylic acid (0.20 g, 0.62 mmol) were added to N, N-dimethylformamide (5 mL) and reacted at room temperature for 12 hours. Then, the reaction mixture was added with water (50 mL) and ethyl acetate (100 mL), and extracted with ethyl acetate (100 mL×4). The combined extract liquor was washed with brine (50 mL), dried over sodium sulfate, filtered, and spin-dried to obtain a crude product. The crude product was separated and purified by a silica gel column (petroleum ether:ethyl acetate (V/V)=20: 1-1:1) to obtain methyl (S)-4-(1-(3-(difluoromethyl)-5-(3-ethyl-4-fluorophenoxy)-1-methyl-1H-pyrazole-4-carboxamido)ethyl)-2-methylbenzoate (Compound I-39F) (0.15 g, yield 59%).

Sixth Step: Synthesis of (S)-4-(1-(3-(difluoromethyl)-5-(3-ethyl-4-fluorophenoxy)-1-methyl-1H-pyrazole-4-carboxamido)ethyl)-2-methylbenzoic Acid (Compound I-39)

I-39

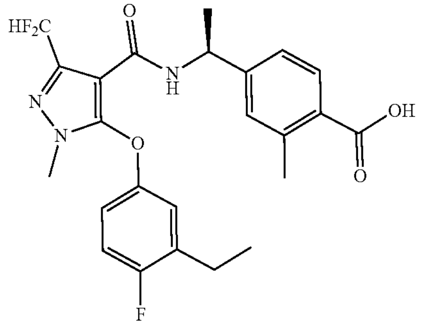

Methyl (S)-4-(1-(3-(difluoromethyl)-5-(3-ethyl-4-fluorophenoxy)-1-methyl-1H-pyrazole-4-carboxamido)ethyl)-2-methylbenzoate (Compound I-39F) (0.15 g, 0.31 mmol) was added to tetrahydrofuran (5 mL), methanol (5 mL) and water (1 mL), and lithium hydroxide (0.03 g, 1.23 mmol) was added at room temperature. The reaction mixture reacted at room temperature for 2 hours, then the mixture was spin-dried. The crude product was added with water (50 mL) and ethyl acetate (100 mL), then the pH was adjusted to 7 with 1N hydrochloric acid, and the mixture was extracted with ethyl acetate (100 mL×2). The organic layers were combined and washed with brine (50 mL), and the organic phase was dried over sodium sulfate and concentrated to obtain a crude product. The crude product was separated and purified by a silica gel column (petroleum ether:ethyl acetate (V/V)=1:1) to obtain a white solid of (S)-4-(1-(3-(difluoromethyl)-5-(3-ethyl-4-fluorophenoxy)-1-methyl-1H-pyrazole-4-carboxamido)ethyl)-2-methylbenzoic acid (Compound I-39) (83 mg, 57% yield).

$^1$H NMR (400 MHz, DMSO) δ 7.94 (d, J=7.6 Hz, 1H), 7.59 (d, J=8.0 Hz, 1H), 7.10 (dd, J=7.6, 6.4 Hz, 2H), 6.99-6.94 (m, 2H), 6.89 (d, J=8.2 Hz, 1H), 6.80-6.75 (m, 1H), 4.84-4.79 (m, 1H), 3.69 (s, 3H), 2.36 (s, 3H), 2.53 (dd, J=14.8, 7.4 Hz, 2H) 1.19 (d, J=7.0 Hz, 3H), 1.06 (t, J=7.6 Hz, 3H).

LC-MS, M/Z (ESI): 476.3 $[M+H]^+$

Example 40: Preparation of Compound I-40

4-(1-(3-(difluoromethyl)-1-methyl-5-(3-(trifluoromethyl)phenoxy)-1H-pyrazole-4-carboxamido)cyclobutyl)benzoic Acid (Compound I-40)

I-40

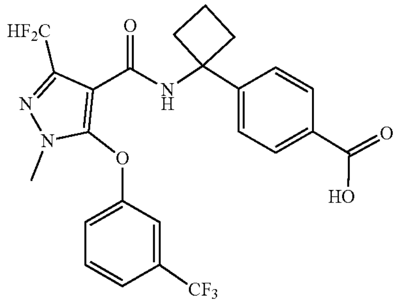

The synthesis scheme for Compound I-40 is shown below:

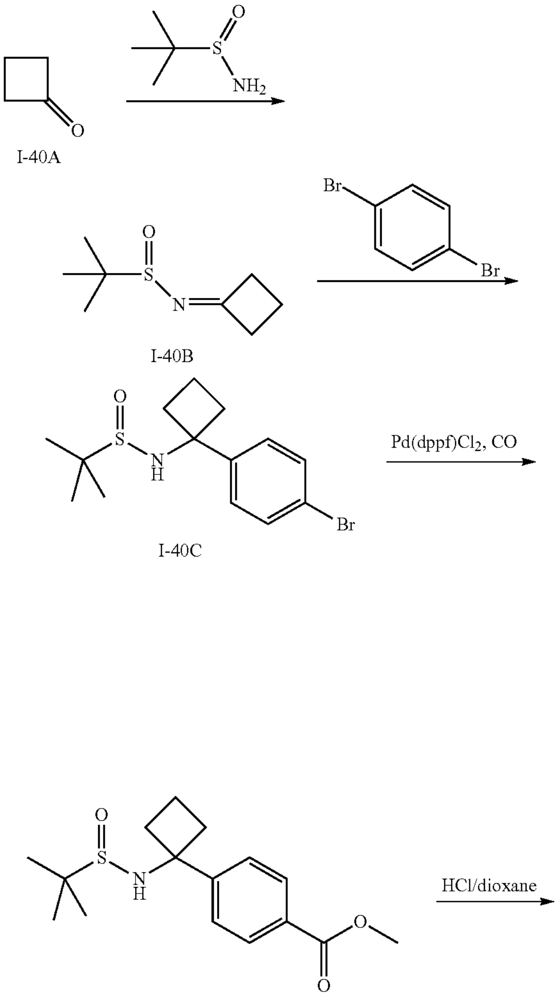

I-40A

I-40B

I-40C

I-40D

-continued

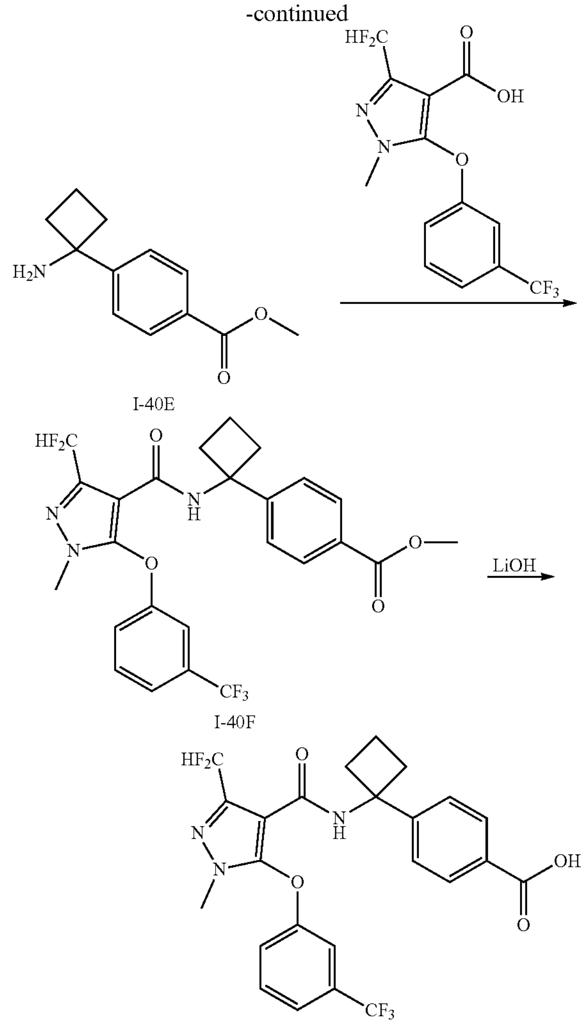

I-40E

I-40F

I-40

First Step: N-cyclobutylidene-2-methylpropane-2-sulfinamide (Compound I-40B)

I-40B

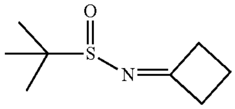

The compound cyclobutanone (5.0 g, 71.4 mmol) was added to dichloromethane (100 mL) at room temperature; tert-butylsulfinamide (10.3 g, 85.6 mmol) and tetraethyl titanate (32.6 g, 143 mmol) were added; and the mixture was heated to 40° C. and stirred for 24 hours. The mixture was cooled to room temperature and added with water (150 mL), and the mixture was extracted with ethyl acetate (100 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a light yellow liquid of N-cyclobutylidene-2-methylpropane-2-sulfinamide (Compound I-40B) (6.5 g, yield 53%).

Second Step: N-(1-(4-bromophenyl)cyclobutyl)-2-methylpropane-2-sulfinamide (Compound I-40C)

I-40C

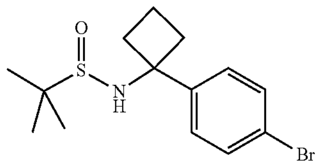

The compound 1, 4-dibromobenzene (14.0 g, 59.8 mmol) was added to tetrahydrofuran (150 mL) at room temperature; the mixture was cooled to −78° C.; and a 2.5 mol/L solution of butyllithium tetrahydrofuran (24.0 mL, 60.0 mmol) was added. The mixture was stirred for 40 min, and then a solution of N-cyclobutylidene-2-methylpropane-2-sulfinamide (Compound I-40B) (7.0 g, 40.4 mmol) in tetrahydrofuran (150 mL) was added dropwise under nitrogen protection. Then, the mixture was naturally warmed to room temperature and stirred for 2.5 hours, and then diluted with saturated aqueous ammonium chloride (200 mL), extracted with ethyl acetate (200 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a yellow solid of N-(1-(4-bromophenyl)cyclobutyl)-2-methylpropane-2-sulfinamide (Compound I-40C) (1.8 g, yield 64%).

LC-MS, M/Z (ESI): 330.0 $[M+H]^+$

Third Step: methyl 4-(1-((tert-butylsulfinyl)amino)cyclobutyl)benzoate (Compound I-40D)

I-40D

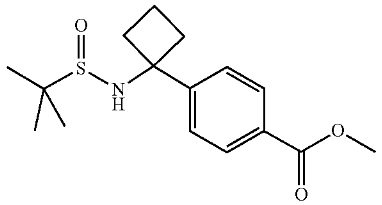

The starting material N-(1-(4-bromophenyl)cyclobutyl)-2-methylpropane-2-sulfinamide (Compound I-40C) (1.80 g, 5.47 mmol) was added to methanol (30 mL) at room temperature; triethylamine (2.76 g, 27.4 mmol) and 1, 1'-bisdiphenylphosphinoferrocene palladium dichloride (450 mg, 0.55 mmol) were added, and carbon monoxide was charged. The mixture was heated to 85° C. and stirred for 24 hours. The mixture was diluted with water (50 mL), extracted with ethyl acetate (50 mL×3) and separated. The organic phases were combined, dried over anhydrous sodium sulfate, filtered and concentrated, and the residue was separated and purified on thin-layer silica gel plate (dichloromethane: methanol (V/V)=10:1) to obtain a yellow liquid of methyl 4-(1-((tert-butylsulfinyl)amino)cyclobutyl)benzoate (Compound I-40D) (1.30 g, 77% yield).

Fourth Step: methyl 4-(1-aminocyclobutyl)benzoate (Compound I-40E)

I-40E

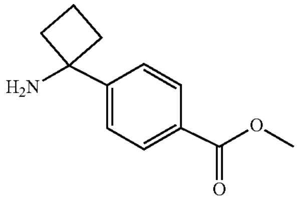

The compound methyl 4-(1-((tert-butylsulfinyl)amino) cyclobutyl)benzoate (Compound I-40D) (600 mg, 1.94 mmol) was added to dichloromethane (10 mL), and a 4 mol/L solution of hydrochloric acid in dioxane (2.0 mL, 8.0 mmol) was added; the mixture was stirred at room temperature for 4 hours; a saturated solution of sodium bicarbonate (30 mL) was added, and the mixture was extracted with dichloromethane (30 mL×3) and separated. The organic phases were combined, dried over anhydrous sodium sulfate, filtered, concentrated and separated to obtain a colorless liquid crude product of methyl 4-(1-aminocyclobutyl) benzoate (Compound I-40E) (350 mg, yield 88%).

LC-MS, M/Z (ESI): 206.5 [M+H]$^+$

Fifth Step: methyl 4-(1-(3-(difluoromethyl)-1-methyl-5-(3-(trifluoromethyl)phenoxy)-1H-pyrazole-4-carboxamido)cyclobutyl)benzoate (Compound I-40F)

I-40F

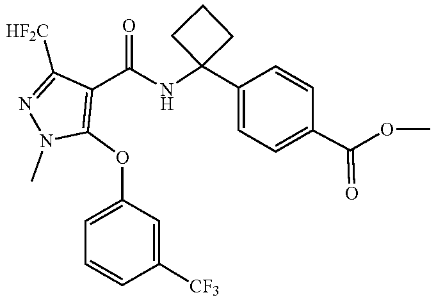

The compound 3-(difluoromethyl)-1-methyl-5-(3-(trifluoromethyl) phenoxy)-1H-pyrazole-4-carboxylic acid (100 mg, 0.30 mmol) was added to N, N-dimethylformamide (3 mL); methyl 4-(1-aminocyclobutyl)benzoate (Compound I-40E) (74 mg, 0.36 mmol), and O-(7-azabenzotriazol-1-yl)-N, N, N, N-tetramethyluronium hexafluorophosphate (125 mg, 0.33 mmol) and N, N-diisopropylethylamine (85 mg, 0.66 mmol) were added at room temperature. The mixture was stirred for 16 hours at room temperature; and the mixture was diluted by addition of water (10 mL), extracted with ethyl acetate (10 mL×3) and separated. The organic phases were combined, dried over anhydrous sodium sulfate, filtered and concentrated, and the residue was separated and purified on a thin-layer silica gel plate (petroleum ether:ethyl acetate (V/V)=1:1) to obtain a white solid of methyl 4-(1-(3-(difluoromethyl)-1-methyl-5-(3-(trifluoromethyl)phenoxy)-1H-pyrazole-4-carboxamido)cyclobutyl) benzoate (Compound I-40F) (60 mg, yield 39%).

LC-MS, M/Z (ESI): 524.5 [M+H]$^+$

Sixth Step: 4-(1-(3-(difluoromethyl)-1-methyl-5-(3-(trifluoromethyl)phenoxy)-1H-pyrazole-4-carboxamido)cyclobutyl)benzoic Acid (Compound I-40)

I-40

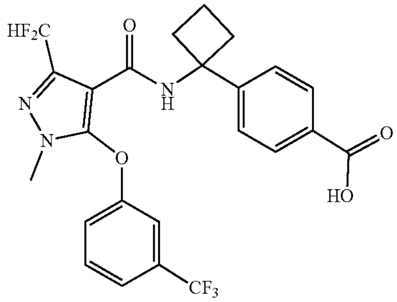

A starting material methyl 4-(1-(3-(difluoromethyl)-1-methyl-5-(3-(trifluoromethyl)phenoxy)-1H-pyrazole-4-carboxamido)cyclobutyl)benzoate (Compound I-40F) (60 mg, 0.12 mmol) was added to tetrahydrofuran (1 mL), methanol (1 mL) and water (1 mL) at room temperature; and lithium hydroxide (20 mg, 0.47 mmol) was added. The mixture was stirred at room temperature for 16 hours; the pH was adjusted to 2 with 1N hydrochloric acid; and the reaction mixture was concentrated to prepare, by the acidic preparation method A, a white solid of 4-(1-(3-(difluoromethyl)-1-methyl-5-(3-(trifluoromethyl)phenoxy)-1H-pyrazole-4-carboxamido)cyclobutyl)benzoic acid (Compound I-40) (16 mg, yield 27%).

$^1$H NMR (400 mHz, DMSO-d6) δ 12.7 (s, 1H), 8.52 (s, 1H), 7.74 (d, 2H), 7.68 (d, 1H), 7.62 (d, 1H), 7.50 (s, 1H), 7.34 (t, 1H), 7.25 (d, 2H), 7.18 (t, 1H), 3.78 (s, 3H), 2.33-2.28 (m, 2H), 2.16-2.13 (m, 2H), 1.70-1.65 (m, 1H), 1.59-1.54 (m, 1H).

LC-MS, M/Z (ESI): 510.5 [M+H]$^+$

Example 41: Preparation of Compound I-41

(S)-4-(1-(3-(difluoromethyl)-1-methyl-5-((5-methylthiophen-3-yl)oxy)-1H-pyrazole-4-carboxamido) ethyl)benzoic Acid (Compound I-41)

I-41

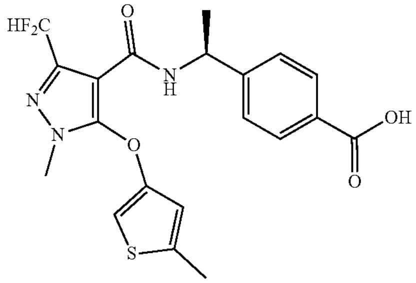

The synthesis scheme for Compound I-41 is shown below:

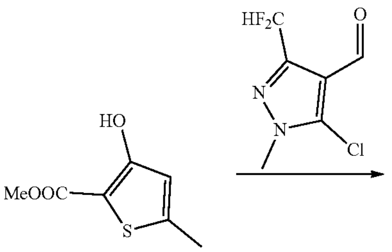

I-41A

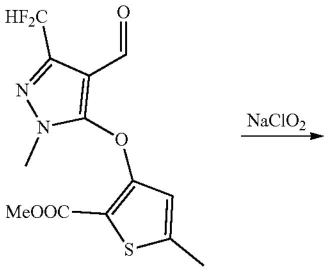

I-41B

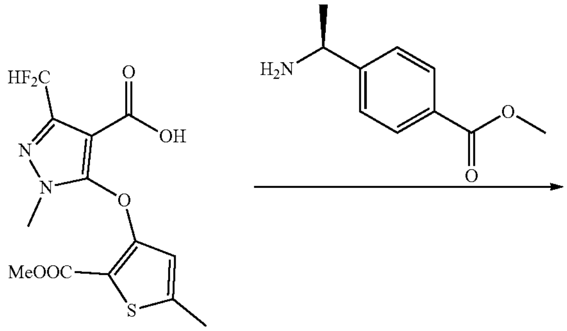

I-41C

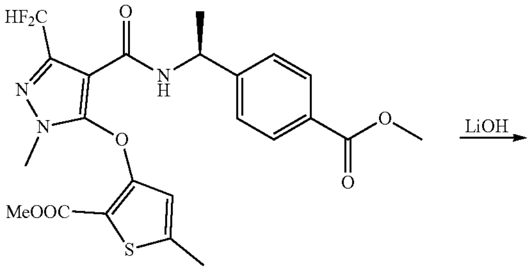

I-41D

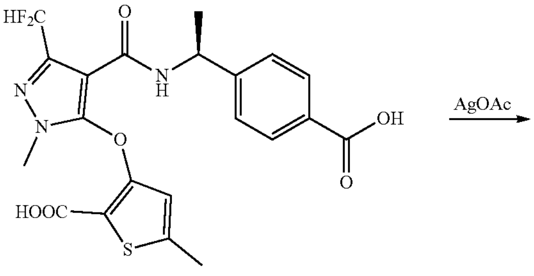

I-41E

-continued

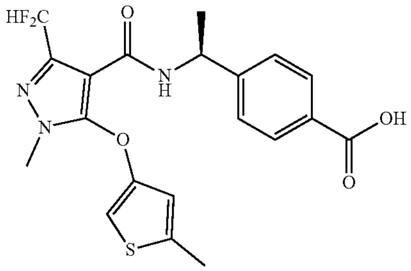

I-41

First Step: methyl 3-((3-(difluoromethyl)-4-formyl-1-methyl-1H-pyrazol-5-yl)oxy)-5-methylthiophene-2-carboxylate (Compound I-41B)

I-41B

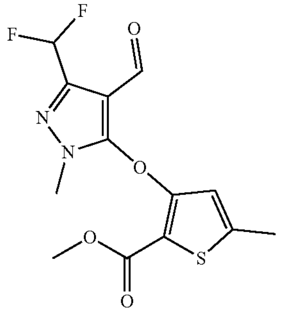

The compound 5-chloro-3-(difluoromethyl)-1-methyl-1H-pyrazole-4-carbaldehyde (120 mg, 0.62 mmol) was added to N, N-dimethylformamide (5 mL); methyl 3-hydroxy-5-methylthiophene-2-carboxylate (143 mg, 0.74 mmol), cesium carbonate (403 mg, 1.24 mmol), cuprous iodide (24.0 mg, 0.12 mmol) and 1, 10-phenanthroline (45.0 mg, 0.25 mmol) were added at room temperature and heated to 130° C. in the microwave and stirred for 1 h; then the mixture was cooled to room temperature, diluted with water (20 mL), extracted with ethyl acetate (15 mL×3) and separated. The organic phases were combined and dried over anhydrous sodium sulfate, filtered and concentrated, and the residue was separated and purified by a silica gel column (petroleum ether:ethyl acetate (V/V)=3:1) to obtain a colorless liquid of methyl 3-((3-(difluoromethyl)-4-formyl-1-methyl-1H-pyrazol-5-yl)oxy)-5-methylthiophene-2-carboxylate (Compound I-41B) (32.0 mg, yield 16%).

LC-MS, M/Z (ESI): 331.4 (M+1).

Second Step: 3-(difluoromethyl)-5-((2-(methoxycarbonyl)-5-methylthiophen-3-yl)oxy)-1-methyl-1H-pyrazole-4-carboxylic Acid (Compound I-41C)

I-41C

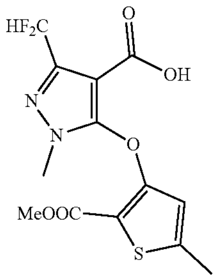

The compound methyl 3-((3-(difluoromethyl)-4-formyl-1-methyl-1H-pyrazol-5-yl)oxy)-5-methylthiophene-2-carboxylate (Compound I-41B) (30.0 mg, 0.09 mmol) was added to tert-butanol (6 mL) and water (3 mL) at room temperature; 2-methyl-2-butene (18.9 mg, 0.27 mmol), sodium chlorite (24.0 mg, 0.27 mmol), and sodium dihydrogen phosphate (27.0 mg, 2.34 mmol) were added. The mixture was stirred for 16 hours at room temperature; and then the mixture was diluted with water (5 mL), extracted with ethyl acetate (10 mL×3) and separated. The organic phases were combined and dried over anhydrous sodium sulfate, filtered, and concentrated to obtain a white solid of 3-(difluoromethyl)-5-((2-(methoxycarbonyl)-5-methylthiophen-3-yl)oxy)-1-methyl-1H-pyrazole-4-carboxylic acid (Compound I-41C) (32.0 mg, yield 100%).

LC-MS, M/Z (ESI): 347.4 (M+1)

Third Step: methyl (S)-3-((3-(difluoromethyl)-4-((1-(4-(methoxycarbonyl)phenyl)ethyl)carbamoyl)-1-methyl-1H-pyrazol-5-yl)oxy)-5-methylthiophene-2-carboxylate (Compound I-41D)

I-41D

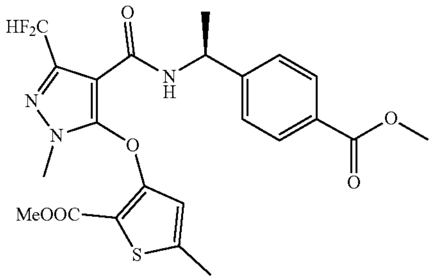

The compound 3-(difluoromethyl)-5-(3-ethyl-4-fluorophenoxy)-1-methyl-1H-pyrazole-4-carboxylic acid (24.0 mg, 0.07 mmol) was added to dichloromethane (5 mL); (S)-methyl 4-(1-aminoethyl) benzoate (15.0 mg, 0.08 mmol), O-(7-azabenzotriazol-1-yl)-N, N, N, N-Tetramethyluronium hexafluorophosphate (40.0 mg, 0.10 mmol) and N, N-diisopropylethylamine (14.0 mg, 0.10 mmol) were added; and the mixture was stirred at room temperature for 16 hours, diluted with water (20 mL), extracted with ethyl acetate (10 mL×3) and separated. The organic phases were combined, dried over anhydrous sodium sulfate, filtered, concentrated, and the residue purified by silica gel column separation (petroleum ether:ethyl acetate (V/V)=3:1) to obtain a colorless liquid of methyl (S)-3-((3-(difluoromethyl)-4-((1-(4-(methoxycarbonyl)phenyl)ethyl)carbamoyl)-1-methyl-1H-pyrazol-5-yl)oxy)-5-methylthiophene-2-carboxylate (Compound I-41D) (25.0 mg, yield 71.0%).

LC-MS, M/Z (ESI): 508.6 (M+1).

Fourth Step: (S)-3-((4-((1-(4-carboxyphenyl)ethyl)carbamoyl)-3-(difluoromethyl)-1-methyl-1H-pyrazol-5-yl)oxy)-5-methylthiophene-2-carboxylic Acid (Compound I-41E)

I-41E

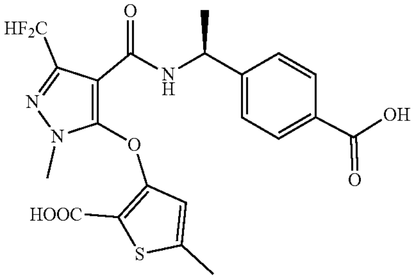

The starting material methyl (S)-3-((3-(difluoromethyl)-4-((1-(4-(methoxycarbonyl)phenyl)ethyl)carbamoyl)-1-methyl-1H-pyrazol-5-yl)oxy)-5-methylthiophene-2-carboxylate (38.0 mg, 0.08 mmol) was added to tetrahydrofuran (5 mL) and water (3 mL) at room temperature, and lithium hydroxide (10.0 mg, 0.22 mmol) was added. The mixture was stirred at room temperature for 3 hours; the pH was adjusted to 6 with 1N hydrochloric acid; and the mixture was extracted with ethyl acetate (10 mL×3) and separated. The organic phases were combined and dried over anhydrous sodium sulfate, filtered and concentrated to obtain a white solid crude product of (S)-3-((4-((1-(4-carboxyphenyl)ethyl)carbamoyl)-3-(difluoromethyl)-1-methyl-1H-pyrazol-5-yl)oxy)-5-methylthiophene-2-carboxylic acid (Compound I-41E) (33.0 mg, yield 92%).

LC-MS, M/Z (ESI): 480.3 (M+1)

Fifth Step: (S)-4-(1-(3-(difluoromethyl)-1-methyl-5-((5-methylthiophen-3-yl)oxy)-1H-pyrazole-4-carboxamido)ethyl)benzoic Acid (Compound I-41)

I-41

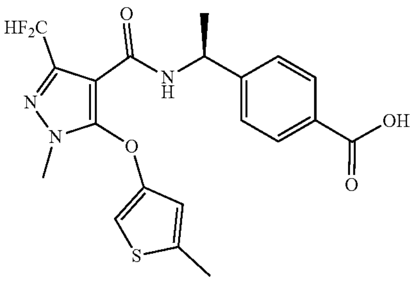

The starting material (S)-3-((4-((1-(4-carboxyphenyl)ethyl)carbamoyl)-3-(difluoromethyl)-1-methyl-1H-pyrazol-5-yl)oxy)-5-methylthiophene-2-carboxylic acid (30.0 mg, 0.06 mmol) was added to N-methylpyrrolidone (6 mL) at room temperature; silver acetate (10.2 mg, 0.06 mmol) was added; and the mixture was heated to 100° C. under nitrogen protection and stirred for 0.5 hour. The reaction mixture was filtered to prepare, via the Acidic Preparation Method A, a white solid of (S)-4-(1-(3-(difluoromethyl)-1-methyl-5-((5-methylthiophen-3-yl)oxy)-1H-pyrazole-4-carboxamido)ethyl)benzoic acid (Compound I-41) (6.7 mg, 25% yield).

$^1$H NMR (400 m Hz, $CDCl_3$) δ 12.8 (s, 1H), 7.99 (d, 2H), 7.20 (t, 1H), 7.20 (d, 2H), 6.51 (s, 1H), 6.39 (d, 1H), 6.20 (s, 1H), 5.22 (t, 1H), 3.75 (s, 3H), 2.45 (s, 3H), 1.43 (d, 3H).

LC-MS, M/Z (ESI): 436.1 (M+1)

Example 42: Preparation of Compound I-42

(S)-4-(1-(3-(difluoromethyl)-1-methyl-5-((5-(trifluoromethyl)thiophen-3-yl)oxy)-1H-pyrazole-4-carboxamido)ethyl)benzoic Acid (Compound I-42)

I-42

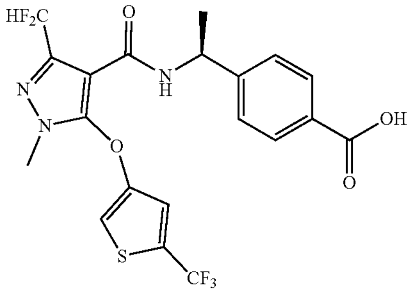

The synthesis scheme for Compound I-42 is shown below:

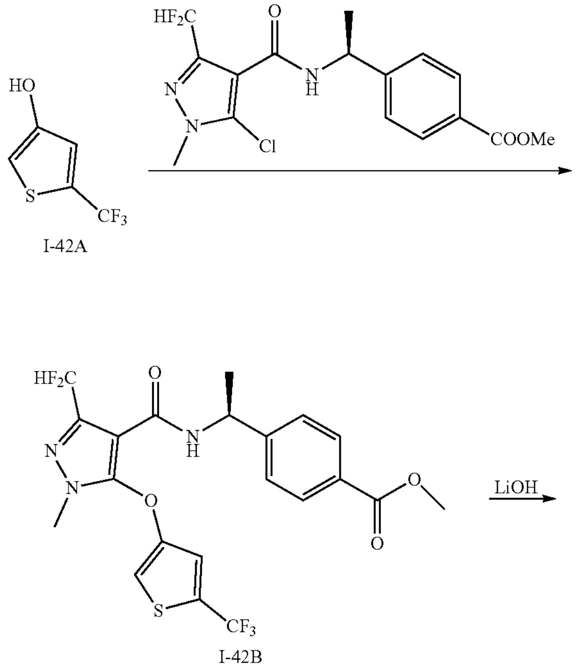

I-42A

I-42B

-continued

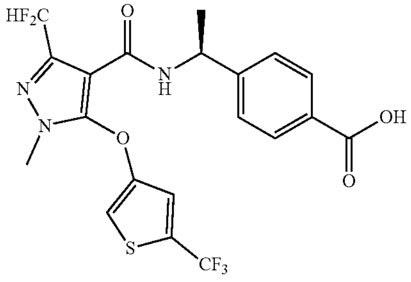

I-42

First Step: methyl (S)-4-(1-(3-(difluoromethyl)-1-methyl-5-((5-(trifluoromethyl)thiophen-3-yl)oxy)-1H-pyrazole-4-carboxamido)ethyl)benzoate (Compound I-42B)

I-42B

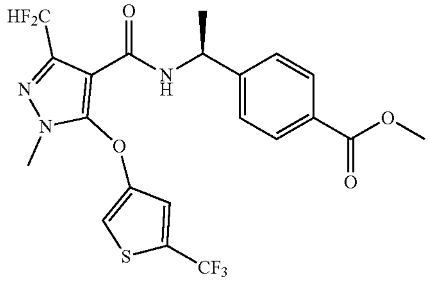

The compound methyl (S)-4-(1-(5-chloro-3-(difluoromethyl)-1-methyl-1H-pyrazole-4-carboxamido)ethyl)benzoat (Intermediate A) (1.0 g, 2.69 mmol) was added to dimethyl sulfoxide (5 mL); 5-(trifluoromethyl) thiophen-3-ol (908 mg, 5.40 mmol), potassium carbonate (1.13 g, 8.18 mmol), cuprous iodide (206 mg, 1.08 mmol), and 1, 10-phenanthroline (388 mg, 2.16 mmol) were added at room temperature; and the mixture was heated to 120° C. in the microwave and stirred for 4 hours. Then, the mixture was cooled to room temperature, diluted with water (20 mL), extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=1:3) to obtain a white solid of methyl (S)-4-(1-(3-(difluoromethyl)-1-methyl-5-((5-(trifluoromethyl)thiophen-3-yl)oxy)-1H-pyrazole-4-carboxamido)ethyl)benzoate (Compound I-42B) (980 mg, yield 72%).

LC-MS, M/Z (ESI): 504.2 (M+1)

Second Step: (S)-4-(1-(3-(difluoromethyl)-1-methyl-5-((5-(trifluoromethyl)thiophen-3-yl)oxy)-1H-pyrazole-4-carboxamido)ethyl)benzoic Acid (Compound I-42)

I-42

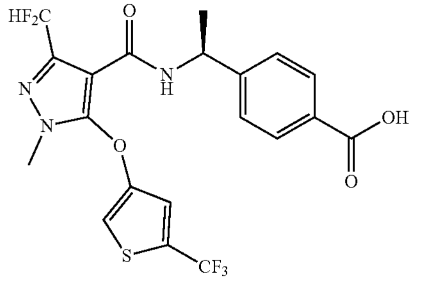

The starting material methyl (S)-4-(1-(3-(difluoromethyl)-1-methyl-5-((5-(trifluoromethyl)thiophen-3-yl)oxy)-1H-pyrazole-4-carboxamido)ethyl)benzoate (Compound I-42B) (980 mg, 1.89 mmol) was added to tetrahydrofuran (5 mL); water (3 mL) and lithium hydroxide (238 mg, 5.67 mmol) were added at room temperature; and the mixture was stirred for 3 hours at room temperature. Then, the reaction mixture was concentrated to prepare, via the acidic preparation method A, a white solid of (S)-4-(1-(3-(difluoromethyl)-1-methyl-5-((5-(trifluoromethyl)thiophen-3-yl)oxy)-1H-pyrazole-4-carboxamido)ethyl)benzoic acid (Compound I-42) (345 mg, 36% yield).

$^1$H NMR (400 m Hz, DMSO-d6) δ 12.8 (s, 1H), 8.20 (d, 1H), 7.79 (d, 2H), 7.67 (s, 1H), 7.25 (d, 2H), 7.23 (d, 1H), 7.09 (t, 1H), 4.99-4.92 (m, 1H), 3.77 (s, 3H), 1.29 (d, 3H).

LC-MS, M/Z (ESI): 490.2 (M+1)

Example 43: Preparation of Compound I-43

(S)-4-(1-(1-methyl-3-(trifluoromethyl)-5-((5-(trifluoromethyl)thiophen-3-yl)oxy)-1H-pyrazole-4-carboxamido)ethyl)benzoic Acid (Compound I-43)

I-43

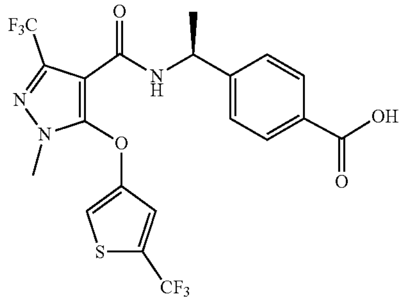

The synthesis scheme for Compound I-43 is shown below:

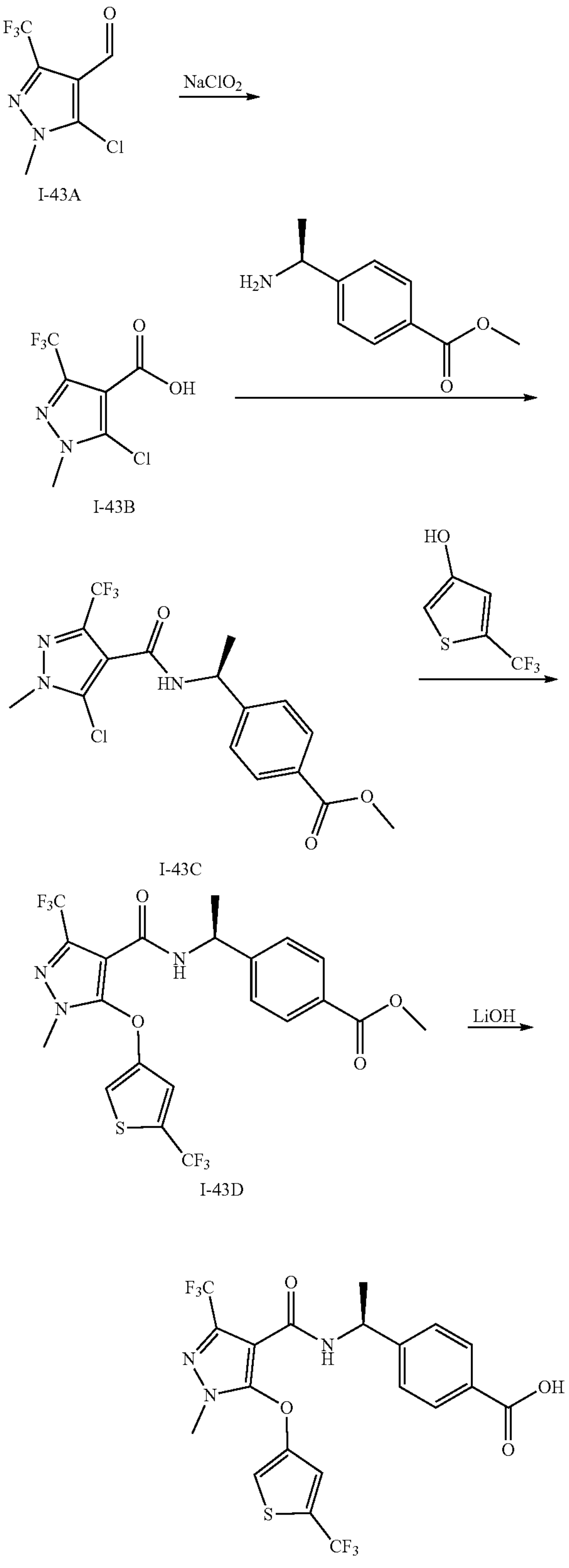

I-43A

I-43B

I-43C

I-43D

I-43

First Step: 5-chloro-1-methyl-3-(trifluoromethyl)-1H-pyrazole-4-carboxylic Acid (Compound I-43B)

I-43B

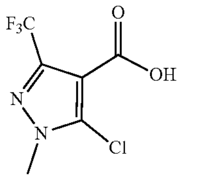

The compound 5-chloro-1-methyl-3-(trifluoromethyl)-1H-pyrazole-4-carbaldehyde (700 mg, 3.30 mmol) was added to tert-butanol (20 mL) and water (5 mL) at room temperature; 2-methyl-2-butene (1.80 g, 25.7 mmol), sodium chlorite (1.48 g, 16.4 mmol) and sodium dihydrogen phosphate (3.10 g, 25.8 mmol) were added. The mixture was stirred for 14 hours at room temperature; and then the mixture was diluted with water (50 mL), extracted with ethyl acetate (30 mL×3) and separated. The organic phases were combined and dried over anhydrous sodium sulfate, filtered and concentrated, and the residue was separated and purified by a silica gel column (petroleum ether:ethyl acetate (V/V)=1:1) to obtain a colorless solid crude product of 5-chloro-1-methyl-3-(trifluoromethyl)-1H-pyrazole-4-carboxylic acid (Compound I-43B) (680 mg, yield 90%).

LC-MS, M/Z (ESI): 229.6 (M+1).

Second Step: methyl (S)-4-(1-(5-chloro-1-methyl-3-(trifluoromethyl)-1H-pyrazole-4-carboxamido)ethyl) benzoate (Compound I-43C)

I-43C

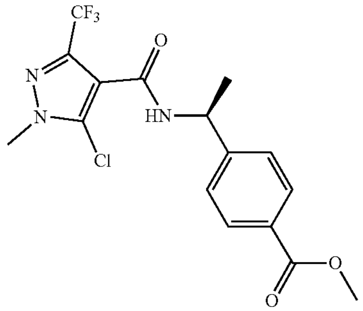

The compound 5-chloro-1-methyl-3-(trifluoromethyl)-1H-pyrazole-4-carboxylic acid (Compound I-43B) (680 mg, 2.98 mmol) was added to N, N-dimethylformamide (20 mL); methyl (S)-4-(1-aminoethyl) benzoate (537 mg, 3.00 mmol), O-(7-azabenzotriazol-1-yl)-N, N, N, N-tetramethyluronium hexafluorophosphate (1.70 g, 4.47 mmol) and N, N-diisopropylethylamine (1.90 g, 14.7 mmol) were added and stirred at room temperature for 16 hours; the mixture was diluted with water (200 mL), extracted with ethyl acetate (30 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a colorless solid of methyl (S)-4-(1-(5-chloro-1-methyl-3-(trifluoromethyl)-1H-pyrazole-4-carboxamido) ethyl)benzoate (Compound I-43C) (700 mg, yield 60%).

LC-MS, M/Z (ESI): 390.5 (M+1).

Third Step: methyl (S)-4-(1-(1-methyl-3-(trifluoromethyl)-5-((5-(trifluoromethyl)thiophen-3-yl)oxy)-1H-pyrazole-4-carboxamido)ethyl)benzoate (Compound I-43D)

I-43D

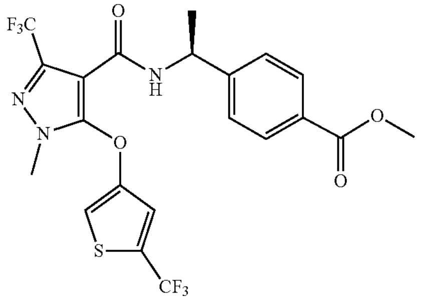

The compound methyl (S)-4-(1-(5-chloro-1-methyl-3-(trifluoromethyl)-1H-pyrazole-4-carboxamido)ethyl)benzoate (500 mg, 1.3 mmol) was added to dimethyl sulfoxide (10 mL); 5-(trifluoromethyl) thiophen-3-ol (216 mg, 1.3 mmol), potassium carbonate (360 mg, 2.6 mmol), cuprous iodide (100 mg, 0.5 mmol) and 1, 10-phenanthroline (100 mg, 0.5 mmol) were added at room temperature; and the mixture was heated to 95° C. in the microwave and stirred for 5 hours. Then, the mixture was cooled to room temperature, diluted with water (50 mL), extracted with ethyl acetate (20 mL×3) and separated. The organic phases were combined, dried over anhydrous sodium sulfate, filtered and concentrated, and the residue was separated and purified by a silica gel column (petroleum ether:ethyl acetate (V/V)=1:1) to obtain a yellow solid of methyl (S)-4-(1-(1-methyl-3-(trifluoromethyl)-5-((5-(trifluoromethyl)thiophen-3-yl)oxy)-1H-pyrazole-4-carboxamido)ethyl)benzoate (Compound I-43D) (200 mg, yield 30%).

LC-MS, M/Z (ESI): 522.1 (M+1).

Fourth Step: (S)-4-(1-(1-methyl-3-(trifluoromethyl)-5-((5-(trifluoromethyl)thiophen-3-yl)oxy)-1H-pyrazole-4-carboxamido)ethyl)benzoic Acid (Compound I-43)

I-43

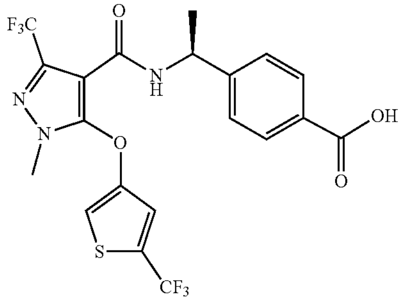

The starting material methyl (S)-4-(1-(1-methyl-3-(trifluoromethyl)-5-((5-(trifluoromethyl)thiophen-3-yl)oxy)-1H-pyrazole-4-carboxamido)ethyl)benzoate (Compound I-43D) (100 mg, 0.19 mmol) was added to tetrahydrofuran (30 mL); water (10 mL) and lithium hydroxide (24 mg, 0.57 mmol) were added at room temperature; and the mixture was heated to 50° C. and stirred for 2 hours. The reaction mixture was concentrated to prepare, by the acidic preparation method A, a yellow solid of (S)-4-(1-(1-methyl-3-(trifluoromethyl)-5-((5-(trifluoromethyl)thiophen-3-yl)oxy)-1H-pyrazole-4-carboxamido)ethyl)benzoic acid (Compound I-43) (54 mg, 56% yield).

$^1$H NMR (400 mHz, DMSO-d6) δ 12.8 (s, 1H), 8.64 (d, 1H), 7.80 (d, 2H), 7.68 (s, 1H), 7.31 (d, 1H), 7.24 (d, 2H), 4.92 (t, 1H), 3.80 (s, 3H), 1.26 (d, 3H).

LC-MS, M/Z (ESI): 508.1 (M+1)

Assay Examples for Biological Activity and Related Properties

Assay Example 1: Assay for EP4 Antagonistic Effect

The control compound and the compounds prepared by Examples 1 to 43 were tested separately for antagonistic effect of EP4, and the assay was performed in a CHO stable cell line, which highly expresses the human EP4 receptor.

After trypsinization, cells were resuspended in a buffer (1×HBSS, 0.1% BSA, 20 mM HEPES, and 500 μM IBMX) and 8000 cells were seeded per well in 384-well plates in a seeding volume of 15 μL. A working solution the compound with a 8× concentration was prepared with an experimental buffer, and then 2.5 μL of the working solution of the compound with 8× concentration was added to the 384-well plate, respectively, and incubated at 37° C. for 30 min. An agonist $PGE_2$ working solution with 8× concentration of (4 nM) was prepared with the experimental buffer and 2.5 μL per well was added to the 384-well plate (the final $PGE_2$ concentration was 0.5 nM) and incubated at 37° C. for 30 min. After the reaction was completed, the amount of cAMP in the cells was quantified according to the method in the instructions of the cAMP test kit (Perkin Elmer, Cat #TRF0263). The antagonistic effects ($IC_{50}$ value) were calculated for the test compounds.

TABLE 1

Antagonistic effects on EP4 by test compounds

| Test compounds | $IC_{50}$ (nM) |
|---|---|
| Control Compound | 44 |
| Compound I-1 | 3.7 |
| Compound I-2 | 1.9 |
| Compound I-3 | 2.8 |
| Compound I-5 | 2.2 |
| Compound I-6 | 8.2 |
| Compound I-9 | 29 |
| Compound I-28 | 5.7 |
| Compound I-29 | 14 |
| Compound I-30 | 12 |
| Compound I-35 | 6.6 |
| Compound I-42 | 8.6 |

Experimental results indicate that the compounds of the present application have a good antagonistic effect on EP4; compared with the control compound, the antagonistic effect of most of compounds is more than 5 times that of the control compound; and the compounds of the present disclosure exhibit a better antagonistic effect on the EP4 receptor.

Assay Example 2: Assay of Calcium Current Inhibition on EP4 Receptor

The control compound and the compounds prepared in Examples 1 to 43 were respectively tested for their inhibitory effect on EP4 calcium current, and the assay was performed on the 293 cells, which overexpress the human EP4 receptor.

The cells were rapidly thawed in a 37° C. water bath, centrifuged, resuspended, and counted. The cell suspensions were seeded at 20 μL/well in two 384-well plates (20,000 cells/well) and placed in an incubator (a 37° C., 5% $CO_2$) overnight. Preparation of a 2× Fluo-4 Direct™ (Invitrogen, Cat #F10471) loading buffer: 77 mg of probenecid was added to 1 mL of a FLIPR buffer, with a concentration of 250 mM. 10 mL of FLIPR buffer and 0.2 mL of probenecid (250 mM) were added to each tube of Fluo-4 Direct™ crystals (F10471).

One of the cell plates was taken out of the incubator and the medium was removed. 20 μL of an assay buffer and 2× Fluo-4 Direct™ non-wash loading buffer were added to the 384-well cell culture plate to a final volume of 40 μL, and then the culture plate was incubated in an incubator (a 37° C., 5% $CO_2$) for 50 minutes, and then at room temperature for 10 minutes, and then the plate was placed in the FLIPR. 10 μL of the buffer was transferred to the cell plate and the fluorescence signal was read. The agonist $PGE_2$ was formulated as a 10 mM stock in a DMSO solvent and 10 concentration points of the 6× working solution were serially diluted using the buffer. 10 μL of the agonist $PGE_2$ was transferred to the cell plate, the fluorescence signal was read to calculate $EC_{80}$ value.

The agonist $PGE_2$ was prepared at 6× $EC_{80}$ concentration and the compound to be tested was formulated as a 10 mM stock solution in the DMSO solvent and 10 concentration points of the 6× compound working solution was serially diluted using the buffer.

Another cell plate was taken to remove media and 20 μL of the assay buffer and 2× Fluo-4 Direct™ non-wash loading buffer were added; the cell plate was incubated in a 37° C., 5% $CO_2$ incubator for 50 minutes and room temperature for 10 minutes and then placed in the FLIPR. 10 μL of the compound working solution, DMSO, and the EP4 full antagonist were transferred to the cell plate and the fluorescence signal was read. 10 μL of the agonist $PGE_2$, with a concentration of 6× $EC_{80}$ was transferred to the cell plate, fluorescence signal was read to calculate the inhibition rate.

Inhibition (%)=100−(test group−*EP*4 full antagonist group)/(DMSO group−*EP*4 full antagonist group)*100

Compound's $IC_{50}$ value of EP4 calcium current inhibition was calculated based on the inhibition rate at different concentrations of the compound.

TABLE 2

Effects of test compounds on EP4 calcium current inhibition

| Test compounds | $IC_{50}$ (nM) |
|---|---|
| Control Compounds | 21 |
| Compound I-1 | 15 |
| Compound I-2 | 7.4 |
| Compound I-3 | 3 |
| Compound I-4 | 4.0 |
| Compound I-5 | 12 |
| Compound I-6 | 8.0 |
| Compound I-8 | 16.5 |
| Compound I-10 | 14 |
| Compound I-11 | 8.0 |
| Compound I-12 | 19 |
| Compound I-13 | 10 |
| Compound I-15 | 18 |
| Compound I-17 | 18 |

TABLE 2-continued

| Effects of test compounds on EP4 calcium current inhibition | |
|---|---|
| Test compounds | $IC_{50}$ (nM) |
| Compound I-26 | 8.5 |
| Compound I-28 | 8 |
| Compound I-30 | 15 |
| Compound I-33 | 12 |
| Compound I-35 | 6 |
| Compound I-41 | 16 |
| Compound I-42 | 15 |

The experimental results indicate that the compounds of the present application exhibit better inhibition effects on the calcium current of EP4, and they are superior to the control compound, especially the Compound I-4; and the inhibition effects of the compounds on the calcium current of EP4 are increased by more than 5 time, compared with the control compound. The compounds of the present disclosure exhibit better inhibition effects on the calcium current of EP4.

Assay Example 3: Radioligand Binding Assay for EP4 Receptor

The bindings, to the radioligand EP4, of a control compound and the compounds prepared by Examples 1 to 43 were tested using recombinant human EP4 receptor membrane protein (prepared from 293 cells overexpressing human EP4 receptor). The compounds to be tested and $PGE_2$ were formulated as 10 mM stocks in a DMSO solvent, and then 8 concentration points of 4× working solution were serially diluted using a buffer (50 mM HBSS, 0.1% BSA, 500 mM NaCl). 1 μL of the compound working solution, DMSO, and the $PGE_2$ working solution were added to the assay plate, respectively; 100 μL of a EP4 receptor membrane protein (20 μg/well) and 100 μL of a radioligand $[^3H]$-$PGE_2$ (PerkinElmer, Cat: NET428250UC, Lot: 2469552) (final concentration of 1.5 nM) were added and incubated at sealed room temperature for 1 hour. Unifilter-96 GF/C filter plate (Perkin Elmer) was soaked with 0.5% BSA, 50 μL per well, for at least 30 min at room temperature. After binding was complete, the reaction mixture was harvested through a GF/C plate using a Perkin Elmer Filtermate Harvester, followed by washing the filter plate and drying the filter plate for 1 hour at 50° C. After drying, the bottom of the filter plate wells was sealed using a Perkin Elmer Unifilter-96 sealing tape, and 50 μL of MicroScint™-20 cocktail (Perkin Elmer) was added to seal the top of the filter plate. The $^3H$ counts captured on the filter were read using a Perkin Elmer MicroBeta2 Reader.

Data were analyzed using GraphPad Prism 5 and inhibition rates were calculated according to the following formula:

$$\text{Inhibition (\%)}=100-(\text{test group}-PGE_2\text{ group})/(\text{DMSO group}-PGE_2\text{ group})*100$$

The $IC_{50}$ and Ki values of the compounds determined by the radioligand binding assay for EP4 receptor were calculated based on the inhibition rate of the different concentrations of the compounds.

TABLE 3

| $IC_{50}$ and Ki values for test compounds determined by radioligand binding assay for EP4 receptor | | |
|---|---|---|
| Test compounds | $IC_{50}$ (nM) | Ki (nM) |
| Control Compounds | 30 | 16 |
| Compound I-1 | 16 | 8.9 |
| Compound I-2 | 5.5 | 3.0 |
| Compound I-3 | 9.0 | 4.9 |
| Compound I-4 | 7.4 | 4.0 |
| Compound I-5 | 5.3 | 2.9 |
| Compound I-6 | 11 | 5.8 |
| Compound I-10 | 4.0 | 2.2 |
| Compound I-11 | 6.8 | 3.7 |
| Compound I-15 | 12 | 6.6 |
| Compound I-23 | 13 | 7.0 |
| Compound I-30 | 12 | 6.6 |
| Compound I-33 | 31 | 17 |
| Compound I-35 | 28 | 15 |
| Compound I-42 | 13 | 7.3 |

The experimental results indicate that, compared with the control compound, the compounds of the present disclosure have a better affinity with the EP4 receptor, which is superior to the control compound, especially Compound I-2 and Compound I-5; and their affinity with the EP4 receptor is increased by more than 5 times, compared with the control compound. The compounds of the present disclosure exhibit better affinity with the EP4 receptor.

Assay Example 4: Pharmacokinetic Assay

In this assay, the pharmacokinetic parameters of a control compound and the compounds prepared by Examples 1 to 43 in mouse, rat, and canine subjects were tested, respectively.

In a mouse pharmacokinetic assay, male ICR mice (20 g to 25 g) were selected and fasted overnight. Three mice were selected and intragastrically administered with 5 mg/kg of the corresponding compound. The blood of the mice was collected before the administration and at 15 min, 30 min, 1 h, 2 h, 4 h, 8 h, 24 h after the administration. Another 3 mice were intravenously administered with 1 mg/kg of the corresponding compound, and the blood thereof was collected before the administration and at 15 min, 30 min, 1 h, 2 h, 4 h, 8 h, 24 h after the administration. The blood samples were centrifuged at 6800 g at 2° C. to 8° C. for 6 minutes, and plasma was collected and stored at −80° C. The plasma was taken at respective time point, mixed with 3-5 times the amount of acetonitrile containing internal standard, vortexed for 1 minute, centrifuged at 4° C. for 10 minutes at 13000 rpm, supernatant was added 3 times the amount of water, and the appropriate mixture was taken for LC-MS/MS analysis. The primary pharmacokinetic parameters were analyzed with a WinNonlin 7.0 software, with non-compartmental model.

In a rat pharmacokinetic assay, male SD rats (180 g to 240 g) were selected and fasted overnight. Three rats were intragastrically administered with 5 mg/kg of the corresponding compound. Another 3 rats were intravenously administered with 1 mg/kg of the corresponding compound. The following operations were the same as the mouse pharmacokinetic assay.

In a canine pharmacokinetic assay, male Beagle dogs (8 kg to 10 Kg) were selected and fasted overnight. Three Beagle dogs were taken and intragastrically administered with 3 mg/kg of the corresponding compound. Another 3 Beagle dogs were intravenously administered with 1 mg/kg of the corresponding compound. The following operations were the same as the mouse pharmacokinetic assay.

TABLE 4-1

Pharmacokinetic assay results for intravenous administration in mouse model

| | Intravenous administration (1 mg/kg) | | | |
|---|---|---|---|---|
| Test compounds | CL (L/h/kg) | $V_z$ (L/kg) | $AUC_{0-t}$ (h*ng/mL) | $T_{1/2}$ (h) |
| Control Compound | 0.88 | 8.38 | 974 | 6.64 |
| Compound I-5 | 0.76 | 5.62 | 1264 | 5.11 |

TABLE 4-2

Pharmacokinetic assay results for intragastric administration in mouse model

| | Oral gavage administration (5 mg/kg) | | | |
|---|---|---|---|---|
| Test compounds | Cmax (ng/mL) | Tmax (hr) | AUC0-t (h*ng/mL) | $T_{1/2}$ (h) |
| Control Compound | 792 | 0.25 | 1766 | 30.93 |
| Compound I-1 | 1114 | 0.33 | 2135 | 4.33 |
| Compound I-2 | 1837 | 0.33 | 2139 | 15.68 |
| Compound I-5 | 1450 | 0.33 | 2709 | 7 |
| Compound I-6 | 1285 | 0.42 | 4436 | 7.22 |
| Compound I-33 | 2528 | 0.33 | 8292 | 8.22 |
| Compound I-35 | 1040 | 0.33 | 3060 | 7.12 |
| Compound I-42 | 570 | 0.33 | 2444 | 23.25 |

TABLE 5-1

Pharmacokinetic assay results for intravenous administration in rat model

| | Intravenous administration (1 mg/kg) | | | |
|---|---|---|---|---|
| Test compounds | CL (L/h/kg) | $V_z$ (L/kg) | $AUC_{0-t}$ (h*ng/mL) | $T_{1/2}$ (h) |
| Control Compound | 0.61 | 9.55 | 1425 | 10.9 |
| Compound I-5 | 0.57 | 7.66 | 1668 | 9.3 |
| Compound I-33 | 0.22 | 2.72 | 4668 | 9.02 |

TABLE 5-2

Pharmacokinetic assay results for intragastric administration in rat model

| | Oral gavage administration (5 mg/kg) | | | |
|---|---|---|---|---|
| Test compounds | Cmax (ng/mL) | Tmax (hr) | AUC0-t (h*ng/mL) | $T_{1/2}$ (h) |
| Control Compounds | 1102 | 0.5 | 6849 | 12.67 |
| Compound I-5 | 993 | 2.00 | 10785 | 9.87 |

TABLE 6-1

Pharmacokinetic assay results for intravenous administration in canine model

| | Intravenous administration (1 mg/kg) | | | |
|---|---|---|---|---|
| Test compounds | CL (L/h/kg) | $V_z$ (L/kg) | $AUC_{0-t}$ (h*ng/mL) | $T_{1/2}$ (h) |
| Control Compound | 0.24 | 3.21 | 3730 | 9.36 |
| Compound I-5 | 0.21 | 2.84 | 4373 | 9.73 |

TABLE 6-2

Pharmacokinetic assay results for intragastric administration in canine model

| | Oral gavage administration (3 mg/kg) | | | |
|---|---|---|---|---|
| Test compounds | Cmax (ng/mL) | Tmax (hr) | AUC0-t (h*ng/mL) | $T_{1/2}$ (h) |
| Control Compound | 1357 | 1.0 | 6802 | 18.6 |
| Compound I-5 | 4822 | 0.25 | 10341 | 19.9 |
| Compound I-42 | 4853 | 0.25 | 7187 | 8.35 |

The experimental results indicate that compared to the control compound, the compounds of the present disclosure have lower clearance for intravenous administration and higher exposure for oral administration, in particular compound 1-5; the exposure after oral administration in rats and canines is about 2 times higher than that of the control compound; and the compounds of the present disclosure exhibit superior pharmacokinetic properties and are good druggability.

Assay Example 5: Anti-Tumor Effect of Test Compounds in a CT-26 Murine Colon Cancer Tumor Model, in Combination with Radiation Therapy In this assay, the anti-tumor effects of the control compound and the compounds prepared in Examples 1 to 43, in combination with radiation therapy, were tested in a CT-26 murine colon cancer tumor model.

After one week of adaptive feeding of mice, CT-26 cells in a log phase were resuspended in PBS, $5\times10^5$ CT-26 cells were inoculated subcutaneously at the right flank at 100 μL per mouse, and tumor growth was observed regularly. When the tumor grew to an average volume of 60 to 80 $mm^3$, the mice carrying the tumor were randomly divided into 5 groups based on the tumor volume size, each group containing 10 mice of 10. These group were a group of Control compound (150 mg/kg) in combination with radiotherapy (3Gry), a group of Compound I-2 (150 mg/kg) in combination with radiotherapy, a group of Compound I-5 (150 mg/kg) in combination with radiotherapy, a group of radiotherapy (3Gry) alone, and a group of vehicle control. The mice were intragastrically administered with the corresponding compound once daily, for 23 days in total; radiation therapy was performed for one-time on the first day of the administration. Tumor volumes and mouse body weights were measured twice a week, and tumor weights were weighed at the end of the experiment. Efficacy evaluations were performed based on relative tumor inhibition (TGI), safety evaluations were performed based on changes in animal body weight and death. Tumor volume and relative tumor inhibition were calculated as follows:

Tumor volume (TV)=½×a×b², where a and b are the length and width of the tumor measurement, respectively.

Relative tumor inhibition rate TGI (%)=(TWc−TWt/TWc)×100%, where TWc is the mean tumor weight of the vehicle control group and TW is the mean tumor weight of the treatment group.

The experimental results are illustrated in FIG. 1. FIG. 1 indicates that the control compound, the test compounds I-2 and I-5, in combination with radiotherapy, all exhibited significant tumor inhibition effect at day 23 after the beginning of administration, and the relative tumor inhibition rates TGI (%) were 54%, 63%, and 79%, respectively, which are all statistically significantly different from the vehicle control group (p-mean smaller than 0.05); the Compound I-5 in combination with radiotherapy group was statistically significantly different from the group of radiotherapy alone (p smaller than 0.05), and better than the group of the control compound in combination with radiotherapy. None of the groups in combination with radiotherapy neither had animal deaths nor exhibited apparent drug toxicity, exhibiting good tolerance during the treatment.

What is claimed is:

1. A compound, represented by Formula V, or a tautomer, stereoisomer, salt or prodrug of the compound represented by Formula V:

V

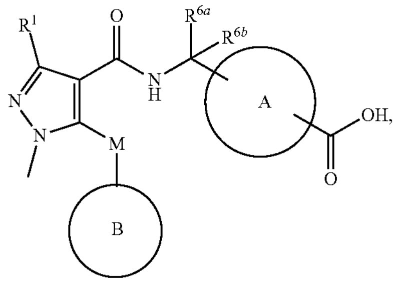

wherein ring A is selected from the group consisting of

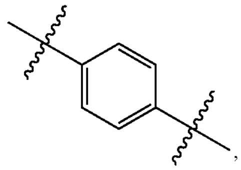

,

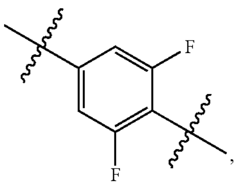

,

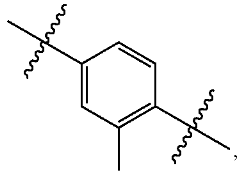

, and

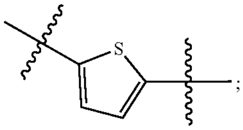

;

ring B is selected from the group consisting of

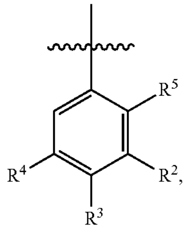

and

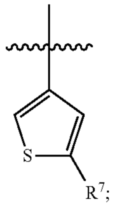

$R^1$ is selected from the group consisting of —$CH_3$, —$CHF_2$, and —$CF_3$;

$R^2$ is selected from the group consisting of $C_2$-$C_6$ alkyl, $C_3$-$C_6$ cycloalkyl, phenyl, trifluoromethyl, $C_2$-$C_6$ halogen-substituted alkyl, $C_3$-$C_6$ halogen-substituted cycloalkyl, $C_2$-$C_6$ hydroxy-substituted alkyl, $C_2$-$C_6$ cyano-substituted alkyl, and —X—$R^{2a}$, where X is selected from sulfur, —CO—, —$SO_2$—, and SO—, and $R^{2a}$ is selected from $C_1$-$C_6$ alkyl and $C_1$-$C_6$ halogen-substituted alkyl;

$R^3$ is selected from the group consisting of hydrogen, halogen, $C_1$-$C_2$ alkyl, $C_1$-$C_2$ fluorine-substituted alkyl, and phenyl;

$R^4$ is selected from the group consisting of hydrogen, halogen, $C_1$-$C_6$ alkyl, $C_1$-$C_6$ alkoxyl, $C_1$-$C_6$ halogen-substituted alkyl, and $C_1$-$C_6$ halogen-substituted alkoxyl;

$R^5$ is selected from the group consisting of hydrogen and halogen;

one of $R^{6a}$ and $R^{6b}$ is hydrogen, and the other one of $R^{6a}$ and $R^{6b}$ is methyl; or $R^{6a}$ and $R^{6b}$ together form cyclobutyl;

$R^7$ is selected from the group consisting of —$CH_3$, —$CHF_2$, and —$CF_3$; and M is selected from the group consisting of oxygen, sulfur, and methylene;

provided that:

when $R^2$ is trifluoromethyl, M is oxygen, one of $R^{6a}$ and $R^{6b}$ is hydrogen, and the other one of $R^{6a}$ and $R^{6b}$ is methyl, ring A is selected from the group consisting of

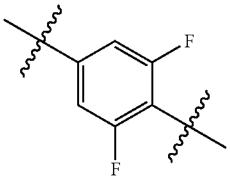

and

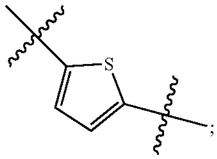

;

and when $R^2$ is trifluoromethyl, M is oxygen, and ring A is

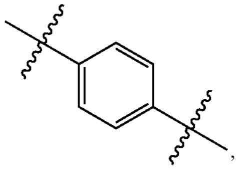 [SMILES: *c1ccc(*)cc1]

, $R^{6a}$ and $R^{6b}$ together form cyclobutyl.

2. The compound according to claim 1, represented by Formula III, or a tautomer, stereoisomer, salt or prodrug of the compound represented by Formula III:

III

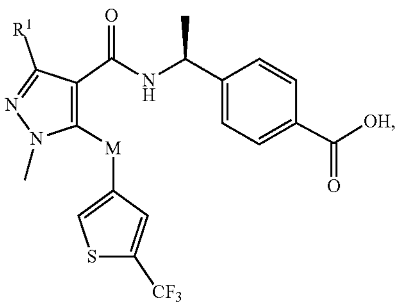

wherein $R^1$ is selected from the group consisting of $—CH_3$, $—CHF_2$, and $—CF_3$;

$R^7$ is selected from the group consisting of $—CH_3$, $—CHF_2$, and $—CF_3$; and M is selected from the group consisting of oxygen, sulfur, and methylene.

3. The compound according to claim 1, represented by Formula II, or a tautomer, stereoisomer, salt or prodrug of the compound represented by Formula II:

II

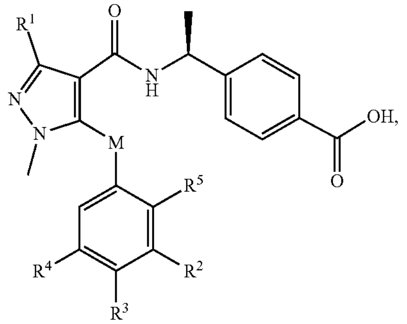

wherein $R^1$ is selected from the group consisting of $—CH_3$, $—CHF_2$, and $—CF_3$;

$R^2$ is selected from the group consisting of ethyl, propyl, isopropyl, n-butyl, isobutyl, tert-butyl, fluoroethyl, fluoropropyl, fluoroisopropyl, fluorobutyl, fluorisobutyl, hydroxyethyl, hydroxyisopropyl, cyanomethyl, cyanoethyl, phenyl, and $—X—R^{2a}$, where X is selected from the group consisting of sulfur, and —CO—, and $R^{2a}$ is selected from the group consisting of methyl, ethyl, fluoromethyl, and fluoroethyl;

$R^3$ is selected from the group consisting of hydrogen, fluorine, chlorine, methyl, ethyl, fluoromethyl, fluoroethyl, and phenyl;

$R^4$ is selected from the group consisting of hydrogen, fluorine, chlorine, methyl, ethyl, fluoromethyl, and fluoroethyl;

$R^5$ is selected from the group consisting of hydrogen, fluorine, and chlorine; and M is selected from the group consisting of oxygen, sulfur, and methylene.

4. The compound according to claim 1, represented by Formula I, or a tautomer, stereoisomer, salt, or prodrug of the compound represented by Formula I:

I

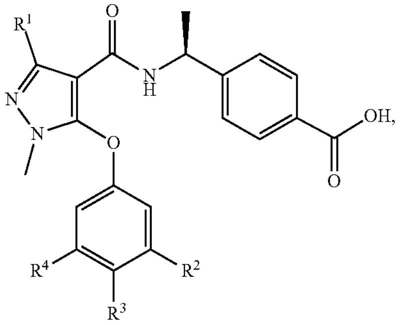

wherein $R^1$ is selected from the group consisting of $—CH_3$, $—CHF_2$, and $—CF_3$;

$R^2$ is selected from the group consisting of $C_2$-$C_6$ alkyl, $C_3$-$C_6$ cycloalkyl, $C_2$-$C_6$ halogen-substituted alkyl, and $C_3$-$C_6$ halogen-substituted cycloalkyl;

$R^3$ is selected from the group consisting of hydrogen, halogen, $C_1$-$C_2$ alkyl, and $C_1$-$C_2$ fluorine-substituted alkyl;

$R^4$ is selected from the group consisting of hydrogen, halogen, $C_1$-$C_6$ alkyl, $C_1$-$C_6$ alkoxyl, $C_1$-$C_6$ halogen-substituted alkyl, and $C_1$-$C_6$ halogen-substituted alkoxyl.

5. The compound according to claim 4, wherein $R^2$ is selected from the group consisting of $C_2$-$C_3$ alkyl, $C_3$-$C_6$ cycloalkyl, $C_2$-$C_3$ fluorine-substituted alkyl, and $C_3$-$C_6$ fluorine-substituted cycloalkyl;

$R^3$ is selected from the group consisting of hydrogen, fluorine, and chlorine;

$R^4$ is selected from the group consisting of hydrogen, fluorine, chlorine, $C_1$-$C_4$ alkyl, $C_1$-$C_4$ alkoxyl, $C_1$-$C_4$ fluorine- or chlorine-substituted alkyl, and $C_1$-$C_4$ fluorine- or chlorine-substituted alkoxyl.

6. A pharmaceutical composition, comprising:

a pharmaceutically acceptable excipient; and the compound according to claim 1.

7. A method for treating a colorectal cancer, the method comprising:

administrating the compound according to claim 1 in combination with a radiation therapy to a patient.

8. The compound according to claim 1, wherein the compound is any one of the following compounds, or a tautomer, stereoisomer, pharmaceutically acceptable salt or prodrug of any one of the following compounds:

I-1

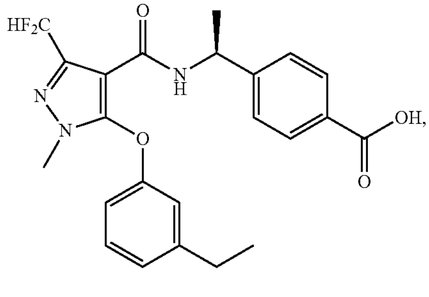

-continued
I-2
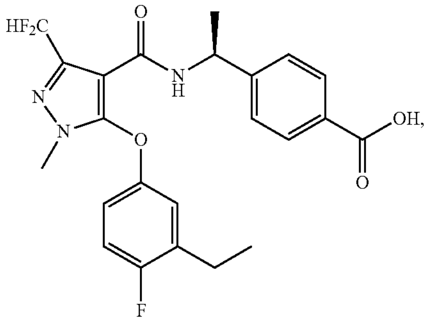
I-3
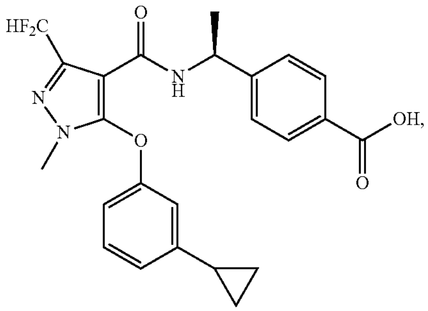
I-4
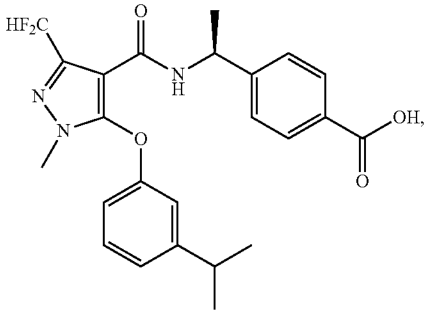
I-5
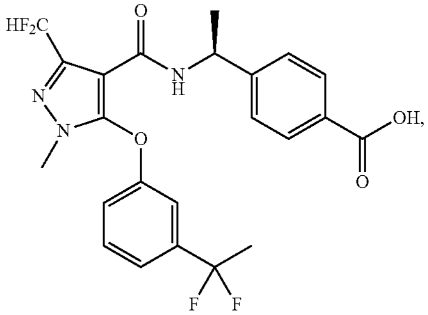
I-6
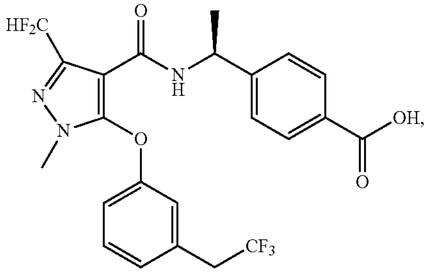
-continued
I-7
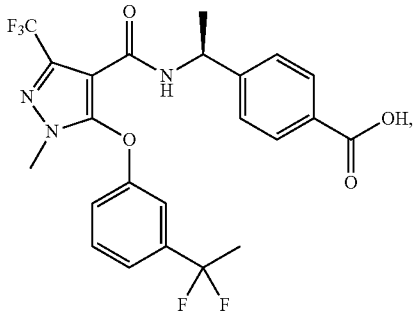
I-8
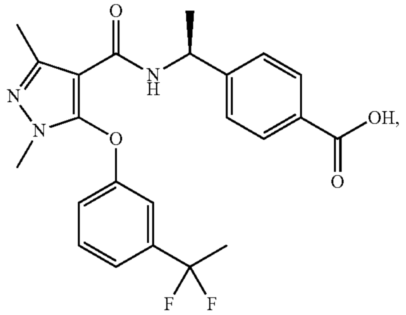
I-9
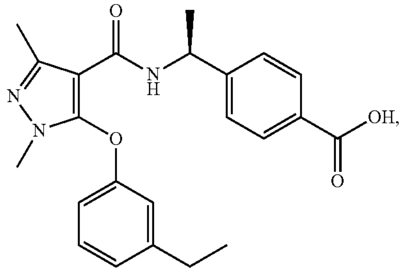
I-10
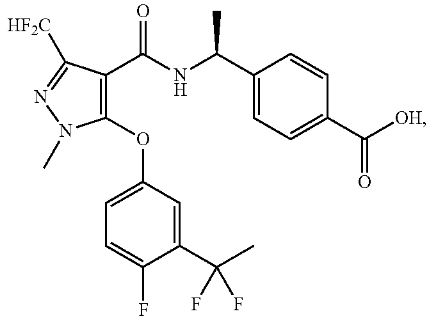
I-11
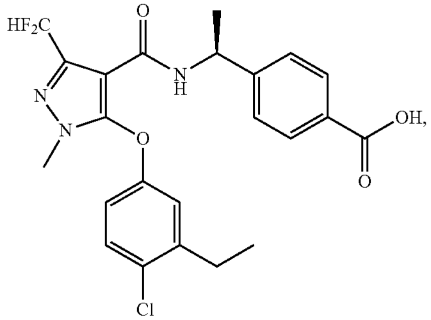

-continued
I-12
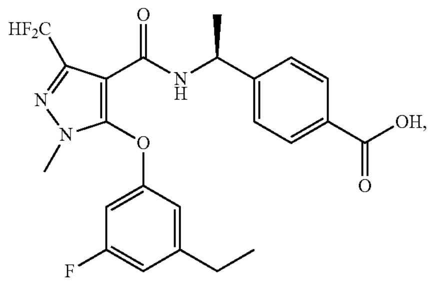
I-13
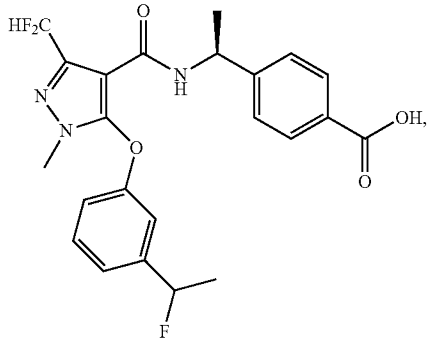
I-14
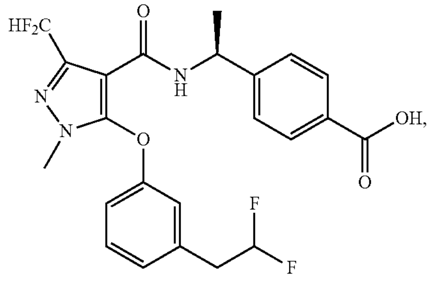
I-15
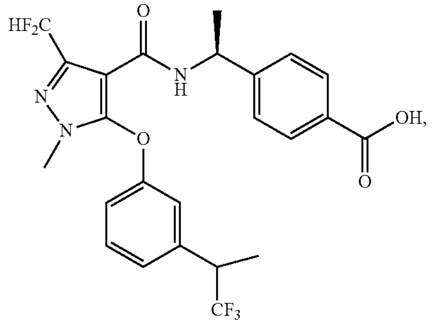
I-16
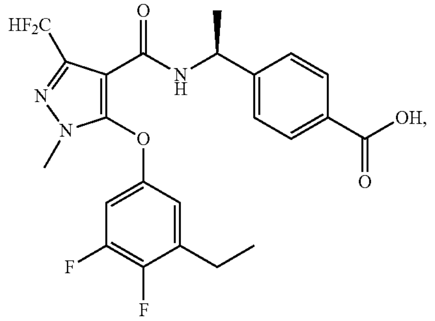
-continued
I-17
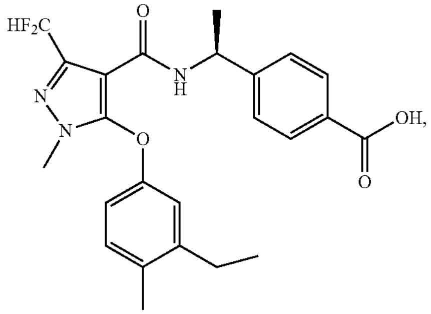
I-21
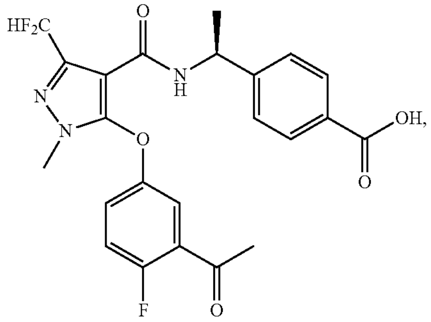
I-22
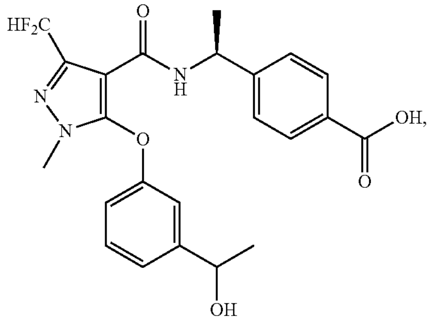
I-23
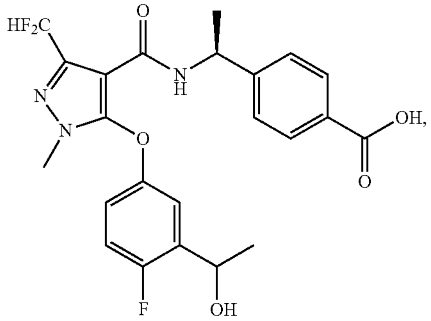
I-24
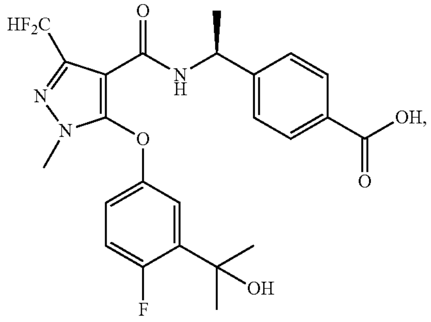

-continued
I-25
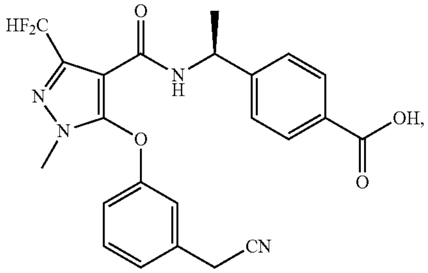
I-27
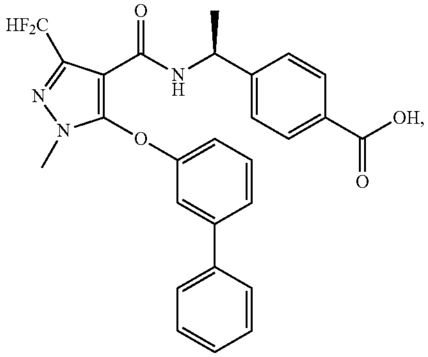
I-29
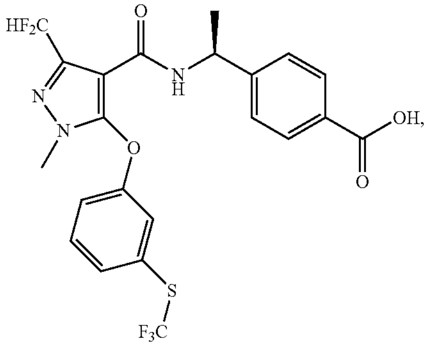
I-30
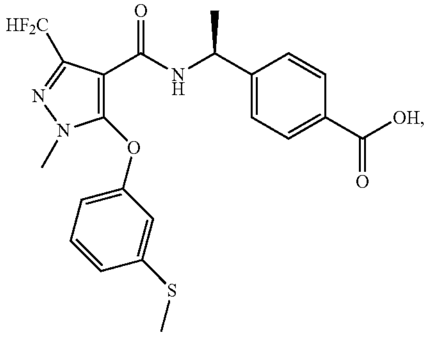
-continued
I-31
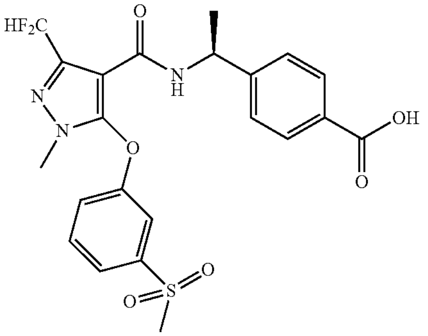
I-32
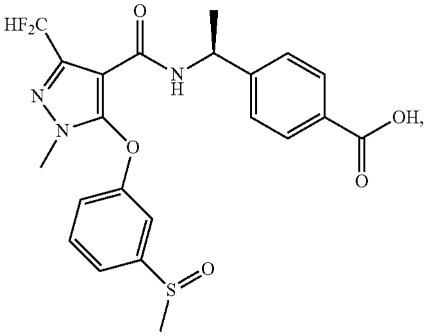
I-35
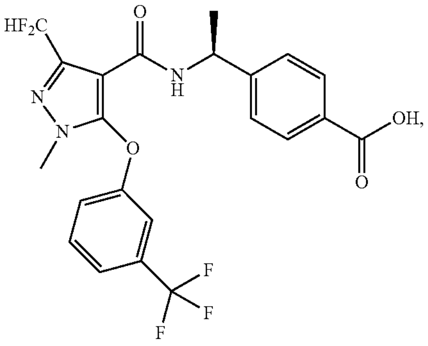
I-37
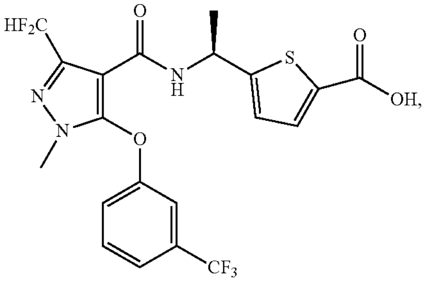
I-38
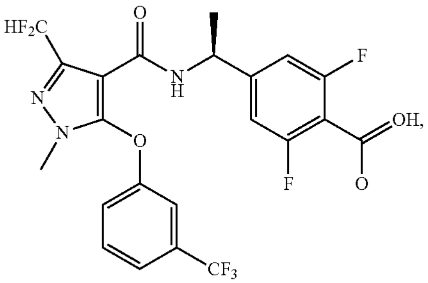

-continued

I-39

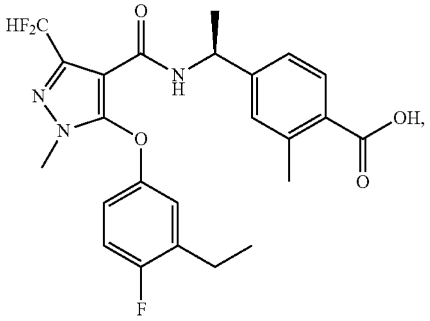

I-40

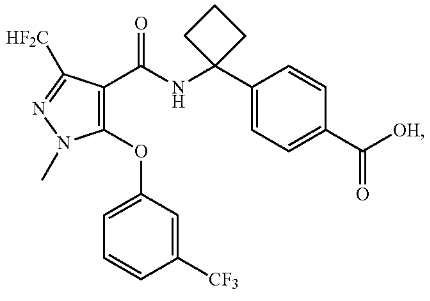

I-41

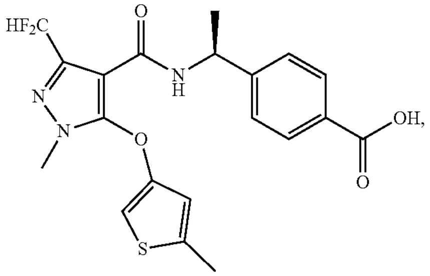

I-42

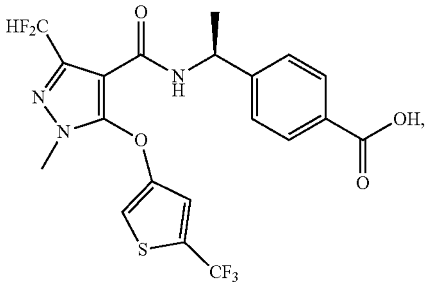

or

-continued

I-43

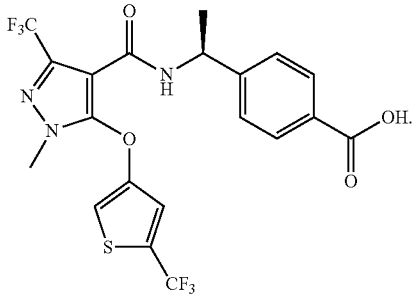

9. The compound of claim 3, wherein $R^1$ is $—CHF_2$.

10. The compound of claim 5, wherein $R^2$ is selected from the group consisting of $—CH_2CH_3$, $—CH(CH_3)_2$, cyclopropyl, $—CF_2CH_3$, and $—CH_2CF_3$.

11. The compound of claim 5, wherein $R^4$ is selected from the group consisting of hydrogen, fluorine, and chlorine.

12. The method according to claim 7, wherein the compound is

I-2

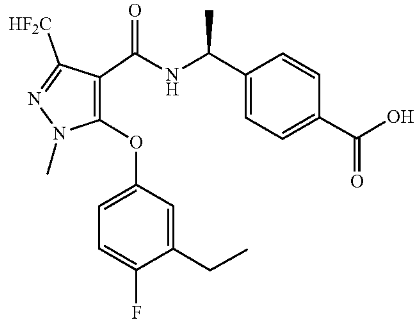

or

I-5

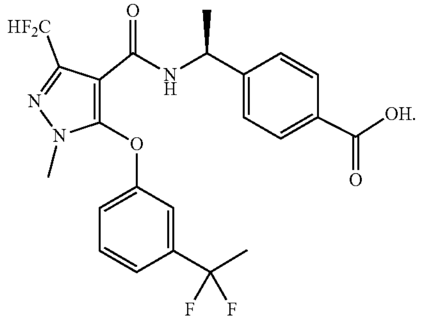

13. The method according to claim 7, wherein a total dose of the radiation therapy is 3 Gry.

* * * * *